US011359028B2

(12) United States Patent
Wilson et al.

(10) Patent No.: US 11,359,028 B2
(45) Date of Patent: Jun. 14, 2022

(54) ANTI-OX40 ANTIBODIES AND ANTI-GITR ANTIBODIES

(71) Applicants: Agenus Inc., Lexington, MA (US); Memorial Sloan-Kettering Cancer Center, New York, NY (US); Ludwig Institute for Cancer Research Ltd., Zurich (CH)

(72) Inventors: Nicholas S. Wilson, San Carlos, CA (US); Jeremy D. Waight, Everett, MA (US); Dennis J. Underwood, Boston, MA (US); Ekaterina V. Breous-Nystrom, Basel (CH); Gerd Ritter, New York, NY (US); David Schaer, Mamaroneck, NY (US); Daniel Hirschhorn-Cymerman, New York, NY (US); Taha Merghoub, Jersey City, NJ (US); Marc Van Dijk, Bosch en Duin (NL)

(73) Assignees: AGENUS INC., Lexington, MA (US); Memorial Sloan-Kettering Cancer Center, New York, NY (US); Ludwig Institute for Cancer Research Ltd., Zurich (CH)

( * ) Notice: Subject to any disclaimer, the term of this patent is extended or adjusted under 35 U.S.C. 154(b) by 303 days.

(21) Appl. No.: 16/407,835

(22) Filed: May 9, 2019

(65) Prior Publication Data
US 2019/0367627 A1    Dec. 5, 2019

Related U.S. Application Data

(63) Continuation of application No. PCT/US2017/060854, filed on Nov. 9, 2017.

(60) Provisional application No. 62/419,907, filed on Nov. 9, 2016.

(51) Int. Cl.
*C07K 16/28* (2006.01)
*A61K 45/06* (2006.01)

(52) U.S. Cl.
CPC ......... *C07K 16/2878* (2013.01); *A61K 45/06* (2013.01); *C07K 16/2818* (2013.01); *C07K 16/2827* (2013.01); *C07K 2317/31* (2013.01); *C07K 2317/565* (2013.01); *C07K 2317/75* (2013.01)

(58) Field of Classification Search
None
See application file for complete search history.

(56) References Cited

U.S. PATENT DOCUMENTS

| | | |
|---|---|---|
| 5,759,546 A | 6/1998 | Weinberg et al. |
| 6,277,962 B1 | 8/2001 | Godfrey et al. |
| 6,566,082 B1 | 5/2003 | Weinberg et al. |
| 7,364,733 B2 | 4/2008 | Godfrey et al. |
| 7,387,271 B2 | 6/2008 | Noelle et al. |
| 7,402,431 B2 | 7/2008 | Har-Noy |
| 7,435,592 B2 | 10/2008 | Har-Noy |
| 7,504,101 B2 | 3/2009 | Weinberg |
| 7,531,170 B1 | 5/2009 | Croft et al. |
| 7,534,808 B2 | 5/2009 | Evenou et al. |
| 7,550,140 B2 | 6/2009 | Bakker et al. |
| 7,563,443 B2 | 7/2009 | Grant et al. |
| 7,592,431 B2 | 9/2009 | Har-Noy |
| 7,635,472 B2 | 12/2009 | Kufer et al. |
| 7,648,989 B2 | 1/2010 | Van Eis et al. |
| 7,807,156 B1 | 10/2010 | Croft et al. |
| 7,812,133 B2 | 10/2010 | Martin |
| 7,820,672 B2 | 10/2010 | Von Matt |
| 7,829,084 B2 | 11/2010 | Ledbetter et al. |
| 7,960,515 B2 | 6/2011 | Min et al. |
| 8,101,175 B1 | 1/2012 | Croft et al. |
| 8,124,085 B2 | 2/2012 | Nielsen et al. |
| 8,133,983 B2 | 3/2012 | Bakker et al. |
| 8,147,835 B2 | 4/2012 | Ledbetter et al. |
| 8,153,765 B2 | 4/2012 | Park et al. |
| 8,197,810 B2 | 6/2012 | Ledbetter et al. |
| 8,236,930 B2 | 8/2012 | Min et al. |
| 8,283,450 B2 | 10/2012 | Kato et al. |

(Continued)

FOREIGN PATENT DOCUMENTS

| | | |
|---|---|---|
| EP | 2100615 A1 | 9/2009 |
| EP | 2637691 A2 | 9/2013 |

(Continued)

OTHER PUBLICATIONS

Rudikoff et al (Proc Natl Acad Sci USA 79: 1979-1983 (1982). (Year: 1982).*
Colman (Research in Immunology 145: 33-36, 1994) (Year: 1994).*
Kussie et al. (J. Immunol. 152: 146-152, 1994) (Year: 1994).*
Chen et al. (EMBO J., 14: 2784-2794, 1995) (Year: 1995).*
D'Angelo et al., Many Routes to an Antibody Heavy-Chain CDR3: Necessary, Yet Insufficient, for Specific Binding; (Frontiers in Immunology vol. 9, Article 395 Mar. 2018; doi:10.3389/fimmu.2018.00395. (Year: 2018).*
Piche-Nicholas et al., Changes in complementarity-determining regions significantly alter IgG binding to the neonatal Fc receptor (FcRN) and pharmacokinetics; MABS 2018, vol. 10, No. 1, 81-94, doi.org/10.1080/19420862.2017.1389355. (Year: 2018).*

(Continued)

*Primary Examiner* — Phillip Gambel
(74) *Attorney, Agent, or Firm* — Dechert LLP; Andrew T. Wilkins; Sharia F. Flohr

(57) ABSTRACT

The present disclosure provides antibodies that specifically bind to human OX40 receptor (OX40) and/or human GITR receptor (GITR), including multispecific antibodies that bind, e.g., to OX40 and GITR, and compositions comprising such antibodies. The antibodies disclosed herein modulate OX40 and/or GITR activity e.g., enhance, activate, induce, reduce, deactivate, or inhibit OX40 and/or GITR activity. The present disclosure also provides methods for treating disorders, such as cancer, autoimmune diseases or disorders, or inflammatory diseases or disorders, by administering an antibody that specifically binds to human OX40 and/or human GITR and modulates OX40 and/or GITR activity.

16 Claims, 8 Drawing Sheets

Figure 1A:
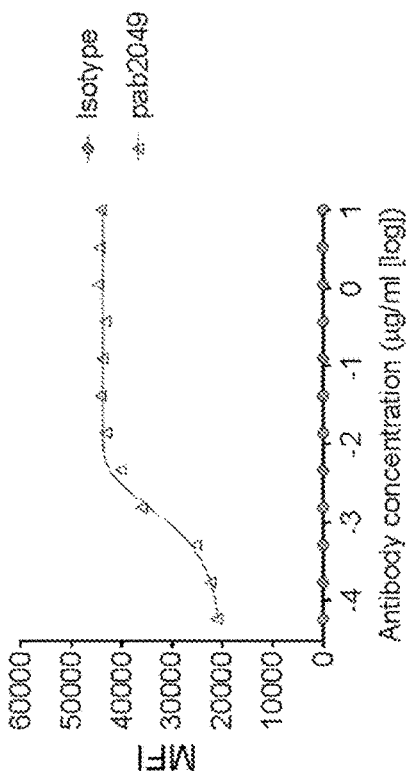

Specification includes a Sequence Listing.

(56) References Cited

U.S. PATENT DOCUMENTS

| | | |
|---|---|---|
| 8,329,197 B2 | 12/2012 | Noelle et al. |
| 8,409,577 B2 | 4/2013 | Thompson et al. |
| 8,440,192 B2 | 5/2013 | Nielsen et al. |
| 8,481,029 B2 | 7/2013 | Glennie et al. |
| 8,551,477 B1 | 10/2013 | Croft et al. |
| 8,614,295 B2 | 12/2013 | Lawson et al. |
| 8,652,836 B2 | 2/2014 | Hu |
| 8,748,585 B2 | 6/2014 | Attinger et al. |
| 8,865,873 B2 | 10/2014 | Liu et al. |
| 8,956,615 B1 | 2/2015 | Croft et al. |
| 8,993,524 B2 | 3/2015 | Bedi et al. |
| 8,993,614 B2 | 3/2015 | Bartkovitz et al. |
| 9,005,612 B2 | 4/2015 | Ledbetter et al. |
| 9,005,619 B2 | 4/2015 | Kohrt et al. |
| 9,006,399 B2 | 4/2015 | Liu et al. |
| 9,028,824 B2 | 5/2015 | Min et al. |
| 9,040,048 B2 | 5/2015 | Adams et al. |
| 9,102,733 B2 | 8/2015 | Endl et al. |
| 9,132,281 B2 | 9/2015 | Zeng et al. |
| 9,161,976 B2 | 10/2015 | Noelle et al. |
| 9,163,085 B2 | 10/2015 | Liu et al. |
| 9,228,016 B2 | 1/2016 | Wang et al. |
| 9,248,183 B2 | 2/2016 | Glennie et al. |
| 9,352,001 B2 | 5/2016 | Har-Noy |
| 9,365,496 B2 | 6/2016 | Cerundolo et al. |
| 9,409,987 B2 | 8/2016 | Toporik et al. |
| 9,428,570 B2 | 8/2016 | Lawson et al. |
| 9,441,044 B2 | 9/2016 | Bedi et al. |
| 9,475,878 B2 | 10/2016 | Kato et al. |
| 9,475,880 B2 | 10/2016 | Simons et al. |
| 9,486,520 B2 | 11/2016 | Borrebaeck et al. |
| 9,493,563 B2 | 11/2016 | Blein et al. |
| 9,511,127 B2 | 12/2016 | Har-Noy |
| 9,527,917 B2 | 12/2016 | Liu et al. |
| 9,540,442 B2 | 1/2017 | Tsurushita et al. |
| 9,695,246 B2 | 7/2017 | Liu et al. |
| 9,700,532 B2 | 7/2017 | Cerundolo et al. |
| 9,713,641 B2 | 7/2017 | Hicklin et al. |
| 9,738,723 B2 | 8/2017 | Hammond et al. |
| 9,758,589 B2 | 9/2017 | Kohrt et al. |
| 9,782,463 B2 | 10/2017 | Har-Noy |
| 9,790,281 B2 | 10/2017 | Simons et al. |
| 9,828,432 B2 | 11/2017 | Curt et al. |
| 9,834,610 B2 | 12/2017 | Tykocinski |
| 9,840,536 B2 | 12/2017 | Currie et al. |
| 9,850,306 B2 | 12/2017 | Bedi et al. |
| 9,873,735 B2 | 1/2018 | Adams et al. |
| 9,873,744 B1 | 1/2018 | Croft et al. |
| 9,926,374 B2 | 3/2018 | Glennie et al. |
| 10,259,882 B2 | 4/2019 | Van Dijk et al. |
| 10,800,849 B2 | 10/2020 | Gonzalez et al. |
| 10,836,830 B2 | 11/2020 | Wilson et al. |
| 2003/0035790 A1 | 2/2003 | Chen et al. |
| 2003/0223989 A1 | 12/2003 | Pluenneke |
| 2004/0009174 A1 | 1/2004 | Arndt et al. |
| 2004/0022760 A1 | 2/2004 | McKenna et al. |
| 2004/0197312 A1 | 10/2004 | Moskalenko et al. |
| 2005/0002916 A1 | 1/2005 | Jooss et al. |
| 2005/0123536 A1 | 6/2005 | Law et al. |
| 2006/0148064 A1 | 7/2006 | Srivastava |
| 2006/0217531 A1 | 9/2006 | Godfrey et al. |
| 2006/0280728 A1 | 12/2006 | Weinberg et al. |
| 2006/0281072 A1 | 12/2006 | Bakker |
| 2007/0036783 A1 | 2/2007 | Humeau et al. |
| 2007/0092511 A1 | 4/2007 | Godfrey et al. |
| 2008/0286286 A1 | 11/2008 | Liu et al. |
| 2008/0317751 A1 | 12/2008 | Heath |
| 2009/0069535 A1 | 3/2009 | Godfrey et al. |
| 2009/0087440 A1 | 4/2009 | Vicari et al. |
| 2009/0130111 A1 | 5/2009 | Wu et al. |
| 2009/0137003 A1 | 5/2009 | Tolstrup et al. |
| 2009/0175867 A1 | 7/2009 | Thompson et al. |
| 2009/0214560 A1 | 8/2009 | Min et al. |
| 2009/0317407 A1 | 12/2009 | LaCelle et al. |
| 2010/0008920 A1 | 1/2010 | Schneck et al. |
| 2010/0015143 A1 | 1/2010 | Hussell et al. |
| 2010/0098712 A1 | 4/2010 | Adler et al. |
| 2010/0136030 A1 | 6/2010 | Salah-Eddine et al. |
| 2010/0196359 A1 | 8/2010 | Kato et al. |
| 2010/0240873 A1 | 9/2010 | Godfrey et al. |
| 2010/0254978 A1 | 10/2010 | Lawson et al. |
| 2011/0008368 A1 | 1/2011 | Liu et al. |
| 2011/0123552 A1 | 5/2011 | Bakker et al. |
| 2011/0206681 A1 | 8/2011 | Min et al. |
| 2011/0256184 A1 | 10/2011 | Lei et al. |
| 2011/0262454 A1 | 10/2011 | Park et al. |
| 2011/0280903 A1 | 11/2011 | Noelle et al. |
| 2011/0318380 A1 | 12/2011 | Brix et al. |
| 2012/0070450 A1 | 3/2012 | Ishikawa et al. |
| 2012/0128687 A1 | 5/2012 | Adler et al. |
| 2012/0141465 A1 | 6/2012 | Croft et al. |
| 2012/0225086 A1 | 9/2012 | Min et al. |
| 2012/0251531 A1 | 10/2012 | Baehner et al. |
| 2012/0269825 A1 | 10/2012 | Liu et al. |
| 2013/0071403 A1 | 3/2013 | Rolland et al. |
| 2013/0183311 A1 | 7/2013 | Nielsen et al. |
| 2013/0183315 A1 | 7/2013 | Attinger et al. |
| 2013/0211050 A1 | 8/2013 | Stennicke et al. |
| 2013/0243772 A1 | 9/2013 | Adams et al. |
| 2013/0280265 A1 | 10/2013 | Rolland et al. |
| 2013/0280275 A1 | 10/2013 | Liu et al. |
| 2013/0295091 A1 | 11/2013 | Esslinger et al. |
| 2013/0330344 A1 | 12/2013 | Lawson et al. |
| 2013/0336977 A1 | 12/2013 | Thompson et al. |
| 2014/0044703 A1 | 2/2014 | Kato et al. |
| 2014/0079706 A1 | 3/2014 | Cannarile et al. |
| 2014/0127203 A1 | 5/2014 | Thompson et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0294765 A1 | 10/2014 | Cojocaru et al. |
| 2014/0294824 A1 | 10/2014 | Attinger et al. |
| 2014/0302033 A1 | 10/2014 | Adams et al. |
| 2014/0308276 A1 | 10/2014 | Liu et al. |
| 2014/0377221 A1 | 12/2014 | Tufaro et al. |
| 2014/0377284 A1 | 12/2014 | Simons et al. |
| 2015/0017141 A1 | 1/2015 | June et al. |
| 2015/0037346 A1 | 2/2015 | Lesokhin et al. |
| 2015/0119555 A1 | 4/2015 | Jung et al. |
| 2015/0132288 A1 | 5/2015 | Simons et al. |
| 2015/0157710 A1 | 6/2015 | Redmond et al. |
| 2015/0158947 A1 | 6/2015 | Cojocaru et al. |
| 2015/0190505 A1 | 7/2015 | Yeung |
| 2015/0190506 A1 | 7/2015 | Cheung et al. |
| 2015/0202291 A1 | 7/2015 | Bosch et al. |
| 2015/0218279 A1 | 8/2015 | Min et al. |
| 2015/0273033 A1 | 10/2015 | Bosch et al. |
| 2015/0307617 A1 | 10/2015 | Du et al. |
| 2015/0307620 A1 | 10/2015 | Vella et al. |
| 2015/0315281 A1 | 11/2015 | Liu et al. |
| 2015/0329617 A1 | 11/2015 | Winther et al. |
| 2015/0353637 A1 | 12/2015 | Wang et al. |
| 2015/0374731 A1 | 12/2015 | Maio et al. |
| 2016/0031974 A1 | 2/2016 | Adams et al. |
| 2016/0068604 A1 | 3/2016 | Liu et al. |
| 2016/0101128 A1 | 4/2016 | Wang et al. |
| 2016/0129095 A1 | 5/2016 | Noelle et al. |
| 2016/0137740 A1 | 5/2016 | Hammond et al. |
| 2016/0152720 A1 | 6/2016 | Kim et al. |
| 2016/0159905 A1 | 6/2016 | Abdiche et al. |
| 2016/0159927 A1 | 6/2016 | Molloy et al. |
| 2016/0193239 A1 | 7/2016 | Baylin et al. |
| 2016/0207995 A1 | 7/2016 | Yansura et al. |
| 2016/0235842 A1 | 8/2016 | Goldstein et al. |
| 2016/0243218 A1 | 8/2016 | Gilboa |
| 2016/0289645 A1 | 10/2016 | Tufaro et al. |
| 2016/0347847 A1 | 12/2016 | Van Dijk et al. |
| 2016/0347848 A1 | 12/2016 | Hammond et al. |
| 2016/0347849 A1 | 12/2016 | Cai et al. |
| 2016/0355589 A1 | 12/2016 | Williams et al. |
| 2016/0355598 A1 | 12/2016 | Lawson et al. |
| 2017/0014496 A1 | 1/2017 | Fotin-Mleczek et al. |
| 2017/0042997 A1 | 2/2017 | Wirth |
| 2017/0051061 A1 | 2/2017 | Snyder et al. |

(56) References Cited

U.S. PATENT DOCUMENTS

| | | |
|---|---|---|
| 2017/0051069 A1 | 2/2017 | Simons et al. |
| 2017/0056391 A1 | 3/2017 | Li |
| 2017/0081417 A1 | 3/2017 | Kato et al. |
| 2017/0106048 A1 | 4/2017 | Kunz et al. |
| 2017/0137530 A1 | 5/2017 | Baehner et al. |
| 2017/0158770 A1 | 6/2017 | Bedi et al. |
| 2017/0165230 A1 | 6/2017 | Rudd et al. |
| 2017/0182156 A1 | 6/2017 | Khleif |
| 2017/0202902 A1 | 7/2017 | McLaughlin et al. |
| 2017/0209574 A1 | 7/2017 | Cao et al. |
| 2017/0216403 A1 | 8/2017 | Wittrup et al. |
| 2017/0224777 A1 | 8/2017 | Wittrup et al. |
| 2017/0239338 A1 | 8/2017 | Szalay et al. |
| 2017/0240634 A1 | 8/2017 | Eisenbach-Schwartz et al. |
| 2017/0261497 A1 | 9/2017 | Schneck et al. |
| 2017/0267759 A1 | 9/2017 | Liang et al. |
| 2017/0267773 A1 | 9/2017 | Liu et al. |
| 2017/0290914 A1 | 10/2017 | Liang et al. |
| 2017/0296659 A1 | 10/2017 | Lebwohl et al. |
| 2017/0320950 A1 | 11/2017 | Snyder et al. |
| 2017/0340733 A1 | 11/2017 | Cao |
| 2017/0362295 A1 | 12/2017 | June et al. |
| 2017/0369586 A1 | 12/2017 | Simons et al. |
| 2018/0044428 A1 | 2/2018 | Gough et al. |
| 2018/0057608 A1 | 3/2018 | Jung et al. |
| 2018/0064765 A1 | 3/2018 | Petit et al. |
| 2018/0078625 A1 | 3/2018 | Moon et al. |
| 2018/0079821 A1 | 3/2018 | Tykocinski |
| 2018/0118823 A1 | 5/2018 | Thompson et al. |
| 2018/0194825 A1 | 7/2018 | Dubinett et al. |
| 2018/0194849 A1 | 7/2018 | Sahin et al. |
| 2018/0194850 A1 | 7/2018 | Faustman |
| 2019/0284291 A1 | 9/2019 | Van Dijk et al. |
| 2019/0367627 A1 | 12/2019 | Wilson |
| 2020/0079861 A1 | 3/2020 | Wilson et al. |
| 2020/0079862 A1 | 3/2020 | Wilson et al. |
| 2020/0123265 A1 | 4/2020 | Wilson et al. |
| 2020/0270356 A1 | 8/2020 | Van Dijk et al. |
| 2020/0317796 A1 | 10/2020 | Van Dijk et al. |
| 2020/0339698 A1 | 10/2020 | Gonzalez et al. |
| 2021/0171648 A1 | 6/2021 | Wilson et al. |

FOREIGN PATENT DOCUMENTS

| | | |
|---|---|---|
| EP | 3148579 A1 | 4/2017 |
| EP | 3292152 A1 | 3/2018 |
| EP | 3498295 A1 | 6/2019 |
| JP | 2008533993 A | 8/2008 |
| JP | 2008278814 A | 11/2008 |
| WO | WO-1994029351 A2 | 12/1994 |
| WO | WO-1995001997 A1 | 1/1995 |
| WO | WO-1997034631 A1 | 9/1997 |
| WO | WO-1998023289 A1 | 6/1998 |
| WO | WO-1999042585 A1 | 8/1999 |
| WO | WO-2000037504 A2 | 6/2000 |
| WO | WO-2000042072 A2 | 7/2000 |
| WO | WO-2001014424 A2 | 3/2001 |
| WO | WO-2001077342 A1 | 10/2001 |
| WO | WO-2002028440 A1 | 4/2002 |
| WO | WO-2002060919 A2 | 8/2002 |
| WO | WO-2003106498 A2 | 12/2003 |
| WO | WO-2004056873 A1 | 7/2004 |
| WO | WO-2004073732 A1 | 9/2004 |
| WO | WO-2005049085 A1 | 6/2005 |
| WO | WO-2006011114 A2 | 2/2006 |
| WO | WO-2006069202 A2 | 6/2006 |
| WO | WO-2006105021 A2 | 10/2006 |
| WO | WO-2007133822 A1 | 11/2007 |
| WO | WO-2008106116 A2 | 9/2008 |
| WO | WO-2009079335 A1 | 6/2009 |
| WO | WO-2009100140 A1 | 8/2009 |
| WO | WO-2010005958 A2 | 1/2010 |
| WO | WO-2010054007 A1 | 5/2010 |
| WO | WO-2010056898 A2 | 5/2010 |
| WO | WO-2011028683 A1 | 3/2011 |
| WO | WO-2011086091 A1 | 7/2011 |
| WO | WO-2012064760 A2 | 5/2012 |
| WO | WO-2012130831 A1 | 10/2012 |
| WO | WO-2012163769 A1 | 12/2012 |
| WO | WO-2013008171 A1 | 1/2013 |
| WO | WO-2013022091 A1 | 2/2013 |
| WO | WO-2013028231 A1 | 2/2013 |
| WO | WO-2013033091 A1 | 3/2013 |
| WO | WO-2013038191 A2 | 3/2013 |
| WO | WO-2013039954 A1 | 3/2013 |
| WO | WO-2013049307 A2 | 4/2013 |
| WO | WO-2013068563 A2 | 5/2013 |
| WO | WO-2013083659 A1 | 6/2013 |
| WO | WO-2013092001 A1 | 6/2013 |
| WO | WO-2014121099 A1 | 8/2014 |
| WO | WO-2014148895 A1 | 9/2014 |
| WO | WO-2014165771 A2 | 10/2014 |
| WO | WO-2015009726 A2 | 1/2015 |
| WO | WO-2015009856 A2 | 1/2015 |
| WO | WO-2015026684 A1 | 2/2015 |
| WO | WO-2015095423 A2 | 6/2015 |
| WO | WO-2015095811 A2 | 6/2015 |
| WO | WO-2015116178 A1 | 8/2015 |
| WO | WO-2015135558 A1 | 9/2015 |
| WO | WO-2015145360 A1 | 10/2015 |
| WO | WO-2015153513 A1 | 10/2015 |
| WO | WO-2015153514 A1 | 10/2015 |
| WO | WO-2015174439 A1 | 11/2015 |
| WO | WO-2015184099 A1 | 12/2015 |
| WO | WO-2016028656 A1 | 2/2016 |
| WO | WO-2016028672 A1 | 2/2016 |
| WO | WO-2016054638 A1 | 4/2016 |
| WO | WO-2016057841 A1 | 4/2016 |
| WO | WO-2016059602 A2 | 4/2016 |
| WO | WO-2016062722 A1 | 4/2016 |
| WO | WO-2016066634 A2 | 5/2016 |
| WO | WO-2016075174 A1 | 5/2016 |
| WO | WO-2016081746 A2 | 5/2016 |
| WO | WO-2016100985 A2 | 6/2016 |
| WO | WO-2016111645 A1 | 7/2016 |
| WO | WO-2016154544 A1 | 9/2016 |
| WO | WO-2016168361 A1 | 10/2016 |
| WO | WO-2016168716 A1 | 10/2016 |
| WO | WO-2016179517 A1 | 11/2016 |
| WO | WO-2017096179 A1 | 6/2017 |
| WO | WO-2017096182 A1 | 6/2017 |
| WO | WO-2017096189 A1 | 6/2017 |
| WO | WO-2017096276 A1 | 6/2017 |
| WO | WO-2017096281 A1 | 6/2017 |
| WO | WO-2017157964 A1 | 9/2017 |
| WO | WO-2017186928 A1 | 11/2017 |
| WO | WO-2018089628 A1 | 5/2018 |

OTHER PUBLICATIONS

Written Opinion of the International Searching Authority of PCT/US2017/060854; dated Mar. 26, 2018. (Year: 2018).*
"A comprehensive immuno-oncology Ecosystem" Cowen and Company 36th Annual Health Care Conference Mar. 2016.
"Agenus Announces Commencement of Phase 1-2 Clinical Trial of anti-OX40 Checkpoint Antibody INCAGN1949 in Patients with Solid Tumors"—PRNewswire—(Nov. 30, 2016).
"Agenus Presents Posters on Checkpoint Antibody Product Candidates at the American Association for Cancer Research (AACR) 2016 Annual Meeting" (Business Wire) (Apr. 18, 2016).
"Agenus R&D Day" (May 14, 2015).
"Agenus R&D Day" New York, NY (Nov. 19, 2015).
"Agenus, Driving the immune system to fight cancer and infectious disease," Mar. 2015.
"Agenus, Driving the immune system to fight cancer and infectious disease," May 15, 2015.
"Agonist Checkpoint Modulators: Challenges and Opportunities" PEGS Boston May 8, 2015.
"Emerging Leader In Immuno-Oncology", Lexington, MA (Nov. 2015).
"Four Agenus Abstracts Accepted for Presentation at the American Association for Cancer Research(AAUI-<) 2017 Annual Meetilly" PRNewswire, Mar. 7, 2017.

(56) References Cited

OTHER PUBLICATIONS

"Immuno-Oncology" RBS Immunotherapy Conference Mar. 27, 2014.
"Integrated Approach to Immuno-Oncology" Blair Maidstone 1-0 Conference NYC, Mar. 31, 2016.
"Integrated Solutions in Immuno-Oncology" Apr. 2016.
"Integrated Solutions in Immuno-Oncology" May 2016.
"Targeting TNFR Family Members: Therapeutic opportunities in immuno-oncology and immuno-inflammation" PEGS Boston 2016.
1984) "Nomenclature and Symbolism for Amino Acids and Peptides. Recommendations 1983", The Biochemical Journal, IUPAC-IUB Joint Commission on Biochemical Nomenclature (JCBN), vol. 219, No. 2, pp. 345-373.
Allan et al., "Activation-induced FOXP3 in Human T Effector Cells Does Not Suppress Proliferation or Cytokine Production," Int Immunol. 2007;19(4):345-54.
Arch, R.H. and Thompson, C.B., (1998) "4-1BB and Ox40 Are Members of a Tumor Necrosis Factor (TNF)-Nerve Growth Factor Receptor Subfamily That Bind TNF Receptor-Associated Factors and Activate Nuclear Factor ?B" Molecular and Cell Biology 18(1):558-565.
Arnett et al., "IBC's 21st Annual Antibody Engineering and 8th Annual Antibody Therapeutics International Conferences and 2010 Annual Meeting of The Antibody Society," mAbs. 2011;3(2):133-152.
Aspeslagh et al., "Rationale for anti-OX40 cancer immunotherapy," Eur J Cancer. 2016;52:50-66.
Aspord et al., "Plasmacytoid dendritic cells support melanoma progression by promoting Th2 and regulatory immunity through OX40L and ICOSL," Cancer Immunol Res. 2013;1(6):402-15.
Avogadri et al., "Modulation of CTLA-4 and GITR for cancer immunotherapy," Curr Top Microbiol Immunol. 2011;344:211-44.
Back, "Dampening Pathological Immune Responses via Targeting OX40 with GBR830, an Antagonist Monoclonal Antibody," PEGS, Biologies for Autoimmune Disease, May 12, 2015.
Baessler et al., "Glucocorticoid-induced Tumor Necrosis Factor Receptor-related Protein Ligand Subverts Immunosurveillance of Acute Myeloid Leukemia in Humans," Cancer Res. 2009;69(3):1037-45.
Baltz et al., "Cancer immunoediting by GITR (glucocorticoid-induced TNF-related protein) ligand in humans: NK cell/tumor cell interactions," FASEB J. 2007;21(10):2442-54.
Barthelemy et al., "Comprehensive analysis of the factors contributing to the stability and solubility of autonomous human VH domains," J Biol Chem. 2008;283(6):3639-3654.
Baum et al., "Identification of OX40 ligand and preliminary characterization of its activities on OX40 receptor," Circ Shock. 1994;44(1):30-4.
Beiboer et al., "Guided selection of a pan carcinoma specific antibody reveals similar binding characteristics yet structural divergence between the original murine antibody and its human equivalent," J Mol Bio. 2000;296(3):833-49.
Bellati et al., "Immunology of gynecologic neoplasms: analysis of the prognostic significance of the immune status," Curr Cancer Drug Targets. 2009;9(4):541-65.
Berrong et al., "Antigen-Specific Antitumor Responses Induced by OX40 Agonist Are Enhanced by the IDO Inhibitor Indoximod," Cancer Immunol Res. 2018;6(2):201-208.
Berrong et al., "Immune combinational therapy targeting OX40 and IDO synergistically enhances efficacy of a cancer vaccine," J Immunother Cancer. 2014;2(Suppl 3):P226.
Bianchini et al., "CD4(+) CD25(low) GITR(+) cells: a novel human CD4(+) T-cell population with regulatory activity," Eur J Immunol. 2011;41 (8):2269-78.
Birebent et al., "Suppressive properties of human CD4+CD25+ regulatory T cells are dependent on CTLA-4 expression," Eur J Immunol. 2004;34(12):3485-96.
Blazar et al., "Ligation of OX40 (CD134) regulates graft-versus-host disease (GVHD) and graft rejection in allogeneic bone marrow transplant recipients," Blood. 2003;101(9):3741-8.

Bossen et al., "Interactions of tumor necrosis factor (TNF) and TNF receptor family members in the mouse and human," J Biol Chem. 2006;281 (20):13964-71.
Bournazos, S., and Ravetch, J.V., (2015) "Fc? receptor pathways during active and passive immunization" Immunological Reviews 268:88-103.
Bowes, J., et al., (2012) "Reducing safety-related drug attrition: the use of in vitro pharmacological profiling" Nature Reviews Drug Discovery 11:911-922.
Bremnes et al., "The role of tumor-infiltrating immune cells and chronic inflammation at the tumor site on cancer development, progression, and prognosis: emphasis on non-small cell lung cancer," J Thorac Oncol. 2011;6(4):824-33.
Brennan et al., "Safety and immunotoxicity assessment of immunomodulatory monoclonal antibodies," MAbs. 2010;2(3):233-55.
Bruhns et al., "Specificity and affinity of human Fcgamma receptors and their polymorphic variants for human IgG subclasses," Blood. 2009;113(16):3716-25.
Buchan et al., "Death receptors is essential for generating optimal protective CD4? T-cell immunity against *Salmonella*," Eur J Immunol. 2012;42(3):580-8.
Buechele et al., "Glucocorticoid-induced TNFR-related protein (GITR) ligand modulates cytokine release and NK cell reactivity in chronic lymphocytic leukemia (CLL)," Leukemia. 2012;26(5):991-1000.
Bulliard et al., "Activating Fc gamma receptors contribute to the antitumor activities of immunoregulatory receptor-targeting antibodies," J Exp Med. 2013;210(9):1685-93.
Bulliard et al., "OX40 engagement depletes intratumoral Tregs via activating Fc?Rs, leading to antitumor efficacy," Immunol Cell Biol. 2014;92(6):475-80.
Capello et al., "Immunoglobulin Kappa Chain Variable Region, Partial [*Homo sapiens*]," National Center for Biotechnology Information. GenBank Entry, Jul. 20, 1999 [Retrieved on Apr. 25, 2016] Retrieved from the Internet, URL: http:--www.ncbi.nlm.nih.gov-protein-5578794, pp. 1-2.
Chan and Carter, "Therapeutic antibodies for autoimmunity and inflammation," Nat Rev Immunol. 2010;10(5):301-16.
Chang et al., "Inflammation-related factors predicting prognosis of gastric cancer," World J Gastroenterol. 2014;20(16):4586-96.
Chapman et al., "Preclinical safety testing of monoclonal antibodies: the significance of species relevance," Nat Rev Drug Discov. 2007;6(2):120-6.
Chattopadhyay et al., "Assembly and structural properties of glucocorticoid-induced TNF receptor ligand: Implications for function," Proc Natl Acad Sci USA. 2007;104(49):19452-7.
Chen and Mellman, "Oncology meets immunology: the cancer-immunity cycle," Immunity. 2013;39(1):1-10.
Chen, L., and Dallas, B.F., (2013) "Molecular mechanisms of T cell co?stimulation and co?inhibition" Nature Reviews Immunology 13(4):227-242.
Choi and Deane, "Predicting antibody complementarity determining region structures without classification," Mol. Biosyst. 2011;7:3327-3334.
Chu et al., "Inhibition of B cell receptor-mediated activation of primary human B cells by coengagement of CD19 and FcgammaRIIb with Fc-engineered antibodies," Mol Immunol. 2008;45(15):3926-33.
Clackson et al., "Making antibody fragments using phage display libraries," Nature. 1991;352(6336):624-8.
Clouthier and Watts, "Cell-specific and context-dependent effects of GITR in cancer, autoimmunity, and infection," Cytokine Growth Factor Rev. 2014;25(2):91-106.
Coe et al., "Depletion of regulatory T cells by anti-GITR mAb as a novel mechanism for cancer immunotherapy," Cancer Immunol Immunother. 2010;59(9):1367-77.
Cohen et al., "Agonist Anti-GITR Antibody Enhances Vaccine-Induced CD8+ T-Cell Responses and Tumor Immunity," Cancer Res. 2006;66(9):4904-4912.
Cohen et al., "Agonist anti-GITR monoclonal antibody induces melanoma tumor immunity in mice by altering regulatory T cell stability and intra-tumor accumulation," PLoS One. 2010;5(5):e10436.

(56) References Cited

OTHER PUBLICATIONS

Coiffier, "Rituximab Therapy in Malignant Lymphoma," Oncogene. 2007;26(25):3603-13.
Collins et al., "The interaction properties of costimulatory molecules revisited," Immunity. 2002;17(2):201-10.
Compaan and Hymowitz, "The crystal structure of the costimulatory OX40-OX40L complex," Structure. 2006;14(8):1321-30.
Cote et al., "Stimulation of the glucocorticoid-induced TNF receptor family-related receptor on CD8 T cells induces protective and high-avidity T cell responses to tumor-specific antigens," J Immunol. 2011;186(1):275-83.
Croft, "Control of immunity by the TNFR-related molecule OX40 (CD134)," Ann Rev Immunol. 2010;28:57-78.
Croft, "The TNF Family in T cell Differentiation and Function—Unanswered Questions and Future Directions," Semin Immunol. 2014;26(3):183-190.
Cui et al., "An isoleucine-zipper motif enhances costimulation of human soluble trimeric GITR ligand," Cell Mol Immunol. 2010;7(4):316-22.
Cunningham and Wells, "High-resolution epitope mapping of hGH-receptor interactions by alanine-scanning mutagenesis," Science. 1989;244(4908):1081-5.
Curti et al., "OX40 is a potent immune-stimulating target in late-stage cancer patients," Cancer Res. 2013;73(24):7189-7198.
Cuzzocrea et al., "Genetic and pharmacological inhibition of GITR-GITRL interaction reduces chronic lung injury induced by bleomycin instillation," FASEB J. 2007;21(1):117-29.
Cuzzocrea et al., "Glucocorticoid-induced TNF receptor family gene (GITR) knockout mice exhibit a resistance to splanchnic artery occlusion (SAO) shock," J Leukoc Biol. 2004;76(5):933-40.
Cuzzocrea et al., "Proinflammatory role of glucocorticoid-induced TNF receptor-related gene in acute lung inflammation," J Immunol. 2006;177(1):631-41.
Dall'Acqua et al., "Properties of human IgG1s engineered for enhanced binding to the neonatal Fc receptor (FcRn)," J Biol Chem. 2006;281(33):23514-24.
Dangl et al., "Segmental flexibility and complement fixation of genetically engineered chimeric human, rabbit and mouse antibodies," EMBO J. 1988;7(7):1989-1994.
De Genst et al., "Antibody repertoire development in camelids," Dev Comp Immunol. 2006;30(1-2):187-98.
Dunn et al., "Cancer immunoediting: from immunosurveillance to tumor escape," Nat Immunol. 2002;3(11):991-8.
DuPage et al., "Expression of Tumor-Specific Antigens Underlies Cancer Immunoediting," Nature. 2012;482(7385):405-9.
EBioscience, an Affymetrix Company "Anti-Human CD357 (AITR/GITR) PE," Product Brochure. Catalog No. 12-5875, (2012).
Ehrenstein and Notley, "The importance of natural IgM: scavenger, protector and regulator," Nat Rev Immunol. 2010;10(11):778-86.
English language translation of JP-2008278814-A (cited as document FP35 above), EPO and Google translate, Apr. 16, 2018.
Ephrem, A., et al., (2013) "Modulation of Treg cells/T effector function by GITR signaling is context-dependent" Eur. J. Immunol. 43:2421-2429.
Esparza and Arch, "Signaling Triggered by Glucocorticoid-induced Tumor Necrosis Factor Receptor Family-related Gene: Regulation at the Interface Between Regulatory T Cells and Immune Effector Cells," Front Biosci. 2006;11:1448-65.
Extended European Search Report received for European Patent Application No. 18204948.6, 6 Pages, dated Mar. 22, 2019.
Finco et al., "Cytokine release assays: current practices and future directions," Cytokine 2014; 66(2):143-55.
Fromm et al., "Gp96-Ig/Costimulator (OX40L, ICOSL, or 4-1 BBL) Combination Vaccine Improves T-cell Priming and Enhances Immunity, Memory, and Tumor Elimination," Cancer Immunol Res. 2016;4(9):766-78.
Fujita, T., et al., (2006) "Functional characterization of OX40 expressed on human CD8+ T cells" Immunology Letters 106:27-33.
Furness et al., "Impact of tumour microenvironment and Fc receptors on the activity of immunomodulatory antibodies," Trends Immunol. 2014;35(7):290-8.
Galon et al., "Type, Density, and Location of Immune Cells Within Human Colorectal Tumors Predict Clinical Outcome," Science. 2006;313(5795):1960-4.
GenBank (Apr. 2, 1999) *Homo sapiens* glucocorticoid-induced TNFR-related protein ligand (TNFSF18) mRNA, complete cds, Accession No. AF125303.1, Retrieved from: <<https://www.ncbi.nlm.nih.gov/nuccore/AF125303>>, 1 Page.
GenBank (Oct. 7, 2016) Tumor Necrosis Factor Receptor Superfamily Member 18 Isoform 2 Precursor [*Homo sapiens*] "Accession No. NP_683699.1, Retrieved from: <<https://www.ncbi.nlm.nih.gov/protein/NP_683699.1/>>", 3 Pages.
GenBank (Oct. 30, 2007) *Homo sapiens* tumor necrosis factor receptor superfamily, member 18, mRNA (cDNA clone IMAGE:100013446) Accession No. BC152386.1, Retrieved from: <<https://www.ncbi.nlm.nih.gov/nuccore/BC152386>>, 2 Pages.
GenBank (Oct. 6, 2016) Tumor Necrosis Factor Ligand Superfamily Member 18 [*Homo Sapiens*], Accession No. NP_005083.2, Retrieved from: <<https://www.ncbi.nlm.nih.gov/protein/NP005083>>, 3 Pages.
GenBank (Oct. 7, 2016) Tumor Necrosis Factor Receptor Superfamily Member 18 Isoform 1 Precursor [*Homo Sapiens*] Accession No. NP_004186.1, Retrieved from: <<https://www.ncbi.nlm.nih.gov/protein/NP_004186.1/>> 3 Pages.
GenBank (Oct. 7, 2016) Tumor Necrosis Factor Receptor Superfamily Member 18 Isoform 3 Precursor [*Homo sapiens*] "Accession No. NP_683700.1, Retrieved from: <<https://www.ncbi.nlm.nih.gov/protein/NP_683700.1/>>", 3 Pages.
GenBank, "*Homo sapiens* cDNA FLJ50815 Complete cds, Highly Similar to Tumor Necrosis Factor Ligand Superfamilymember 4", Accession No. AK297932.1, accessed at https:--www.ncbi.nlm.nih.gov-nuccore-AK297932.1.
GenBank, "*Homo sapiens* Glucocorticoid-induced TNFR-related Protein Ligand (TNFSF18) mRNA, Complete Cds," Accession No. AF125303.1, accessed at https://www.ncbi.nlm.nih.gov/nuccore/AF125303, Apr. 2, 1999.
GenBank, "*Homo sapiens* mRNA for Glycoprotein 34, Complete CDS," Accession No. D90224.1, accessed at https://www.ncbi.nlm.nih.gov-nuccore-D90224.1.
"Gene ID: 8784 by Entrez Gene, TNFRSF18, accessed at https://www.ncbi.nlm.nih.gov/gene/8784, Feb. 20, 2017."
Gerondakis et al., "NF-KB Control of T Cell Development," Nat Immunol. 2014; 15(1):15-25.
Glaus et al., "n Vivo SPECT/CT Imaging of an Anti-GITR Antibody: A Novel Cancer Immunotherapeutic," J Nucl Med. 2013;54(Supp2):327.
Gobert et al., "Regulatory T Cells Recruited through CCL22/CCR4 are Selectively Activated in Lymphoid Infiltrates Surrounding Primary Breast Tumors and Lead to an Adverse Clinical Outcome," Cancer Res. 2009;69(5):2000-9.
Godfrey et al., "Identification of a human OX-40 ligand, a costimulator of CD4+ T cells with homology to tumor necrosis factor," J Exp Med. 1994;180(2):757-62.
Goede et al., "Obinutuzumab plus chlorambucil in patients with CLL and coexisting conditions," N Engl J Med. 2014;370(12):1101-10.
Golay et al., "Glycoengineered CD20 antibody obinutuzumab activates neutrophils and mediates phagocytosis through CD16B more efficiently than rituximab," Blood. 2013;122(20):3482-91.
Gong et al., "A heat shock protein 70-based vaccine with enhanced immunogenicity for clinical use," J Immunol. 2010;184(1):488-96.
Gonzalez et al., "A Novel Agonist Antibody (INCAGN01876) That Targets the Costimulatory Receptor GITR," American Association for Cancer Research Annual Meeting 2016, Poster #3220. Presented Apr. 2016.
Gonzalez, et al., "INCAGN1876, a Unique GITR Agonist Antibody That Facilitates GITR Oligomerization" 3643 Presented at the American Association for Cancer Research Annual Meeting 2017 Washington, DC, USA Apr. 1-5, 2017.

(56) References Cited

OTHER PUBLICATIONS

Gooden, et al. (Jun. 2011) "The Prognostic Influence of Tumor-Infiltrating Lymphocytes in Cancer: A Systematic Review with Meta-Analysis", British Journal of Cancer, vol. 105, No. 1, pp. 93-103.

Gough et al., "Targeting macrophages in the tumour environment to enhance the efficacy of ?OX40 therapy," Immunology. 2012;136(4):437-47.

Gramaglia et al., "Ox-40 ligand: a potent costimulatory molecule for sustaining primary CD4 T cell responses," J Immunol. 1998;161(12):6510-7.

Gramaglia et al., "The OX40 costimulatory receptor determines the development of CD4 memory by regulating primary clonal expansion," J Immunol. 2000;165(6):3043-50.

Gravekamp and Jahangir, "Is cancer vaccination feasible at older age?" Exp Gerontol. 2014;54:138-144.

Grewal, I.S., "Overview of TNF Superfamily: A Chest Full of Potential Therapeutic Targets," Advances in Experimental Medicine and Biology 647:1-7, Kluwer Academic/Plenum Publishers, United States (2009).

Griffiths et al., "Human anti-self antibodies with high specificity from phage display libraries.," EMBO J. 1993;12(2):725-734.

Grohmann, et al. (Apr. 8, 2007) "Reverse Signaling Through GITR Ligand Enables Dexamethasone to Activate IDO in Allergy", Nature Medicine, Nature Publishing Company, United States, 13, pp. 579-586.

Grosso, et al. (Feb. 2013) "CTLA-4 Blockade in Tumor Models: An Overview of Preclinical and Translational Research", Cancer Immunity, vol. 13, No. 1, pp. 1-14.

Guilliams et al., "The function of Fcgamma receptors in dendritic cells and macrophages," Nat Rev Immunol. 2014;14(2):94-108.

Guilliams, et al. (Jul. 18, 2014) "Dendritic Cells, Monocytes and Macrophages: A Unified Nomenclature Based on Ontogeny", Nature Reviews Immunology, vol. 14, No. 8, pp. 571-578.

Guo et al., "PD-1 blockade and OX40 triggering synergistically protects against tumor growth in a murine model of ovarian cancer," PLoS One. 2014;9(2):e89350.

Gurney, et al. (Feb. 25, 1999) "Identification of A New Member of the Tumor Necrosis Factor Family and Its Receptor, A Human Ortholog Of Mouse GITR", Current biology, vol. 9, Issue 4, GenBank™ accession No. AF125303, Retrieved from: https://www.ncbi.nlm.nih.gov/nuccore/AF125303.1/, pp. 215-218.

Hanabuchi, et al. (May 1, 2006) "Human Plasmacytoid Predendritic Cells Activate NK Cells Through Glucocorticoid-Induced Tumor Necrosis Factor Receptor-Ligand (GITRL)", Blood, vol. 107, No. 9, pp. 3617-3623.

Hattori et al., "Blockade of the OX40 ligand prolongs corneal allograft survival," Eur J Immunol. 2007;37(12):3597-604.

Hauer, J., et al., (2005) "TNF receptor (TNFR)-associated factor (TRAF) 3 serves as an inhibitor of TRAF2/5-mediated activation of the noncanonical NF-?B pathway by TRAF-binding TNFRs" PNAS 102(8):2874-7879.

Hebb et al., "Administration of low-dose combination anti-CTLA4, anti-CD137, and anti-OX40 into murine tumor or proximal to the tumor draining lymph node induces systemic tumor regression," Cancer Immunol Immunother. 2018;67(1):47-60.

Herber, et al. (Jun. 2007) "Meeting Report: Mechanism and Therapeutic Reversal of Immune Suppression in Cancer,", Cancer Research, vol. 67, Issue 11, pp. 5067-5069.

Herter, et al. (Mar. 1, 2014) "Glycoengineering of Therapeutic Antibodies Enhances Monocyte/macrophage-mediated Phagocytosis and Cytotoxicity", The Journal of Immunology, vol. 192, No. 5, pp. 2252-2260.

Hindley, J.P., et al., (2011) "Analysis of the T-Cell Receptor Repertoires of Tumor-Infiltrating Conventional and Regulatory T Cells Reveals No Evidence for Conversion in Carcinogen-Induced Tumors" Cancer Res. 71(3):736-746.

Hirschhorn-Cymerman et al., "OX40 engagement and chemotherapy combination provides potent antitumor immunity with concomitant regulatory T cell apoptosis," J Exp Med. 2009;206(5):1103-16.

Hogarth and Pietersz, "Fc receptor-targeted therapies for the treatment of inflammation, cancer and beyond," Nat Rev Drug Discov. 2012;11(4):311-31.

Hornbach et al., "OX40 costimulation by a chimeric antigen receptor abrogates CD28 and IL-2 induced IL-10 secretion by redirected CD4(+) T cells," Oncoimmunology. 2012;1(4):458-466.

Hulett, et al. (Sep. 8, 1995) "Multiple Regions of Human Fc Gamma RII (CD32) Contribute to the Binding of IgG", The Journal of Biological Chemistry, vol. 270, No. 36, pp. 21188-21194.

Imai-Nishiya, et al. (Nov. 30, 2007) "Double Knockdown of ?1, 6-Fucosyltransferase (FUT8) and GDP-Mannose 4, 6-Dehydratase (GMD) in Antibody-Producing Cells: A New Strategy for Generating Fully Non-Fucosylated Therapeutic Antibodies with Enhanced ADCC", BMC biotechnology, vol. 7, No. 1, pp. 1-13.

Imura et al., "The human OX40/gp34 system directly mediates adhesion of activated T cells to vascular endothelial cells," J Exp Med. 1996;183(5):2185-95.

International Preliminary Report on Patentability and Written Opinion for International Application No. PCT/US2015/032895, The International Bureau of WIPO, Geneva, Switzerland, dated Nov. 29, 2016, 8 pages.

International Preliminary Report on Patentability for PCT-US2016-031257 dated Nov. 7, 2017.

International Search Report and Written Opinion received for PCT/US2016/031257, dated Jul. 18, 2016.

International Search Report for International Application No. PCT/US2015/032895, European Patent Office, Netherlands, dated Oct. 21, 2015, 8 pages.

Jacobsen (Jan. 1, 2011) "Molecular and Functional Characterization of Cynomolgus Monkey IgG Subclasses", Journal of Immunology, vol. 186, No. 1, pp. 341-349.

Jensen et al., "Signaling through OX40 enhances antitumor immunity," Semin Oncol. 2010;37(5):524-32.

Ji, et al. (May 15, 2004) "Cutting Edge: The Natural Ligand for Glucocorticoid-induced TNF Receptor-related Protein Abrogates Regulatory T Cell Suppression", Journal of Immunology, vol. 172, Issue 10, pp. 5823-5827.

Kamb, et al. (Dec. 8, 2006) "Why Is Cancer Drug Discovery So Difficult?", Nature Reviews Drug Discovery, pp. 115-120.

Kanamaru, et al. (Jun. 15, 2004) "Costimulation via Glucocorticoid-Induced TNF Receptor in Both Conventional and CD25+ Regulatory CD4+ T Cells", The Journal of Immunology, vol. 172, Issue 12, pp. 7306-7314.

Katschke et al., "A novel inhibitor of the alternative pathway of complement reverses inflammation and bone destruction in experimental arthritis," J Exp Med. 2007;204(6):1319-1325.

Kim and Ashkenazi, "Fcgamma receptors enable anticancer action of proapoptotic and immune-modulatory antibodies," J Exp Med. 2013;210(9):1647-51.

Kim, et al. (Aug. 17, 2015) "Glucocorticoid-induced Tumor Necrosis Factor Receptor-related Protein Co-stimulation Facilitates Tumor Regression by Inducing IL-9-producing Helper T Cells", Nature Medicine, vol. 21, No. 9, pp. 1010-1017.

Kim, et al. (Jun. 2013) "Tumor-infiltrating Lymphocytes, Tumor Characteristics, and Recurrence in Patients with Early Breast Cancer", American Journal of Clinical Oncology, vol. 36, No. 3, pp. 224-231.

Kim, et al. (Nov. 15, 2015) "Authentic GITR Signaling Fails to Induce Tumor Regression unless Foxp3+ Regulatory T Cells Are Depleted", Journal of Immunology, vol. 195, No. 10, pp. 4721-4729.

Kim, et al. (Nov. 2006) "Glucocorticoid-induced Tumor Necrosis Factor Receptor Family Related Protein (GITR) Mediates Inflammatory Activation of Macrophages that Can Destabilize Atherosclerotic Plaques", Immunology, vol. 119, Issue 3, pp. 421-429.

Kim, et al. (Nov. 26, 2003) "Cloning and Characterization of GITR Ligand", Genes and Immunity, vol. 4, No. 8, pp. 564-569.

(56) References Cited

OTHER PUBLICATIONS

Kim, et al. (Oct. 24, 2007) "Guided Selection of Human Antibody Light Chains Against TAG-72 Using A Phage Display Chain Shuffling Approach", The Journal of Microbiology, vol. 45, No. 6, pp. 572-577.

Kirk, R., "Risk Factors. CD8+:FOXP3+ Cell Ratio is a Novel Survival Marker for Colorectal Cancer," Nature Reviews. Clinical Oncology 7(6):299, Nature Pub. Group, England (2010).

Kjaergaard et al., "Therapeutic efficacy of OX-40 receptor antibody depends on tumor immunogenicity and anatomic site of tumor growth," Cancer Res. 2000;60(19):5514-21.

Klimka et al., "Human anti-CD30 recombinant antibodies by guided phage antibody selection using cell panning," Br J Cancer. 2000;83(2):252-260.

Knee, et al. (Nov. 2016) "Rationale for Anti-GITR Cancer Immunotherapy", European Journal of Cancer, vol. 67, pp. 1-10.

Ko, et al. (Aug. 2007) "A Combination of Chemoimmunotherapies Can Efficiently Break Self-Tolerance and Induce Antitumor Immunity in a Tolerogenic Murine Tumor Model", Cancer Research, vol. 67, No. 15, pp. 7477-7486.

Ko, et al. (Oct. 3, 2005) "Treatment of Advanced Tumors with Agonistic Anti-GITR Mab and Its Effects on Tumor-infiltrating Foxp3+Cd25+Cd4+ Regulatory T Cells", The Journal of Experimental Medicine, vol. 202, No. 7, pp. 885-891.

Kober et al., "The capacity of the TNF family members 4-1 BBL, OX40L, CD70, GITRL, CD30L and LIGHT to costimulate human T cells," Eur J Immunol. 2008;38(10):2678-88.

Koene et al., "Fc gammaRIIIa-158V/F polymorphism influences the binding of IgG by natural killer cell FcgammaRIIIa, independently of the FcgammaRIIIa-48L/R/H phenotype," Blood. 1997;90(3):1109-14.

Krause et al., "Prostaglandin E2 enhances T-cell proliferation by inducing the costimulatory molecules OX40L, CD70, and 4-1BBL on dendritic cells," Blood. 2009;113(11):2451-2460.

Krausz, et al. (May 1, 2007) "GITR-GITRL System, A Novel Player in Shock and Inflammation", The Scientific World Journal, vol. 7, pp. 533-566.

Kunitomi et al., "Vascular endothelial cells provide T cells with costimulatory signals via the OX40/gp34 system," J Leukoc Biol. 2000;68(1):111-8.

Kwon, B., et al., "Identification of a Novel Activation-inducible Protein of the Tumor Necrosis Factor Receptor Superfamily and Its Ligand," The Journal of Biological Chemistry 274(10):6056-6061, American Society for Biochemistry and Molecular Biology, United States (1999).

Lacal, et al. (Oct. 1, 2013) "Glucocorticoid-induced Tumor Necrosis Factor Receptor Family-related Ligand Triggering Upregulates Vascular Cell Adhesion Molecule-1 and Intercellular Adhesion Molecule-1 and Promotes Leukocyte Adhesion", The Journal of Pharmacology and Experimental Therapeutics, vol. 347, Issue 1, pp. 164-172.

Lazar, G.A., et al., (2006) "Engineered antibody Fc variants with enhanced effector function" PNAS 103(11):4005-4010.

Leach et al. (Mar. 22, 1996) "Enhancement of Antitumor Immunity by CTLA-4 Blockade", Science, vol. 271, No. 5256, pp. 1734-1736.

Levings, et al. (Nov. 11, 2002) "Human CD25+CD4+ T Suppressor Cell Clones Produce Transforming Growth Factor Beta, but not Interleukin 10, and Are Distinct from Type 1 T Regulatory Cells", The Journal of Experimental Medicine, vol. 196, No. 10, p. 1335-1346.

Li and Ravetch, "Inhibitory Fc? receptor engagement drives adjuvant and anti-tumor activities of agonistic CD40 antibodies," Science. 2011;333(6045):1030-1034.

Li, et al. (Aug. 2003) "Expression of Glucocorticoid Induced TNF Receptor Family Related Protein (GITR) On Peripheral T Cells from Normal Human Donors and Patients with Non-Infectious Uveitis", Journal of autoimmunity, vol. 21, No. 1, pp. 83-92.

Liao, et al. (Feb. 3, 2014) "Glucocorticoid-Induced TNF Receptor Family-Related Protein Ligand is Requisite for Optimal Functioning of Regulatory CD4(+) T Cells", Frontiers in Immunology, vol. 5, Article 35, pp. 1-7.

Lightle et al., "Mutations within a human IgG2 antibody form distinct and homogeneous disulfide isomers but do not affect Fc gamma receptor or C1q binding," Protein Sci. 2010;19(4):753-762.

Linch and Redmond, "Combined OX40 ligation plus CTLA-4 blockade More than the sum of its parts," Oncoimmunology. 2014;3:e28245.

Linch et al., "Combination OX40 agonism/CTLA-4 blockade with HER2 vaccination reverses T-cell anergy and promotes survival in tumor-bearing mice," Proc. Natl. Acad. Sci. USA. 2016;113(3):E319-27.

Linch et al., "OX40 Agonists and Combination Immunotherapy: Putting the Pedal to the Metal," Front Oncol. 2015;5:34.

Linton et al., "Costimulation via OX40L expressed by B cells is sufficient to determine the extent of primary CD4 cell expansion and Th2 cytokine secretion in vivo," J Exp Med. 2003;197(7):875-83.

Liu, et al. (Nov. 2011) "CD8+ cytotoxic T cell and FOXP3+ Regulatory T Cell Infiltration in Relation to Breast Cancer Survival and Molecular Subtypes", Breast Cancer Research and Treatment, vol. 130, Issue 2, pp. 645-655.

Li-Weber, et al. (Jul. 1, 2003) "Regulation of IL4 Gene Expression by T Cells and Therapeutic Perspectives", Nature Reviews Immunology, vol. 3, No. 7, pp. 534-543.

Locksley (Feb. 23, 2001) "The TNF and TNF Receptor Superfamilies: Integrating Mammalian Biology", Cell, vol. 104, Issue 4, pp. 487-501.

Lu, et al. (Feb. 7, 2014) "Combined PD-1 Blockade and GITR Triggering Induce a Potent Antitumor Immunity in Murine Cancer Models and Synergizes with Chemotherapeutic Drugs", Journal of Translational Medicine, vol. 12, No. 36, pp. 1-11.

Mahmud et al., "Costimulation via the tumor-necrosis factor receptor superfamily couples TCR signal strength to the thymic differentiation of regulatory T cells," Nat Immunol. 2014;15(5):473-81.

Mahne, A.E., et al., "Dual Roles for Regulatory T-cell Depletion and Costimulatory Signaling in Agonistic GITR Targeting for Tumor Immunotherapy," Cancer Research 77(5):1108-1118, American Association for Cancer Research, United States (2017).

Malia et al., "Epitope mapping and structural basis for the recognition of phosphorylated tau by the anti-tau antibody AT8," Proteins. 2016;84(4):427-34.

Mallett et al., "Characterization of the MRC 0X40 antigen of activated CD4 positive T lymphocytes—a molecule related to nerve growth factor receptor," EMBO J. 1990;9(4):1063-1068.

Marabelle et al., "Depleting tumor-specific Tregs at a single site eradicates disseminated tumors," J Clin Invest. 2013;123(6):2447-63.

Mathai, et al. (Jul. 2012) "Role of Foxp3-positive Tumor-infiltrating Lymphocytes in the Histologic Features and Clinical Outcomes of Hepatocellular Carcinoma", The American Journal of Surgical Pathology, vol. 36, Issue 7, pp. 980-986.

Matsushita, et al. (Feb. 8, 2012) "Cancer Exome Analysis Reveals a T-Cell-Dependent Mechanism of Cancer Immunoediting", Nature, vol. 482, No. 7385, pp. 400-404.

McHugh, et al. (Feb. 2002) "CD4+ CD25+ Immunoregulatory T Cells: Gene Expression Analysis Reveals A Functional Role for The Glucocorticoid-Induced TNF Receptor", Immunity, vol. 16, Issue 2, pp. 311-323.

Mei, Z., et al., "Tumour-infiltrating Inflammation and Prognosis in Colorectal Cancer: Systematic Review and Meta-analysis ," British Journal of Cancer 110(6):1595-1605, Cancer Research UK, England (Feb. 2014).

Melero et al., "Agonist antibodies to TNFR molecules that costimulate T and NK cells," Clin Cancer Res. 2013;19(5):1044-53.

Mellman et al., "Cancer immunotherapy comes of age," Nature. 2011;480(7378):480-9.

Mellor, J.D., et al., (2013) "A critical review of the role of Fc gamma receptor polymorphisms in the response to monoclonal antibodies in cancer" Journal of Hematology & Oncology 6:1-10.

(56) References Cited

OTHER PUBLICATIONS

Messenheimer et al., "Timing of PD-1 Blockade Is Critical to Effective Combination Immunotherapy with Anti-OX40," Clin Cancer Res. 2017;23(20):6165-6177.
Meylan et al., "TL1A and DR3, a TNF family ligand-receptor pair that promotes lymphocyte costimulation, mucosal hyperplasia, and autoimmune inflammation," Immunol Rev. 2011;244(1):188-96.
"Miltenyi Biotec ""Human Anti-GITR Antibodies,"" Product Brochure. Catalog Nos. 130-092-895, 130-092-575, 130-092-886, and 130-092-885, (2012)."
Mimoto, et al. (Oct. 2013) "Engineered Antibody Fc Variant with Selectively Enhanced Fc?RIIb Binding Over Both Fc?RIIa(R131) and Fc?RIIa(H131)", Protein Engineering, Design and Selection, vol. 26, No. 10, pp. 589-598.
Mitsui, et al. (May 2010) "Two Distinct Mechanisms of Augmented Antitumor Activity by Modulation of Immunostimulatory/inhibitory Signals", Clinical Cancer Research, vol. 16, Issue 10, pp. 2781-2791.
Miura et al., "Molecular cloning and characterization of a novel glycoprotein, gp34, that is specifically induced by the human T-cell leukemia virus type I transactivator p40tax," Mol Cell Biol. 1991;11(3):1313-25.
Montler et al., "OX40, PD-1 and CTLA-4 are selectively expressed on tumor-infiltrating T cells in head and neck cancer," Clin Transl Immunology. 2016;5(4):e70.
Moran et al., "The TNFRs OX40, 4-1BB, and CD40 as targets for cancer immunotherapy," Curr Opin Immunol. 2013;25(2):230-7.
Moreau et al. (Mar. 1996) "Transient Increase in Symptoms Associated with Cytokine Release in Patients with Multiple Sclerosis", Brain, vol. 119, No. 1, pp. 225-237.
Murphy et al., "CD8+ T cell-independent tumor regression induced by Fc-OX40L and therapeutic vaccination in a mouse model of glioma," J Immunol. 2014:192(1):224-33.
Murphy, et al. (2014) "Anaphylaxis Caused by Repetitive Doses of a GITR Agonist Monoclonal Antibody in Mice", Blood, vol. 123, Issue 14, pp. 2172-2180.
Nimmerjahn and Ravetch, "Antibodies, Fc receptors and cancer," Curr Opin Immunol. 2007;19(2):239-45.
Nimmerjahn and Ravetch, "Fcgamma receptors as regulators of immune responses," Nat Rev Immunol. 2008;8(1):34-47.
Nimmerjahn and Ravetch, "Translating basic mechanisms of IgG effector activity into next generation cancer therapies," Cancer Immun. 2012; 12:13.
Nishikawa, H., et al., (2005) "Definition of target antigens for naturally occurring CD4+ CD25+ regulatory T cells" J. Exp. Med. 201 (5):681-686.
Nishioka, et al. (Dec. 22, 2008) "In Vivo Expansion of CD4+ Foxp3+ regulatory T Cells Mediated by GITR Molecules", Immunology Letters, vol. 121, Issue 2, pp. 97-104.
Nocentini, et al. (2007) "GITR/GITRL: More Than an Effector T Cell Co?Stimulatory System", European journal of immunology, vol. 37, No. 5, pp. 1165-1169.
Nocentini, et al. (2009) "GITR: A Modulator of Immune Response and Inflammation", Advances in Experimental Medicine and Biology, pp. 156-173.
Nocentini, et al. (2012) "Pharmacological Modulation of GITRL/GITR System: Therapeutic Perspectives", British journal of pharmacology, vol. 165, No. 7, pp. 2089-2099.
Nocentini, et al. (Jun. 10, 1997) "A New Member of the Tumor Necrosis Factor/Nerve Growth Factor Receptor Family Inhibits T Cell Receptor-Induced Apoptosis", Proceedings of the National Academy of Sciences, vol. 94, No. 12, pp. 6216-6221.
Nocentini, et al. (Mar. 22, 2005) "GITR: A Multifaceted Regulator of Immunity Belonging to The Tumor Necrosis Factor Receptor Superfamily", European journal of immunology, vol. 35, No. 4, pp. 1016-1022.
Non-Final Office Action dated Jun. 18, 2018, in U.S. Appl. No. 14/724,452, Gonzalez, A. M et al., filed May 28, 2015, 5 pages.
Non-Final Office Action dated Sep. 19, 2017, in U.S. Appl. No. 14/724,452, Gonzalez, A. M et al., filed May 28, 2015, 10 pages.

Nosho, et al. (Aug. 31, 2010) "Tumor-infiltrating T-cell Subsets, Molecular Changes in Colorectal Cancer, and Prognosis: Cohort Study and Literature Review", The Journal of Pathology, vol. 222, Issue 4, pp. 350-366.
Notice of Allowance dated Oct. 17, 2018, in U.S. Appl. No. 14/724,452, Seibert, V., et al., filed May 28, 2015, 7 pages.
Nuebling et al., "The Immune Checkpoint Modulator OX40 and Its Ligand OX40L in NK-Cell Immunosurveillance and Acute Myeloid Leukemia," Cancer Immunol Res. 2018;6(2):209-221.
Oble, et al. (Jan. 2009) "Focus on TILs: Prognostic Significance of Tumor Infiltrating Lymphocytes in Human Melanoma", Cancer Immunity, vol. 9, Issue 1, pp. 1-20.
Ohshima et al., "Expression and function of OX40 ligand on human dendritic cells," J Immunol. 1997;159(8):3838-48.
Oken, et al. (Dec. 1982) "Toxicity and response criteria of the Eastern Cooperative Oncology Group", American Journal of Clinical Oncology, vol. 5, No. 6, pp. 649-655.
Oncomed Pharmaceuticals (Sep. 2015) "OncoMed Presents Immuno-Oncology Data for GITRL-Fc Candidate at the Inaugural International Cancer Immunotherapy Conference".
Ono, et al. (Apr. 15, 2006) "Control of Autoimmune Myocarditis and Multiorgan Inflammation by Glucocorticoid-induced TNF Receptor Family-related Protein(high), Foxp3-expressing CD25+ and CD25− Regulatory T Cells", Journal of Immunology, vol. 176, Issue 8, pp. 4748-4756.
Park, Moon Soo (2005) "The Role of AITR and AITRL In the Lumbar Disc Herniation", Yonsei University Department of Medicine, vol. 48, No. 5, pp. 839-846.
Patel, et al. (May 17, 2016) "Agonist Anti-GITR Monoclonal Antibody and Stereotactic Radiation Induce Immune-mediated Survival Advantage in Murine Intracranial Glioma", Journal for Immunotherapy of Cancer, vol. 4, No. 28, pp. 1-13.
Paterson et al., "Antigens of activated rat T lymphocytes including a molecule of 50,000 Mr detected only on CD4 positive T blasts," Mol Immunol. 1987;24(12):1281-90.
Piao, et al. (Aug. 2009) "Enhancement of T-cell-mediated Antitumor Immunity via the Ectopically Expressed Glucocorticoid-induced Tumor Necrosis Factor Receptor-related Receptor Ligand (GITRL) on Tumours", Immunology, vol. 127, No. 4, pp. 489-499.
Piconese et al., "'Hardcore' OX40+ immunosuppressive regulatory T cells in hepatic cirrhosis and cancer," Oncoimmunology. 2014;3:e29257.
Piconese et al., "Human OX40 tunes the function of regulatory T cells in tumor and nontumor areas of hepatitis C virus-infected liver tissue," Hepatology. 2014;60(5):1494-507.
Piconese et al., "OX40 triggering blocks suppression by regulatory T cells and facilitates tumor rejection," J Exp Med. 2008;205(4):825-39.
Placke, et al. (2010) "Glucocorticoid-induced TNFR-related (GITR) Protein and Its Ligand in Antitumor Immunity: Functional Role and Therapeutic Modulation", Clinical and Developmental Immunology, vol. 2010, No. 239083, 10 Pages.
Ponte, et al. (Jun. 2010) "Enhancement of Humoral and Cellular Immunity with an Anti-glucocorticoid-induced Tumor Necrosis Factor Receptor Monoclonal Antibody", Immunology, vol. 130, Issue 2, pp. 231-242.
Prell et al., "OX40-mediated memory T cell generation is TNF receptor-associated factor 2 dependent," J Immunol. 2003;171(11):5997-6005.
Presta (Aug. 2008) "Molecular Engineering and Design of Therapeutic Antibodies", Current Opinion in Immunology, vol. 20, No. 4, pp. 460-470.
Preston, et al. (Nov. 14, 2013) "The Ratios of CD8+ T Cells to CD4+CD25+ FOXP3+ and FOXP3− T Cells Correlate with Poor Clinical Outcome in Human Serous Ovarian Cancer", PLoS One, vol. 8, No. 11, pp. e80063.
R & D Systems, "Human GITR/TNFRSF18 Antibody," Monoclonal Mouse IgG 1 Clone #110416, accessed at: https://resources.rndsystems.com/pdfs/datasheetsimab689.pdf, dated Jun. 10, 2010, 1 page.
Rader, et al. (Jul. 21, 1998) "A Phage Display Approach for Rapid Antibody Humanization: Designed Combinatorial V Gene Libraries", Proceedings of the National Academy of Sciences, vol. 95, No. 15, pp. 8910-8915.

(56) References Cited

OTHER PUBLICATIONS

Ramirez-Montagut, et al. (Jun. 1, 2006) "Glucocorticoid-induced TNF Receptor Family Related Gene Activation Overcomes Tolerance/ignorance to Melanoma Differentiation Antigens and Enhances Antitumor Immunity", The Journal of Immunology, vol. 176, Issue 11, pp. 6434-6442.
Ravetch and Lanier, "Immune inhibitory receptors," Science. 2000;290(5489):84-9.
Redmond and Weinberg, "Targeting OX40 and OX40L for the treatment of autoimmunity and cancer," Crit Rev Immunol. 2007;27(5):415-36.
Redmond et al., "Combined targeting of costimulatory (OX40) and coinhibitory (CTLA-4) pathways elicits potent effector T cells capable of driving robust antitumor immunity," Cancer Immunol Res. 2014;2(2):142-53.
Redmond et al., "Dual anti-OX40/IL-2 therapy augments tumor immunotherapy via IL-2R-mediated regulation of OX40 expression," PLoS One. 2012;7(4):e34467.
Richard et al., "The TNF-family ligand TL1A and its receptor DR3 promote T cell-mediated allergic immunopathology by enhancing differentiation and pathogenicity of IL-9-producing T cells," J Immunol. 2015;194(8):3567-82.
Rodman & Renshaw Annual Global Investment Conference Sep. 2015.
Rogers et al., "OX40 promotes Bcl-xL and Bcl-2 expression and is essential for long-term survival of CD4 T cells," Immunity. 2001;15(3):445-55.
Ronchetti, et al. (2015) "Glucocorticoid-induced Tumor Necrosis Factor Receptor-related Protein: A Key Marker of Functional Regulatory T Cells", Journal of Immunology Research, vol. 2015, Article ID 171520, 17 Pages.
Ronchetti, et al. (Apr. 2012) "CD8+ T Cells: GITR Matters", The Scientific World Journal, vol. 2012, Article ID 308265, 7 Pages.
Ronchetti, et al. (Feb. 25, 2004) "Frontline: GITR, A Member of the Tnf Receptor Superfamily, Is Costimulatory to Mouse T Lymphocyte Subpopulations", European journal of immunology, vol. 34, No. 3, pp. 613-622.
Ronchetti, et al. (Jul. 1, 2002) "Role of GITR in Activation Response of T Lymphocytes", Blood, vol. 100, No. 1, pp. 350-352.
Ronchetti, S., et al., "GITR, a Member of the TNF Receptor Superfamily, is Costimulatory to Mouse T Lymphocyte Subpopulations," European Journal of Immunology 34(3):613-622, Wiley-VCH, Germany (2004).
Rosenzweig, et al. (Sep. 22, 2016) "Development of TRX518, An Aglycosyl Humanized Monoclonal Antibody (Mab) Agonist of huGITR", Journal of Clinical Oncology, vol. 28, No. 15, pp. e13028.
Ruby et al., "Cutting Edge: OX40 agonists can drive regulatory T cell expansion if the cytokine milieu is right," J Immunol. 2009;183(8):4853-7.
Sagiv-Barfi et al., "Eradication of spontaneous malignancy by local immunotherapy," Sci Transl Med. 2018;10(426):eaan4488.
Sainz-Perez, A., et al., (2012) "The T-cell receptor repertoire of tumor-infiltrating regulatory T lymphocytes is skewed towards public sequences" Cancer Research.
Salek-Ardakani et al., "OX40 (CD134) controls memory T helper 2 cells that drive lung inflammation," J Exp Med.2003;198(2):315-24.
Salgado, et al. (Sep. 11, 2014) "The Evaluation of Tumor-infiltrating Lymphocytes (TILs) in Breast Cancer: Recommendations by an International TILs Working Group 2014", Annals of Oncology, vol. 26, No. 2, pp. 259-271.
Saxena, A. and Wu, D., et al., (2016) "Advances in Therapeutic Fc engineering—Modulation of igG-Associated effector Functions and Serum Half-life" 7:570.
Schaer, D.A., et al., "GITR Pathway Activation Abrogates Tumor Immune Suppression Through Loss of Regulatory T Cell Lineage Stability," Cancer Immunology Research 1(5):320-331, American Association for Cancer Research, United States (2013).
Schaer, D.A., et al., "Modulation of GITR for Cancer Immunotherapy," Current Opinion in Immunology 24(2):217-224, Elsevier Ltd., England (Apr. 2012).
Schaer, D.A., et al., "Targeting Tumor-necrosis Factor Receptor Pathways for Tumor Immunotherapy," Journal for Immunotherapy of Cancer 2:7, BioMed Central, England (Apr. 2014).
Schreiber and Podack, "Immunobiology of TNFSFI5 and TNFRSF25," Immunol Res. 2013;57(1-3):3-11.
Schreiber et al., "T Cell Costimulation by TNFRSF4 and TNFRSF25 in the Context of Vaccination," J Immunol. 2012;189(7):3311-3318.
Schreiber et al., "Therapeutic Treg expansion in mice by TNFRSF25 prevents allergic lung inflammation," J Clin Invest. 2010;120(10):3629-40.
Schwende, et al. (Apr. 1, 1996) "Differences in the State of Differentiation of THP-1 Cells Induced by Phorbol Ester and 1,25-dihydroxyvitamin D3", Journal of Leukocyte Biology, vol. 59, Issue 4, pp. 555-561.
Search Report and Written Opinion for Singaporean Patent Application No. 11201609721W, Intellectual Property Office of Singapore, Singapore, dated Apr. 17, 2018, 13 pages.
Selby et al. (Jul. 2013) "Anti-CTLA-4 Antibodies of IgG2a Isotype Enhance Antitumor Activity Through Reduction of Intratumoral Regulatory T Cells", Cancer Immunology Research, vol. 1, No. 1, pp. 32-42.
Seshasayee et al., "In vivo blockade of OX40 ligand inhibits thymic stromal lymphopoietin driven atopic inflammation," J Clin Invest. 2007;117(12):3868-78.
Sharma et al., (2015) "Immune Checkpoint Targeting In Cancer Therapy: Towards Combination Strategies With Curative Potential" Cell 161(2): 205-214.
Sheridan, "IDO inhibitors move center stage in immuno-oncology," Nat Biotechnol. 2015;33(4):321-2.
Shevach., E.M. and Stephens, G.L., "The GITR-GITRL Interaction: Co-stimulation or Contrasuppression of Regulatory Activity?," Nature Reviews Immunology 6(8):613-618, Nature Publishing Group, England (2006).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. 2001;276(9):6591-604.
Shimizu, et al. (Jan. 22, 2002) "Stimulation of CD25+ CD4+ regulatory T Cells Through GITR Breaks Immunological Self-Tolerance", Nature Immunology, vol. 3, No. 2, pp. 135-142.
Shirabe, et al. (Dec. 2010) "Tumor-infiltrating Lymphocytes and Hepatocellular Carcinoma: Pathology and Clinical Management", International Journal of Clinical Oncology, vol. 15, No. 6, pp. 552-558.
Shrimali et al., "Concurrent PD-1 Blockade Negates the Effects of OX40 Agonist Antibody in Combination Immunotherapy through Inducing T-cell Apoptosis," Cancer Immunol Res. 2017;5(9):755-766.
Simpson et al., "Fc-dependent depletion of tumor-infiltrating regulatory T cells co-defines the efficacy of anti-CTLA-4 therapy against melanoma," J Exp Med. 2013;210(9):1695-710.
Smith, et al. (Apr. 17, 2012) "Mouse Model Recapitulating Human Fc? Receptor Structural and Functional Diversity", Proceedings of the National Academy of Sciences, vol. 109, No. 16, pp. 6181-6186.
Smith, et al. (Mar. 25, 1994) "The TNF Receptor Superfamily of Cellular and Viral Proteins: Activation, Costimulation, and Death", Cell, vol. 76, Issue 6, pp. 959-962.
Smyth et al., "Targeting regulatory T cells in tumor immunotherapy," Immunology and Cell Biology. 2014;92:473-474.
Snell, et al. (Dec. 15, 2010) "CD8 T Cell-Intrinsic GITR Is Required for T Cell Clonal Expansion And Mouse Survival Following Severe Influenza Infection", The Journal of Immunology 185.12, pp. 7223-7234.
Snell, et al. (Oct. 21, 2011) "T-cell intrinsic Effects of GITR and 4-1 BB during Viral Infection and Cancer Immunotherapy", Immunological Reviews, vol. 244, Issue 1, pp. 197-217.
So et al., "Immune Regulation and Control of Regulatory T cells by OX40 and 4-1 BB," Cytokine Growth Factor Rev. 2008;19(3-4):253-262.

(56) References Cited

OTHER PUBLICATIONS

So, T., et al., (2015) "TNF Receptor-Associated Factor (TRAF) Signaling Network in CD4+ T-Lymphocytes" J. Exp. Med. 236:139-154.
Soroosh et al., "OX40-OX40 ligand interaction through T cell-T cell contact contributes to CD4 T cell longevity," J Immunol. 2006;176(10):5975-87.
Stebbings et al., "'Cytokine storm' in the phase I trial of monoclonal antibody TGN1412: better understanding the causes to improve preclinical testing of immunotherapeutics," J Immunol. 2007;179(5):3325-31.
Stephens, et al. (Oct. 15, 2004) "Engagement of Glucocorticoid-induced TNFR Family-related Receptor on Effector T Cells by its Ligand Mediates Resistance to Suppression by CD4+CD25+ T Cells", Journal of Immunology, vol. 173, No. 8, pp. 5008-5020.
Strbo et al., "Secreted heat shock protein gp96-Ig: next-generation vaccines for cancer and infectious diseases," Immunol Res. 2013;57(1-3):311-25.
Strohl (Dec. 2009) "Optimization of Fc-Mediated Effector Functions of Monoclonal Antibodies", Current Opinion in Biotechnology, vol. 20, No. 6, pp. 685-691.
Sugamura et al., "Therapeutic targeting of the effector T-cell co-stimulatory molecule OX40," Nat Rev Immunol. 2004;4(6):420-31.
Supplemental Partial European Search Report from EP 16871583 dated Jul. 3, 2019.
Swiss-Prot (Feb. 15, 2017) Tumor Necrosis Factor Ligand Superfamily Member 18 (TNF18_HUMAN) Accession No. Q9UNG2, Retrieved From: <<http://www.uniprot.org/uniprot/Q9UNG2>> 11 Pages.
Swiss-Prot (Nov. 1, 1999) Tumor Necrosis Factor Receptor Superfamily Member 18 (TNR18_HUMAN), Accession No. Q9Y5U5-1, Retrieved From: <<http://www.uniprot.org/uniprot/Q9Y5U5#Q9Y5U5-1>>, 11 Pages.
Swiss-Prot, Tumor Necrosis Factor Receptor Superfamily Member 18 (TNR18_HUMAN), Accession No. Q9Y5U5-2, Retrieved From: <<http://www.uniprot.org/uniprot/Q9Y5U5#Q9Y5U5-2>>.
Swiss-Prot, Tumor Necrosis Factor Receptor Superfamily Member 18 (TNR18_HUMAN), Accession No. Q9Y5U5-3, Retrieved From: <<http://www.uniprot.org/uniprot/Q9Y5U5#Q9Y5U5-3>>.
Talmadge, James E. (Apr. 2011) "Immune Cell Infiltration of Primary and Metastatic Lesions: Mechanisms and Clinical Impact", Seminars in Cancer Biology, vol. 21, Issue 2, pp. 131-138.
Tanaka, A. and Sakaguchi, S. (2016) "Regulatory T cells in cancer immunotherapy" Cell Research 27:109-118.
Taylor and Schwarz, "Identification of a soluble OX40 isoform: development of a specific and quantitative immunoassay," J Immunol Methods. 2001;255(1-2):67-72.
Tian, et al. (Oct. 15, 2012) "Up-Regulation of GITRL On Dendritic Cells by WGP Improves Anti-Tumor Immunity In Murine Lewis Lung Carcinoma", PloS one, vol. 7, No. 10, pp. e46936.
Tone et al., "Gene Expression in the Gitr Locus Is Regulated by NF-?B and Foxp3 through an Enhancer," J Immunol. 2014;192(8):3915-3924.
Tone, et al. (Dec. 9, 2003) "Mouse Glucocorticoid-Induced Tumor Necrosis Factor Receptor Ligand Is Costimulatory for T Cells", Proceedings of the National Academy of Sciences, vol. 100, No. 25, pp. 15059-15064.
Tran Janco, J.M., "Tumor-Infiltrating Dendritic Cells in Cancer Pathogenesis," The Journal of Immunology /94:2985-2991, The American Association of Immunologists, Inc., United States (Mar. 20, 2015).
Triplett et al., "STAT3 Signaling Is Required for Optimal Regression of Large Established Tumors in Mice Treated with Anti-OX40 and TGF? Receptor Blockade," Cancer Immunol Res. 2015;3(5):526-35.
Turk, et al. (Sep. 20, 2004) "Concomitant Tumor Immunity to a Poorly Immunogenic Melanoma Is Prevented by Regulatory T Cells", The Journal of Experimental Medicine, vol. 200, No. 6, pp. 771-782.

Twohig et al., "The death receptor 3/TL1A pathway is essential for efficient development of antiviral CD4+ and CD8+ T-cell immunity," FASEB J. 2012;26(8):3575-3586.
Ukyo et al., "Costimulation through OX40 is crucial for induction of an alloreactive human T-cell response," Immunology. 2003;109(2):226-231.
Valzasina, Barbara et al. "Triggering of OX40 (CD134) on CD4+ CD25+T Cells Blocks Their Inhibitory Activity: a Novel Regulatory Role for OX40 and its Comparison with GITR," Blood 105(7):2845-2851, (Dec. 9, 2004).
Van Olffen, et al. (Jun. 15, 2009) "GITR Triggering Induces Expansion of Both Effector and Regulatory CD4+ T Cells In Vivo", Journal of Immunology, vol. 182, No. 12, pp. 7490-7500.
Vesely et al., "Natural innate and adaptive immunity to cancer," Annu Rev Immunol. 2011;29:235-71.
Vessillier, S., et al., "Cytokine Release Assays for the Prediction of Therapeutic mAb Safety in First-in Man Trials—Whole Blood Cytokine Release Assays Are Poorly Predictive for TGN1412 Cytokine Storm," Journal of Immunological Methods 424:43-52, Elsevier, Netherlands (May 2015).
Vidal et al. (Aug. 2010) "In Vitro Cytokine Release Assays for Predicting Cytokine Release Syndrome: The Current State-of-the-Science", Report of a European Medicines Agency Workshop, Cytokine, vol. 51, No. 2, pp. 213-215.
Vilgelm, A.E., et al., (2016) "Combinatorial approach to cancer immunotherapy: strength in numbers" J. Leukoc. Biol. 100:275-290.
Voo et al., "Antibodies targeting human OX40 expand effector T cells and block inducible and natural regulatory T cell function," J Immunol. 2013;191(7):3641-50.
Vu, M.D., et al., (2007) "OX40 costimulation turns off Foxp3+ Tregs" Blood 110:2501-2510.
Waight et al., "Cutting edge: epigenetic regulation of Foxp3 defines a stable population of CD4+ regulatory T cells in tumors from mice and humans," J Immunol. 2015;194(3):878-82.
Ward et al., "Binding activities of a repertoire of single immunoglobulin variable domains secreted from *Escherichia coli*," Nature. 1989;341:544-546.
Warncke et al. (May 1, 2012) "Different Adaptations of IgG Effector Function in Human and Nonhuman Primates and Implications for Therapeutic Antibody Treatment", Journal of Immunology, vol. 188, No. 9, pp. 4405-4411.
Watanabe et al., "Combination of adoptive cell transfer and antibody injection can eradicate established tumors in mice-an in vivo study using anti-OX40mAb, anti-CD25mAb and anti-CTLA4mAb-," Immunopharmacol Immunotoxicol. 2010;32(2):238-45.
Watts, Tania H. (Apr. 23, 2005) "TNF/TNFR Family Members in Costimulation of T Cell Responses", Annual Review of Immunology, vol. 23, pp. 23-68.
Weinberg et al., "Anti-OX40 (CD134) administration to nonhuman primates: immunostimulatory effects and toxicokinetic study," J Immunother. 2006;29(6):575-85.
Weinberg et al., "Blocking OX-40/OX-40 ligand interaction in vitro and in vivo leads to decreased T cell function and amelioration of experimental allergic encephalomyelitis," J Immunol. 1999;162(3):1818-26.
Weinberg et al., "Engagement of the OX-40 receptor in vivo enhances antitumor immunity," J Immunol. 2000;164(4):2160-9.
Weinberg et al., "Science gone translational: the OX40 agonist story," Immunol Rev. 2011;244(1):218-31.
Weinberg et al., "Selective depletion of myelin-reactive T cells with the anti-OX-40 antibody ameliorates autoimmune encephalomyelitis," Nat Med. 1996;2(2):183-9.
Weixler et al., "OX40 expression enhances the prognostic significance of CD8 positive lymphocyte infiltration in colorectal cancer," Oncotarget. 2015;6(35):37588-37599.
Wells, J.A., "Systematic Mutational Analyses of Protein-protein Interfaces," Methods in Enzymology 202:390-411, Academic Press, United States (1991).
Weng et al. (Nov. 1, 2003) "Two Immunoglobulin G Fragment C Receptor Polymorphisms Independently Predict Response to Rituximab in Patients With Follicular Lymphoma", Journal of Clinical Oncology, vol. 21, No. 21, pp. 3940-3947.

(56) References Cited

OTHER PUBLICATIONS

White, A.L., et al., "Conformation of the human immunoglobulin G2 hinge imparts superagonistic properties to immunostimulatory anticancer antibodies," Cancer Cell 27(1):138-148, Cell Press, United States (Jan. 2015).

White, et al. (Aug. 15, 2011) "Interaction with Fc?RIIB is Critical for the Agonistic Activity of Anti-CD40 Monoclonal Antibody", Journal of Immunology, vol. 187, Issue 4, pp. 1754-1763.

Wilson et al., "An Fcgamma Receptor-Dependent mechanism Drives Antibody-Mediated Target-Receptor Signaling in Cancer Cells," Cancer Cell. 2011;19(1):101-13.

Wilson, et al. (2005) "Regulation of Antigen Presentation and Cross-Presentation in the Dendritic Cell Network: Facts, Hypothesis, and Immunological Implications", Advances in Immunology, vol. 86, pp. 241-305.

Wing et al. (Oct. 10, 2008) "CTLA-4 Control over Foxp3+ Regulatory T Cell Function", Science, vol. 322, No. 5899, pp. 271-275.

Wolchok, et al. (Oct. 2008) "The Mechanism of Anti-CTLA-4 Activity and The Negative Regulation of T-cell Activation", The Oncologist, vol. 13, No. 4, pp. 2-9.

Wolchok, J.D., et al., "Guidelines for the Evaluation of Immune Therapy Activity in Solid Tumors: Immune-related Response Criteria," Clinical Cancer Research 15(23):7412-7420, The Association, United States (2009).

Wolf et al., "A whole blood in vitro cytokine release assay with aqueous monoclonal antibody presentation for the prediction of therapeutic protein induced cytokine release syndrome in humans," Cytokine. 2012;60(3):828-37.

Wu et al., "The effect of OX40/OX40L and CD27/CD70 pathways on allogeneic islet graft rejection," Transplant Proc. 2001;33(1-2):217-8.

Xiao et al., "The Costimulatory Receptor OX40 Inhibits Interleukin-17 Expression through Activation of Repressive Chromatin Remodeling Pathways," Immunity. 2016;44(6):1271-83.

Xie et al., "Characterization and application of two novel monoclonal antibodies against human OX40: costimulation of T cells and expression on tumor as well as normal gland tissues," Tissue Antigens. 2006;67(4):307-17.

Xie, "TRAF molecules in cell signaling and in human diseases," J mol Signal. 2013;8(1):7.

Yao et al., "Advances in targeting cell surface signalling molecules for immune modulation," Nat Rev Drug Discov. 2013;12(2):130-46.

Yoon, et al. (Aug. 6, 2012) "Prognostic Impact of FoxP3+ Regulatory T Cells in Relation to CD8+ T Lymphocyte Density in Human Colon Carcinomas", PloS One, vol. 7, No. 8, pp. e42274.

Yu et al., "Combinational Immunotherapy with Allo-DRibble Vaccines and Anti-OX40 CoStimulation Leads to Generation of Cross-Reactive Effector T Cells and Tumor Regression," Sci Rep. 2016;6:37558.

Yu, et al. (Oct. 17, 2003) "Identification of A Ligand For Glucocorticoid-Induced Tumor Necrosis Factor Receptor Constitutively Expressed In Dendritic Cells", Biochemical and biophysical research communications, vol. 310, No. 2, pp. 433-438.

Zhan, Y., et al., "Glucocorticoid-induced TNF Receptor Expression by T Cells is Reciprocally Regulated by NF-kappaB and NFAT," Journal of Immunology 181(8):5405-5413, American Association of Immunologists, United States (2008).

Zhang et al., "Fc Engineering Approaches to Enhance the Agonism and Effector Functions of an Anti-OX40 Antibody," J Biol Chem. 2016;291(53):27134-27146.

Zhang, et al. (Apr. 1, 2010) "Regulatory T Cell Depletion Enhances Tumor Specific CD8 T-cell Responses, Elicited by Tumor Antigen NY-ES0-1 b in Hepatocellular Carcinoma Patients, in Vitro", International Journal of Oncology, vol. 36, Issue 4, pp. 841-848.

Zheng, Song Guo et al. "Natural and Induced CD4+CD25+ Cells Educate CD4+CD25− Cells to Develop Suppressive Activity: The Role of IL-2, TGF-I3, and IL-10," J Immunol 172:5213-5221, (2004).

Zhou, et al. (Apr. 8, 2008) "Human Glucocorticoid-induced TNF Receptor Ligand Regulates Its Signaling Activity Through Multiple Oligomerization States", Proceedings of the National Academy of Sciences USA, vol. 105, No. 14, pp. 5465-5470.

Zhou, et al. (Oct. 2010) "Mature B Cells Are Critical to T-cell-mediated Tumor Immunity Induced by an Agonist Anti-GITR Monoclonal Antibody", Journal of Immunotherapy, vol. 33, Issue 8, pp. 789-797.

Zhou, P., et al., (2007) "Pivotal Roles of CD4 Effector T cells in Mediating Agonistic Anti-GITR mAb-Induced-Immune Activation and Tumor Immunity in CT26 Tumors" Journal of Immunology 179:7365-7375.

Zipfel, P.F. and Skerka, C., "Complement Regulators and Inhibitory Proteins," Nature Reviews. Immunology 9(10):729-740, Nature Pub. Group, England (2009).

Zou, et al. (Apr. 2006) "Regulatory T cells, Tumor Immunity and Immunotherapy", Nature Reviews Immunology, vol. 6, No. 4, pp. 295-307.

* cited by examiner

SEQUENCE LISTING

```
<160> NUMBER OF SEQ ID NOS: 109

<210> SEQ ID NO 1
<211> LENGTH: 121
<212> TYPE: PRT
<213> ORGANISM: Artificial Sequence
<220> FEATURE:
<223> OTHER INFORMATION: pab1949 VH

<400> SEQUENCE: 1

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
```

```
                100             105             110

Gln Gly Thr Leu Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: pab1949 VH N56Y

<400> SEQUENCE: 2

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Tyr Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Gly Tyr Asp Tyr Trp Gly
            100                 105                 110

Gln Gly Thr Leu Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: pab1949 VH Y103A

<400> SEQUENCE: 3

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Ala Asp Ser Gly Tyr Asp Tyr Trp Gly
            100                 105                 110

Gln Gly Thr Leu Val Thr Val Ser Ser
        115                 120

<210> SEQ ID NO 4
<211> LENGTH: 121
<212> TYPE: PRT
<213> ORGANISM: Artificial Sequence
<220> FEATURE:
```

<223> OTHER INFORMATION: pab1949 VH D104A

<400> SEQUENCE: 4

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Ala Ser Ser Gly Tyr Asp Tyr Trp Gly
            100                 105                 110

Gln Gly Thr Leu Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: pab1949 VH Y108A

<400> SEQUENCE: 5

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Ala Asp Tyr Trp Gly
            100                 105                 110

Gln Gly Thr Leu Val Thr Val Ser Ser
        115                 120

<210> SEQ ID NO 6
<211> LENGTH: 121
<212> TYPE: PRT
<213> ORGANISM: Artificial Sequence
<220> FEATURE:
<223> OTHER INFORMATION: pab1949 VH D109A

<400> SEQUENCE: 6

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val

```
                35                  40                  45
Gly Arg Ile Arg Ser Lys Ala Asn Ser Tyr Ala Thr Ala Tyr Ala Ala
            50                  55                  60
Ser Val Lys Gly Arg Phe Thr Ile Ser Arg Asp Asp Ser Lys Asn Thr
65                  70                  75                  80
Ala Tyr Leu Gln Met Asn Ser Leu Lys Thr Glu Asp Thr Ala Val Tyr
                85                  90                  95
Tyr Cys Thr Ser Gly Ile Tyr Asp Ser Ser Gly Tyr Ala Tyr Trp Gly
                100                 105                 110
Gln Gly Thr Leu Val Thr Val Ser Ser
            115                 120

<210> SEQ ID NO 7
<211> LENGTH: 121
<212> TYPE: PRT
<213> ORGANISM: Artificial Sequence
<220> FEATURE:
<223> OTHER INFORMATION: pab1949 VH AM-1

<400> SEQUENCE: 7

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser Gln Glu
                20                  25                  30
Gly Met His Trp Val Arg Gln Ala Ser Gly Lys Gly Leu Glu Trp Val
                35                  40                  45
Gly Arg Ile Arg Ser Lys Ala Asn Ser Tyr Ala Thr Ala Tyr Ala Ala
            50                  55                  60
Ser Val Lys Gly Arg Phe Thr Ile Ser Arg Asp Asp Ser Glu Asn Thr
65                  70                  75                  80
Ala Tyr Leu Gln Met Asn Ser Leu Lys Thr Glu Asp Thr Ala Val Tyr
                85                  90                  95
Tyr Cys Thr Ser Gly Ile Tyr Asp Thr Leu Ala Tyr Asp Tyr Trp Gly
                100                 105                 110
Gln Gly Thr Leu Val Thr Val Ser Ser
            115                 120

<210> SEQ ID NO 8
<211> LENGTH: 121
<212> TYPE: PRT
<213> ORGANISM: Artificial Sequence
<220> FEATURE:
<223> OTHER INFORMATION: pab1949 VH AM-2

<400> SEQUENCE: 8

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser His Glu
                20                  25                  30
Gly Met His Trp Val Arg Gln Ala Ser Gly Lys Gly Leu Glu Trp Val
                35                  40                  45
Gly Arg Ile Arg Ser Lys Tyr Tyr Gln Glu Glu Thr Ala Tyr Ala Ala
            50                  55                  60
Ser Val Lys Gly Arg Phe Thr Ile Ser Arg Asp Asp Ser Lys Asn Thr
65                  70                  75                  80
Ala Tyr Leu Gln Met Asn Ser Leu Lys Thr Glu Asp Thr Ala Val Tyr
                85                  90                  95
```

Tyr Cys Thr Ser Gly Ile Tyr Asp Ser Gly Tyr Asp Tyr Trp Gly
            100                 105                 110

Gln Gly Thr Leu Val Thr Val Ser Ser
        115                 120

<210> SEQ ID NO 9
<211> LENGTH: 121
<212> TYPE: PRT
<213> ORGANISM: Artificial Sequence
<220> FEATURE:
<223> OTHER INFORMATION: pab1949 VH AM-3

<400> SEQUENCE: 9

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Tyr
            20                  25                  30

Ser Met His Trp Val Arg Gln Ala Ser Gly Lys Gly Leu Glu Trp Val
        35                  40                  45

Gly Arg Ile Arg Ser Lys Ser Glu Gly Gln Leu Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Gly Tyr Asp Tyr Trp Gly
            100                 105                 110

Gln Gly Thr Leu Val Thr Val Ser Ser
        115                 120

<210> SEQ ID NO 10
<211> LENGTH: 121
<212> TYPE: PRT
<213> ORGANISM: Artificial Sequence
<220> FEATURE:
<223> OTHER INFORMATION: pab1949 VH AM-4

<400> SEQUENCE: 10

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Glu Glu
            20                  25                  30

Ser Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Trp Glu Gly Tyr Asp Tyr Trp Gly
            100                 105                 110

Gln Gly Thr Leu Val Thr Val Ser Ser
        115                 120

<210> SEQ ID NO 11
<211> LENGTH: 112
<212> TYPE: PRT
<213> ORGANISM: Artificial Sequence
<220> FEATURE:
<223> OTHER INFORMATION: pab1949 VL

<400> SEQUENCE: 11

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: pab1949 VL A96G/L97S

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ser Gln Thr Pro Leu Thr Phe Gly Gly Gly Thr Lys Val Glu Ile Lys
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: pab1949 VL Q98K

<400> SEQUENCE: 13

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Lys Thr Pro Leu Thr Phe Gly Gly Gly Thr Lys Val Glu Ile Lys
            100                 105                 110
```

<210> SEQ ID NO 14
<211> LENGTH: 112
<212> TYPE: PRT
<213> ORGANISM: Artificial Sequence
<220> FEATURE:
<223> OTHER INFORMATION: pab1949 VL T99W

<400> SEQUENCE: 14

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Trp Pro Leu Thr Phe Gly Gly Gly Thr Lys Val Glu Ile Lys
            100                 105                 110
```

<210> SEQ ID NO 15
<211> LENGTH: 112
<212> TYPE: PRT
<213> ORGANISM: Artificial Sequence
<220> FEATURE:
<223> OTHER INFORMATION: pab2049 VL

<400> SEQUENCE: 15

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Ile Tyr Tyr Cys Met Gln Gly
                 85                  90                  95

Ser Lys Trp Pro Leu Thr Phe Gly Gly Gly Thr Lys Leu Glu Ile Lys
            100                 105                 110
```

<210> SEQ ID NO 16
<211> LENGTH: 5
<212> TYPE: PRT
<213> ORGANISM: Artificial Sequence
<220> FEATURE:
<223> OTHER INFORMATION: VH CDR1

```
<400> SEQUENCE: 16

Gly Ser Ala Met His
1               5

<210> SEQ ID NO 17
<211> LENGTH: 5
<212> TYPE: PRT
<213> ORGANISM: Artificial Sequence
<220> FEATURE:
<223> OTHER INFORMATION: VH CDR1

<400> SEQUENCE: 17

Gln Glu Gly Met His
1               5

<210> SEQ ID NO 18
<211> LENGTH: 5
<212> TYPE: PRT
<213> ORGANISM: Artificial Sequence
<220> FEATURE:
<223> OTHER INFORMATION: VH CDR1

<400> SEQUENCE: 18

His Glu Gly Met His
1               5

<210> SEQ ID NO 19
<211> LENGTH: 5
<212> TYPE: PRT
<213> ORGANISM: Artificial Sequence
<220> FEATURE:
<223> OTHER INFORMATION: VH CDR1

<400> SEQUENCE: 19

Gly Tyr Ser Met His
1               5

<210> SEQ ID NO 20
<211> LENGTH: 5
<212> TYPE: PRT
<213> ORGANISM: Artificial Sequence
<220> FEATURE:
<223> OTHER INFORMATION: VH CDR1

<400> SEQUENCE: 20

Glu Glu Ser Met His
1               5

<210> SEQ ID NO 21
<211> LENGTH: 19
<212> TYPE: PRT
<213> ORGANISM: Artificial Sequence
<220> FEATURE:
<223> OTHER INFORMATION: VH CDR2

<400> SEQUENCE: 21

Arg Ile Arg Ser Lys Ala Asn Ser Tyr Ala Thr Ala Tyr Ala Ala Ser
1               5                   10                  15

Val Lys Gly

<210> SEQ ID NO 22
<211> LENGTH: 19
<212> TYPE: PRT
<213> ORGANISM: Artificial Sequence
<220> FEATURE:
<223> OTHER INFORMATION: VH CDR2
```

<400> SEQUENCE: 22

Arg Ile Arg Ser Lys Ala Tyr Ser Tyr Ala Thr Ala Tyr Ala Ala Ser
1               5                   10                  15

Val Lys Gly

<210> SEQ ID NO 23
<211> LENGTH: 19
<212> TYPE: PRT
<213> ORGANISM: Artificial Sequence
<220> FEATURE:
<223> OTHER INFORMATION: VH CDR2

<400> SEQUENCE: 23

Arg Ile Arg Ser Lys Tyr Tyr Gln Glu Glu Thr Ala Tyr Ala Ala Ser
1               5                   10                  15

Val Lys Gly

<210> SEQ ID NO 24
<211> LENGTH: 19
<212> TYPE: PRT
<213> ORGANISM: Artificial Sequence
<220> FEATURE:
<223> OTHER INFORMATION: VH CDR2

<400> SEQUENCE: 24

Arg Ile Arg Ser Lys Ser Glu Gly Gln Leu Thr Ala Tyr Ala Ala Ser
1               5                   10                  15

Val Lys Gly

<210> SEQ ID NO 25
<211> LENGTH: 10
<212> TYPE: PRT
<213> ORGANISM: Artificial Sequence
<220> FEATURE:
<223> OTHER INFORMATION: VH CDR3

<400> SEQUENCE: 25

Gly Ile Tyr Asp Ser Ser Gly Tyr Asp Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: VH CDR3

<400> SEQUENCE: 26

Gly Ile Ala Asp Ser Ser Gly Tyr Asp Tyr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: VH CDR3

<400> SEQUENCE: 27

Gly Ile Tyr Ala Ser Ser Gly Tyr Asp Tyr
1               5                   10

<210> SEQ ID NO 28

```
<211> LENGTH: 10
<212> TYPE: PRT
<213> ORGANISM: Artificial Sequence
<220> FEATURE:
<223> OTHER INFORMATION: VH CDR3

<400> SEQUENCE: 28

Gly Ile Tyr Asp Ser Ser Gly Ala Asp Tyr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: VH CDR3

<400> SEQUENCE: 29

Gly Ile Tyr Asp Ser Ser Gly Tyr Ala Tyr
1               5                   10

<210> SEQ ID NO 30
<211> LENGTH: 10
<212> TYPE: PRT
<213> ORGANISM: Artificial Sequence
<220> FEATURE:
<223> OTHER INFORMATION: VH CDR3

<400> SEQUENCE: 30

Gly Ile Tyr Asp Thr Leu Ala Tyr Asp Tyr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: VH CDR3

<400> SEQUENCE: 31

Gly Ile Tyr Asp Trp Glu Gly Tyr Asp Tyr
1               5                   10

<210> SEQ ID NO 32
<211> LENGTH: 16
<212> TYPE: PRT
<213> ORGANISM: Artificial Sequence
<220> FEATURE:
<223> OTHER INFORMATION: VL CDRL1

<400> SEQUENCE: 32

Arg Ser Ser Gln Ser Leu Leu His Ser Asn Gly Tyr Asn Tyr Leu Asp
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: VL CDR2

<400> SEQUENCE: 33

Leu Gly Ser Asn Arg Ala Ser
1               5

<210> SEQ ID NO 34
<211> LENGTH: 9
```

```
<212> TYPE: PRT
<213> ORGANISM: Artificial Sequence
<220> FEATURE:
<223> OTHER INFORMATION: VL CDR3

<400> SEQUENCE: 34

Met Gln Ala Leu Gln Thr Pro Leu Thr
1               5

<210> SEQ ID NO 35
<211> LENGTH: 9
<212> TYPE: PRT
<213> ORGANISM: Artificial Sequence
<220> FEATURE:
<223> OTHER INFORMATION: VL CDR3

<400> SEQUENCE: 35

Met Gln Gly Ser Gln Thr Pro Leu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: VL CDR3

<400> SEQUENCE: 36

Met Gln Ala Leu Lys Thr Pro Leu Thr
1               5

<210> SEQ ID NO 37
<211> LENGTH: 9
<212> TYPE: PRT
<213> ORGANISM: Artificial Sequence
<220> FEATURE:
<223> OTHER INFORMATION: VL CDR3

<400> SEQUENCE: 37

Met Gln Ala Leu Gln Trp Pro Leu Thr
1               5

<210> SEQ ID NO 38
<211> LENGTH: 9
<212> TYPE: PRT
<213> ORGANISM: Artificial Sequence
<220> FEATURE:
<223> OTHER INFORMATION: VL CDR3

<400> SEQUENCE: 38

Met Gln Gly Ser Lys Trp Pro Leu Thr
1               5

<210> SEQ ID NO 39
<211> LENGTH: 100
<212> TYPE: PRT
<213> ORGANISM: Artificial Sequence
<220> FEATURE:
<223> OTHER INFORMATION: OX40 VH germline IGHV3-73*01

<400> SEQUENCE: 39

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
                20                  25                  30

Ala Met His Trp Val Arg Gln Ala Ser Gly Lys Gly Leu Glu Trp Val
```

-continued

```
                35                  40                  45
Gly Arg Ile Arg Ser Lys Ala Asn Ser Tyr Ala Thr Ala Tyr Ala Ala
         50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg
            100

<210> SEQ ID NO 40
<211> LENGTH: 100
<212> TYPE: PRT
<213> ORGANISM: Artificial Sequence
<220> FEATURE:
<223> OTHER INFORMATION: OX40 VL germline IGKV2-28*01

<400> SEQUENCE: 40

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100

<210> SEQ ID NO 41
<211> LENGTH: 5
<212> TYPE: PRT
<213> ORGANISM: Artificial Sequence
<220> FEATURE:
<223> OTHER INFORMATION: CDRH1 consensus sequence 1
<220> FEATURE:
<221> NAME/KEY: MOD_RES
<222> LOCATION: (1)..(1)
<223> OTHER INFORMATION: Xaa is Gly, Gln, His, or Glu
<220> FEATURE:
<221> NAME/KEY: MOD_RES
<222> LOCATION: (2)..(2)
<223> OTHER INFORMATION: Xaa is Ser, Glu, or Tyr
<220> FEATURE:
<221> NAME/KEY: MOD_RES
<222> LOCATION: (3)..(3)
<223> OTHER INFORMATION: Xaa is Ala, Ser, or Gly

<400> SEQUENCE: 41

Xaa Xaa Xaa Met His
 1               5

<210> SEQ ID NO 42
<211> LENGTH: 19
<212> TYPE: PRT
<213> ORGANISM: Artificial Sequence
<220> FEATURE:
<223> OTHER INFORMATION: CDRH2 consensus sequence 1
<220> FEATURE:
<221> NAME/KEY: MOD_RES
```

```
<222> LOCATION: (6)..(6)
<223> OTHER INFORMATION: Xaa is Ala, Ser, or Tyr
<220> FEATURE:
<221> NAME/KEY: MOD_RES
<222> LOCATION: (7)..(7)
<223> OTHER INFORMATION: Xaa is Asn, Glu, or Tyr
<220> FEATURE:
<221> NAME/KEY: MOD_RES
<222> LOCATION: (8)..(8)
<223> OTHER INFORMATION: Xaa is Ser, Gln, or Gly
<220> FEATURE:
<221> NAME/KEY: MOD_RES
<222> LOCATION: (9)..(9)
<223> OTHER INFORMATION: Xaa is Tyr, Glu, or Gln
<220> FEATURE:
<221> NAME/KEY: MOD_RES
<222> LOCATION: (10)..(10)
<223> OTHER INFORMATION: Xaa is Ala, Glu, or Leu

<400> SEQUENCE: 42

Arg Ile Arg Ser Lys Xaa Xaa Xaa Xaa Xaa Thr Ala Tyr Ala Ala Ser
1               5                   10                  15

Val Lys Gly

<210> SEQ ID NO 43
<211> LENGTH: 10
<212> TYPE: PRT
<213> ORGANISM: Artificial Sequence
<220> FEATURE:
<223> OTHER INFORMATION: CDRH3 consensus sequence 1
<220> FEATURE:
<221> NAME/KEY: MOD_RES
<222> LOCATION: (3)..(3)
<223> OTHER INFORMATION: Xaa is Tyr or Ala
<220> FEATURE:
<221> NAME/KEY: MOD_RES
<222> LOCATION: (4)..(4)
<223> OTHER INFORMATION: Xaa is Asp or Ala
<220> FEATURE:
<221> NAME/KEY: MOD_RES
<222> LOCATION: (5)..(5)
<223> OTHER INFORMATION: Xaa is Ser, Thr, or Trp
<220> FEATURE:
<221> NAME/KEY: MOD_RES
<222> LOCATION: (6)..(6)
<223> OTHER INFORMATION: Xaa is Ser, Glu, or Leu
<220> FEATURE:
<221> NAME/KEY: MOD_RES
<222> LOCATION: (7)..(7)
<223> OTHER INFORMATION: Xaa is Gly or Ala
<220> FEATURE:
<221> NAME/KEY: MOD_RES
<222> LOCATION: (8)..(8)
<223> OTHER INFORMATION: Xaa is Tyr or Ala
<220> FEATURE:
<221> NAME/KEY: MOD_RES
<222> LOCATION: (9)..(9)
<223> OTHER INFORMATION: Xaa is Asp or Ala

<400> SEQUENCE: 43

Gly Ile Xaa Xaa Xaa Xaa Xaa Xaa Xaa Tyr
1               5                   10

<210> SEQ ID NO 44
<211> LENGTH: 19
<212> TYPE: PRT
<213> ORGANISM: Artificial Sequence
<220> FEATURE:
<223> OTHER INFORMATION: CDRH2 consensus sequence 2
<220> FEATURE:
<221> NAME/KEY: MOD_RES
<222> LOCATION: (7)..(7)
<223> OTHER INFORMATION: Xaa is Asn or Tyr
```

-continued

```
<400> SEQUENCE: 44

Arg Ile Arg Ser Lys Ala Xaa Ser Tyr Ala Thr Ala Tyr Ala Ala Ser
1               5                   10                  15

Val Lys Gly

<210> SEQ ID NO 45
<211> LENGTH: 10
<212> TYPE: PRT
<213> ORGANISM: Artificial Sequence
<220> FEATURE:
<223> OTHER INFORMATION: CDRH3 consensus sequence 2
<220> FEATURE:
<221> NAME/KEY: MOD_RES
<222> LOCATION: (3)..(3)
<223> OTHER INFORMATION: Xaa is Tyr or Ala
<220> FEATURE:
<221> NAME/KEY: MOD_RES
<222> LOCATION: (4)..(4)
<223> OTHER INFORMATION: Xaa is Asp or Ala
<220> FEATURE:
<221> NAME/KEY: MOD_RES
<222> LOCATION: (8)..(8)
<223> OTHER INFORMATION: Xaa is Tyr or Ala
<220> FEATURE:
<221> NAME/KEY: MOD_RES
<222> LOCATION: (9)..(9)
<223> OTHER INFORMATION: Xaa is Asp or Ala

<400> SEQUENCE: 45

Gly Ile Xaa Xaa Ser Ser Gly Xaa Xaa Tyr
1               5                   10

<210> SEQ ID NO 46
<211> LENGTH: 9
<212> TYPE: PRT
<213> ORGANISM: Artificial Sequence
<220> FEATURE:
<223> OTHER INFORMATION: CDRL3 consensus sequence
<220> FEATURE:
<221> NAME/KEY: MOD_RES
<222> LOCATION: (3)..(3)
<223> OTHER INFORMATION: Xaa is Ala or Gly
<220> FEATURE:
<221> NAME/KEY: MOD_RES
<222> LOCATION: (4)..(4)
<223> OTHER INFORMATION: Xaa is Leu or Ser
<220> FEATURE:
<221> NAME/KEY: MOD_RES
<222> LOCATION: (5)..(5)
<223> OTHER INFORMATION: Xaa is Gln or Lys
<220> FEATURE:
<221> NAME/KEY: MOD_RES
<222> LOCATION: (6)..(6)
<223> OTHER INFORMATION: Xaa is Thr or Trp

<400> SEQUENCE: 46

Met Gln Xaa Xaa Xaa Xaa Pro Leu Thr
1               5

<210> SEQ ID NO 47
<211> LENGTH: 121
<212> TYPE: PRT
<213> ORGANISM: Artificial Sequence
<220> FEATURE:
<223> OTHER INFORMATION: VH consensus sequence 1
<220> FEATURE:
<221> NAME/KEY: MOD_RES
<222> LOCATION: (31)..(31)
<223> OTHER INFORMATION: Xaa is Gly, Gln, His, or Glu
<220> FEATURE:
<221> NAME/KEY: MOD_RES
<222> LOCATION: (32)..(32)
```

```
<223> OTHER INFORMATION: Xaa is Ser, Glu, or Tyr
<220> FEATURE:
<221> NAME/KEY: MOD_RES
<222> LOCATION: (33)..(33)
<223> OTHER INFORMATION: Xaa is Ala, Ser, or Gly
<220> FEATURE:
<221> NAME/KEY: MOD_RES
<222> LOCATION: (55)..(55)
<223> OTHER INFORMATION: Xaa is Ala, Ser, or Tyr
<220> FEATURE:
<221> NAME/KEY: MOD_RES
<222> LOCATION: (56)..(56)
<223> OTHER INFORMATION: Xaa is Asn, Glu, or Tyr
<220> FEATURE:
<221> NAME/KEY: MOD_RES
<222> LOCATION: (57)..(57)
<223> OTHER INFORMATION: Xaa is Ser, Gln, or Gly
<220> FEATURE:
<221> NAME/KEY: MOD_RES
<222> LOCATION: (58)..(58)
<223> OTHER INFORMATION: Xaa is Tyr, Glu, or Gln
<220> FEATURE:
<221> NAME/KEY: MOD_RES
<222> LOCATION: (59)..(59)
<223> OTHER INFORMATION: Xaa is Ala, Glu, or Leu
<220> FEATURE:
<221> NAME/KEY: MOD_RES
<222> LOCATION: (78)..(78)
<223> OTHER INFORMATION: Xaa is Lys or Glu
<220> FEATURE:
<221> NAME/KEY: MOD_RES
<222> LOCATION: (103)..(103)
<223> OTHER INFORMATION: Xaa is Tyr or Ala
<220> FEATURE:
<221> NAME/KEY: MOD_RES
<222> LOCATION: (104)..(104)
<223> OTHER INFORMATION: Xaa is Asp or Ala
<220> FEATURE:
<221> NAME/KEY: MOD_RES
<222> LOCATION: (105)..(105)
<223> OTHER INFORMATION: Xaa is Ser, Thr, or Trp
<220> FEATURE:
<221> NAME/KEY: MOD_RES
<222> LOCATION: (106)..(106)
<223> OTHER INFORMATION: Xaa is Ser, Glu, or Leu
<220> FEATURE:
<221> NAME/KEY: MOD_RES
<222> LOCATION: (107)..(107)
<223> OTHER INFORMATION: Xaa is Gly or Ala
<220> FEATURE:
<221> NAME/KEY: MOD_RES
<222> LOCATION: (108)..(108)
<223> OTHER INFORMATION: Xaa is Tyr or Ala
<220> FEATURE:
<221> NAME/KEY: MOD_RES
<222> LOCATION: (109)..(109)
<223> OTHER INFORMATION: Xaa is Asp or Ala

<400> SEQUENCE: 47

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Xaa Xaa
            20                  25                  30

Xaa Met His Trp Val Arg Gln Ala Ser Gly Lys Gly Leu Glu Trp Val
        35                  40                  45

Gly Arg Ile Arg Ser Lys Xaa Xaa Xaa Xaa Xaa Thr Ala Tyr Ala Ala
    50                  55                  60

Ser Val Lys Gly Arg Phe Thr Ile Ser Arg Asp Asp Ser Xaa Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Xaa Xaa Xaa Xaa Xaa Xaa Xaa Tyr Trp Gly
```

```
                    100                 105                 110

Gln Gly Thr Leu Val Thr Val Ser Ser
            115                 120

<210> SEQ ID NO 48
<211> LENGTH: 121
<212> TYPE: PRT
<213> ORGANISM: Artificial Sequence
<220> FEATURE:
<223> OTHER INFORMATION: VH consensus sequence 2
<220> FEATURE:
<221> NAME/KEY: MOD_RES
<222> LOCATION: (56)..(56)
<223> OTHER INFORMATION: Xaa is Asn or Tyr
<220> FEATURE:
<221> NAME/KEY: MOD_RES
<222> LOCATION: (103)..(103)
<223> OTHER INFORMATION: Xaa is Tyr or Ala
<220> FEATURE:
<221> NAME/KEY: MOD_RES
<222> LOCATION: (104)..(104)
<223> OTHER INFORMATION: Xaa is Asp or Ala
<220> FEATURE:
<221> NAME/KEY: MOD_RES
<222> LOCATION: (108)..(108)
<223> OTHER INFORMATION: Xaa is Tyr or Ala
<220> FEATURE:
<221> NAME/KEY: MOD_RES
<222> LOCATION: (109)..(109)
<223> OTHER INFORMATION: Xaa is Asp or Ala

<400> SEQUENCE: 48

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Xaa Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Xaa Xaa Ser Ser Gly Xaa Xaa Tyr Trp Gly
            100                 105                 110

Gln Gly Thr Leu Val Thr Val Ser Ser
            115                 120

<210> SEQ ID NO 49
<211> LENGTH: 112
<212> TYPE: PRT
<213> ORGANISM: Artificial Sequence
<220> FEATURE:
<223> OTHER INFORMATION: VL consensus sequence
<220> FEATURE:
<221> NAME/KEY: MOD_RES
<222> LOCATION: (72)..(72)
<223> OTHER INFORMATION: Xaa is Ser or Ala
<220> FEATURE:
<221> NAME/KEY: MOD_RES
<222> LOCATION: (90)..(90)
<223> OTHER INFORMATION: Xaa is Val or Ile
<220> FEATURE:
<221> NAME/KEY: MOD_RES
<222> LOCATION: (96)..(96)
<223> OTHER INFORMATION: Xaa is Ala or Gly
<220> FEATURE:
```

-continued

```
<221> NAME/KEY: MOD_RES
<222> LOCATION: (97)..(97)
<223> OTHER INFORMATION: Xaa is Leu or Ser
<220> FEATURE:
<221> NAME/KEY: MOD_RES
<222> LOCATION: (98)..(98)
<223> OTHER INFORMATION: Xaa is Gln or Lys
<220> FEATURE:
<221> NAME/KEY: MOD_RES
<222> LOCATION: (99)..(99)
<223> OTHER INFORMATION: Xaa is Thr or Trp
<220> FEATURE:
<221> NAME/KEY: MOD_RES
<222> LOCATION: (109)..(109)
<223> OTHER INFORMATION: Xaa is Val or Leu

<400> SEQUENCE: 49

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Xaa Gly Thr Asp Phe Thr Leu Lys Ile
65                  70                  75                  80

Ser Arg Val Glu Ala Glu Asp Val Gly Xaa Tyr Tyr Cys Met Gln Xaa
                85                  90                  95

Xaa Xaa Xaa Pro Leu Thr Phe Gly Gly Gly Thr Lys Xaa Glu Ile Lys
            100                 105                 110

<210> SEQ ID NO 50
<211> LENGTH: 450
<212> TYPE: PRT
<213> ORGANISM: Artificial Sequence
<220> FEATURE:
<223> OTHER INFORMATION: pab1949/pab2049 heavy chain (IgG1)

<400> SEQUENCE: 50

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 51
<211> LENGTH: 219
<212> TYPE: PRT
<213> ORGANISM: Artificial Sequence
<220> FEATURE:
<223> OTHER INFORMATION: pab1949 light chain

<400> SEQUENCE: 51

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 52
<211> LENGTH: 118
<212> TYPE: PRT
<213> ORGANISM: Artificial Sequence
<220> FEATURE:
<223> OTHER INFORMATION: pab1876 VH

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser
        115
```

```
<210> SEQ ID NO 53
<211> LENGTH: 118
<212> TYPE: PRT
<213> ORGANISM: Artificial Sequence
<220> FEATURE:
<223> OTHER INFORMATION: pab1876 VH D57G

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30
```

-continued

Ala Met Tyr Trp Val Arg Gln Ala Pro Gly Gln Gly Leu Glu Trp Ile
        35                  40                  45

Gly Val Ile Arg Thr Tyr Ser Gly Gly Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser
        115

<210> SEQ ID NO 54
<211> LENGTH: 118
<212> TYPE: PRT
<213> ORGANISM: Artificial Sequence
<220> FEATURE:
<223> OTHER INFORMATION: pab1967 VH

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Gly Tyr
            20                  25                  30

Ala Met His Trp Val Arg Gln Ala Pro Gly Gln Gly Leu Glu Trp Met
        35                  40                  45

Gly Leu Ile Arg Thr Tyr Ser Gly Gly Val Ser Tyr Asn Gln Lys Phe
    50                  55                  60

Arg Glu Arg Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Ile Thr Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: pab1975 VH

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Ala Met His Trp Val Arg Gln Ala Pro Gly Gln Gly Leu Glu Trp Met
        35                  40                  45

Gly Leu Ile Arg Thr Tyr Ser Gly Gly Val Ser Tyr Asn Gln Lys Phe
    50                  55                  60

Gln Gly Arg Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys

```
                85                  90                  95
Ala Lys Ser Gly Thr Val Arg Gly Phe Ala Tyr Trp Gly Gln Gly Thr
            100                 105                 110

Leu Val Thr Val Ser Ser
        115

<210> SEQ ID NO 56
<211> LENGTH: 118
<212> TYPE: PRT
<213> ORGANISM: Artificial Sequence
<220> FEATURE:
<223> OTHER INFORMATION: pab1979 VH

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Ala Met His Trp Val Arg Gln Ala Pro Gly Gln Gly Leu Glu Trp Met
            35                  40                  45

Gly Val Ile Arg Thr Tyr Ser Gly Gly Val Ser Tyr Asn Gln Lys Phe
        50                  55                  60

Gln Glu Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser
        115

<210> SEQ ID NO 57
<211> LENGTH: 113
<212> TYPE: PRT
<213> ORGANISM: Artificial Sequence
<220> FEATURE:
<223> OTHER INFORMATION: pab1876 VL

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr His Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 58
<211> LENGTH: 113
<212> TYPE: PRT
```

<213> ORGANISM: Artificial Sequence
<220> FEATURE:
<223> OTHER INFORMATION: pab1967 VL

<400> SEQUENCE: 58

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Ser Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Val Ala Val Tyr His Cys Gln Asn
                85                  90                  95

Glu Tyr Ser Phe Pro Tyr Thr Phe Gly Gln Gly Thr Lys Leu Glu Ile
            100                 105                 110

Lys

<210> SEQ ID NO 59
<211> LENGTH: 113
<212> TYPE: PRT
<213> ORGANISM: Artificial Sequence
<220> FEATURE:
<223> OTHER INFORMATION: pab1975/pab1979 VL

<400> SEQUENCE: 59

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 60
<211> LENGTH: 5
<212> TYPE: PRT
<213> ORGANISM: Artificial Sequence
<220> FEATURE:
<223> OTHER INFORMATION: VH CDR1

<400> SEQUENCE: 60

Asp Tyr Ala Met Tyr
1               5

<210> SEQ ID NO 61
<211> LENGTH: 5
<212> TYPE: PRT

```
<213> ORGANISM: Artificial Sequence
<220> FEATURE:
<223> OTHER INFORMATION: VH CDR1

<400> SEQUENCE: 61

Gly Tyr Ala Met His
1               5

<210> SEQ ID NO 62
<211> LENGTH: 5
<212> TYPE: PRT
<213> ORGANISM: Artificial Sequence
<220> FEATURE:
<223> OTHER INFORMATION: VH CDR1

<400> SEQUENCE: 62

Glu Tyr Ala Met His
1               5

<210> SEQ ID NO 63
<211> LENGTH: 17
<212> TYPE: PRT
<213> ORGANISM: Artificial Sequence
<220> FEATURE:
<223> OTHER INFORMATION: VH CDR2

<400> SEQUENCE: 63

Val Ile Arg Thr Tyr Ser Gly Asp Val Thr Tyr Asn Gln Lys Phe Lys
1               5                   10                  15

Asp

<210> SEQ ID NO 64
<211> LENGTH: 17
<212> TYPE: PRT
<213> ORGANISM: Artificial Sequence
<220> FEATURE:
<223> OTHER INFORMATION: VH CDR2

<400> SEQUENCE: 64

Val Ile Arg Thr Tyr Ser Gly Gly Val Thr Tyr Asn Gln Lys Phe Lys
1               5                   10                  15

Asp

<210> SEQ ID NO 65
<211> LENGTH: 17
<212> TYPE: PRT
<213> ORGANISM: Artificial Sequence
<220> FEATURE:
<223> OTHER INFORMATION: VH CDR2

<400> SEQUENCE: 65

Leu Ile Arg Thr Tyr Ser Gly Gly Val Ser Tyr Asn Gln Lys Phe Arg
1               5                   10                  15

Glu

<210> SEQ ID NO 66
<211> LENGTH: 17
<212> TYPE: PRT
<213> ORGANISM: Artificial Sequence
<220> FEATURE:
<223> OTHER INFORMATION: VH CDR2

<400> SEQUENCE: 66

Leu Ile Arg Thr Tyr Ser Gly Gly Val Ser Tyr Asn Gln Lys Phe Gln
1               5                   10                  15
```

Gly

<210> SEQ ID NO 67
<211> LENGTH: 17
<212> TYPE: PRT
<213> ORGANISM: Artificial Sequence
<220> FEATURE:
<223> OTHER INFORMATION: VH CDR2

<400> SEQUENCE: 67

Val Ile Arg Thr Tyr Ser Gly Gly Val Ser Tyr Asn Gln Lys Phe Gln
1               5                   10                  15

Glu

<210> SEQ ID NO 68
<211> LENGTH: 9
<212> TYPE: PRT
<213> ORGANISM: Artificial Sequence
<220> FEATURE:
<223> OTHER INFORMATION: VH CDR3

<400> SEQUENCE: 68

Ser Gly Thr Val Arg Gly Phe Ala Tyr
1               5

<210> SEQ ID NO 69
<211> LENGTH: 17
<212> TYPE: PRT
<213> ORGANISM: Artificial Sequence
<220> FEATURE:
<223> OTHER INFORMATION: VL CDR1

<400> SEQUENCE: 69

Lys Ser Ser Gln Ser Leu Leu Asn Ser Gly Asn Gln Lys Asn Tyr Leu
1               5                   10                  15

Thr

<210> SEQ ID NO 70
<211> LENGTH: 17
<212> TYPE: PRT
<213> ORGANISM: Artificial Sequence
<220> FEATURE:
<223> OTHER INFORMATION: VL CDR1

<400> SEQUENCE: 70

Lys Ser Ser Gln Ser Leu Leu Asn Ser Ser Asn Gln Lys Asn Tyr Leu
1               5                   10                  15

Thr

<210> SEQ ID NO 71
<211> LENGTH: 7
<212> TYPE: PRT
<213> ORGANISM: Artificial Sequence
<220> FEATURE:
<223> OTHER INFORMATION: VL CDR2

<400> SEQUENCE: 71

Trp Ala Ser Thr Arg Glu Ser
1               5

<210> SEQ ID NO 72
<211> LENGTH: 9
<212> TYPE: PRT
<213> ORGANISM: Artificial Sequence

```
<220> FEATURE:
<223> OTHER INFORMATION: VL CDR3

<400> SEQUENCE: 72

Gln Asn Asp Tyr Ser Tyr Pro Tyr Thr
1               5

<210> SEQ ID NO 73
<211> LENGTH: 9
<212> TYPE: PRT
<213> ORGANISM: Artificial Sequence
<220> FEATURE:
<223> OTHER INFORMATION: VL CDR3

<400> SEQUENCE: 73

Gln Asn Glu Tyr Ser Phe Pro Tyr Thr
1               5

<210> SEQ ID NO 74
<211> LENGTH: 98
<212> TYPE: PRT
<213> ORGANISM: Artificial Sequence
<220> FEATURE:
<223> OTHER INFORMATION: GITR VH germline

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 75
<211> LENGTH: 101
<212> TYPE: PRT
<213> ORGANISM: Artificial Sequence
<220> FEATURE:
<223> OTHER INFORMATION: GITR VL germline

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Tyr Tyr Ser Thr Pro
            100

<210> SEQ ID NO 76
<211> LENGTH: 5
<212> TYPE: PRT
<213> ORGANISM: Artificial Sequence
<220> FEATURE:
<223> OTHER INFORMATION: CDRH1 consensus sequence 1
<220> FEATURE:
<221> NAME/KEY: MOD_RES
<222> LOCATION: (1)..(1)
<223> OTHER INFORMATION: Xaa is Asp, Glu, or Gly
<220> FEATURE:
<221> NAME/KEY: MOD_RES
<222> LOCATION: (3)..(3)
<223> OTHER INFORMATION: Xaa is Ala or Val
<220> FEATURE:
<221> NAME/KEY: MOD_RES
<222> LOCATION: (5)..(5)
<223> OTHER INFORMATION: Xaa is Tyr or His

<400> SEQUENCE: 76

Xaa Tyr Xaa Met Xaa
1               5

<210> SEQ ID NO 77
<211> LENGTH: 17
<212> TYPE: PRT
<213> ORGANISM: Artificial Sequence
<220> FEATURE:
<223> OTHER INFORMATION: CDRH2 consensus sequence 1
<220> FEATURE:
<221> NAME/KEY: MOD_RES
<222> LOCATION: (1)..(1)
<223> OTHER INFORMATION: Xaa is Val or Leu
<220> FEATURE:
<221> NAME/KEY: MOD_RES
<222> LOCATION: (3)..(3)
<223> OTHER INFORMATION: Xaa is Arg, Lys, or Gln
<220> FEATURE:
<221> NAME/KEY: MOD_RES
<222> LOCATION: (5)..(5)
<223> OTHER INFORMATION: Xaa is Tyr or Phe
<220> FEATURE:
<221> NAME/KEY: MOD_RES
<222> LOCATION: (8)..(8)
<223> OTHER INFORMATION: Xaa is Asp, Glu, or Gly
<220> FEATURE:
<221> NAME/KEY: MOD_RES
<222> LOCATION: (9)..(9)
<223> OTHER INFORMATION: Xaa is Val or Leu
<220> FEATURE:
<221> NAME/KEY: MOD_RES
<222> LOCATION: (10)..(10)
<223> OTHER INFORMATION: Xaa is Thr or Ser
<220> FEATURE:
<221> NAME/KEY: MOD_RES
<222> LOCATION: (16)..(16)
<223> OTHER INFORMATION: Xaa is Lys, Arg, or Gln
<220> FEATURE:
<221> NAME/KEY: MOD_RES
<222> LOCATION: (17)..(17)
<223> OTHER INFORMATION: Xaa is Asp, Glu, or Gly

<400> SEQUENCE: 77

Xaa Ile Xaa Thr Xaa Ser Gly Xaa Xaa Xaa Tyr Asn Gln Lys Phe Xaa
1               5                   10                  15

Xaa

<210> SEQ ID NO 78
<211> LENGTH: 5
<212> TYPE: PRT

<213> ORGANISM: Artificial Sequence
<220> FEATURE:
<223> OTHER INFORMATION: CDRH1 consensus sequence 2
<220> FEATURE:
<221> NAME/KEY: MOD_RES
<222> LOCATION: (1)..(1)
<223> OTHER INFORMATION: Xaa is Asp, Gly, or Glu
<220> FEATURE:
<221> NAME/KEY: MOD_RES
<222> LOCATION: (5)..(5)
<223> OTHER INFORMATION: Xaa is Tyr or His

<400> SEQUENCE: 78

Xaa Tyr Ala Met Xaa
1               5

<210> SEQ ID NO 79
<211> LENGTH: 17
<212> TYPE: PRT
<213> ORGANISM: Artificial Sequence
<220> FEATURE:
<223> OTHER INFORMATION: CDRH2 consensus sequence 2
<220> FEATURE:
<221> NAME/KEY: MOD_RES
<222> LOCATION: (1)..(1)
<223> OTHER INFORMATION: Xaa is Val or Leu
<220> FEATURE:
<221> NAME/KEY: MOD_RES
<222> LOCATION: (8)..(8)
<223> OTHER INFORMATION: Xaa is Asp or Gly
<220> FEATURE:
<221> NAME/KEY: MOD_RES
<222> LOCATION: (10)..(10)
<223> OTHER INFORMATION: Xaa is Thr or Ser
<220> FEATURE:
<221> NAME/KEY: MOD_RES
<222> LOCATION: (16)..(16)
<223> OTHER INFORMATION: Xaa is Lys, Arg, or Gln
<220> FEATURE:
<221> NAME/KEY: MOD_RES
<222> LOCATION: (17)..(17)
<223> OTHER INFORMATION: Xaa is Asp, Glu, or Gly

<400> SEQUENCE: 79

Xaa Ile Arg Thr Tyr Ser Gly Xaa Val Xaa Tyr Asn Gln Lys Phe Xaa
1               5                   10                  15

Xaa

<210> SEQ ID NO 80
<211> LENGTH: 17
<212> TYPE: PRT
<213> ORGANISM: Artificial Sequence
<220> FEATURE:
<223> OTHER INFORMATION: CDRL1 consensus sequence 1
<220> FEATURE:
<221> NAME/KEY: MOD_RES
<222> LOCATION: (10)..(10)
<223> OTHER INFORMATION: Xaa is Gly or Ser
<220> FEATURE:
<221> NAME/KEY: MOD_RES
<222> LOCATION: (17)..(17)
<223> OTHER INFORMATION: Xaa is Thr or Ser

<400> SEQUENCE: 80

Lys Ser Ser Gln Ser Leu Leu Asn Ser Xaa Asn Gln Lys Asn Tyr Leu
1               5                   10                  15

Xaa

<210> SEQ ID NO 81
<211> LENGTH: 9
<212> TYPE: PRT

<213> ORGANISM: Artificial Sequence
<220> FEATURE:
<223> OTHER INFORMATION: CDRL3 consensus sequence 1
<220> FEATURE:
<221> NAME/KEY: MOD_RES
<222> LOCATION: (3)..(3)
<223> OTHER INFORMATION: Xaa is Asp, Glu, or Ala
<220> FEATURE:
<221> NAME/KEY: MOD_RES
<222> LOCATION: (6)..(6)
<223> OTHER INFORMATION: Xaa is Tyr, Phe, or Ser

<400> SEQUENCE: 81

Gln Asn Xaa Tyr Ser Xaa Pro Tyr Thr
1               5

<210> SEQ ID NO 82
<211> LENGTH: 17
<212> TYPE: PRT
<213> ORGANISM: Artificial Sequence
<220> FEATURE:
<223> OTHER INFORMATION: CDRL1 consensus sequence 2
<220> FEATURE:
<221> NAME/KEY: MOD_RES
<222> LOCATION: (10)..(10)
<223> OTHER INFORMATION: Xaa is Gly or Ser

<400> SEQUENCE: 82

Lys Ser Ser Gln Ser Leu Leu Asn Ser Xaa Asn Gln Lys Asn Tyr Leu
1               5                   10                  15

Thr

<210> SEQ ID NO 83
<211> LENGTH: 9
<212> TYPE: PRT
<213> ORGANISM: Artificial Sequence
<220> FEATURE:
<223> OTHER INFORMATION: CDRL3 consensus sequence 2
<220> FEATURE:
<221> NAME/KEY: MOD_RES
<222> LOCATION: (3)..(3)
<223> OTHER INFORMATION: Xaa is Asp, Glu, or Ala
<220> FEATURE:
<221> NAME/KEY: MOD_RES
<222> LOCATION: (6)..(6)
<223> OTHER INFORMATION: Xaa is Tyr or Phe

<400> SEQUENCE: 83

Gln Asn Xaa Tyr Ser Xaa Pro Tyr Thr
1               5

<210> SEQ ID NO 84
<211> LENGTH: 118
<212> TYPE: PRT
<213> ORGANISM: Artificial Sequence
<220> FEATURE:
<223> OTHER INFORMATION: VH consensus
<220> FEATURE:
<221> NAME/KEY: MOD_RES
<222> LOCATION: (24)..(24)
<223> OTHER INFORMATION: Xaa is Gly or Ala
<220> FEATURE:
<221> NAME/KEY: MOD_RES
<222> LOCATION: (31)..(31)
<223> OTHER INFORMATION: Xaa is Asp, Gly, or Glu
<220> FEATURE:
<221> NAME/KEY: MOD_RES
<222> LOCATION: (35)..(35)
<223> OTHER INFORMATION: Xaa is Tyr or His
<220> FEATURE:
<221> NAME/KEY: MOD_RES
<222> LOCATION: (48)..(48)

```
<223> OTHER INFORMATION: Xaa is Ile or Met
<220> FEATURE:
<221> NAME/KEY: MOD_RES
<222> LOCATION: (50)..(50)
<223> OTHER INFORMATION: Xaa is Val or Leu
<220> FEATURE:
<221> NAME/KEY: MOD_RES
<222> LOCATION: (57)..(57)
<223> OTHER INFORMATION: Xaa is Asp or Gly
<220> FEATURE:
<221> NAME/KEY: MOD_RES
<222> LOCATION: (59)..(59)
<223> OTHER INFORMATION: Xaa is Thr or Ser
<220> FEATURE:
<221> NAME/KEY: MOD_RES
<222> LOCATION: (65)..(65)
<223> OTHER INFORMATION: Xaa is Lys, Arg, or Gln
<220> FEATURE:
<221> NAME/KEY: MOD_RES
<222> LOCATION: (66)..(66)
<223> OTHER INFORMATION: Xaa is Asp, Glu, or Gly
<220> FEATURE:
<221> NAME/KEY: MOD_RES
<222> LOCATION: (68)..(68)
<223> OTHER INFORMATION: Xaa is Ala or Val
<220> FEATURE:
<221> NAME/KEY: MOD_RES
<222> LOCATION: (74)..(74)
<223> OTHER INFORMATION: Xaa is Lys or Thr
<220> FEATURE:
<221> NAME/KEY: MOD_RES
<222> LOCATION: (103)..(103)
<223> OTHER INFORMATION: Xaa is Arg or Ala
<220> FEATURE:
<221> NAME/KEY: MOD_RES
<222> LOCATION: (114)..(114)
<223> OTHER INFORMATION: Xaa is Val or Ile

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Xaa Ser Gly Tyr Thr Phe Thr Xaa Tyr
            20                  25                  30

Ala Met Xaa Trp Val Arg Gln Ala Pro Gly Gln Gly Leu Glu Trp Xaa
        35                  40                  45

Gly Xaa Ile Arg Thr Tyr Ser Gly Xaa Val Xaa Tyr Asn Gln Lys Phe
    50                  55                  60

Xaa Xaa Arg Xaa Thr Met Thr Val Asp Xaa Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Xaa Gly Phe Ala Tyr Trp Gly Gln Gly Thr
            100                 105                 110

Leu Xaa Thr Val Ser Ser
        115

<210> SEQ ID NO 85
<211> LENGTH: 113
<212> TYPE: PRT
<213> ORGANISM: Artificial Sequence
<220> FEATURE:
<223> OTHER INFORMATION: VL consensus
<220> FEATURE:
<221> NAME/KEY: MOD_RES
<222> LOCATION: (33)..(33)
<223> OTHER INFORMATION: Xaa is Gly or Ser
<220> FEATURE:
<221> NAME/KEY: MOD_RES
<222> LOCATION: (69)..(69)
<223> OTHER INFORMATION: Xaa is Ser or Thr
```

```
<220> FEATURE:
<221> NAME/KEY: MOD_RES
<222> LOCATION: (84)..(84)
<223> OTHER INFORMATION: Xaa is Leu or Val
<220> FEATURE:
<221> NAME/KEY: MOD_RES
<222> LOCATION: (93)..(93)
<223> OTHER INFORMATION: Xaa is His or Tyr
<220> FEATURE:
<221> NAME/KEY: MOD_RES
<222> LOCATION: (97)..(97)
<223> OTHER INFORMATION: Xaa is Asp, Glu, or Ala
<220> FEATURE:
<221> NAME/KEY: MOD_RES
<222> LOCATION: (100)..(100)
<223> OTHER INFORMATION: Xaa is Tyr or Phe

<400> SEQUENCE: 85

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Xaa Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Val Ala Val Tyr Xaa Cys Gln Asn
                85                  90                  95

Xaa Tyr Ser Xaa Pro Tyr Thr Phe Gly Gln Gly Thr Lys Leu Glu Ile
            100                 105                 110

Lys

<210> SEQ ID NO 86
<211> LENGTH: 447
<212> TYPE: PRT
<213> ORGANISM: Artificial Sequence
<220> FEATURE:
<223> OTHER INFORMATION: pab1876 heavy chain (IgG1)

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met Tyr Trp Val Arg Gln Ala Pro Gly Gln Gly Leu Glu Trp Ile
        35                  40                  45

Gly Val Ile Arg Thr Tyr Ser Gly Asp Val Thr Tyr Asn Gln Lys Phe
    50                  55                  60

Lys Asp Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Gly Thr Val Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

-continued

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 87
<211> LENGTH: 220
<212> TYPE: PRT
<213> ORGANISM: Artificial Sequence
<220> FEATURE:
<223> OTHER INFORMATION: pab1876 light chain

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr His Cys Gln Asn
                 85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 88
<211> LENGTH: 329
<212> TYPE: PRT
<213> ORGANISM: Artificial Sequence
<220> FEATURE:
<223> OTHER INFORMATION: Human IgG1 constant region consensus sequence
<220> FEATURE:
<221> NAME/KEY: MOD_RES
<222> LOCATION: (97)..(97)
<223> OTHER INFORMATION: Xaa is Lys or Arg
<220> FEATURE:
<221> NAME/KEY: MOD_RES
<222> LOCATION: (239)..(239)
<223> OTHER INFORMATION: Xaa is Asp or Glu
<220> FEATURE:
<221> NAME/KEY: MOD_RES
<222> LOCATION: (241)..(241)
<223> OTHER INFORMATION: Xaa is Leu or Met
<220> FEATURE:
<221> NAME/KEY: MOD_RES
<222> LOCATION: (314)..(314)
<223> OTHER INFORMATION: Xaa is Gly or Ala

<400> SEQUENCE: 88

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Xaa Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Xaa Glu
225                 230                 235                 240

Xaa Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Xaa Leu His Asn His Tyr Thr
305                 310                 315                 320

Gln Lys Ser Leu Ser Leu Ser Pro Gly
            325

<210> SEQ ID NO 89
<211> LENGTH: 329
<212> TYPE: PRT
<213> ORGANISM: Artificial Sequence
<220> FEATURE:
<223> OTHER INFORMATION: Human IgG1 G1m3 allotype

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 90
<211> LENGTH: 329
<212> TYPE: PRT
<213> ORGANISM: Artificial Sequence
<220> FEATURE:
<223> OTHER INFORMATION: Human IgG1 G1m17,1 allotype

<400> SEQUENCE: 90

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 91
<211> LENGTH: 329
<212> TYPE: PRT
<213> ORGANISM: Artificial Sequence
<220> FEATURE:
<223> OTHER INFORMATION: Human IgG1, G1m17,1,2 allotype

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Gly Leu His Asn His Tyr Thr
305                 310                 315                 320

Gln Lys Ser Leu Ser Leu Ser Pro Gly
                325

<210> SEQ ID NO 92
<211> LENGTH: 329
<212> TYPE: PRT
<213> ORGANISM: Artificial Sequence
<220> FEATURE:
<223> OTHER INFORMATION: Human IgG1 G1m3 allotype N297A

<400> SEQUENCE: 92

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 93
<211> LENGTH: 326
<212> TYPE: PRT
<213> ORGANISM: Artificial Sequence
<220> FEATURE:
<223> OTHER INFORMATION: Human IgG4 S228P

<400> SEQUENCE: 93

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
        290                 295                 300
Cys Ser Val Met His Glu Ala Leu His Asn His Tyr Thr Gln Lys Ser
305                 310                 315                 320
Leu Ser Leu Ser Leu Gly
                325

<210> SEQ ID NO 94
<211> LENGTH: 107
<212> TYPE: PRT
<213> ORGANISM: Artificial Sequence
<220> FEATURE:
<223> OTHER INFORMATION: Human kappa light chain constant region IGKC*01
      Km3 allotype

<400> SEQUENCE: 94

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 95
<211> LENGTH: 118
<212> TYPE: PRT
<213> ORGANISM: Artificial Sequence
<220> FEATURE:
<223> OTHER INFORMATION: pab1876 VH R103A

<400> SEQUENCE: 95

Gln Val Gln Leu Val Gln Ser Gly Ala Glu Val Lys Lys Pro Gly Ala
1               5                   10                  15
Ser Val Lys Val Ser Cys Lys Gly Ser Gly Tyr Thr Phe Thr Asp Tyr
            20                  25                  30
Ala Met Tyr Trp Val Arg Gln Ala Pro Gly Gln Gly Leu Glu Trp Ile
        35                  40                  45
Gly Val Ile Arg Thr Tyr Ser Gly Asp Val Thr Tyr Asn Gln Lys Phe
    50                  55                  60
Lys Asp Arg Ala Thr Met Thr Val Asp Lys Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Lys Ser Gly Thr Val Ala Gly Phe Ala Tyr Trp Gly Gln Gly Thr
            100                 105                 110
Leu Val Thr Val Ser Ser
            115

<210> SEQ ID NO 96
<211> LENGTH: 113
```

```
<212> TYPE: PRT
<213> ORGANISM: Artificial Sequence
<220> FEATURE:
<223> OTHER INFORMATION: pab1876 VL D97A

<400> SEQUENCE: 96

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr His Cys Gln Asn
                85                  90                  95

Ala Tyr Ser Tyr Pro Tyr Thr Phe Gly Gln Gly Thr Lys Leu Glu Ile
            100                 105                 110

Lys

<210> SEQ ID NO 97
<211> LENGTH: 9
<212> TYPE: PRT
<213> ORGANISM: Artificial Sequence
<220> FEATURE:
<223> OTHER INFORMATION: VH CDR3

<400> SEQUENCE: 97

Ser Gly Thr Val Ala Gly Phe Ala Tyr
1               5

<210> SEQ ID NO 98
<211> LENGTH: 9
<212> TYPE: PRT
<213> ORGANISM: Artificial Sequence
<220> FEATURE:
<223> OTHER INFORMATION: VL CDR3

<400> SEQUENCE: 98

Gln Asn Ala Tyr Ser Tyr Pro Tyr Thr
1               5

<210> SEQ ID NO 99
<211> LENGTH: 9
<212> TYPE: PRT
<213> ORGANISM: Artificial Sequence
<220> FEATURE:
<223> OTHER INFORMATION: CDRH3 consensus sequence 1
<220> FEATURE:
<221> NAME/KEY: MOD_RES
<222> LOCATION: (5)..(5)
<223> OTHER INFORMATION: Xaa is Arg or Ala

<400> SEQUENCE: 99

Ser Gly Thr Val Xaa Gly Phe Ala Tyr
1               5

<210> SEQ ID NO 100
<211> LENGTH: 249
<212> TYPE: PRT
<213> ORGANISM: Artificial Sequence
<220> FEATURE:
```

<223> OTHER INFORMATION: Mature human OX40 sequence

<400> SEQUENCE: 100

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245

<210> SEQ ID NO 101
<211> LENGTH: 277
<212> TYPE: PRT
<213> ORGANISM: Homo sapiens

<400> SEQUENCE: 101

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly

```
            100                 105                 110
Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
                260                 265                 270

Thr Leu Ala Lys Ile
            275

<210> SEQ ID NO 102
<211> LENGTH: 216
<212> TYPE: PRT
<213> ORGANISM: Homo sapiens

<400> SEQUENCE: 102

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
            20                  25                  30

Cys Arg Asp Tyr Pro Gly Glu Glu Cys Cys Ser Glu Trp Asp Cys Met
        35                  40                  45

Cys Val Gln Pro Glu Phe His Cys Gly Asp Pro Cys Cys Thr Thr Cys
    50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro Leu Gly Trp Leu Thr Val Val
        130                 135                 140

Leu Leu Ala Val Ala Ala Cys Val Leu Leu Thr Ser Ala Gln Leu
145                 150                 155                 160

Gly Leu His Ile Trp Gln Leu Arg Ser Gln Cys Met Trp Pro Arg Glu
                165                 170                 175

Thr Gln Leu Leu Leu Glu Val Pro Pro Ser Thr Glu Asp Ala Arg Ser
            180                 185                 190
```

```
Cys Gln Phe Pro Glu Glu Arg Gly Glu Arg Ser Ala Glu Glu Lys
            195                 200                 205

Gly Arg Leu Gly Asp Leu Trp Val
    210                 215

<210> SEQ ID NO 103
<211> LENGTH: 241
<212> TYPE: PRT
<213> ORGANISM: Homo sapiens

<400> SEQUENCE: 103

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
50                  55                  60

Glu Cys Cys Ser Glu Trp Asp Cys Met Cys Val Gln Pro Glu Phe His
65                  70                  75                  80

Cys Gly Asp Pro Cys Thr Thr Cys Arg His His Pro Cys Pro Pro
            85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val

<210> SEQ ID NO 104
<211> LENGTH: 255
<212> TYPE: PRT
<213> ORGANISM: Homo sapiens

<400> SEQUENCE: 104

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
```

```
                50                  55                  60
Glu Cys Cys Ser Glu Trp Asp Cys Met Cys Val Gln Pro Glu Phe His
 65                  70                  75                  80

Cys Gly Asp Pro Cys Cys Thr Thr Cys Arg His His Pro Cys Pro Pro
                 85                  90                  95

Gly Gln Gly Val Gln Ser Gln Gly Lys Phe Ser Phe Gly Phe Gln Cys
                100                 105                 110

Ile Asp Cys Ala Ser Gly Thr Phe Ser Gly Gly His Glu Gly His Cys
                115                 120                 125

Lys Pro Trp Thr Asp Cys Cys Trp Arg Cys Arg Arg Pro Lys Thr
                130                 135                 140

Pro Glu Ala Ala Ser Ser Pro Arg Lys Ser Gly Ala Ser Asp Arg Gln
145                 150                 155                 160

Arg Arg Arg Gly Gly Trp Glu Thr Cys Gly Cys Glu Pro Gly Arg Pro
                165                 170                 175

Pro Gly Pro Pro Thr Ala Ala Ser Pro Ser Pro Gly Ala Pro Gln Ala
                180                 185                 190

Ala Gly Ala Leu Arg Ser Ala Leu Gly Arg Ala Leu Leu Pro Trp Gln
                195                 200                 205

Gln Lys Trp Val Gln Glu Gly Gly Ser Asp Gln Arg Pro Gly Pro Cys
210                 215                 220

Ser Ser Ala Ala Ala Ala Gly Pro Cys Arg Arg Glu Arg Glu Thr Gln
225                 230                 235                 240

Ser Trp Pro Pro Ser Ser Leu Ala Gly Pro Asp Gly Val Gly Ser
                245                 250                 255

<210> SEQ ID NO 105
<211> LENGTH: 234
<212> TYPE: PRT
<213> ORGANISM: Homo sapiens

<400> SEQUENCE: 105

Met Ala Gln His Gly Ala Met Gly Ala Phe Arg Ala Leu Cys Gly Leu
 1               5                  10                  15

Ala Leu Leu Cys Ala Leu Ser Leu Gly Gln Arg Pro Thr Gly Gly Pro
                 20                  25                  30

Gly Cys Gly Pro Gly Arg Leu Leu Leu Gly Thr Gly Thr Asp Ala Arg
                 35                  40                  45

Cys Cys Arg Val His Thr Thr Arg Cys Cys Arg Asp Tyr Pro Gly Glu
 50                  55                  60

Glu Cys Cys Ser Glu Trp Asp Cys Met Cys Val Gln Pro Glu Phe His
 65                  70                  75                  80

Cys Gly Asp Pro Cys Cys Thr Thr Cys Arg His His Pro Cys Pro Pro
                 85                  90                  95

Gly Gln Gly Val Gln Ser Gln Gly Lys Phe Ser Phe Gly Phe Gln Cys
                100                 105                 110

Ile Asp Cys Ala Ser Gly Thr Phe Ser Gly Gly His Glu Gly His Cys
                115                 120                 125

Lys Pro Trp Thr Asp Cys Thr Gln Phe Gly Phe Leu Thr Val Phe Pro
                130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175
```

Val Leu Leu Leu Thr Ser Ala Gln Leu Gly Leu His Ile Trp Gln Leu
            180                 185                 190

Arg Lys Thr Gln Leu Leu Glu Val Pro Pro Ser Thr Glu Asp Ala
        195                 200                 205

Arg Ser Cys Gln Phe Pro Glu Glu Arg Gly Glu Arg Ser Ala Glu
        210                 215                 220

Glu Lys Gly Arg Leu Gly Asp Leu Trp Val
225                 230

<210> SEQ ID NO 106
<211> LENGTH: 234
<212> TYPE: PRT
<213> ORGANISM: Macaca fascicularis

<400> SEQUENCE: 106

Val Ala Arg His Gly Ala Met Cys Ala Cys Gly Thr Leu Cys Cys Leu
1               5                   10                  15

Ala Leu Leu Cys Ala Ala Ser Leu Gly Gln Arg Pro Thr Gly Gly Pro
            20                  25                  30

Gly Cys Gly Pro Gly Arg Leu Leu Leu Gly Thr Gly Lys Asp Ala Arg
        35                  40                  45

Cys Cys Arg Val His Pro Thr Arg Cys Cys Arg Asp Tyr Gln Ser Glu
    50                  55                  60

Glu Cys Cys Ser Glu Trp Asp Cys Val Cys Val Gln Pro Glu Phe His
65                  70                  75                  80

Cys Gly Asn Pro Cys Cys Thr Thr Cys Gln His His Pro Cys Pro Ser
                85                  90                  95

Gly Gln Gly Val Gln Pro Gln Gly Lys Phe Ser Phe Gly Phe Arg Cys
            100                 105                 110

Val Asp Cys Ala Leu Gly Thr Phe Ser Arg Gly His Asp Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Pro Gly Trp Leu Thr Ile Val Leu Leu Ala Val Ala Ala Cys
                165                 170                 175

Val Leu Leu Leu Thr Ser Ala Gln Leu Gly Leu His Ile Trp Gln Leu
            180                 185                 190

Gly Lys Thr Gln Leu Leu Leu Glu Val Pro Pro Ser Thr Glu Asp Ala
        195                 200                 205

Ser Ser Cys Gln Phe Pro Glu Glu Glu Arg Gly Glu Arg Leu Ala Glu
    210                 215                 220

Glu Lys Gly Arg Leu Gly Asp Leu Trp Val
225                 230

<210> SEQ ID NO 107
<211> LENGTH: 329
<212> TYPE: PRT
<213> ORGANISM: Artificial Sequence
<220> FEATURE:
<223> OTHER INFORMATION: Human IgG1 S239D/I332E

<400> SEQUENCE: 107

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr 20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 108
<211> LENGTH: 329
<212> TYPE: PRT
<213> ORGANISM: Artificial Sequence
<220> FEATURE:
<223> OTHER INFORMATION: Human IgG1 S239D/A330L/I332E

<400> SEQUENCE: 108

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser

```
            50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 109
<211> LENGTH: 329
<212> TYPE: PRT
<213> ORGANISM: Artificial Sequence
<220> FEATURE:
<223> OTHER INFORMATION: Human IgG1 L235V/F243L/R292P/Y300L/P396L

<400> SEQUENCE: 109

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
```

```
                85                  90                  95
Arg Val Glu Pro Lys Ser Cys Asp Lys Thr His Thr Cys Pro Pro Cys
                100                 105                 110

Pro Ala Pro Glu Leu Val Gly Gly Pro Ser Val Phe Leu Leu Pro Pro
                115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Pro Glu
                165                 170                 175

Glu Gln Tyr Asn Ser Thr Leu Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Leu Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

ANTI-OX40 ANTIBODIES AND ANTI-GITR ANTIBODIES

This application is a continuation of International Patent Application No. PCT/US2017/060854, filed Nov. 9, 2017, which claims priority to U.S. Patent Application Ser. No. 62/419,907, filed Nov. 9, 2016, the entire disclosures of which are hereby incorporated herein by reference.

1. FIELD

The present disclosure relates to antibodies, including monospecific and multispecific (e.g., bispecific) antibodies, that specifically bind to human OX40 receptor ("OX40"), compositions comprising such antibodies, and methods of producing and using those antibodies. Also provided are antibodies, including monospecific and multispecific (e.g., bispecific) antibodies, that specifically bind to human glucocorticoid-induced TNFR family related receptor (GITR), compositions comprising such antibodies, and methods of producing and using those antibodies. Exemplary multispecific (e.g., bispecific) antibodies provided herein bind to human OX40 and human GITR.

2. BACKGROUND

The contributions of the innate and adaptive immune response in the control of human tumor growth are well-characterized (Vesely M D et al., (2011) Annu Rev Immunol 29: 235-271). As a result, antibody-based strategies have emerged that aim to enhance T cell responses for the purpose of cancer therapy, such as targeting T cell expressed stimulatory receptors with agonist antibodies, or inhibitory receptors with functional antagonists (Mellman I et al., (2011) Nature 480: 480-489). Antibody-mediated agonist and antagonist approaches have shown preclinical, and more recently clinical, activity. An important stimulatory receptor that modulates T cell, Natural Killer T (NKT) cell, and NK cell function is the OX40 receptor (also known as OX40, CD134, TNFRSF4, TXGP1L, ACT35, and ACT-4) (Sugamura K et al., (2004) Nat Rev Immunol 4: 420-431). OX40 is a member of the tumor necrosis factor receptor superfamily (TNFRSF) and signaling via OX40 can modulate important immune functions.

OX40 can be upregulated by antigen-specific T cells following T cell receptor (TCR) stimulation by professional antigen presenting cells (APCs) displaying MHC class I or II molecules loaded with a cognate peptide (Sugamura K et al., (2004) Nat Rev Immunol 4: 420-431). Upon maturation APCs such as dendritic cells (DCs) upregulate stimulatory B7 family members (e.g., CD80 and CD86), as well as accessory co-stimulatory molecules including OX40 ligand (OX40L), which help to sculpt the kinetics and magnitude of the T cell immune response, as well as effective memory cell differentiation. Notably, other cell types can also express constitutive and/or inducible levels of OX40L such as B cells, vascular endothelial cells, mast cells, and in some instances activated T cells (Soroosh P et al., (2006) J Immunol 176: 5975-5987). OX40:OX40L co-engagement is believed to drive the higher order clustering of receptor trimers and subsequent signal transduction (Compaan D M et al., (2006) Structure 14: 1321-1330).

OX40 expression by T cells within the tumor microenvironment has been observed in murine and human tumor tissues (Bulliard Y et al., (2014) Immunol Cell Biol 92: 475-480 and Piconese S et al., (2014) Hepatology 60: 1494-1507). OX40 is highly expressed by intratumoral populations of regulatory T cells (Tregs) relative to conventional T cell populations, a feature attributed to their proliferative status (Waight J D et al., (2015) J Immunol 194: 878-882 and Bulliard Y et al., (2014) Immunol Cell Biol 92: 475-480). Early studies demonstrated that OX40 agonist antibodies were able to elicit tumor rejection in mouse models (Weinberg A D et al., (2000) J Immunol 164: 2160-2169 and Piconese S et al., (2008) J Exp Med 205: 825-839). A mouse antibody that agonizes human OX40 signaling has also been shown to enhance immune functions in cancer patients (Curti B D et al., (2013) Cancer Res 73: 7189-7198).

OX40 and OX40L interactions also have been associated with immune responses in inflammatory and autoimmune diseases and disorders, including mouse models of asthma/atopy, encephalomyelitis, rheumatoid arthritis, colitis/inflammatory bowel disease, graft-versus-host disease (e.g., transplant rejection), diabetes in non-obese diabetic mice, and atherosclerosis (Croft M et al., (2009) Immunol Rev 229(1): 173-191, and references cited therein). Reduced symptomatology associated with the diseases and disorders has been reported in OX40- and OX40L-deficient mice, in mice receiving anti-OX40 liposomes loaded with a cytostatic drug, and in mice in which OX40 and OX40L interactions were blocked with an anti-OX40L blocking antibody or a recombinant OX40 fused to the Fc portion of human immunoglobulin (Croft M et al.; Boot E P J et al., (2005) Arthritis Res Ther 7: R604-615; Weinberg A D et al., (1999) J Immunol 162: 1818-1826). Treatment with a blocking anti-OX40L antibody was also shown to inhibit Th2 inflammation in a rhesus monkey model of asthma (Croft M et al., Seshasayee D et al., (2007) J Clin Invest 117: 3868-3878). Additionally, polymorphisms in OX40L have been associated with lupus (Croft M et al.).

Another important stimulator of immune responses is glucocorticoid-induced TNFR-related protein (GITR). GITR (also known as activation-inducible TNFR family receptor (AITR), GITR-D, CD357, and tumor necrosis factor receptor superfamily member 18 (TNFRSF18)), is expressed in many components of the innate and adaptive immune system and stimulates both acquired and innate immunity (Nocentini G et al., (1994) PNAS 94: 6216-6221; Hanabuchi S et al., (2006) Blood 107:3617-3623; Nocentini G & Riccardi C (2005) Eur J Immunol 35: 1016-1022; Nocentini G et al., (2007) Eur J Immunol 37:1165-1169). It is expressed in several cells and tissues, including T, B, dendritic (DC) and Natural Killer (NK) cells and is activated by its ligand, GITRL, mainly expressed on antigen presenting cells (APCs), endothelial cells, and also tumor cells. The GITR/GITRL system participates in the development of autoimmune/inflammatory responses and potentiates response to infection and tumors. For example, treating animals with GITR-Fc fusion protein ameliorates autoimmune/inflammatory diseases while GITR triggering is effective in treating viral, bacterial, and parasitic infections, as well in boosting immune response against tumors (Nocentini G et al., (2012) Br J Pharmacol 165: 2089-99). These effects are due to several concurrent mechanisms including: co-activation of effector T cells, inhibition of regulatory T (Treg) cells, NK-cell co-activation, activation of macrophages, modulation of dendritic cell function and regulation of the extravasation process. The membrane expression of GITR is increased following T cell activation (Hanabuchi S et al., (2006) supra; Nocentini G & Riccardi C supra). Its triggering coactivates effector T lymphocytes (McHugh R S et al., (2002) Immunity 16: 311-323; Shimizu J et al., (2002) Nat Immunol 3: 135-142; Roncheti S et al., (2004) Eur J Immunol 34: 613-622; Tone M et al., (2003) PNAS 100: 15059-15064). GITR activation increases resistance to tumors and viral infections, is involved in autoimmune/inflammatory processes and regulates leukocyte extravasation (Nocentini G & Riccardi C (2005) supra; Cuzzocrea S et al., (2004) J Leukoc Biol 76: 933-940; Shevach E M & Stephens G L (2006) Nat Rev Immunol 6: 613-618; Cuzzocrea S et al., (2006) J Immunol 177: 631-641; Cuzzocrea S et al., (2007) FASEB J 21: 117-129).

Human GITR is expressed at very low levels in peripheral (non-activated) T cells. After T cell activation, GITR is strongly up-regulated for several days in both $CD4^+$ and $CD8^+$ cells (Kwon B et al., (1999) J Biol Chem 274: 6056-6061; Gurney A L et al., (1999) Curr Biol 9: 215-218; Ronchetti S et al., (2004) supra; Shimizu J et al., (2002) supra; Ji H B et al., (2004) supra; Ronchetti S et al., (2002) Blood 100: 350-352; Li Z et al., (2003) J Autoimmun 21: 83-92), with $CD4^+$ cells having a higher GITR expression than $CD8^+$ cells (Kober J et al., (2008) Eur J Immunol 38(10): 2678-88; Bianchini R et al., (2011) Eur J Immunol 41(8): 2269-78).

Given the role of human OX40 and GITR in modulating immune responses, provided herein are antibodies that specifically bind to OX40 or GITR. Such antibodies include multispecific antibodies, for example bispecific antibodies that specifically bind to OX40 and/or GITR. Thus use of such antibodies to modulate OX40 activity and/or GITR activity are also provided herein.

3. SUMMARY

In one embodiment, provided herein is an isolated antibody that specifically binds to human OX40, the antibody comprising a heavy chain variable region comprising complementarity determining regions CDRH1, CDRH2, and CDRH3 and a light chain variable region comprising complementarity determining regions CDRL1, CDRL2, and CDRL3, wherein: (a) CDRH1 comprises the amino acid sequence of $X_1X_2X_3MH$ (SEQ ID NO: 41), wherein $X_1$ is G, Q, H, or E, $X_2$ is S, E, or Y, and $X_3$ is A, S, or G; (b) CDRH2 comprises the amino acid sequence of RIRSKX$_1$X$_2$X$_3$X$_4$X$_5$TAYAASVKG (SEQ ID NO: 42), wherein $X_1$ is A, S, or Y, $X_2$ is N, E, or Y, $X_3$ is S, Q, or G, $X_4$ is Y, E, or Q, and $X_5$ is A, E, or L; (c) CDRH3 comprises the amino acid sequence of GIX$_1$X$_2$X$_3$X$_4$X$_5$X$_6$X$_7$Y (SEQ ID NO: 43), wherein $X_1$ is Y or A, $X_2$ is D or A, $X_3$ is S, T, or W, $X_4$ is S, E, or L, $X_5$ is G or A, $X_6$ is Y or A, and $X_7$ is D or A; (d) CDRL1 comprises the amino acid sequence of RSSQSLLHSNGYNYLD (SEQ ID NO: 32); (e) CDRL2 comprises the amino acid sequence of LGSNRAS (SEQ ID NO: 33); and (f) CDRL3 comprises the amino acid sequence of MQX$_1$X$_2$X$_3$X$_4$PLT (SEQ ID NO: 46), wherein $X_1$ is A or G, $X_2$ is L or S, $X_3$ is Q or K, and $X_4$ is T or W, and wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38.

In one embodiment, CDRH2 comprises the amino acid sequence of RIRSKAXSYATAYAASVKG (SEQ ID NO: 44), wherein: X is N or Y. In one embodiment, CDRH3 comprises the amino acid sequence of GIX$_1$X$_2$SSGX$_3$X$_4$Y (SEQ ID NO: 45), wherein: $X_1$ is Y or A; $X_2$ is D or A; $X_3$ is Y or A; and $X_4$ is D or A.

In one embodiment, CDRH1 comprises an amino acid sequence selected from the group consisting of SEQ ID NOs: 16-20. In one embodiment, CDRH2 comprises an amino acid sequence selected from the group consisting of SEQ ID NOs: 21-24. In one embodiment, CDRH3 comprises an amino acid sequence selected from the group consisting of SEQ ID NOs: 25-31. In one embodiment, CDRL3 comprises an amino acid sequence selected from the group consisting of SEQ ID NOs: 34-38.

In one embodiment, CDRH1, CDRH2, and CDRH3 comprise the CDRH1, CDRH2, and CDRH3 amino acid sequences set forth in SEQ ID NOs: 16, 21, and 25; 16, 22, and 25; 16, 21, and 26; 16, 21, and 27; 16, 21, and 28; 16, 21, and 29; 17, 21, and 30; 18, 23, and 25; 19, 24, and 25; or 20, 21, and 31, respectively.

In one embodiment, CDRL1, CDRL2, and CDRL3 comprise the CDRL1, CDRL2, and CDRL3 amino acid sequences set forth in SEQ ID NOs: 32, 33, and 34; 32, 33, and 35; 32, 33, and 36; 32, 33, and 37; or 32, 33, and 38, respectively.

In one embodiment, CDRH1, CDRH2, CDRH3, CDRL1, CDRL2, and CDRL3 comprise the amino acid sequences set forth in SEQ ID NOs: 16, 22, 25, 32, 33, and 34; 16, 21, 26, 32, 33, and 34; 16, 21, 27, 32, 33, and 34; 16, 21, 28, 32, 33, and 34; 16, 21, 29, 32, 33, and 34; 17, 21, 30, 32, 33, and 38; 18, 23, 25, 32, 33, and 38; 19, 24, 25, 32, 33, and 38; 20, 21, 31, 32, 33, and 38; 16, 21, 25, 32, 33, and 35; 16, 21, 25, 32, 33, and 36; or 16, 21, 25, 32, 33, and 37, respectively.

In one embodiment, provided herein is an isolated antibody that specifically binds to human OX40, the antibody comprising a heavy chain variable region comprising complementarity determining regions CDRH1, CDRH2, and CDRH3 and a light chain variable region comprising complementarity determining regions CDRL1, CDRL2, and CDRL3, wherein CDRH1, CDRH2, CDRH3, CDRL1, CDRL2, and CDRL3 comprise the amino acid sequences set forth in SEQ ID NOs: 16, 22, 25, 32, 33, and 34, respectively.

In one embodiment, provided herein is an isolated antibody that specifically binds to human OX40, the antibody comprising a heavy chain variable region comprising complementarity determining regions CDRH1, CDRH2, and CDRH3 and a light chain variable region comprising complementarity determining regions CDRL1, CDRL2, and CDRL3, wherein CDRH1, CDRH2, CDRH3, CDRL1, CDRL2, and CDRL3 comprise the amino acid sequences set forth in SEQ ID NOs: 16, 21, 25, 32, 33, and 37, respectively.

In one embodiment, the antibody comprises a heavy chain variable region comprising the amino acid sequence of SEQ ID NO: 47 or 48.

In one embodiment, the antibody comprises a heavy chain variable region comprising an amino acid sequence which is at least 75%, 80%, 85%, 90%, 95%, or 100% identical to an amino acid sequence selected from the group consisting of SEQ ID NOs: 1-10.

In one embodiment, the heavy chain variable region comprises an amino acid sequence selected from the group consisting of SEQ ID NOs: 1-10.

In one embodiment, the antibody comprises a light chain variable region comprising the amino acid sequence of SEQ ID NO: 49.

In one embodiment, the antibody comprises a light chain variable region comprising an amino acid sequence which is at least 75%, 80%, 85%, 90%, 95%, or 100% identical to an amino acid sequence selected from the group consisting of SEQ ID NOs: 11-15. In one embodiment, the light chain variable region comprises an amino acid sequence selected from the group consisting of SEQ ID NOs: 11-15.

In one embodiment, provided herein is an isolated antibody that specifically binds to human OX40, the antibody comprising a heavy chain variable region comprising an amino acid sequence selected from the group consisting of SEQ ID NOs: 2-10.

In one embodiment, provided herein is an isolated antibody that specifically binds to human OX40, the antibody comprising a light chain variable region comprising an amino acid sequence selected from the group consisting of SEQ ID NOs: 12-14.

In one embodiment, provided herein is an isolated antibody that specifically binds to human OX40, the antibody comprising a heavy chain variable region and a light chain variable region, wherein the heavy chain variable region and the light chain variable region comprise the amino acid sequences set forth in SEQ ID NOs: 2 and 11; 3 and 11; 4 and 11; 5 and 11; 6 and 11; 7 and 15; 8 and 15; 9 and 15; 10 and 15; 1 and 12; 1 and 13; or 1 and 14, respectively.

In one embodiment, the heavy chain variable region and the light chain variable region comprise the amino acid sequences set forth in SEQ ID NOs: 2 and 11, respectively. In one embodiment, the heavy chain variable region and the light chain variable region comprise the amino acid sequences set forth in SEQ ID NOs: 1 and 14, respectively.

In one embodiment, the antibody comprises a heavy chain variable region having an amino acid sequence derived from a human IGHV3-73 germline sequence.

In one embodiment, the antibody comprises a light chain variable region having an amino acid sequence derived from a human IGKV2-28 germline sequence.

In one embodiment, the antibody comprises a heavy chain constant region selected from the group consisting of human IgG$_1$, IgG$_2$, IgG$_3$, IgG$_4$, IgA$_1$, and IgA$_2$.

In one embodiment, the heavy chain constant region is IgG$_1$. In one embodiment, the antibody comprises a heavy chain constant region comprising the amino acid sequence of SEQ ID NO: 88, 89, 90, or 91. In one embodiment, the amino acid sequence of IgG$_1$ comprises S239D and I332E mutations, numbered according to the EU numbering system. In one embodiment, the antibody comprises a heavy chain constant region comprising the amino acid sequence of SEQ ID NO: 107. In one embodiment, the amino acid sequence of IgG$_1$ comprises S239D, A330L, and I332E mutations, numbered according to the EU numbering system. In one embodiment, the antibody comprises a heavy chain constant region comprising the amino acid sequence of SEQ ID NO: 108. In one embodiment, the amino acid sequence of IgG$_1$ comprises L235V, F243L, R292P, Y300L, and P396L mutations, numbered according to the EU numbering system. In one embodiment, the antibody comprises a heavy chain constant region comprising the amino acid sequence of SEQ ID NO: 109. In one embodiment, the IgG$_1$ is non-fucosylated IgG$_1$. In one embodiment, the amino acid sequence of IgG$_1$ comprises a N297A or N297Q mutation, numbered according to the EU numbering system. In one embodiment, the antibody comprises a heavy chain constant region comprising the amino acid sequence of SEQ ID NO: 92.

In one embodiment, the heavy chain constant region is IgG4. In one embodiment, the amino acid sequence of IgG4 comprises a S228P mutation, numbered according to the EU numbering system. In one embodiment, the antibody comprises a heavy chain constant region comprising the amino acid sequence of SEQ ID NO: 93.

In one embodiment, the antibody comprises a light chain constant region selected from the group consisting of human IgGκ and IgGλ. In one embodiment, the antibody comprises a light chain constant region comprising the amino acid sequence of SEQ ID NO: 94.

In one embodiment, provided herein is an isolated antibody that comprises a heavy chain variable region comprising complementarity determining regions CDRH1, CDRH2, and CDRH3 and a light chain variable region comprising complementarity determining regions CDRL1, CDRL2, and CDRL3, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38, and wherein the antibody cross-competes for binding to human OX40 with an anti-OX40 antibody provided herein.

In one embodiment, provided herein is an isolated antibody that comprises a heavy chain variable region comprising complementarity determining regions CDRH1, CDRH2, and CDRH3 and a light chain variable region comprising complementarity determining regions CDRL1, CDRL2, and CDRL3, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38, and wherein the antibody binds to the same epitope of human OX40 as an antibody provided herein.

In one embodiment, the antibody is human.

In one embodiment, the antibody is conjugated to a cytotoxic agent, cytostatic agent, toxin, radionuclide, or detectable label.

In any antibody embodiments as disclosed herein, the N-terminal amino acid residue of a heavy chain variable region of the antibody has been converted to pyroglutamate (e.g., as a result of post-translational cyclization of the free amino group of the N-terminal glutamic acid or glutamine residue of the heavy chain variable region). In any antibody embodiments as disclosed herein, the N-terminal amino acid residue of a heavy chain of the antibody has been converted to pyroglutamate (e.g., as a result of post-translational cyclization of the free amino group of the N-terminal glutamic acid or glutamine residue of the heavy chain).

In one embodiment, provided herein is an isolated multispecific antibody comprising a first antigen-binding domain of an antibody provided herein, wherein the first antigen-binding domain specifically binds to human OX40 and comprises a heavy chain variable region comprising complementarity determining regions CDRH1, CDRH2, and CDRH3 and a light chain variable region comprising complementarity determining regions CDRL1, CDRL2, and CDRL3, and wherein the isolated multispecific antibody further comprises a second antigen-binding domain.

In one embodiment, CDRH1, CDRH2, and CDRH3 of the first antigen-binding domain that specifically binds to human OX40 comprise the CDRH1, CDRH2, and CDRH3 amino acid sequences set forth in SEQ ID NOs: 16, 21, and 25; 16, 22, and 25; 16, 21, and 26; 16, 21, and 27; 16, 21, and 28; 16, 21, and 29; 17, 21, and 30; 18, 23, and 25; 19, 24, and 25; or 20, 21, and 31, respectively.

In one embodiment, CDRL1, CDRL2, and CDRL3 of the first antigen-binding domain that specifically binds to human OX40 comprise the CDRL1, CDRL2, and CDRL3 amino acid sequences set forth in SEQ ID NOs: 32, 33, and 34; 32, 33, and 35; 32, 33, and 36; 32, 33, and 37; or 32, 33, and 38, respectively.

In one embodiment, CDRH1, CDRH2, CDRH3, CDRL1, CDRL2, and CDRL3 of the first antigen-binding domain that specifically binds to human OX40 comprise the amino acid sequences set forth in SEQ ID NOs: 16, 22, 25, 32, 33, and 34; 16, 21, 26, 32, 33, and 34; 16, 21, 27, 32, 33, and 34; 16, 21, 28, 32, 33, and 34; 16, 21, 29, 32, 33, and 34; 17, 21, 30, 32, 33, and 38; 18, 23, 25, 32, 33, and 38; 19, 24, 25, 32, 33, and 38; 20, 21, 31, 32, 33, and 38; 16, 21, 25, 32, 33, and 35; 16, 21, 25, 32, 33, and 36; or 16, 21, 25, 32, 33, and 37, respectively.

In one embodiment, the heavy chain variable region of the first antigen-binding domain that specifically binds to human OX40 comprises an amino acid sequence selected from the group consisting of SEQ ID NOs: 1-10.

In one embodiment, the light chain variable region of the first antigen-binding domain that specifically binds to human OX40 comprises an amino acid sequence selected from the group consisting of SEQ ID NOs: 11-15.

In one embodiment, the heavy chain variable region and the light chain variable region of the first antigen-binding domain that specifically binds to human OX40 comprise the amino acid sequences set forth in SEQ ID NOs: 2 and 11; 3 and 11; 4 and 11; 5 and 11; 6 and 11; 7 and 15; 8 and 15; 9 and 15; 10 and 15; 1 and 12; 1 and 13; or 1 and 14, respectively.

In one embodiment, the second antigen-binding domain specifically binds to human GITR. In one embodiment, the second antigen-binding domain that specifically binds to human GITR comprises a heavy chain variable region comprising complementarity determining regions CDRH1, CDRH2, and CDRH3 and a light chain variable region comprising complementarity determining regions CDRL1, CDRL2, and CDRL3, wherein: (a) CDRH1 comprises the amino acid sequence of $X_1YX_2MX_3$ (SEQ ID NO: 76), wherein $X_1$ is D, E or G, $X_2$ is A or V, and $X_3$ is Y or H; (b) CDRH2 comprises the amino acid sequence of $X_1IX_2TX_3SGX_4X_5X_6YNQKFX_7X_8$ (SEQ ID NO: 77), wherein $X_1$ is V or L, $X_2$ is R, K or Q, $X_3$ is Y or F, $X_4$ is D, E or G, $X_5$ is V or L, $X_6$ is T or S, $X_7$ is K, R or Q, and $X_8$ is D, E or G; (c) CDRH3 comprises the amino acid sequence of SGTVXGFAY (SEQ ID NO: 99), wherein; X is R or A; (d) CDRL1 comprises the amino acid sequence of $KSSQSLLNSX_1NQKNYLX_2$ (SEQ ID NO: 80), wherein $X_1$ is G or S, and $X_2$ is T or S; (e) CDRL2 comprises the amino acid sequence of WASTRES (SEQ ID NO: 71); and (f) CDRL3 comprises the amino acid sequence of $QNX_1YSX_2PYT$ (SEQ ID NO: 81), wherein $X_1$ is D, E, or A; and $X_2$ is Y, F, or S.

In one embodiment, CDRH1 of the second antigen-binding domain that specifically binds to human GITR comprises the amino acid sequence of $X_1YAMX_2$ (SEQ ID NO: 78), wherein: $X_1$ is D, G, or E; and $X_2$ is Y or H.

In one embodiment, CDRH2 of the second antigen-binding domain that specifically binds to human GITR comprises the amino acid sequence of $X_1IRTYSGX_2VX_3YNQKFX_4X_5$ (SEQ ID NO: 79), wherein: $X_1$ is V or L; $X_2$ is D or G; $X_3$ is T or S; $X_4$ is K, R, or Q; and $X_5$ is D, E, or G.

In one embodiment, CDRL1 of the second antigen-binding domain that specifically binds to human GITR comprises the amino acid sequence of KSSQSLLNSXNQKNYLT (SEQ ID NO: 82), wherein: X is G or S.

In one embodiment, CDRL3 of the second antigen-binding domain that specifically binds to human GITR comprises the amino acid sequence of $QNX_1YSX_2PYT$ (SEQ ID NO: 83), wherein: $X_1$ is D, E, or A; and $X_2$ is Y or F.

In one embodiment, CDRH1 of the second antigen-binding domain that specifically binds to human GITR comprises an amino acid sequence selected from the group consisting of SEQ ID NOs: 60-62. In one embodiment, CDRH2 of the second antigen-binding domain that specifically binds to human GITR comprises an amino acid sequence selected from the group consisting of SEQ ID NOs: 63-67. In one embodiment, CDRH3 of the second antigen-binding domain that specifically binds to human GITR comprises an amino acid sequence selected from the group consisting of SEQ ID NOs: 68 and 97. In one embodiment, CDRL1 of the second antigen-binding domain that specifically binds to human GITR comprises an amino acid sequence selected from the group consisting of SEQ ID NOs: 69 and 70. In one embodiment, CDRL3 of the second antigen-binding domain that specifically binds to human GITR comprises an amino acid sequence selected from the group consisting of SEQ ID NOs: 72, 73, and 98.

In one embodiment, CDRH1, CDRH2, and CDRH3 of the second antigen-binding domain that specifically binds to human GITR comprise the CDRH1, CDRH2, and CDRH3 amino acid sequences set forth in SEQ ID NOs: 60, 63, and 68; 60, 64, and 68; 60, 63, and 97; 61, 65, and 68; 62, 66, and 68; or 62, 67, and 68, respectively.

In one embodiment, CDRL1, CDRL2, and CDRL3 of the second antigen-binding domain that specifically binds to human GITR comprise the CDRL1, CDRL2, and CDRL3 amino acid sequences set forth in SEQ ID NOs: 69, 71, and 72; 69, 71, and 98; 70, 71, and 73; or 69, 71, and 72, respectively.

In one embodiment, CDRH1, CDRH2, CDRH3, CDRL1, CDRL2, and CDRL3 of the second antigen-binding domain that specifically binds to human GITR comprise the amino acid sequences set forth in SEQ ID NOs: 60, 63, 68, 69, 71, and 72; 60, 64, 68, 69, 71, and 72; 60, 63, 97, 69, 71, and 72; 60, 63, 68, 69, 71, and 98; 61, 65, 68, 70, 71, and 73; 62, 66, 68, 69, 71, and 72; or 62, 67, 68, 69, 71, and 72, respectively.

In one embodiment, the second antigen-binding domain that specifically binds to human GITR comprises a heavy chain variable region comprising the amino acid sequence of SEQ ID NO: 84.

In one embodiment, the second antigen-binding domain that specifically binds to human GITR comprises a heavy chain variable region comprising an amino acid sequence which is at least 75%, 80%, 85%, 90%, 95%, or 100% identical to an amino acid sequence selected from the group consisting of SEQ ID NOs: 52-56, and 95.

In one embodiment, the heavy chain variable region of the second antigen-binding domain that specifically binds to human GITR comprises an amino acid sequence selected from the group consisting of SEQ ID NOs: 52-56, and 95.

In one embodiment, the second antigen-binding domain that specifically binds to human GITR comprises a light chain variable region comprising the amino acid sequence of SEQ ID NO: 85.

In one embodiment, the second antigen-binding domain that specifically binds to human GITR comprises a light chain variable region comprising an amino acid sequence which is at least 75%, 80%, 85%, 90%, 95%, or 100% identical to an amino acid sequence selected from the group consisting of SEQ ID NOs: 57-59, and 96.

In one embodiment, the light chain variable region of the second antigen-binding domain that specifically binds to human GITR comprises an amino acid sequence selected from the group consisting of SEQ ID NOs: 57-59, and 96.

In one embodiment, the heavy chain variable region and the light chain variable region of the second antigen-binding domain that specifically binds to human GITR comprise the amino acid sequences set forth in SEQ ID NOs: 52 and 57; 53 and 57; 95 and 57; 52 and 96; 54 and 58; 55 and 59; or 56 and 59, respectively.

In one embodiment, the second antigen-binding domain that specifically binds to human GITR comprises a heavy chain variable region having an amino acid sequence derived from a human IGHV1-2 germline sequence.

In one embodiment, the second antigen-binding domain that specifically binds to human GITR comprises a light chain variable region having an amino acid sequence derived from a human IGKV4-1 germline sequence.

In one embodiment, the second antigen-binding domain that specifically binds to human GITR comprises a heavy chain constant region selected from the group consisting of human IgG$_1$, IgG2, IgG3, IgG4, IgA$_1$, and IgA$_2$.

In one embodiment, the heavy chain constant region of the second antigen-binding domain that specifically binds to human GITR is IgG$_1$.

In one embodiment, the second antigen-binding domain that specifically binds to human GITR comprises a heavy chain constant region comprising the amino acid sequence of SEQ ID NO: 88, 89, 90, or 91.

In one embodiment, the amino acid sequence of IgG$_1$ comprises S239D and I332E mutations, numbered according to the EU numbering system.

In one embodiment, the second antigen-binding domain that specifically binds to human GITR comprises a heavy chain constant region comprising the amino acid sequence of SEQ ID NO: 107.

In one embodiment, the amino acid sequence of IgG$_1$ comprises S239D, A330L, and I332E mutations, numbered according to the EU numbering system.

In one embodiment, the second antigen-binding domain that specifically binds to human GITR comprises a heavy chain constant region comprising the amino acid sequence of SEQ ID NO: 108.

In one embodiment, the amino acid sequence of IgG$_1$ comprises L235V, F243L, R292P, Y300L, and P396L mutations, numbered according to the EU numbering system.

In one embodiment, the second antigen-binding domain that specifically binds to human GITR comprises a heavy chain constant region comprising the amino acid sequence of SEQ ID NO: 109.

In one embodiment, the IgG$_1$ is non-fucosylated IgG$_1$.

In one embodiment, the amino acid sequence of IgG$_1$ of the second antigen-binding domain that specifically binds to human GITR comprises a N297A or N297Q mutation, numbered according to the EU numbering system.

In one embodiment, the second antigen-binding domain that specifically binds to human GITR comprises a heavy chain constant region comprising the amino acid sequence of SEQ ID NO: 92.

In one embodiment, the heavy chain constant region of the second antigen-binding domain that specifically binds to human GITR is IgG4.

In one embodiment, the amino acid sequence of IgG4 of the second antigen-binding domain that specifically binds to human GITR comprises a S228P mutation, numbered according to the EU numbering system.

In one embodiment, the second antigen-binding domain that specifically binds to human GITR comprises a heavy chain constant region comprising the amino acid sequence of SEQ ID NO: 93.

In one embodiment, the second antigen-binding domain that specifically binds to human GITR comprises a light chain constant region selected from the group consisting of human IgGκ and IgGλ.

In one embodiment, the second antigen-binding domain that specifically binds to human GITR comprises a light chain constant region comprising the amino acid sequence of SEQ ID NO: 94.

In one embodiment, the second antigen-binding domain that specifically binds to human GITR is humanized.

In one embodiment, CDRH1, CDRH2, CDRH3, CDRL1, CDRL2, and CDRL3 of the first antigen-binding domain that specifically binds to human OX40 and CDRH1, CDRH2, CDRH3, CDRL1, CDRL2, and CDRL3 of the second antigen-binding domain that specifically binds to human GITR comprise the amino acid sequences listed in a single row of Table 12.

In one embodiment, provided herein is an isolated multispecific antibody comprising a first antigen-binding domain that specifically binds to human OX40 and a second antigen-binding domain that specifically binds to human GITR, wherein the first antigen-binding domain comprises a heavy chain variable region comprising CDRH1, CDRH2, and CDRH3 and a light chain variable region comprising CDRL1, CDRL2, and CDRL3, and wherein the second antigen-binding domain comprises a heavy chain variable region comprising CDRH1, CDRH2, and CDRH3 and a light chain variable region comprising CDRL1, CDRL2, and CDRL3, wherein CDRH1, CDRH2, CDRH3, CDRL1, CDRL2, and CDRL3 of the first antigen-binding domain and CDRH1, CDRH2, CDRH3, CDRL1, CDRL2, and CDRL3 of the second antigen-binding domain comprise the amino acid sequences listed in a single row of Table 12.

In one embodiment, the heavy chain variable region and the light chain variable region of the first antigen-binding domain that specifically binds to human OX40 and the heavy chain variable region and the light chain variable region of the second antigen-binding domain that specifically binds to human GITR comprise the amino acid sequences listed in a single row of Table 13.

In one embodiment, provided here in is an isolated multispecific antibody comprising a first antigen-binding domain that specifically binds to human OX40 and a second antigen-binding domain that specifically binds to human GITR, wherein the first antigen-binding domain comprises a heavy chain variable region and a light chain variable region, and wherein the second antigen-binding domain comprises a heavy chain variable region and a light chain variable region, wherein the heavy chain variable region and the light chain variable region of the first antigen-binding domain and the heavy chain variable region and the light chain variable region of the second antigen-binding domain comprise the amino acid sequences listed in a single row of Table 13.

In one embodiment, provided herein is an isolated antibody that specifically binds to human GITR, the antibody comprising a heavy chain variable region comprising complementarity determining regions CDRH1, CDRH2, and CDRH3 and a light chain variable region comprising complementarity determining regions CDRL1, CDRL2, and CDRL3, wherein the CDRH1, CDRH2, CDRH3, CDRL1, CDRL2, and CDRL3 regions comprise the amino acid sequences set forth in SEQ ID NOs: 60, 64, 68, 69, 71, and 72, respectively.

In one embodiment, the heavy chain variable region and the light chain variable region of the antibody comprise the amino acid sequences set forth in SEQ ID NOs: 53 and 57, respectively.

In one embodiment, provided herein is an isolated antibody that specifically binds to human GITR, the antibody comprising a heavy chain variable region comprising the amino acid sequence of SEQ ID NO: 53.

In one embodiment, provided herein is an isolated multispecific antibody comprising a first antigen-binding domain and a second antigen-binding domain, wherein the second antigen-binding domain specifically binds to human GITR and comprises a heavy chain variable region comprising complementarity determining regions CDRH1, CDRH2, and CDRH3 and a light chain variable region comprising complementarity determining regions CDRL1, CDRL2, and CDRL3, wherein the CDRH1, CDRH2, CDRH3, CDRL1, CDRL2, and CDRL3 regions of the second antigen-binding domain that specifically binds to human GITR comprise the amino acid sequences set forth in SEQ ID NOs: 60, 64, 68, 69, 71, and 72, respectively.

In one embodiment, the heavy chain variable region and the light chain variable region of the second antigen-binding domain that specifically binds to human GITR comprise the amino acid sequences set forth in SEQ ID NOs: 53 and 57, respectively.

In one embodiment, provided herein is an isolated multispecific antibody comprising a first antigen-binding domain and a second antigen-binding domain, wherein the second antigen-binding domain specifically binds to human GITR and comprises a heavy chain variable region comprising the amino acid sequence of SEQ ID NO: 53.

In one embodiment, the first antigen-binding domain specifically binds to human OX40.

In one embodiment, the first antigen-binding domain that specifically binds to human OX40 comprises a heavy chain variable region comprising complementarity determining regions CDRH1, CDRH2, and CDRH3 and a light chain variable region comprising complementarity determining regions CDRL1, CDRL2, and CDRL3, wherein: (a) CDRH1 comprises the amino acid sequence of $X_1X_2X_3MH$ (SEQ ID NO: 41), wherein $X_1$ is G, Q, H, or E, $X_2$ is S, E, or Y, and $X_3$ is A, S, or G; (b) CDRH2 comprises the amino acid sequence of $RIRSKX_1X_2X_3X_4X_5TAYAASVKG$ (SEQ ID NO: 42), wherein $X_1$ is A, S, or Y, $X_2$ is N, E, or Y, $X_3$ is S, Q, or G, $X_4$ is Y, E, or Q, and $X_5$ is A, E, or L; (c) CDRH3 comprises the amino acid sequence of $GIX_1X_2X_3X_4X_5X_6X_7Y$ (SEQ ID NO: 43), wherein $X_1$ is Y or A, $X_2$ is D or A, $X_3$ is S, T, or W, $X_4$ is S, E, or L, $X_5$ is G or A, $X_6$ is Y or A, and $X_7$ is D or A; (d) CDRL1 comprises the amino acid sequence of RSSQSLLHSNGYNYLD (SEQ ID NO: 32); (e) CDRL2 comprises the amino acid sequence of LGSNRAS (SEQ ID NO: 33); and (f) CDRL3 comprises the amino acid sequence of $MQX_1X_2X_3X_4PLT$ (SEQ ID NO: 46), wherein $X_1$ is A or G, $X_2$ is L or S, $X_3$ is Q or K, and $X_4$ is T or W.

In one embodiment, the CDRH1, CDRH2, CDRH3, CDRL1, CDRL2, and CDRL3 regions of the first antigen-binding domain that specifically binds to human OX40 comprise the amino acid sequences set forth in SEQ ID NOs: 16, 21, 25, 32, 33, and 34, respectively.

In one embodiment, the CDRH1, CDRH2, CDRH3, CDRL1, CDRL2, and CDRL3 regions of the first antigen-binding domain that specifically binds to human OX40 comprise the amino acid sequences set forth in SEQ ID NOs: 16, 21, 25, 32, 33, and 38, respectively.

In any multispecific antibody embodiments as disclosed herein, the N-terminal amino acid residues of one or more heavy chain variable regions of the antibody (e.g., the heavy chain variable regions of a first antigen-binding domain and/or of a second antigen-binding domain) has been converted to pyroglutamate (e.g., as a result of post-translational cyclization of the free amino group of the N-terminal glutamic acid or glutamine residue of the heavy chain variable region). In any multispecific antibody embodiments as disclosed herein, the N-terminal amino acid residue of one or more heavy chains of the antibody has been converted to pyroglutamate (e.g., as a result of post-translational cyclization of the free amino group of the N-terminal glutamic acid or glutamine residue of the heavy chain).

In one embodiment, provided herein is a pharmaceutical composition comprising an antibody or a multispecific antibody provided herein and a pharmaceutically acceptable carrier or excipient.

In one embodiment, provided herein is an isolated polynucleotide encoding a heavy and/or light chain of an antibody or a multispecific antibody provided herein.

In one embodiment, provided herein is an isolated polynucleotide encoding an antibody or a multispecific antibody provided herein.

In one embodiment, provided herein is a vector comprising a polynucleotide provided herein.

In one embodiment, provided herein is a recombinant host cell comprising a polynucleotide or vector provided herein.

In one embodiment, provided herein is a method of producing an antibody that specifically binds to human OX40, a multispecific antibody comprising a first antigen-binding domain that specifically binds to human OX40 and a second antigen-binding domain, an antibody that specifically binds to human GITR, or a multispecific antibody comprising a first antigen-binding domain and a second antigen-binding domain that specifically binds to human GITR, the method comprising culturing a host cell provided herein so that the polynucleotide is expressed and the antibody or the multispecific antibody is produced.

In one embodiment, provided herein is a method of modulating an immune response in a subject, the method comprising administering to the subject an effective amount of an antibody, a multispecific antibody, or a pharmaceutical composition provided herein.

In one embodiment, provided herein is a method of enhancing or inducing an immune response in a subject, the method comprising administering to the subject an effective amount of an antibody, a multispecific antibody, or a pharmaceutical composition provided herein.

In one embodiment, provided herein is a method of treating cancer in a subject, the method comprising administering to the subject an effective amount of an antibody, a multispecific antibody, or a pharmaceutical composition provided herein.

In one embodiment, the cancer is selected from the group consisting of melanoma, renal cancer, prostate cancer, colon cancer, and lung cancer.

In one embodiment, the method further comprises administering an additional therapeutic agent to the subject. In one embodiment, the additional therapeutic agent is a chemotherapeutic, a radiotherapeutic, or a checkpoint targeting agent. In one embodiment, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, and an agonist anti-OX40 antibody. In one embodiment, the additional therapeutic agent is an inhibitor of indoleamine-2,3-dioxygenase (IDO). In one embodiment, the inhibitor is selected from the group consisting of epacadostat, F001287, indoximod, and NLG919. In one embodiment, the additional therapeutic agent is a vaccine. In one embodiment, the vaccine comprises a heat shock protein peptide complex (HSPPC) comprising a heat shock protein complexed with an antigenic peptide. In one embodiment, the heat shock protein is hsc70 and is complexed with a tumor-associated antigenic peptide. In one embodiment, the heat shock protein is gp96 and is complexed with a tumor-associated antigenic peptide, wherein the HSPPC is derived from a tumor obtained from a subject.

In one embodiment, provided herein is a method for reducing or inhibiting an immune response in a subject, the method comprising administering to the subject an effective amount of an antibody, a multispecific antibody, or a pharmaceutical composition provided herein.

In one embodiment, provided herein is a method for treating an autoimmune or inflammatory disease or disorder in a subject, the method comprising administering to the subject an effective amount of an antibody, a multispecific antibody, or a pharmaceutical composition provided herein.

In one embodiment, the autoimmune or inflammatory disease or disorder is selected from the group consisting of transplant rejection, graft-versus-host disease, vasculitis, asthma, rheumatoid arthritis, dermatitis, inflammatory bowel disease, uveitis, lupus, colitis, diabetes, multiple sclerosis, and airway inflammation.

In one embodiment, the present invention relates to an antibody (e.g., a monospecific or multispecific antibody) of the invention, or a pharmaceutical composition of the invention, or a polynucleotide of the invention, or a vector of the invention, or a recombinant host cell of the invention for use as a medicament.

In one embodiment, the present invention relates to an antibody (e.g., a monospecific or multispecific antibody) of the invention, or a pharmaceutical composition of the invention, or a polynucleotide of the invention, or a vector of the invention, or a recombinant host cell of the invention for use as a diagnostic.

In one aspect, the present invention relates to an antibody (e.g., a monospecific or multispecific antibody), polynucleotide, vector, recombinant host cell, and/or pharmaceutical composition of the present invention for use in a method for increasing an immune response.

In one aspect, the present invention relates to an antibody (e.g., a monospecific or multispecific antibody), polynucleotide, vector, recombinant host cell, and/or pharmaceutical composition of the present invention for use in a method for increasing an immune response in a subject comprising administering to the subject an effective amount of an antibody (e.g., a monospecific or multispecific antibody), polynucleotide, vector, recombinant host cell, and/or pharmaceutical composition of the invention.

In one aspect, the present invention relates to an antibody (e.g., a monospecific or multispecific antibody), polynucleotide, vector, recombinant host cell, and/or pharmaceutical composition of the present invention for use in a method for the treatment of cancer.

In one aspect, the present invention relates to an antibody (e.g., a monospecific or multispecific antibody), polynucleotide, vector, recombinant host cell, and/or pharmaceutical composition of the present invention for use in a method for the treatment of cancer in a subject comprising administering to the subject an effective amount of an antibody (e.g., a monospecific or multispecific antibody), polynucleotide, vector, recombinant host cell, and/or pharmaceutical composition of the invention.

In one aspect, the present invention relates to an antibody (e.g., a monospecific or multispecific antibody), polynucleotide, vector, recombinant host cell, and/or pharmaceutical composition of the present invention for use in a method for the treatment of an infectious disease.

In one aspect, the present invention relates to an antibody (e.g., a monospecific or multispecific antibody), polynucleotide, vector, recombinant host cell, and/or pharmaceutical composition of the present invention for use in a method for the treatment of an infectious disease in a subject comprising administering to the subject an effective amount of an antibody (e.g., a monospecific or multispecific antibody), polynucleotide, vector, recombinant host cell, and/or pharmaceutical composition of the invention.

In one aspect, the present invention relates to an antibody (e.g., a monospecific or multispecific antibody), polynucleotide, vector, recombinant host cell, and/or pharmaceutical composition of the present invention for use in a method for inhibiting an immune response.

In one aspect, the present invention relates to an antibody (e.g., a monospecific or multispecific antibody), polynucleotide, vector, recombinant host cell, and/or pharmaceutical composition of the present invention for use in a method for inhibiting an immune response in a subject comprising administering to the subject an effective amount of an antibody (e.g., a monospecific or multispecific antibody), polynucleotide, vector, recombinant host cell, and/or pharmaceutical composition of the invention.

In one aspect, the present invention relates to an antibody (e.g., a monospecific or multispecific antibody), polynucleotide, vector, recombinant host cell, and/or pharmaceutical composition of the present invention for use in a method for the treatment of an autoimmune or inflammatory disease or disorder.

In one aspect, the present invention relates to an antibody (e.g., a monospecific or multispecific antibody), polynucleotide, vector, recombinant host cell, and/or pharmaceutical composition of the present invention for use in a method for the treatment of an autoimmune or inflammatory disease or disorder in a subject comprising administering to the subject an effective amount of an antibody (e.g., a monospecific or multispecific antibody), polynucleotide, vector, recombinant host cell, and/or pharmaceutical composition of the invention.

In one aspect, the present invention relates to (a) an antibody (e.g., a monospecific or multispecific antibody), polynucleotide, vector, recombinant host cell, and/or pharmaceutical composition of the present invention and (b) an additional therapeutic agent for use as a medicament.

In one aspect, the present invention relates to (a) an antibody (e.g., a monospecific or multispecific antibody), polynucleotide, vector, recombinant host cell, and/or pharmaceutical composition of the present invention and (b) an additional therapeutic agent for use in a method for the treatment of cancer.

In one aspect, the present invention relates to (a) an antibody (e.g., a monospecific or multispecific antibody), polynucleotide, vector, recombinant host cell, and/or pharmaceutical composition of the present invention and (b) an additional therapeutic agent for use in a method for the treatment of an infectious disease.

In one aspect, the present invention relates to (a) an antibody (e.g., a monospecific or multispecific antibody), polynucleotide, vector, recombinant host cell, and/or pharmaceutical composition of the present invention and (b) an additional therapeutic agent for use in a method for the treatment of an autoimmune or inflammatory disease or disorder.

In one aspect, the present invention relates to a pharmaceutical composition, kit or kit-of-parts comprising (a) an antibody (e.g., a monospecific or multispecific antibody), polynucleotide, vector, recombinant host cell, and/or pharmaceutical composition of the present invention and (b) an additional therapeutic agent.

4. BRIEF DESCRIPTION OF THE FIGURES

Figure 1C:
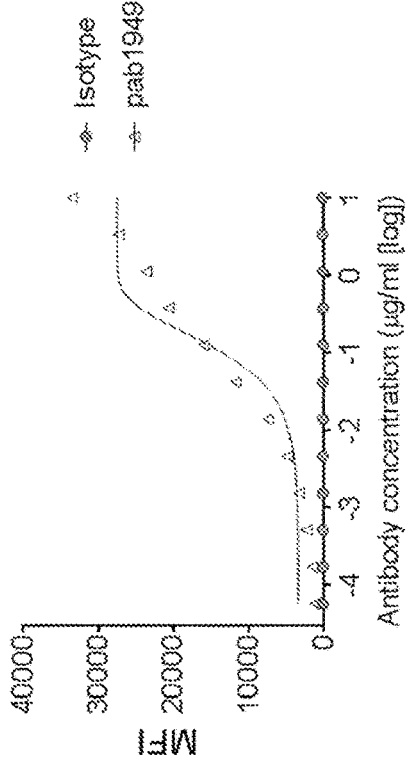
Figure 1B:
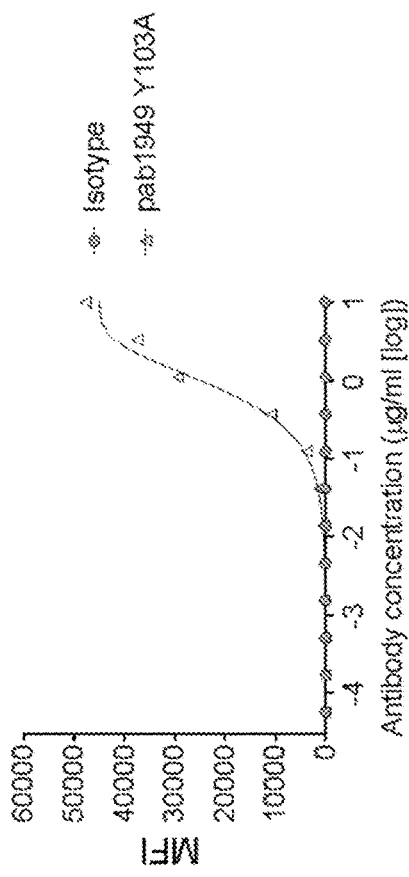
Figure 1D:
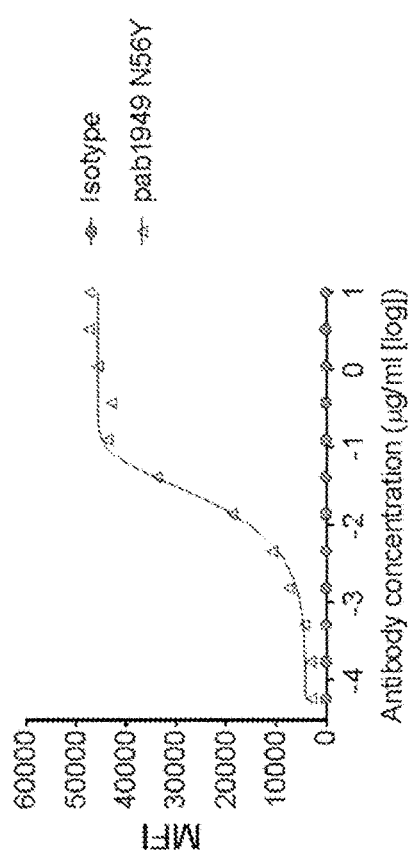
Figure 1E:
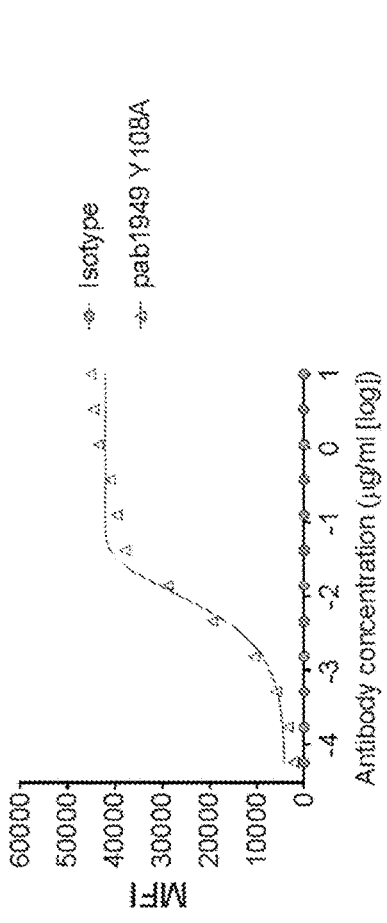
Figure 1F:
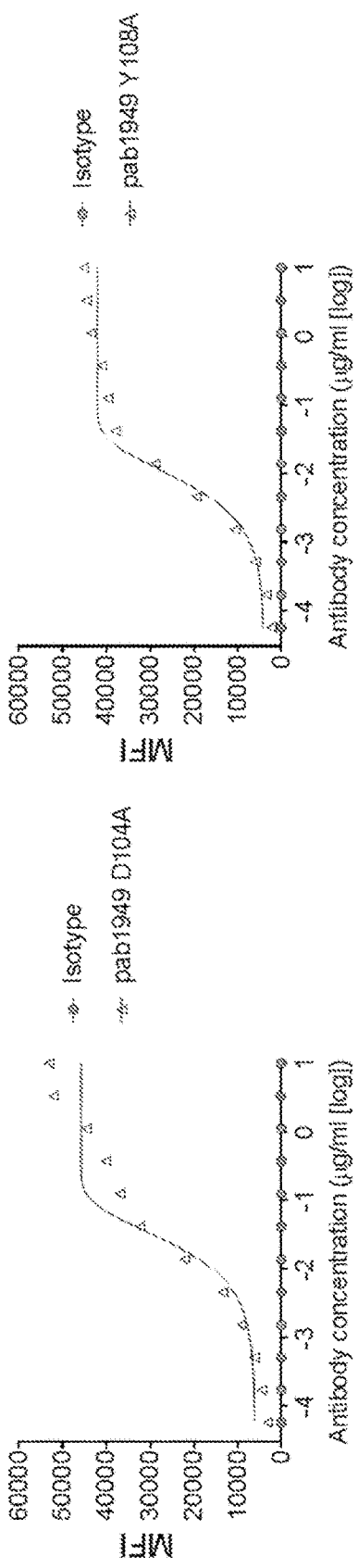
Figure 1G:
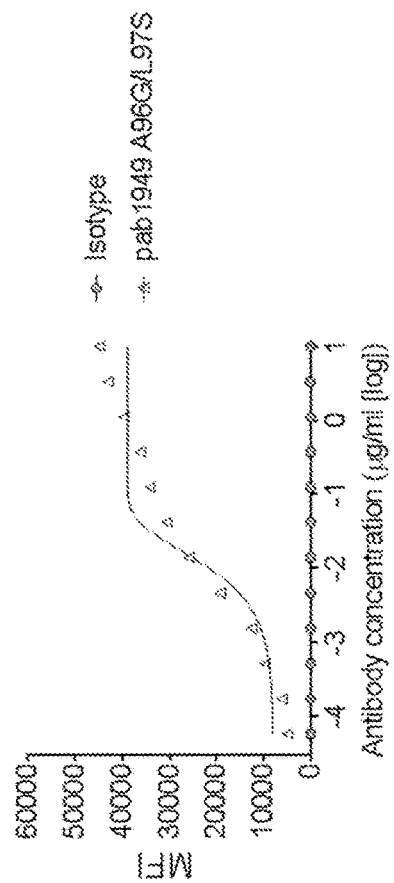
Figure 1H:
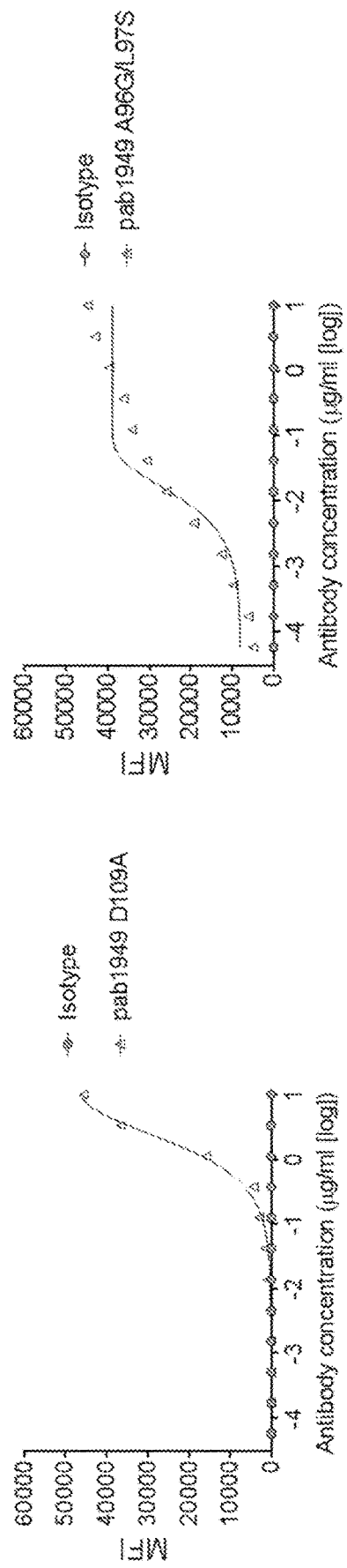
Figure 1I:
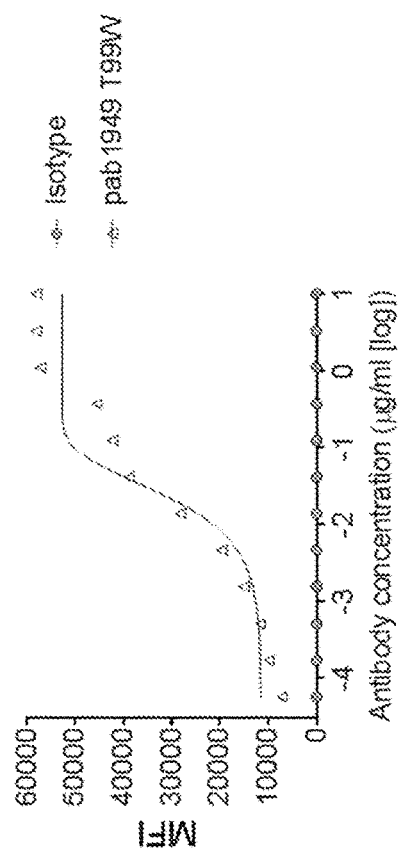
Figure 1J:
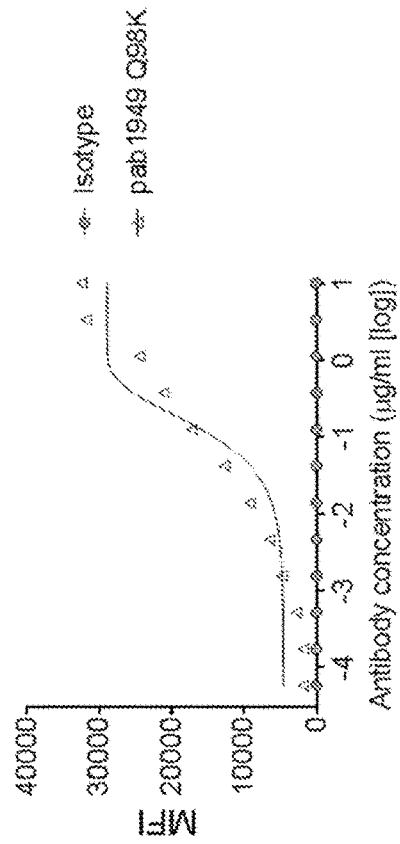

FIGS. 1A, 1B, 1C, 1D, 1E, 1F, 1G, 1H, 1I, and 1J are a set of flow cytometry plots showing the binding of anti-OX40 antibodies or an isotype control antibody to Jurkat cells expressing human OX40. The anti-OX40 antibodies tested include pab1949, pab2049, heavy chain variants of pab1949 (pab1949 N56Y, pab1949 Y103A, pab1949 D104A, pab1949 Y108A, and pab1949 D109A), and light chain variants of pab1949 (pab1949 A96G/L97S, pab1949 Q98K, and pab1949 T99W). All the anti-OX40 antibodies tested are $IgG_1$ antibodies. MFI values are plotted over a range of antibody concentrations.

Figure 2A:
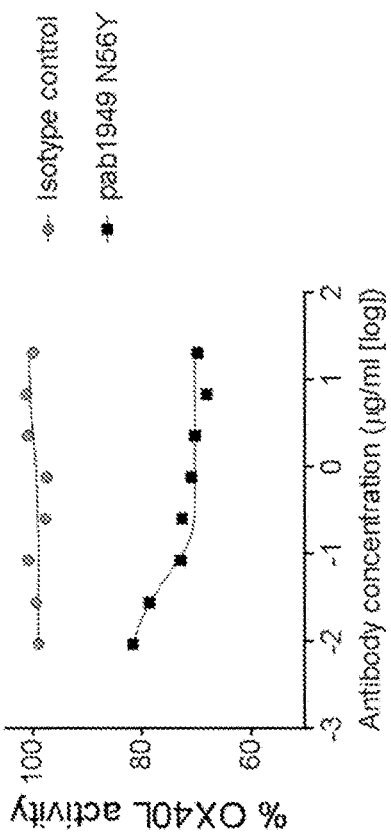
Figure 2B:
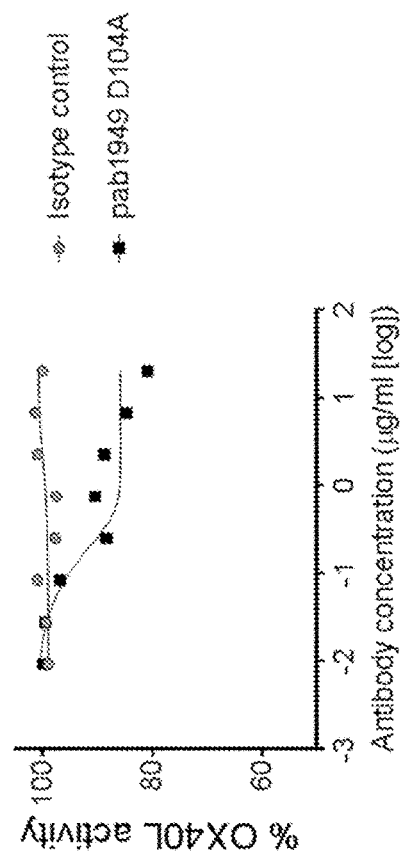
Figure 2C:
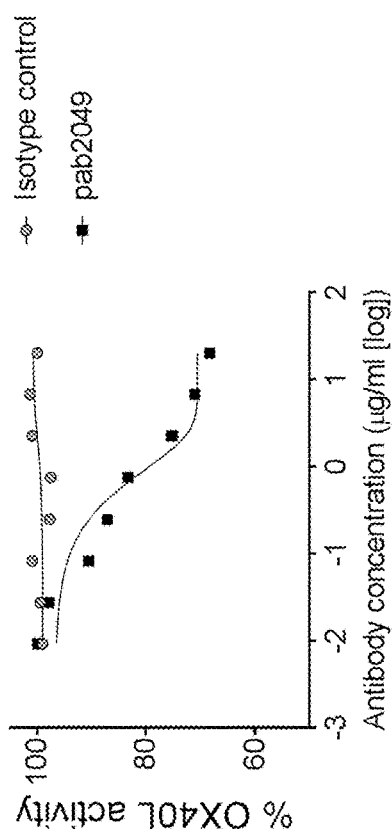
Figure 2D:
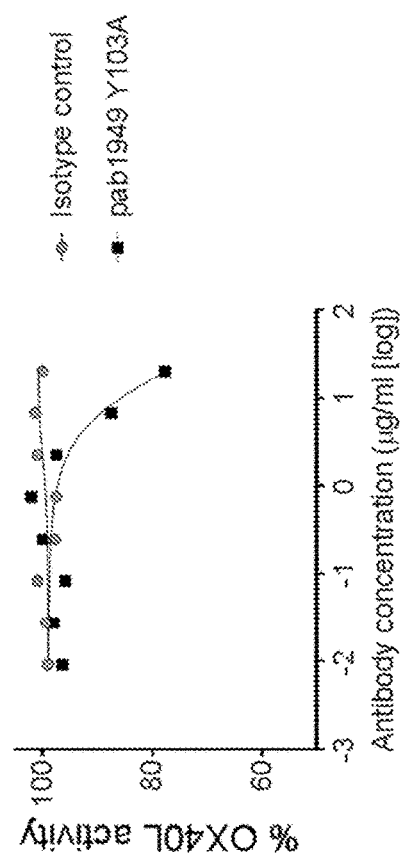
Figure 2E:
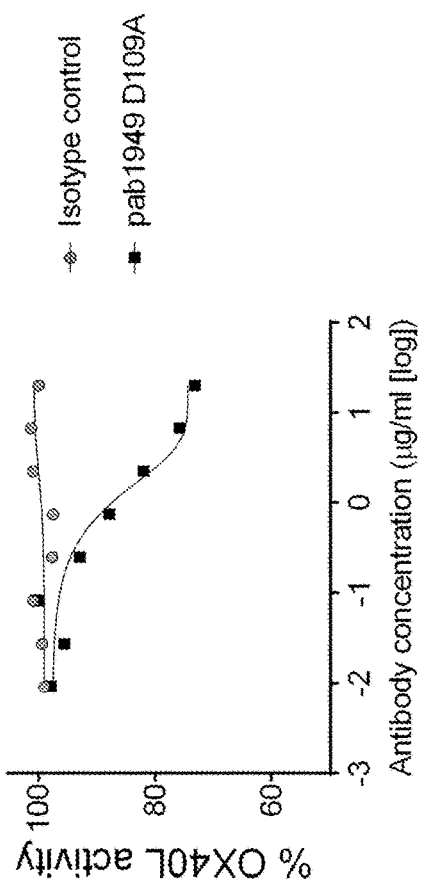
Figure 2F:
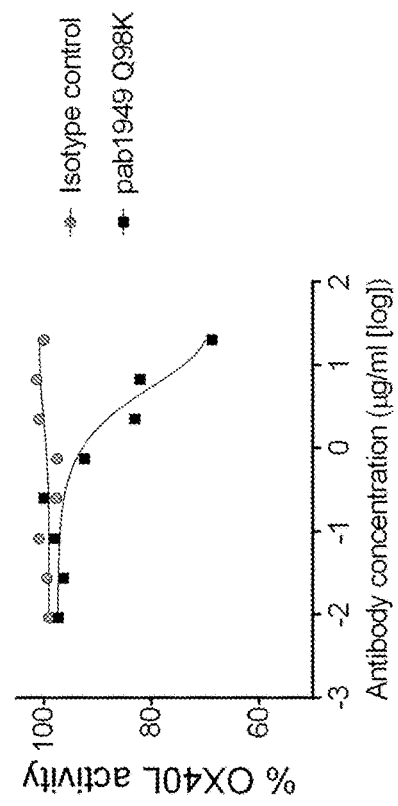
Figure 2G:
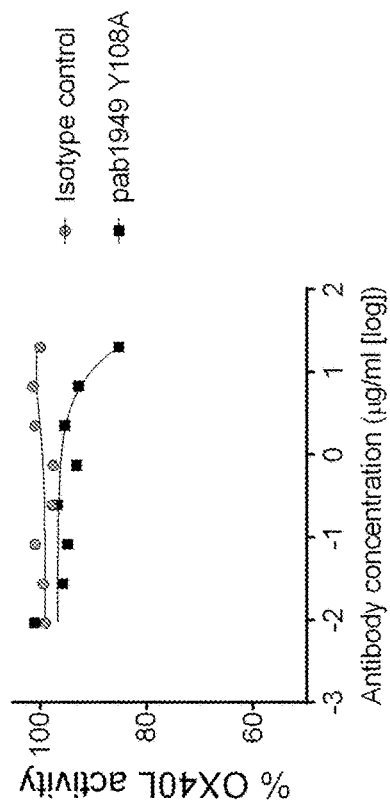
Figure 2H:
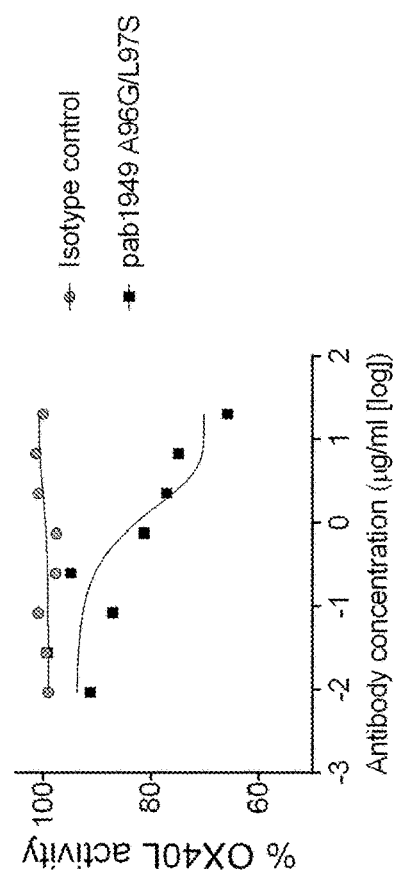
Figure 2I:
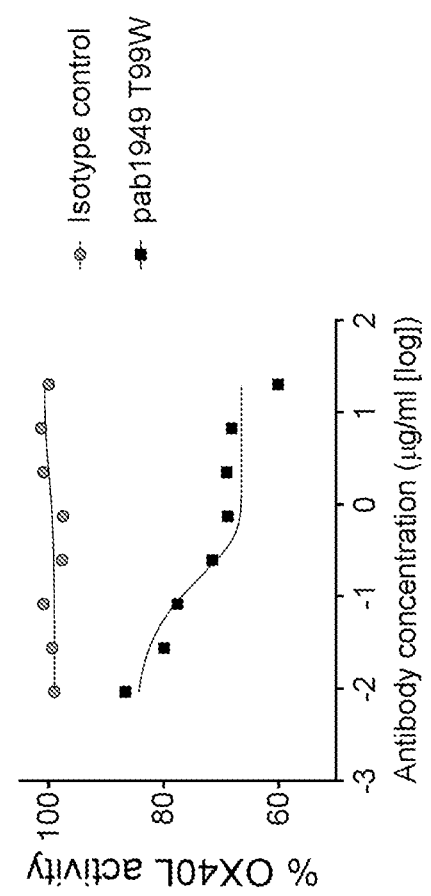

FIGS. 2A, 2B, 2C, 2D, 2E, 2F, 2G, 2H, and 2I are results from an assay where Jurkat-huOX40-NF-κB-luciferase reporter cells were pre-incubated with anti-OX40 antibodies or an isotype control antibody before activated by multimeric OX40L. The anti-OX40 antibodies tested include pab2049, heavy chain variants of pab1949 (pab1949 N56Y, pab1949 Y103A, pab1949 D104A, pab1949 Y108A, and pab1949 D109A), and light chain variants of pab1949 (pab1949 A96G/L97S, pab1949 Q98K, and pab1949 T99W). All the anti-OX40 antibodies tested are $IgG_1$ antibodies. The % OX40L activity is plotted against a range of antibody concentrations.

Figure 3A:
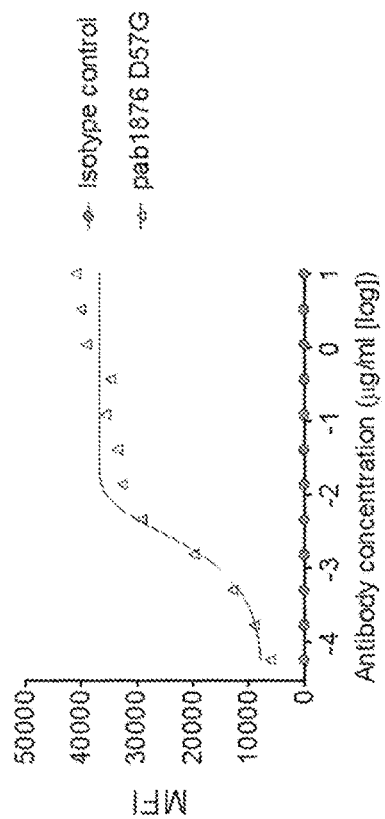
Figure 3B:
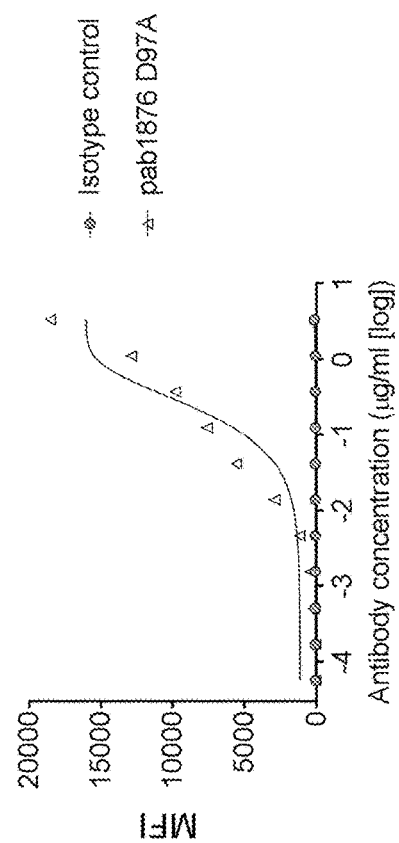
Figure 3C:
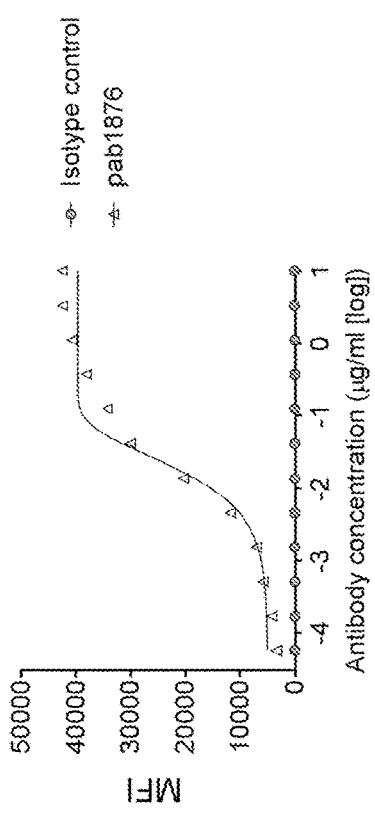
Figure 3D:
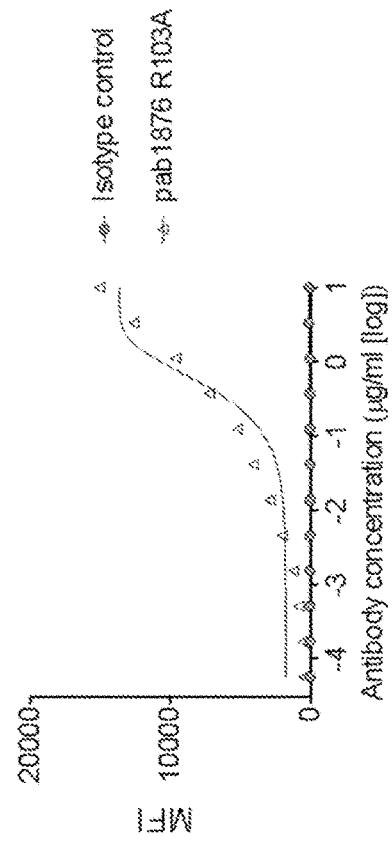
Figure 3F:
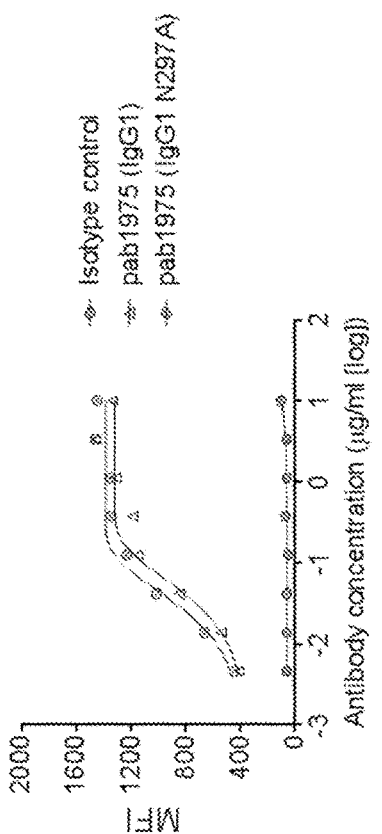
Figure 3E:
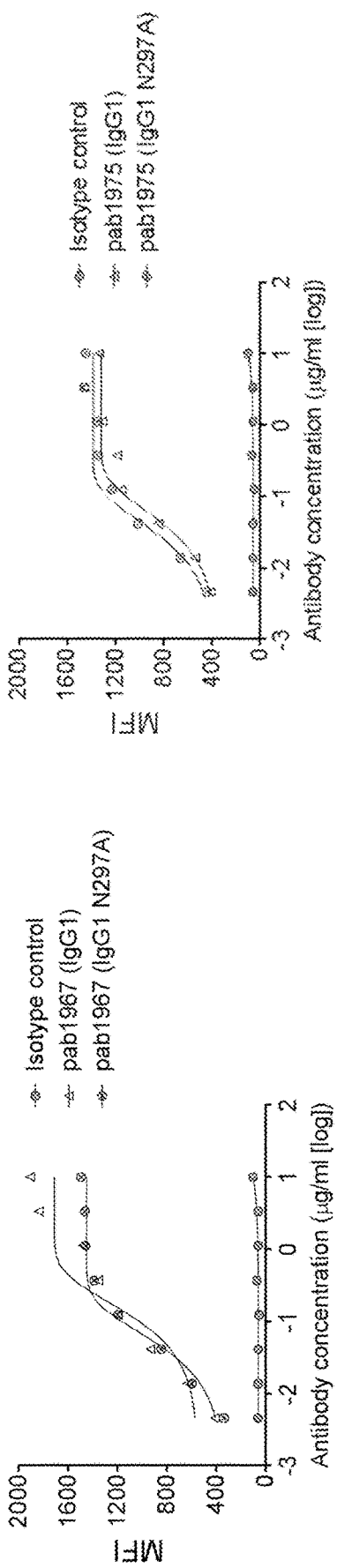
Figure 3G:
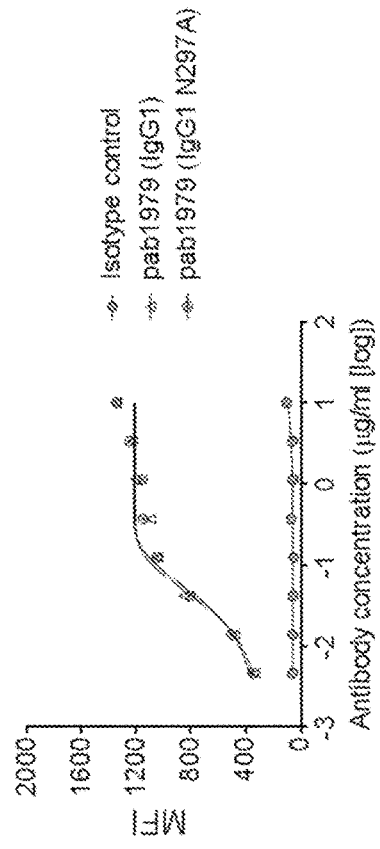

FIGS. 3A, 3B, 3C, 3D, 3E, 3F, and 3G are a set of flow cytometry plots showing the binding of anti-GITR antibodies or an isotype control antibody to Jurkat cells expressing human GITR. The anti-GITR antibodies tested include pab1876 (IgG1), heavy chain variants of pab1876 (pab1876 D57G (IgG1) and pab1876 R103A (IgG1)), a light chain variant of pab1876 (pab1876 D97A (IgG1)), pab1967 ($IgG_1$), pab1967 (IgG1 N297A), pab1975 ($IgG_1$), pab1975 (IgG1 N297A), pab1979 (IgG1), and pab1979 (IgG1 N297A). MFI values are plotted over a range of antibody concentrations.

5. DETAILED DESCRIPTION

Provided herein is an antibody (e.g., a monospecific antibody) that specifically binds to OX40 (e.g., human OX40) and modulates OX40 activity. For example, in one aspect, provided herein is an antibody that specifically binds to OX40 and enhances, induces, or increases one or more OX40 activities. For example, in another aspect, provided herein is an antibody that specifically binds to OX40 (e.g., human OX40) and deactivates, reduces, or inhibits one or more OX40 activities. In a specific embodiment, the antibody is isolated.

Also provided is an antibody (e.g., a monospecific antibody) that specifically binds to GITR (e.g., human GITR) and modulates GITR activity. For example, in one aspect, provided herein is an antibody that specifically binds to GITR and enhances, induces, or increases one or more GITR activities. For example, in another aspect, provided herein is an antibody that specifically binds to GITR (e.g., human GITR) and deactivates, reduces, or inhibits one or more GITR activities. In a specific embodiment, the antibody is isolated.

Further provided is a multispecific (e.g., bispecific) antibody that specifically binds to OX40 (e.g., human OX40) and/or GITR (e.g., human GITR). For example, in one aspect, a multispecific (e.g., bispecific) antibody provided herein can contain a first antigen-binding domain that specifically binds to OX40 (e.g., human OX40) and a second antigen-binding domain. The second antigen-binding domain can be distinct from the first antigen-binding domain. The second antigen-binding domain can bind to a different antigen (i.e., an antigen that is not OX40) than the first antigen-binding domain. The second antigen-binding domain can bind to a different epitope than the first antigen-binding domain. In one instance, a multispecific (e.g., bispecific) antibody provided herein contains a first antigen-binding domain that specifically binds to OX40 (e.g., human OX40) and a second antigen-binding domain that specifically binds to GITR (e.g., human GITR). In a specific embodiment, the multispecific antibody is isolated.

In another example, a multispecific (e.g., bispecific) antibody provided herein can contain a first antigen-binding domain and a second antigen-binding domain that binds to GITR. The first antigen-binding domain can be distinct from the second antigen-binding domain. The first antigen-binding domain can bind to a different antigen (i.e., an antigen that is not GITR) than the first antigen-binding domain. The second antigen-binding domain can bind to a different epitope than the first antigen-binding domain. In one instance, a multispecific (e.g., bispecific) antibody provided herein contains a first antigen-binding domain that specifically binds to OX40 (e.g., human OX40) and a second antigen-binding domain that specifically binds to GITR (e.g., human GITR). In a specific embodiment, the multispecific antibody is isolated.

In one aspect, provided herein is a multispecific (e.g., bispecific) antibody that specifically binds to OX40 and GITR and enhances, induces, or increases one or more OX40 and/or GITR activities. In another aspect, provided herein is a multispecific (e.g., bispecific) antibody that specifically binds to OX40 and GITR and reduces, inhibits, or decreases one or more OX40 or GITR activities. In a specific embodiment, the multispecific antibody is isolated.

Also provided are isolated nucleic acids (polynucleotides), such as complementary DNA (cDNA), encoding such antibodies (e.g., monospecific or multispecific antibodies). Further provided are vectors (e.g., expression vectors) and cells (e.g., host cells) comprising nucleic acids (polynucleotides) encoding such antibodies (e.g., monospecific or multispecific antibodies). Also provided are methods of making such antibodies (e.g., monospecific or multispecific antibodies). In other aspects, provided herein are methods and uses for inducing, increasing, or enhancing OX40 and/or GITR activity, and treating certain conditions, such as cancer. Further provided are methods and uses for inhibiting, decreasing, or reducing OX40 and/or GITR activity, and treating certain conditions, such as inflammatory or autoimmune diseases and disorders. Related compositions (e.g., pharmaceutical compositions), kits, and detection methods are also provided.

5.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, B is a "substantially increasing function" of A over a specified domain of A values if B substantially increases as A increases over the specified domain, e.g., in a given experiment, or using mean values from multiple experiments. This definition allows for a value of B corresponding to a specified value of A to be up to 1%, 2%, 3%, 4%, 5%, 10%, 15%, or 20% lower relative to a value of B corresponding to any lower value of A.

As used herein, B is a "substantially decreasing function" of A over a specified domain of A values if B substantially decreases as A increases over the specified domain, e.g., in a given experiment, or using mean values from multiple experiments. This definition allows for a value of B corresponding to a specified value of A to be up to 1%, 2%, 3%, 4%, 5%, 10%, 15%, or 20% higher relative to a value of B corresponding to any lower value of A.

As used herein, the terms "antibody" and "antibodies" are terms of art and can be used interchangeably herein and refer to a molecule with an antigen-binding site that specifically binds an antigen.

As used herein, the terms "antibody" and "antibodies" include full length antibodies, antigen-binding fragments of full length antibodies, and molecules comprising antibody CDRs, VH regions or VL regions. Examples of antibodies include monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., $IgG_1$, IgG2, IgG3, IgG4, $IgA_1$ or $IgA_2$), or any subclass (e.g., $IgG2_a$ or IgG2b) of immunoglobulin molecule. In certain embodiments, antibodies described herein are IgG antibodies, or a class (e.g., human $IgG_1$ or IgG4) or subclass thereof. In a specific embodiment, the antibody is a humanized monoclonal antibody. In another specific embodiment, the antibody is a human monoclonal antibody.

"Multispecific" antibodies are antibodies with at least two different antigen-binding sites. Multispecific antibodies include bispecific antibodies that contain two different antigen-binding sites (exclusive of the Fc region). Examples of multispecific antibodies include recombinantly produced antibodies, human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, $F(ab')_2$ fragments, disulfide-linked Fvs (sdFv), anti-idiotypic (anti-Id) antibodies (including, e.g., anti-anti-Id antibodies), and antigen-binding fragments of any of the above. Multispecific antibodies can be of any type (e.g., IgG, IgE, IgM, IgD, IgA or IgY), any class (e.g., $IgG_1$, $IgG_2$, $IgG_3$, $IgG_4$, $IgA_1$ or $IgA_2$), or any subclass (e.g., $IgG_{2a}$ or $IgG_{2b}$) of immunoglobulin molecule. In certain embodiments, multispecific antibodies described herein are IgG antibodies, or a class (e.g., human $IgG_1$ or $IgG_4$) or subclass thereof.

As used herein, the terms "antigen-binding domain," "antigen-binding region," "antigen-binding site," and similar terms refer to the portion of antibody molecules which comprises the amino acid residues that confer on the antibody molecule its specificity for the antigen (e.g., the complementarity determining regions (CDR)). The antigen-binding region can be derived from any animal species, such as rodents (e.g., mouse, rat, or hamster) and humans.

As used herein, the term "anti-OX40/GITR" antibody refers to a multispecific antibody (e.g., a bispecific antibody) that contains an antigen-binding domain that binds to OX40 (e.g., human OX40) and an antigen-binding domain that binds to GITR (e.g., human GITR).

As used herein, the terms "variable region" and "variable domain" are used interchangeably and are common in the art. The variable region typically refers to a portion of an antibody, generally, a portion of a light or heavy chain, typically about the amino-terminal 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann N Y Acad Sci 190: 382-391 and Kabat E A et al., (1991) Sequences of Proteins of Immunological Interest, Fifth Edition, U.S. Department of Health and Human Services, NIH Publication No. 91-3242, each of which is herein incorporated by reference in its entirety). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

As used herein, the terms "constant region" and "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha ($\alpha$), delta ($\delta$), epsilon ($\epsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

As used herein, the term "EU numbering system" refers to the EU numbering convention for the constant regions of an antibody, as described in Edelman, G. M. et al., Proc. Natl. Acad. USA, 63, 78-85 (1969) and Kabat et al., Sequences of Proteins of Immunological Interest, U.S. Dept. Health and Human Services, 5th edition, 1991, each of which is herein incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation rate constant of, e.g., an antibody to an antigen. The $k_{on}$ and $k_{off}$ can be determined by techniques known to one of ordinary skill in the art, such as BIAcore® or KinExA. As used herein, a "lower affinity" refers to a larger $K_D$.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody can be replaced with an amino acid residue with a similar side chain.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays (e.g., constraining peptides using CLIPS (Chemical Linkage of Peptides onto Scaffolds) to map discontinuous or conformational epitopes), and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50 (Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.,; U.S. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter C W; Roversi P et al., (2000) Acta Crystallogr D Biol Crystallogr 56 (Pt 10): 1316-1323), each of which is herein incorporated by reference in its entirety. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. CLIPS (Chemical Linkage of Peptides onto Scaffolds) is a technology to present one or more peptides in a structurally constrained configuration to behave as functional mimics of complex protein domains. See, e.g., U.S. Publication Nos. US 2008/0139407 A1 and US 2007/099240 A1, and U.S. Pat. No. 7,972,993, each of which is herein incorporated by reference in its entirety. In a specific embodiment, the epitope of an antibody is determined using alanine scanning mutagenesis studies. In a specific embodiment, the epitope of an antibody is determined using hydrogen/deuterium exchange coupled with mass spectrometry. In a specific embodiment, the epitope of an antibody is determined using CLIPS Epitope Mapping Technology from Pepscan Therapeutics.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that immunospecifically bind to an antigen bind to the antigen with a $K_A$ that is at least 2 logs, 2.5 logs, 3 logs, 4 logs or greater than the $K_A$ when the molecules bind non-specifically to another antigen. In the context of multispecific (e.g., bispecific) antibodies, the terms "immunospecifically binds," "immunospecifically recognizes," "specifically binds," and "specifically recognizes" refer to antibodies that have distinct specificities for more than one antigen or for more than one epitope on a single antigen. For example, a bispecific antibody may, e.g., specifically bind each of human OX40 and human GITR, e.g., with distinct antigen-binding domains.

In another specific embodiment, antigen-binding domains that immunospecifically bind to an antigen do not cross react with other proteins under similar binding conditions. In another specific embodiment, antigen-binding domains that immunospecifically bind to OX40 antigen do not cross react with other non-OX40 proteins. In another specific embodiment, antigen-binding domains that immunospecifically bind to GITR antigen do not cross react with other non-GITR proteins. In a specific embodiment, provided herein is an antibody containing an antigen-binding domain that binds to OX40 or GITR with higher affinity than to another unrelated antigen. In certain embodiments, provided herein is an antibody containing an antigen-binding domain that binds to OX40 or GITR (e.g., human OX40 or human GITR) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-OX40 antigen-binding domain described herein to an unrelated, non-OX40 protein is less than 10%, 15%, or 20% of the binding of the antigen-binding domain to OX40 protein as measured by, e.g., a radioimmunoassay. In a specific embodiment, the extent of binding of an anti-GITR antigen-binding domain described herein to an unrelated, non-GITR protein is less than 10%, 15%, or 20% of the binding of the antigen-binding domain to GITR protein as measured by, e.g., a radioimmunoassay.

In a specific embodiment, provided herein is an antibody containing an antigen-binding domain that binds to human OX40 with higher affinity than to another species of OX40 and/or an antigen-binding domain that binds to human GITR with higher affinity than to another species of GITR. In certain embodiments, provided herein is an antibody containing an antigen-binding domain that binds to human OX40 with a 5%, 10%, 15%, 20%, 25%, 30%, 35%, 40%, 45%, 50%, 55%, 60%, 65%, 70% or higher affinity than to another species of OX40 as measured by, e.g., a radioimmunoassay, surface plasmon resonance, or kinetic exclusion assay and/or that binds to human GITR with a 5%, 10%, 15%, 20%, 25%, 30%, 35%, 40%, 45%, 50%, 55%, 60%, 65%, 70% or higher affinity than to another species of GITR as measured by, e.g., a radioimmunoassay, surface plasmon resonance, or kinetic exclusion assay. In a specific embodiment, an antibody described herein, which binds to human OX40 and human GITR, will bind to another species of OX40 and/or GITR protein with less than 10%, 15%, or 20% of the binding of the antibody to the human OX40 and/or GITR protein as measured by, e.g., a radioimmunoassay, surface plasmon resonance, or kinetic exclusion assay.

As used herein, the term "OX40 receptor" or "OX40" refers to tumor necrosis factor receptor superfamily member 4 (TNFRSF4) (also known as CD134). As used herein, the term "human OX40" refers to a human OX40 protein encoded by a wild type human OX40 gene, e.g., GenBank™ accession number BC105070. An exemplary immature amino acid sequence of human OX40 is provided as SEQ ID NO: 101. An exemplary mature amino acid sequence of human OX40 is provided as SEQ ID NO: 100.

As used herein, the term "OX40 ligand" or "OX40L" refers to tumor necrosis factor ligand superfamily member 4 (TNFSF4). OX40L is otherwise known as CD252, GP34, TXGP1, and CD134L. As used herein, the term "human OX40L" refers to a human OX40L protein encoded by a wild type human OX40L gene, e.g., GenBank™ accession number D90224.1. RefSeq number NP 003317.1 and Swiss-Prot accession number P23510-1 provide exemplary human OX40L amino acid sequences for isoform 1. RefSeq number NP_001284491.1 and Swiss-Prot accession number P23510-2 provide exemplary human OX40L amino acid sequences for isoform 2. Human OX40L is designated GeneID: 7292 by Entrez Gene.

As used herein, the term "GITR" refers to glucocorticoid-induced TNFR family related receptor (also known as tumor necrosis factor receptor superfamily member 18 (TNFRSF18), activation-inducible TNFR family receptor (AITR), GITR-D, or CD357). As used herein, the term "human GITR" refers to a human GITR protein encoded by a wild type human GITR gene, e.g., GenBank™ accession numbers BC152381 and BC152386. Exemplary immature amino acid sequences of human GITR are provided as SEQ ID NOs: 103, 104, and 105. An exemplary mature amino acid sequence of human GITR is provided as SEQ ID NO: 102. An exemplary immature amino acid sequence of cynomolgus GITR is provided as SEQ ID NO: 106.

As used herein, the terms "GITR ligand" and "GITRL" refer to glucocorticoid-induced TNFR-related protein ligand. GITRL is otherwise known as activation-induced TNF-related ligand (AITRL) and tumor necrosis factor ligand superfamily member 18 (TNFSF18). As used herein, the term "human GITRL" refers to a human GITRL protein encoded by a wild type human GITRL gene, e.g., GenBank™ accession number AF125303. GenBank™ accession number NP_005083 and Swiss-Prot accession number Q9UNG2 provide exemplary human GITRL amino acid sequences.

TABLE 1

Exemplary OX40 and GITR sequences.

| SEQ ID NO: | Description | Amino acid Sequence |
|---|---|---|
| 100 | Mature human OX40 sequence | LHCVGDTYPSNDRCCHECRPGNGMVSRCSRSQNTVCRP CGPGFYNDVVSSKPCKPCTWCNLRSGSERKQLCTATQD TVCRCRAGTQPLDSYKPGVDCAPCPPGHFSPGDNQACK PWTNCTLAGKHTLQPASNSSDAICEDRDPPATQPQETQ GPPARPITVQPTEAWPRTSQGPSTRPVEVPGGRAVAAI LGLGLVLGLLGPLAILLALYLLRRDQRLPPDAHKPPGG GSFRTPIQEEQADAHSTL AKI |
| 101 | Immature human OX40 sequence | MCVGARRLGRGPCAALLLLGLGLSTVTGLHCVGDTYPS NDRCCHECRPGNGMVSRCSRSQNTVCRPCGPGFYNDVV SSKPCKPCTWCNLRSGSERKQLCTATQDTVCRCRAGTQ PLDSYKPGVDCAPCPPGHFSPGDNQACKPWTNCTLAGK HTLQPASNSSDAICEDRDPPATQPQETQGPPARPITVQ PTEAWPRTSQGPSTRPVEVPGGRAVAAILGLGLVLGLL GPLAILLALYLLRRDQRLPPDAHKPPGGGSFRTPIQEE QADAHSTLAKI |
| 102 | Mature human GITR sequence | QRPTGGPGCGPGRLLLGTGTDARCCRVHTTRCCRDYPG EECCSEWDCMCVQPEFHCGDPCCTTCRHHPCPPGQGVQ SQGKFSFGFQCIDCASGTFSGGHEGHCKPWTDCTQFGF LTVFPGNKTHNAVCVPGSPPAEPLGWLTVVLLAVAACV LLLTSAQLGLHIWQLRSQCMWPRETQLLLEVPPSTEDA |

TABLE 1-continued

Exemplary OX40 and GITR sequences.

| SEQ ID NO: | Description | Amino acid Sequence |
|---|---|---|
| | (Isoform 1) | RSCQFPEEERGERSAEEKGRLGDLWV |
| 103 | Immature human GITR sequence (Isoform 1) | MAQHGAMGAFRALCGLALLCALSLGQRPTGGPGCGPGR LLLGTGTDARCCRVHTTRCCRDYPGEECCSEWDCMCVQ PEFHCGDPCCTTCRHHPCPPGQGVQSQGKFSFGFQCID CASGTFSGGHEGHCKPWTDCTQFGFLTVFPGNKTHNAV CVPGSPPAEPLGWLTVVLLAVAACVLLLTSAQLGLHIW QLRSQCMWPRETQLLLEVPPSTEDARSCQFPEEERGER SAEEKGRLGDLWV |
| 104 | Immature human GITR sequence (Isoform 2) | MAQHGAMGAFRALCGLALLCALSLGQRPTGGPGCGPGR LLLGTGTDARCCRVHTTRCCRDYPGEECCSEWDCMCVQ PEFHCGDPCCTTCRHHPCPPGQGVQSQGKFSFGFQCID CASGTFSGGHEGHCKPWTDCCWRCRRRPKTPEAASSPR KSGASDRQRRRGGWETCGCEPGRPPGPPTAASPSPGAP QAAGALRSALGRALLPWQQKWVQEGGSDQRPGPCSSAA AAGPCRRERETQSWPPSSLAGPDGVGS |
| 105 | Immature human GITR sequence (Isoform 3) | MAQHGAMGAFRALCGLALLCALSLGQRPTGGPGCGPGR LLLGTGTDARCCRVHTTRCCRDYPGEECCSEWDCMCVQ PEFHCGDPCCTTCRHHPCPPGQGVQSQGKFSFGFQCID CASGTFSGGHEGHCKPWTDCTQFGFLTVFPGNKTHNAV CVPGSPPAEPLGWLTVVLLAVAACVLLLTSAQLGLHIW QLRKTQLLLEVPPSTEDARSCQFPEEERGERSAEEKGR LGDLWV |
| 106 | Immature cynomolgus GITR sequence | VARHGAMCACGTLCCLALLCAASLGQRPTGGPGCGPGR LLLGTGKDARCCRVHPTRCCRDYQSEECCSEWDCVCVQ PEFHCGNPCCTTCQHHPCPSGQGVQPQGKFSFGFRCVD CALGTFSRGHDGHCKPWTDCTQFGFLTVFPGNKTHNAV CVPGSPPAEPPGWLTIVLLAVAACVLLLTSAQLGLHIW QLGKTQLLLEVPPSTEDASSCQFPEEERGERLAEEKGR LGDLWV |

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell are not necessarily identical to the parent cell transfected with the nucleic acid molecule, e.g., due to mutations or environmental influences that may occur in succeeding generations or integration of the nucleic acid molecule into the host cell genome.

As used herein, the term "effective amount" in the context of the administration of a therapy to a subject refers to the amount of a therapy that achieves a desired prophylactic or therapeutic effect.

As used herein, the terms "subject" and "patient" are used interchangeably. The subject can be an animal. In some embodiments, the subject is a mammal such as a non-primate (e.g., cow, pig, horse, cat, dog, rat, etc.) or a primate (e.g., monkey or human), for example a human. In some embodiments, the subject is a cynomolgus monkey. In certain embodiments, such terms refer to a non-human animal (e.g., a non-human animal such as a pig, horse, cow, cat, or dog). In some embodiments, such terms refer to a pet or farm animal. In specific embodiments, such terms refer to a human.

The determination of "percent identity" between two sequences (e.g., amino acid sequences or nucleic acid sequences) can also be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and)(BLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the)(BLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389 3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of) (BLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

5.2 Antibodies 5.2.1 Anti-OX40 Antibodies

In a specific aspect, provided herein is an antibody (e.g., a monoclonal antibody, such as a chimeric, humanized, or human antibody) that specifically binds to OX40 (e.g., human OX40). Also provided herein is a multispecific antibody that comprises a first antigen-binding domain that specifically binds to OX40 (e.g., human OX40) and, optionally, a second antigen-binding domain that does not specifically bind to OX40 (e.g., human OX40).

The amino acid sequences of exemplary antibodies are set forth in Tables 2-5, herein.

TABLE 2

Amino acid sequences of exemplary anti-OX40 antibodies.*

| SEQ ID NO: | Description | Amino acid Sequence |
|---|---|---|
| 1 | pab1949 VH | EVQLVESGGGLVQPGGSLKLSCAASGFTFSGSAMHWVR QASGKGLEWVGRIRSKANSYATAYAASVKGRFTISRDD SKNTAYLQMNSLKTEDTAVYYCTSGIYDSSGYDYWGQG TLVTVSS |

TABLE 2-continued

Amino acid sequences of exemplary anti-OX40 antibodies.*

| SEQ ID NO: | Description | Amino acid Sequence |
|---|---|---|
| 2 | pab1949 VH N56Y | EVQLVESGGGLVQPGGSLKLSCAASGFTFSGSAMHWVRQASGKGLEWVGRIRSKAYSYATAYAASVKGRFTISRDDSKNTAYLQMNSLKTEDTAVYYCTSGIYDSSGYDYWGQGTLVTVSS |
| 3 | pab1949 VH Y103A | EVQLVESGGGLVQPGGSLKLSCAASGFTFSGSAMHWVRQASGKGLEWVGRIRSKANSYATAYAASVKGRFTISRDDSKNTAYLQMNSLKTEDTAVYYCTSGIADSSGYDYWGQGTLVTVSS |
| 4 | pab1949 VH D104A | EVQLVESGGGLVQPGGSLKLSCAASGFTFSGSAMHWVRQASGKGLEWVGRIRSKANSYATAYAASVKGRFTISRDDSKNTAYLQMNSLKTEDTAVYYCTSGIYASSGYDYWGQGTLVTVSS |
| 5 | pab1949 VH Y108A | EVQLVESGGGLVQPGGSLKLSCAASGFTFSGSAMHWVRQASGKGLEWVGRIRSKANSYATAYAASVKGRFTISRDDSKNTAYLQMNSLKTEDTAVYYCTSGIYDSSGADYWGQGTLVTVSS |
| 6 | pab1949 VH D109A | EVQLVESGGGLVQPGGSLKLSCAASGFTFSGSAMHWVRQASGKGLEWVGRIRSKANSYATAYAASVKGRFTISRDDSKNTAYLQMNSLKTEDTAVYYCTSGIYDSSGYAYWGQGTLVTVSS |
| 7 | pab1949 VH AM-1 | EVQLVESGGGLVQPGGSLKLSCAASGFTFSQEGMHWVRQASGKGLEWVGRIRSKANSYATAYAASVKGRFTISRDDSENTAYLQMNSLKTEDTAVYYCTSGIYDTLAYDYWGQGTLVTVSS |
| 8 | pab1949 VH AM-2 | EVQLVESGGGLVQPGGSLKLSCAASGFTFSHEGMHWVRQASGKGLEWVGRIRSKYYQEETAYAASVKGRFTISRDDSKNTAYLQMNSLKTEDTAVYYCTSGIYDSSGYDYWGQGTLVTVSS |
| 9 | pab1949 VH AM-3 | EVQLVESGGGLVQPGGSLKLSCAASGFTFSGYSMHWVRQASGKGLEWVGRIRSKSEGQLTAYAASVKGRFTISRDDSKNTAYLQMNSLKTEDTAVYYCTSGIYDSSGYDYWGQGTLVTVSS |
| 10 | pab1949 VH AM-4 | EVQLVESGGGLVQPGGSLKLSCAASGFTFSEESMHWVRQASGKGLEWVGRIRSKANSYATAYAASVKGRFTISRDDSKNTAYLQMNSLKTEDTAVYYCTSGIYDWEGYDYWGQGTLVTVSS |
| 11 | pab1949 VL | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPLTFGGGTKVEIK |
| 12 | pab1949 VL A96G/L97S | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQGSQTPLTFGGGTKVEIK |
| 13 | pab1949 VL Q98K | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALKTPLTFGGGTKVEIK |
| 14 | pab1949 VL I99W | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQWPLTFGGGTKVEIK |
| 15 | pab2049 VL | DIVMTQSPLSLPVTPGEPASISCRSSQSLLHSNGYNYLDWYLQKPGQSPQLLIYLGSNRASGVPDRFSGSGSGAGTDFTLKISRVEAEDVGIYYCMQGSKWPLTFGGGTKLEIK |
| 16 | VH CDR1 | GSAMH |
| 17 | VH CDR1 | QEGMH |
| 18 | VH CDR1 | HEGMH |
| 19 | VH CDR1 | GYSMH |
| 20 | VH CDR1 | EESMH |
| 21 | VH CDR2 | RIRSKANSYATAYAASVKG |
| 22 | VH CDR2 | RIRSKAYSYATAYAASVKG |
| 23 | VH CDR2 | RIRSKYYQEETAYAASVKG |
| 24 | VH CDR2 | RIRSKSEGQLTAYAASVKG |
| 25 | VH CDR3 | GIYDSSGYDY |
| 26 | VH CDR3 | GIADSSGYDY |
| 27 | VH CDR3 | GIYASSGYDY |
| 28 | VH CDR3 | GIYDSSGADY |
| 29 | VH CDR3 | GIYDSSGYAY |
| 30 | VH CDR3 | GIYDTLAYDY |
| 31 | VH CDR3 | GIYDWEGYDY |
| 32 | VL CDR1 | RSSQSLLHSNGYNYLD |
| 33 | VL CDR2 | LGSNRAS |
| 34 | VL CDR3 | MQALQTPLT |
| 35 | VL CDR3 | MQGSQTPLT |
| 36 | VL CDR3 | MQALKTPLT |
| 37 | VL CDR3 | MQALQWPLT |
| 38 | VL CDR3 | MQGSKWPLT |
| 39 | OX40 VH germline IGHV3-73*01 | EVQLVESGGGLVQPGGSLKLSCAASGFTFSGSAMHWVRQASGKGLEWVGRIRSKANSYATAYAASVKGRFTISRDDSKNTAYLQMNSLKTEDTAVYYCTR |
| 40 | OX40 VL germ0line IGKV2-28*01 | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTP |
| 41 | CDRH1 consensus sequence 1 | $X_1X_2X_3MH$, wherein: $X_1$ is G, Q, H, or E; $X_2$ is S, E, or Y; and $X_3$ is A, S, or G |
| 42 | CDRH2 consensus sequence 1 | $RIRSKX_1X_2X_3X_4X_5TAYAASVKG$, wherein: $X_1$ is A, S, or Y; $X_2$ is N, E, or Y; $X_3$ is S, Q, or G; $X_4$ is Y, E, or Q; and $X_5$ is A, E, or L |
| 43 | CDRH3 consensus sequence | $GIX_1X_2X_3X_4X_5X_6X_7Y$, wherein: $X_1$ is Y or A; $X_2$ is D or A; $X_3$ is S, T, or W; $X_4$ is S, E, or L; |

TABLE 2-continued

Amino acid sequences of exemplary anti-OX40 antibodies.*

| SEQ ID NO: | Description | Amino acid Sequence |
|---|---|---|
| | | $X_5$ is G or A; $X_6$ is Y or A; and $X_7$ is D or A |
| 44 | CDRH2 consensus sequence 2 | RIRSKAXSYATAYAASVKG, wherein X is N or Y |
| 45 | CDRH3 consensus sequence 2 | GIX$_1$X$_2$SSGX$_3$X$_4$Y, wherein X$_1$ is Y or A; X$_2$ is D or A; X$_3$ is Y or A; and X$_4$ is D or A |
| 46 | CDRL3 consensus sequence | MQX$_1$X$_2$X$_3$X$_4$PLT, wherein X$_1$ is A or G; X$_2$ is L or S; X$_3$ is Q or K; and X$_4$ is T or W |
| 47 | VH consensus sequence 1 | EVQLVESGGGLVQPGGSLKLSCAASGFTFSX$_1$X$_2$X$_3$MH WVRQASGKGLEWVGRIRSKX$_4$X$_5$X$_6$X$_7$X$_8$TAYAASVKG RFTISRDDSX$_9$NTAYLQMNSLKTEDTAVYYCTSGIX$_{10}$ X$_{11}$X$_{12}$X$_{13}$X$_{14}$X$_{15}$X$_{16}$YWGQGTLVTVSS, wherein X$_1$ is G, Q, H, or E; X$_2$ is S, E, or Y; X$_3$ is A, S, or G; X$_4$ is A, S, or Y; X$_5$ is N, E, or Y; X$_6$ is S, Q, or G; X$_7$ is Y, E, or Q; X$_8$ is A, E, or L; X$_9$ is K or E; X$_{10}$ is Y or A; X$_{11}$ is D or A; X$_{12}$ is S, T, or W; X$_{13}$ is S, E, or L; X$_{14}$ is G or A; X$_{15}$ is Y or A; and X$_{16}$ is D or A |
| 48 | VH consensus sequence 2 | EVQLVESGGGLVQPGGSLKLSCAASGFTFSGSAMHWV RQASGKGLEWVGRIRSKAX$_1$SYATAYAASVKGRFTISR DDSKNTAYLQMNSLKTEDTAVYYCTSGIX$_2$X$_3$ SSGX$_4$X$_5$YWGQGTLVTVSS, wherein X$_1$ is N or Y; X$_2$ is Y or A; X$_3$ is D or A; X$_4$ is Y or A; and X$_5$ is D or A |
| 49 | VL consensus sequence | DIVMTQSPLSLPVTPGEPASISCRSSQSLLHSNGYNY LDWYLQKPGQSPQLLIYLGSNRASGVPDRFSGSGX$_1$GT DFTLKISRVEAEDVGX$_2$YYCMQX$_3$X$_4$X$_5$X$_6$PLTFGGGT KX$_7$EIK, wherein X$_1$ is S or A; X$_2$ is V or I; X$_3$ is A or G; X$_4$ is L or S; X$_5$ is Q or K; X$_6$ is T or W; and X$_7$ is V or L |

TABLE 2-continued

Amino acid sequences of exemplary anti-OX40 antibodies.*

| SEQ ID NO: | Description | Amino acid Sequence |
|---|---|---|
| 50 | pab1949/ pab2049 heavy chain (IgG1) | EVQLVESGGGLVQPGGSLKLSCAASGFTFSGSAMHWV RQASGKGLEWVGRIRSKANSYATAYAASVKGRFTISR DDSKNTAYLQMNSLKTEDTAVYYCTSGIYDSSGYDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYNSTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 51 | pab1949 light chain | DIVMTQSPLSLPVTPGEPASISCRSSQSLLHSNGYNY LDWYLQKPGQSPQLLIYLGSNRASGVPDRFSGSGSGT DFTLKISRVEAEDVGVYYCMQALQTPLTFGGGTKVEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGEC |

*CDRs are defined according to the Kabat numbering system.

TABLE 3

Heavy chain CDR amino acid sequences of exemplary anti-OX40 antibodies.*

| VH | VH CDR1 (SEQ ID NO:) | VH CDR2 (SEQ ID NO:) | VH CDR3 (SEQ ID NO:) |
|---|---|---|---|
| pab1949 VH (1) | GSAMH (16) | RIRSKANSYATAYAASVKG (21) | GIYDSSGYDY (25) |
| pab1949 VH N56Y (2) | GSAMH (16) | RIRSKAYSYATAYAASVKG (22) | GIYDSSGYDY (25) |
| pab1949 VH Y103A (3) | GSAMH (16) | RIRSKANSYATAYAASVKG (21) | GIADSSGYDY (26) |
| pab1949 VH D104A (4) | GSAMH (16) | RIRSKANSYATAYAASVKG (21) | GIYASSGYDY (27) |
| pab1949 VH Y108A (5) | GSAMH (16) | RIRSKANSYATAYAASVKG (21) | GIYDSSGADY (28) |
| pab1949 VH D109A (6) | GSAMH (16) | RIRSKANSYATAYAASVKG (21) | GIYDSSGYAY (29) |
| pab1949 VH AM-1 (7) | QEGMH (17) | RIRSKANSYATAYAASVKG (21) | GIYDTLAYDY (30) |
| pab1949 VH AM-2 (8) | HEGMH (18) | RIRSKYYQEETAYAASVKG (23) | GIYDSSGYDY (25) |

TABLE 3-continued

Heavy chain CDR amino acid sequences of exemplary anti-OX40 antibodies.*

| VH (SEQ ID NO:) | VH CDR1 (SEQ ID NO:) | VH CDR2 (SEQ ID NO:) | VH CDR3 (SEQ ID NO:) |
|---|---|---|---|
| pab1949 VH AM-3 (9) | GYSMH (19) | RIRSKSEGQLTAYAASVKG (24) | GIYDSSGYDY (25) |
| pab1949 VH AM-4 (10) | EESMH (20) | RIRSKANSYATAYAASVKG (21) | GIYDWEGYDY (31) |

*Defined according to the Kabat numbering system.

TABLE 4

Light chain CDR amino acid sequences of exemplary anti-OX40 antibodies.*

| VL (SEQ ID NO:) | VL CDR1 (SEQ ID NO:) | VL CDR2 (SEQ ID NO:) | VL CDR3 (SEQ ID NO:) |
|---|---|---|---|
| pab1949 VL (11) | RSSQSLLHSNGYNYLD (32) | LGSNRAS (33) | MQALQTPLT (34) |
| pab1949 VL A96G/L97S (12) | RSSQSLLHSNGYNYLD (32) | LGSNRAS (33) | MQGSQTPLT (35) |
| pab1949 VL Q98K (13) | RSSQSLLHSNGYNYLD (32) | LGSNRAS (33) | MQALKTPLT (36) |
| pab1949 VL 199W (14) | RSSQSLLHSNGYNYLD (32) | LGSNRAS (33) | MQALQWPLT (37) |
| pab2049 VL (15) | RSSQSLLHSNGYNYLD (32) | LGSNRAS (33) | MQGSKWPLT (38) |

*Defined according to the Kabat numbering system.

TABLE 5

Heavy chain variable region (VH) and light chain variable region (VL) sequences of exemplary anti-OX40 antibodies.

| Antibody | Heavy chain variable region | SEQ ID NO: | Light chain variable region | SEQ ID NO: |
|---|---|---|---|---|
| pab1949 | pab1949 VH | 1 | pab1949 VL | 11 |
| pab1949 N56Y | pab1949 VH N56Y | 2 | pab1949 VL | 11 |
| pab1949 Y103A | pab1949 VH Y103A | 3 | pab1949 VL | 11 |
| pab1949 D104A | pab1949 VH D104A | 4 | pab1949 VL | 11 |
| pab1949 Y108A | pab1949 VH Y108A | 5 | pab1949 VL | 11 |
| pab1949 D109A | pab1949 VH D109A | 6 | pab1949 VL | 11 |
| pab1949 AM-1 | pab1949 VH AM-1 | 7 | pab2049 VL | 15 |
| pab1949 AM-2 | pab1949 VH AM-2 | 8 | pab2049 VL | 15 |
| pab1949 AM-3 | pab1949 VH AM-3 | 9 | pab2049 VL | 15 |
| pab1949 AM-4 | pab1949 VH AM-4 | 10 | pab2049 VL | 15 |
| pab2049 | pab1949 VH | 1 | pab2049 VL | 15 |
| pab1949 A96G/L97S | pab1949 VH | 1 | pab1949 VL A96G/L97S | 12 |
| pab1949 Q98K | pab1949 VH | 1 | pab1949 VL Q98K | 13 |
| pab1949 T99W | pab1949 VH | 1 | pab1949 VL T99W | 14 |

TABLE 6

Closest germline genes for exemplary anti-OX40 antibodies.

| Closest germline gene | SEQ ID NO: |
|---|---|
| IGHV3-73*01 | 39 |
| IGKV2-28*01 | 40 |

In certain embodiments, the instant disclosure provides an isolated antibody that specifically binds to OX40 (e.g., human OX40), the antibody comprising a heavy chain variable region comprising one, two, or all three of the CDRs of a heavy chain variable region set forth in Table 2 herein. In certain embodiments, the antibody comprises the CDRH1 of one of heavy chain variable regions set forth in Table 2. In certain embodiments, the antibody comprises the CDRH2 of one of the heavy chain variable regions set forth in Table 2. In certain embodiments, the antibody comprises the CDRH3 of one of the heavy chain variable regions set forth in Table 2.

In certain embodiments, the instant disclosure provides an isolated antibody that specifically binds to OX40 (e.g., human OX40), the antibody comprising a light chain variable region comprising one, two, or all three of the CDRs of a light chain variable region disclosed in Table 2 herein. In certain embodiments, the antibody comprises the CDRL1 of one of light chain variable regions set forth in Table 2. In certain embodiments, the antibody comprises the CDRL2 of one of the light chain variable regions set forth in Table 2. In certain embodiments, the antibody comprises the CDRL3 of one of the light chain variable regions set forth in Table 2.

In certain embodiments, the CDRs of an antibody can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817;

Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the instant disclosure provides an isolated antibody that specifically binds to OX40 (e.g., human OX40), the antibody comprising the Chothia V H CDRs of a VH disclosed in Table 2 herein. In certain embodiments, the instant disclosure provides an isolated antibody that specifically binds to OX40 (e.g., human OX40), the antibody comprising the Chothia V L CDRs of a VL disclosed in Table 2 herein. In certain embodiments, the instant disclosure provides an isolated antibody that specifically binds to OX40 (e.g., human OX40), the antibody comprising the Chothia V H CDRs and Chothia V L CDRs of an antibody disclosed in Table 2 herein. In certain embodiments, antibodies that specifically bind to OX40 (e.g., human OX40) comprise one or more CDRs, in which the Chothia and Kabat CDRs have the same amino acid sequence. In certain embodiments, the instant disclosure provides an isolated antibody that specifically binds to OX40 (e.g., human OX40) and comprises combinations of Kabat CDRs and Chothia CDRs.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212, each of which is herein incorporated by reference in its entirety. In certain embodiments, the instant disclosure provides antibodies that specifically bind to OX40 (e.g., human OX40) and comprise CDRs of an antibody disclosed in Table 2 herein, as determined by the IMGT numbering system, for example, as described in Lefranc M-P (1999) supra and Lefranc M-P et al., (1999) supra.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to OX40 (e.g., human OX40) and comprise CDRs of an antibody disclosed in Table 2 herein as determined by the AbM numbering scheme.

In certain embodiments, the CDRs of an antibody can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in *Antibody Engineering*, Kontermann and Dithel, eds., Chapter 31, pp. 422-439, Springer-Verlag, Berlin (2001), herein incorporated by reference in its entirety. In a particular embodiment, the instant disclosure provides antibodies that specifically bind to OX40 (e.g., human OX40) and comprise CDRs of an antibody disclosed in Table 2 herein as determined by the MacCallum numbering scheme.

In certain embodiments, the instant disclosure provides an isolated antibody that specifically binds to OX40 (e.g., human OX40), wherein the antibody comprises a heavy chain variable region comprising the CDRH1, CDRH2, and CDRH3 region amino acid sequences of a heavy chain variable region set forth in SEQ ID NO: 1, 2, 3, 4, 5, 6, 7, 8, 9, or 10, and a light chain variable region comprising the CDRL1, CDRL2, and CDRL3 region amino acid sequences of a light chain variable region set forth in SEQ ID NO: 11, 12, 13, 14, or 15, wherein each CDR is defined in accordance with the MacCallum definition, the Kabat definition, the Chothia definition, the combination of the Kabat definition and the Chothia definition, the IMGT numbering system, or the AbM definition of CDR.

In certain embodiments, the instant disclosure provides an isolated antibody that specifically binds to OX40 (e.g., human OX40), the antibody comprising:
(a) a CDRH1 comprises the amino acid sequence of $X_1X_2X_3MH$ (SEQ ID NO: 41), wherein
 $X_1$ is G, Q, H, or E,
 $X_2$ is S, E, or Y, and
 $X_3$ is A, S, or G; and/or
(b) a CDRH2 comprises the amino acid sequence of RIRSK$X_1X_2X_3X_4X_5$TAYAASVKG (SEQ ID NO: 42), wherein
 $X_1$ is A, S, or Y,
 $X_2$ is N, E, or Y,
 $X_3$ is S, Q, or G,
 $X_4$ is Y, E, or Q, and
 $X_5$ is A, E, or L; and/or
(c) a CDRH3 comprises the amino acid sequence of GI$X_1X_2X_3X_4X_5X_6X_7$Y (SEQ ID NO: 43), wherein
 $X_1$ is Y or A,
 $X_2$ is D or A,
 $X_3$ is S, T, or W,
 $X_4$ is S, E, or L,
 $X_5$ is G or A,
 $X_6$ is Y or A, and
 $X_7$ is D or A; and/or
(d) a CDRL1 comprises the amino acid sequence of RSSQSLLHSNGYNYLD (SEQ ID NO: 32); and/or
(e) a CDRL2 comprises the amino acid sequence of LGSNRAS (SEQ ID NO: 33); and/or
(f) a CDRL3 comprises the amino acid sequence of MQ$X_1X_2X_3X_4$PLT (SEQ ID NO: 46), wherein
 $X_1$ is A or G,
 $X_2$ is L or S,
 $X_3$ is Q or K, and
 $X_4$ is T or W,
and wherein the CDRH1, CDRH2, CDRH3, CDRL1, CDRL2, and CDRL3 sequences of the antibody are not SEQ ID NOs: 16, 21, 25, 32, 33, and 34, respectively.

In certain embodiments, the instant disclosure provides an isolated antibody that specifically binds to OX40 (e.g., human OX40), the antibody comprising:
(a) a CDRH1 comprises the amino acid sequence of $X_1X_2X_3MH$ (SEQ ID NO: 41), wherein
 $X_1$ is G, Q, H, or E,
 $X_2$ is S, E, or Y, and
 $X_3$ is A, S, or G; and/or (b) a CDRH2 comprises the amino acid sequence of RIRSKX$_1$X$_2$X$_3$X$_4$X$_5$TAYAASVKG (SEQ ID NO: 42), wherein
  X$_1$ is A, S, or Y,
  X$_2$ is N, E, or Y,
  X$_3$ is S, Q, or G,
  X$_4$ is Y, E, or Q, and
  X$_5$ is A, E, or L; and/or
(c) a CDRH3 comprises the amino acid sequence of GIX$_1$X$_2$X$_3$X$_4$X$_5$X$_6$X$_7$Y (SEQ ID NO: 43), wherein
  X$_1$ is Y or A,
  X$_2$ is D or A,
  X$_3$ is S, T, or W,
  X$_4$ is S, E, or L,
  X$_5$ is G or A,
  X$_6$ is Y or A, and
  X$_7$ is D or A; and/or
(d) a CDRL1 comprises the amino acid sequence of RSSQSLLHSNGYNYLD (SEQ ID NO: 32); and/or
(e) a CDRL2 comprises the amino acid sequence of LGSNRAS (SEQ ID NO: 33); and/or
(f) a CDRL3 comprises the amino acid sequence of MQX$_1$X$_2$X$_3$X$_4$PLT (SEQ ID NO: 46), wherein
  X$_1$ is A or G,
  X$_2$ is L or S,
  X$_3$ is Q or K, and
  X$_4$ is T or W,
and wherein the CDRH1, CDRH2, CDRH3, CDRL1, CDRL2, and CDRL3 sequences of the antibody are not SEQ ID NOs: 16, 21, 25, 32, 33, and 38, respectively.

In certain embodiments, the instant disclosure provides an isolated antibody that specifically binds to OX40 (e.g., human OX40), the antibody comprising:
(a) a CDRH1 comprises the amino acid sequence of X$_1$X$_2$X$_3$MH (SEQ ID NO: 41), wherein
  X$_1$ is G, Q, H, or E,
  X$_2$ is S, E, or Y, and
  X$_3$ is A, S, or G; and/or
(b) a CDRH2 comprises the amino acid sequence of RIRSKX$_1$X$_2$X$_3$X$_4$X$_5$TAYAASVKG (SEQ ID NO: 42), wherein
  X$_1$ is A, S, or Y,
  X$_2$ is N, E, or Y,
  X$_3$ is S, Q, or G,
  X$_4$ is Y, E, or Q, and
  X$_5$ is A, E, or L; and/or
(c) a CDRH3 comprises the amino acid sequence of GIX$_1$X$_2$X$_3$X$_4$X$_5$X$_6$X$_7$Y (SEQ ID NO: 43), wherein
  X$_1$ is Y or A,
  X$_2$ is D or A,
  X$_3$ is S, T, or W,
  X$_4$ is S, E, or L,
  X$_5$ is G or A,
  X$_6$ is Y or A, and
  X$_7$ is D or A; and/or
(d) a CDRL1 comprises the amino acid sequence of RSSQSLLHSNGYNYLD (SEQ ID NO: 32); and/or
(e) a CDRL2 comprises the amino acid sequence of LGSNRAS (SEQ ID NO: 33); and/or
(f) a CDRL3 comprises the amino acid sequence of MQX$_1$X$_2$X$_3$X$_4$PLT (SEQ ID NO: 46), wherein
  X$_1$ is A or G,
  X$_2$ is L or S,
  X$_3$ is Q or K, and
  X$_4$ is T or W,
and wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38.

In certain embodiments, CDRH2 comprises the amino acid sequence of RIRSKAXSYATAYAASVKG (SEQ ID NO: 44), wherein: X is N or Y. In certain embodiments, CDRH3 comprises the amino acid sequence of GIX$_1$X$_2$SSGX$_3$X$_4$Y (SEQ ID NO: 45), wherein: X$_1$ is Y or A; X$_2$ is D or A; X$_3$ is Y or A; and X$_4$ is D or A. In certain embodiments, CDRH1 comprises an amino acid sequence selected from the group consisting of SEQ ID NOs: 16-20. In certain embodiments, CDRH2 comprises an amino acid sequence selected from the group consisting of SEQ ID NOs: 21-24. In certain embodiments, CDRH3 comprises an amino acid sequence selected from the group consisting of SEQ ID NOs: 25-31. In certain embodiments, CDRL3 comprises an amino acid sequence selected from the group consisting of SEQ ID NOs: 34-38.

In certain embodiments, the instant disclosure provides an isolated antibody that specifically binds to OX40 (e.g., human OX40), wherein the antibody comprises a heavy chain variable region comprising the CDRH1, CDRH2 and CDRH3 amino acid sequences set forth in SEQ ID NOs: 16, 21, and 25; 16, 22, and 25; 16, 21, and 26; 16, 21, and 27; 16, 21, and 28; 16, 21, and 29; 17, 21, and 30; 18, 23, and 25; 19, 24, and 25; or 20, 21, and 31, respectively, and wherein the CDRH1, CDRH2, CDRH3, CDRL1, CDRL2, and CDRL3 sequences of the antibody are not SEQ ID NOs: 16, 21, 25, 32, 33, and 34, respectively.

In certain embodiments, the instant disclosure provides an isolated antibody that specifically binds to OX40 (e.g., human OX40), wherein the antibody comprises a heavy chain variable region comprising the CDRH1, CDRH2 and CDRH3 amino acid sequences set forth in SEQ ID NOs: 16, 21, and 25; 16, 22, and 25; 16, 21, and 26; 16, 21, and 27; 16, 21, and 28; 16, 21, and 29; 17, 21, and 30; 18, 23, and 25; 19, 24, and 25; or 20, 21, and 31, respectively, and wherein the CDRH1, CDRH2, CDRH3, CDRL1, CDRL2, and CDRL3 sequences of the antibody are not SEQ ID NOs: 16, 21, 25, 32, 33, and 38, respectively.

In certain embodiments, the instant disclosure provides an isolated antibody that specifically binds to OX40 (e.g., human OX40), wherein the antibody comprises a heavy chain variable region comprising the CDRH1, CDRH2 and CDRH3 amino acid sequences set forth in SEQ ID NOs: 16, 21, and 25; 16, 22, and 25; 16, 21, and 26; 16, 21, and 27; 16, 21, and 28; 16, 21, and 29; 17, 21, and 30; 18, 23, and 25; 19, 24, and 25; or 20, 21, and 31, respectively, and wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38.

In certain embodiments, the instant disclosure provides an isolated antibody that specifically binds to OX40 (e.g., human OX40), wherein the antibody comprises a light chain variable region comprising the CDRL1, CDRL2 and CDRL3 amino acid sequences set forth in SEQ ID NOs: 32, 33, and 34; 32, 33, and 35; 32, 33, and 36; 32, 33, and 37; or 32, 33, and 38, respectively, and wherein the CDRH1, CDRH2, CDRH3, CDRL1, CDRL2, and CDRL3 sequences of the antibody are not SEQ ID NOs: 16, 21, 25, 32, 33, and 34, respectively.

In certain embodiments, the instant disclosure provides an isolated antibody that specifically binds to OX40 (e.g., human OX40), wherein the antibody comprises a light chain variable region comprising the CDRL1, CDRL2 and CDRL3 amino acid sequences set forth in SEQ ID NOs: 32, 33, and 34; 32, 33, and 35; 32, 33, and 36; 32, 33, and 37;

or 32, 33, and 38, respectively, and wherein the CDRH1, CDRH2, CDRH3, CDRL1, CDRL2, and CDRL3 sequences of the antibody are not SEQ ID NOs: 16, 21, 25, 32, 33, and 38, respectively.

In certain embodiments, the instant disclosure provides an isolated antibody that specifically binds to OX40 (e.g., human OX40), wherein the antibody comprises a light chain variable region comprising the CDRL1, CDRL2 and CDRL3 amino acid sequences set forth in SEQ ID NOs: 32, 33, and 34; 32, 33, and 35; 32, 33, and 36; 32, 33, and 37; or 32, 33, and 38, respectively, and wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38.

In certain embodiments, the instant disclosure provides an isolated antibody that specifically binds to OX40 (e.g., human OX40), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 16, 22, 25, 32, 33, and 34; 16, 21, 26, 32, 33, and 34; 16, 21, 27, 32, 33, and 34; 16, 21, 28, 32, 33, and 34; 16, 21, 29, 32, 33, and 34; 17, 21, 30, 32, 33, and 38; 18, 23, 25, 32, 33, and 38; 19, 24, 25, 32, 33, and 38; 20, 21, 31, 32, 33, and 38; 16, 21, 25, 32, 33, and 35; 16, 21, 25, 32, 33, and 36; or 16, 21, 25, 32, 33, and 37, respectively.

In certain embodiments, the instant disclosure provides an isolated antibody that specifically binds to OX40 (e.g., human OX40), comprising a heavy chain variable region comprising an amino acid sequence of SEQ ID NO: 47 or 48, wherein the CDRH1, CDRH2, CDRH3, CDRL1, CDRL2, and CDRL3 sequences of the antibody are not SEQ ID NOs: 16, 21, 25, 32, 33, and 34, respectively. In certain embodiments, the instant disclosure provides an isolated antibody that specifically binds to OX40 (e.g., human OX40), comprising a heavy chain variable region comprising an amino acid sequence of SEQ ID NO: 47 or 48, wherein the CDRH1, CDRH2, CDRH3, CDRL1, CDRL2, and CDRL3 sequences of the antibody are not SEQ ID NOs: 16, 21, 25, 32, 33, and 38, respectively. In certain embodiments, the instant disclosure provides an isolated antibody that specifically binds to OX40 (e.g., human OX40), comprising a heavy chain variable region comprising an amino acid sequence of SEQ ID NO: 47 or 48, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38. In certain embodiments, the instant disclosure provides an isolated antibody that specifically binds to OX40 (e.g., human OX40), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, wherein the CDRH1, CDRH2, CDRH3, CDRL1, CDRL2, and CDRL3 sequences of the antibody are not SEQ ID NOs: 16, 21, 25, 32, 33, and 34, respectively. In certain embodiments, the instant disclosure provides an isolated antibody that specifically binds to OX40 (e.g., human OX40), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, wherein the CDRH1, CDRH2, CDRH3, CDRL1, CDRL2, and CDRL3 sequences of the antibody are not SEQ ID NOs: 16, 21, 25, 32, 33, and 38, respectively. In certain embodiments, the instant disclosure provides an isolated antibody that specifically binds to OX40 (e.g., human OX40), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38.

In certain embodiments, the antibody comprises a heavy chain variable region having the amino acid sequence set forth in SEQ ID NO: 1, 2, 3, 4, 5, 6, 7, 8, 9, or 10. In certain embodiments, the antibody comprises a heavy chain variable region having the amino acid sequence set forth in SEQ ID NO: 1. In certain embodiments, the antibody comprises a heavy chain variable region having the amino acid sequence set forth in SEQ ID NO: 2. In certain embodiments, the antibody comprises a heavy chain variable region having the amino acid sequence set forth in SEQ ID NO: 3. In certain embodiments, the antibody comprises a heavy chain variable region having the amino acid sequence set forth in SEQ ID NO: 4. In certain embodiments, the antibody comprises a heavy chain variable region having the amino acid sequence set forth in SEQ ID NO: 5. In certain embodiments, the antibody comprises a heavy chain variable region having the amino acid sequence set forth in SEQ ID NO: 6. In certain embodiments, the antibody comprises a heavy chain variable region having the amino acid sequence set forth in SEQ ID NO: 7. In certain embodiments, the antibody comprises a heavy chain variable region having the amino acid sequence set forth in SEQ ID NO: 8. In certain embodiments, the antibody comprises a heavy chain variable region having the amino acid sequence set forth in SEQ ID NO: 9. In certain embodiments, the antibody comprises a heavy chain variable region having the amino acid sequence set forth in SEQ ID NO: 10.

In certain embodiments, the instant disclosure provides an isolated antibody that specifically binds to OX40 (e.g., human OX40), comprising a light chain variable region comprising an amino acid sequence of SEQ ID NO: 49, wherein the CDRH1, CDRH2, CDRH3, CDRL1, CDRL2, and CDRL3 sequences of the antibody are not SEQ ID NOs: 16, 21, 25, 32, 33, and 34, respectively. In certain embodiments, the instant disclosure provides an isolated antibody that specifically binds to OX40 (e.g., human OX40), comprising a light chain variable region comprising an amino acid sequence of SEQ ID NO: 49, wherein the CDRH1, CDRH2, CDRH3, CDRL1, CDRL2, and CDRL3 sequences of the antibody are not SEQ ID NOs: 16, 21, 25, 32, 33, and 38, respectively. In certain embodiments, the instant disclosure provides an isolated antibody that specifically binds to OX40 (e.g., human OX40), comprising a light chain variable region comprising an amino acid sequence of SEQ ID NO: 49, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38. In certain embodiments, the instant disclosure provides an isolated antibody that specifically binds to OX40 (e.g., human OX40), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the antibody are not SEQ ID NOs: 16, 21, 25, 32, 33, and 34, respectively. In certain embodiments, the instant disclosure provides an isolated antibody that specifically binds to OX40 (e.g., human OX40), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the antibody are not SEQ ID NOs: 16, 21, 25, 32, 33, and 38, respectively. In certain embodiments, the instant disclosure provides an isolated antibody that specifically binds to OX40 (e.g., human OX40), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38. In certain embodiments, the antibody comprises a light chain variable region having the amino acid sequence set forth in SEQ ID NO: 11, 12, 13, 14, or 15. In certain embodiments, the antibody comprises a light chain variable region having the amino acid sequence set forth in SEQ ID NO: 11. In certain embodiments, the antibody comprises a light chain variable region having the amino acid sequence set forth in SEQ ID NO: 12. In certain embodiments, the antibody comprises a light chain variable region having the amino acid sequence set forth in SEQ ID NO: 13. In certain embodiments, the antibody comprises a light chain variable region having the amino acid sequence set forth in SEQ ID NO: 14. In certain embodiments, the antibody comprises a light chain variable region having the amino acid sequence set forth in SEQ ID NO: 15.

In certain embodiments, the instant disclosure provides an isolated antibody that specifically binds to OX40 (e.g., human OX40), comprising a heavy chain variable region comprising an amino acid sequence of SEQ ID NO: 47 or 48, and a light chain variable region comprising an amino acid sequence of SEQ ID NO: 49, wherein the CDRH1, CDRH2, CDRH3, CDRL1, CDRL2, and CDRL3 sequences of the antibody are not SEQ ID NOs: 16, 21, 25, 32, 33, and 34, respectively. In certain embodiments, the instant disclosure provides an isolated antibody that specifically binds to OX40 (e.g., human OX40), comprising a heavy chain variable region comprising an amino acid sequence of SEQ ID NO: 47 or 48, and a light chain variable region comprising an amino acid sequence of SEQ ID NO: 49, wherein the CDRH1, CDRH2, CDRH3, CDRL1, CDRL2, and CDRL3 sequences of the antibody are not SEQ ID NOs: 16, 21, 25, 32, 33, and 38, respectively. In certain embodiments, the instant disclosure provides an isolated antibody that specifically binds to OX40 (e.g., human OX40), comprising a heavy chain variable region comprising an amino acid sequence of SEQ ID NO: 47 or 48, and a light chain variable region comprising an amino acid sequence of SEQ ID NO: 49, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38. In certain embodiments, the instant disclosure provides an isolated antibody that specifically binds to OX40 (e.g., human OX40), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the antibody are not SEQ ID NOs: 16, 21, 25, 32, 33, and 34, respectively. In certain embodiments, the instant disclosure provides an isolated antibody that specifically binds to OX40 (e.g., human OX40), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the antibody are not SEQ ID NOs: 16, 21, 25, 32, 33, and 38, respectively. In certain embodiments, the instant disclosure provides an isolated antibody that specifically binds to OX40 (e.g., human OX40), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38. In certain embodiments, the antibody comprises a heavy chain variable region having the amino acid sequence set forth in SEQ ID NO: 1, 2, 3, 4, 5, 6, 7, 8, 9, or 10, and a light chain variable region having the amino acid sequence set forth in SEQ ID NO: 11, 12, 13, 14, or 15. In certain embodiments, the antibody comprises a heavy chain variable region and light chain variable region having the amino acid sequences set forth in SEQ ID NO: 2 and 11; 3 and 11; 4 and 11; 5 and 11; 6 and 11; 7 and 15; 8 and 15; 9 and 15; 10 and 15; 1 and 12; 1 and 13; or 1 and 14, respectively. In certain embodiments, the antibody comprises a heavy chain variable region and light chain variable region having the amino acid sequences set forth in SEQ ID NO: 2 and 11, respectively. In certain embodiments, the antibody comprises a heavy chain variable region and light chain variable region having the amino acid sequences set forth in SEQ ID NO: 3 and 11, respectively. In certain embodiments, the antibody comprises a heavy chain variable region and light chain variable region having the amino acid sequences set forth in SEQ ID NO: 4 and 11, respectively. In certain embodiments, the antibody comprises a heavy chain variable region and light chain variable region having the amino acid sequences set forth in SEQ ID NO: 5 and 11, respectively. In certain embodiments, the antibody comprises a heavy chain variable region and light chain variable region having the amino acid sequences set forth in SEQ ID NO: 6 and 11, respectively. In certain embodiments, the antibody comprises a heavy chain variable region and light chain variable region having the amino acid sequences set forth in SEQ ID NO: 7 and 15, respectively. In certain embodiments, the antibody comprises a heavy chain variable region and light chain variable region having the amino acid sequences set forth in SEQ ID NO: 8 and 15, respectively. In certain embodiments, the antibody comprises a heavy chain variable region and light chain variable region having the amino acid sequences set forth in SEQ ID NO: 9 and 15, respectively. In certain embodiments, the antibody comprises a heavy chain variable region and light chain variable region having the amino acid sequences set forth in SEQ ID NO: 10 and 15, respectively. In certain embodiments, the antibody comprises a heavy chain variable region and light chain variable region having the amino acid sequences set forth in SEQ ID NO: 1 and 12, respectively. In certain embodiments, the antibody comprises a heavy chain variable region and light chain variable region having the amino acid sequences set forth in SEQ ID NO: 1 and 13, respectively. In certain embodiments, the antibody comprises a heavy chain variable region and light chain variable region having the amino acid sequences set forth in SEQ ID NO: 1 and 14, respectively.

In certain embodiments, the instant disclosure provides an isolated antibody that specifically binds to OX40 (e.g., human OX40), comprising a heavy chain variable region having an amino acid sequence derived from a human IGHV3-73 germline sequence (e.g., IGHV3-73*01, e.g., having the amino acid sequence of SEQ ID NO: 39), wherein the CDRH1, CDRH2, CDRH3, CDRL1, CDRL2, and CDRL3 sequences of the antibody are not SEQ ID NOs: 16, 21, 25, 32, 33, and 34, respectively. In certain embodiments, the instant disclosure provides an isolated antibody that specifically binds to OX40 (e.g., human OX40), comprising a heavy chain variable region having an amino acid sequence derived from a human IGHV3-73 germline sequence (e.g., IGHV3-73*01, e.g., having the amino acid sequence of SEQ ID NO: 39), wherein the CDRH1, CDRH2, CDRH3, CDRL1, CDRL2, and CDRL3 sequences of the antibody are not SEQ ID NOs: 16, 21, 25, 32, 33, and 38, respectively. In certain embodiments, the instant disclosure provides an isolated antibody that specifically binds to OX40 (e.g., human OX40), comprising a heavy chain variable region having an amino acid sequence derived from a human IGHV3-73 germline sequence (e.g., IGHV3-73*01, e.g., having the amino acid sequence of SEQ ID NO: 39), wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38. One or more regions selected from framework 1, framework 2, framework 3, CDRH1, and CDRH2 (e.g., two, three, four or five of these regions) can be derived from a human IGHV3-73 germline sequence (e.g., IGHV3-73*01, e.g., having the amino acid sequence of SEQ ID NO: 39). In one embodiment, framework 1, framework 2, framework 3, CDRH1, and CDRH2 are all derived from a human IGHV3-73 germline sequence (e.g., IGHV3-73*01, e.g., having the amino acid sequence of SEQ ID NO: 39).

In certain embodiments, the instant disclosure provides an isolated antibody that specifically binds to OX40 (e.g., human OX40), comprising a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the antibody are not SEQ ID NOs: 16, 21, 25, 32, 33, and 34, respectively. In certain embodiments, the instant disclosure provides an isolated antibody that specifically binds to OX40 (e.g., human OX40), comprising a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the antibody are not SEQ ID NOs: 16, 21, 25, 32, 33, and 38, respectively. In certain embodiments, the instant disclosure provides an isolated antibody that specifically binds to OX40 (e.g., human OX40), comprising a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38. One or more regions selected from framework 1, framework 2, framework 3, CDRL1, and CDRL2 (e.g., two, three, four or five of these regions) can be derived from a human IGKV2-28 germline sequence (e.g., IGKV2-28*01, e.g., having the amino acid sequence of SEQ ID NO: 40). In one embodiment, framework 1, framework 2, framework 3, CDRL1, and CDRL2 are all derived from a human IGKV2-28 germline sequence (e.g., IGKV2-28*01, e.g., having the amino acid sequence of SEQ ID NO: 40).

In certain embodiments, the instant disclosure provides an isolated antibody that specifically binds to OX40 (e.g., human OX40), comprising a heavy chain variable region having an amino acid sequence derived from a human IGHV3-73 germline sequence (e.g., IGHV3-73*01, e.g., having the amino acid sequence of SEQ ID NO: 39), and a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the antibody are not SEQ ID NOs: 16, 21, 25, 32, 33, and 34, respectively. In certain embodiments, the instant disclosure provides an isolated antibody that specifically binds to OX40 (e.g., human OX40), comprising a heavy chain variable region having an amino acid sequence derived from a human IGHV3-73 germline sequence (e.g., IGHV3-73*01, e.g., having the amino acid sequence of SEQ ID NO: 39), and a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the antibody are not SEQ ID NOs: 16, 21, 25, 32, 33, and 38, respectively. In certain embodiments, the instant disclosure provides an isolated antibody that specifically binds to OX40 (e.g., human OX40), comprising a heavy chain variable region having an amino acid sequence derived from a human IGHV3-73 germline sequence (e.g., IGHV3-73*01, e.g., having the amino acid sequence of SEQ ID NO: 39), and a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38.

In certain embodiments, the instant disclosure provides an isolated antibody, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38, and wherein the antibody cross-competes for binding to OX40 (e.g., human OX40) with an antibody described herein., e.g., an antibody comprising the heavy and light chain variable region amino acid sequences set forth in SEQ ID NOs: 2 and 11; 3 and 11; 4 and 11; 5 and 11; 6 and 11; 7 and 15; 8 and 15; 9 and 15; 10 and 15; 1 and 12; 1 and 13; or 1 and 14, respectively.

In certain embodiments, the instant disclosure provides an isolated antibody, wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38, and wherein the antibody binds to the same or an overlapping epitope of OX40 (e.g., an epitope of human OX40) as an antibody described herein, e.g., an antibody comprising the heavy and light chain variable region amino acid sequences set forth in SEQ ID NOs: 2 and 11; 3 and 11; 4 and 11; 5 and 11; 6 and 11; 7 and 15; 8 and 15; 9 and 15; 10 and 15; 1 and 12; 1 and 13; or 1 and 14, respectively.

As further provided herein, antibodies that bind to OX40 can increase OX40 activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to OX40 activity without any antibody or with an unrelated antibody (e.g., an antibody that does not bind to OX40). For instance, an antibody that binds to OX40, e.g., an antibody that binds to OX40 and comprises a combination of CDR sequences specified herein, a VH and/or VL sequence having at least 70%, at least 75%, at least 80%, at least 85%, at least 90%, at least 95%, at least 98%, at least 99%, or 100% sequence identity with VH and/or VL sequences specified herein, or heavy and/or light chains specified herein, can increase OX40 (e.g., human OX40) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to OX40 (e.g., human OX40) activity without any antibody or with an unrelated antibody (e.g., an antibody that does not bind to OX40). Non-limiting examples of OX40 (e.g., human OX40) activity can include OX40 (e.g., human OX40) signaling, OX40 (e.g., human OX40) binding to OX40 (e.g., human OX40) ligand, cell proliferation, cell survival, and cytokine production (e.g., IL-2, TNF-α, IFN-γ, IL-4, IL-10, and/or IL-13).

As further provided herein, antibodies that bind to OX40 can agonize OX40 function, for example, by stimulating T cell activation. For instance, an antibody that binds to OX40, e.g., an antibody that binds to OX40 and comprises a combination of CDR sequences specified herein, a VH and/or VL sequence having at least 70%, at least 75%, at least 80%, at least 85%, at least 90%, at least 95%, at least 98%, at least 99%, or 100% sequence identity with VH and/or VL sequences specified herein, or heavy and/or light chains specified herein, can stimulate T cell activation, optionally wherein T cell activation is a substantially increasing function of antibody concentrations.

As further provided herein, antibodies that bind to OX40 can agonize OX40 function, for example, by stimulating IL-2 release in an SEA assay. For instance, an antibody that binds to OX40, e.g., an antibody that binds to OX40 and comprises a combination of CDR sequences specified herein, a VH and/or VL sequence having at least 70%, at least 75%, at least 80%, at least 85%, at least 90%, at least 95%, at least 98%, at least 99%, or 100% sequence identity with VH and/or VL sequences specified herein, or heavy and/or light chains specified herein, can, in combination with *Staphylococcus* Enterotoxin A (SEA) (e.g., 100 ng/ml), induce IL-2 production in, e.g., PBMCs upon stimulation for, e.g., 5 days at, e.g., 37° C., 5% $CO_2$, and 97% humidity, as measured by, e.g., electrochemiluminescence. In some embodiments, the IL-2 production is a substantially increasing function of antibody concentrations. In certain embodiments, an antibody that binds to OX40, e.g., an antibody that binds to OX40 and comprises a combination of CDR sequences specified herein, a VH and/or VL sequence having at least 70%, at least 75%, at least 80%, at least 85%, at least 90%, at least 95%, at least 98%, at least 99%, or 100% sequence identity with VH and/or VL sequences specified herein, or heavy and/or light chains specified herein, can, in combination with *Staphylococcus* Enterotoxin A (SEA), induce IL-2 production in, e.g., PBMCs, optionally wherein the IL-2 production is a substantially increasing function of antibody concentrations as assessed in, e.g., an assay comprising the following steps: (a) culturing the PBMCs (e.g., $10^5$ cells in a well) in the absence or presence of varying concentrations of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence.

As further provided herein, antibodies that bind to OX40 can agonize OX40 function, for example, by stimulating NF-κB signaling. For instance, an antibody that binds to OX40, e.g., an antibody that binds to OX40 and comprises a combination of CDR sequences specified herein, a VH and/or VL sequence having at least 70%, at least 75%, at least 80%, at least 85%, at least 90%, at least 95%, at least 98%, at least 99%, or 100% sequence identity with VH and/or VL sequences specified herein, or heavy and/or light chains specified herein, can stimulate NF-κB signaling, e.g., in a Jurkat-huOX40-NF-κB-luciferase reporter assay as described in the examples herein, optionally wherein the NF-κB signaling is a substantially increasing function of antibody concentrations.

As further provided herein, antibodies that bind to OX40 can decrease OX40 activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to OX40 activity without any antibody or with an unrelated antibody (e.g., an antibody that does not bind to OX40). For instance, an antibody that binds to OX40, e.g., an antibody that binds to OX40 and comprises a combination of CDR sequences specified herein, a VH and/or VL sequence having at least 70%, at least 75%, at least 80%, at least 85%, at least 90%, at least 95%, at least 98%, at least 99%, or 100% sequence identity with VH and/or VL sequences specified herein, or heavy and/or light chains specified herein, can decrease OX40 (e.g., human OX40) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to OX40 (e.g., human OX40) activity without any antibody or with an unrelated antibody (e.g., an antibody that does not bind to OX40). Non-limiting examples of OX40 (e.g., human OX40) activity can include OX40 (e.g., human OX40) signaling, OX40 (e.g., human OX40) binding to OX40 (e.g., human OX40) ligand, cell proliferation, cell survival, and cytokine production (e.g., IL-2, TNF-α, IFN-γ, IL-4, IL-10, and/or IL-13).

5.2.2 Anti-GITR Antibodies

In a specific aspect, provided herein is an antibody (e.g., a monoclonal antibody, such as a chimeric, humanized, or human antibody) that specifically binds to GITR (e.g., human GITR). Also provided herein is a multispecific antibody that comprises a first antigen-binding domain that specifically binds to GITR (e.g., human GITR) and, optionally, a second antigen-binding domain that does not specifically bind to GITR (e.g., human GITR).

The amino acid sequences of exemplary antibodies are set forth in Tables 7-10, herein.

TABLE 7

Amino acid sequences of exemplary anti-GITR antibodies.*

| SEQ ID NO: | Description* | Amino acid Sequence |
|---|---|---|
| 52 | pab1876 VH | QVQLVQSGAEVKKPGASVKVSCKGSYTFTDYAMYWVRQAPGQGLEWIGVIRTYSGDVTYNQKFKDRATMTVDKSISTAYMELSRLRSDDTAVYYCAKSGTVRGFAYWGQGTLVTVSS |
| 53 | pab1876 VH D57G | QVQLVQSGAEVKKPGASVKVSCKGSYTFTDYAMYWVRQAPGQGLEWIGVIRTYSGGVTYNQKFKDRATMTVDKSISTAYMELSRLRSDDTAVYYCAKSGTVRGFAYWGQGTLVTVSS |
| 95 | pab1876 VH R103A | QVQLVQSGAEVKKPGASVKVSCKGSYTFTDYAMYWVRQAPGQGLEWIGVIRTYSGDVTYNQKFKDRATMTVDKSISTAYMELSRLRSDDTAVYYCAKSGTVAGFAYWGQGTLVTVSS |
| 54 | pab1967 VH | QVQLVQSGAEVKKPGASVKVSCKGSYTFTGYAMHWVRQAPGQGLEWMGLIRTYSGGVSYNQKFRERATMTVDTSISTAYMELSRLRSDDTAVYYCAKSGTVRGFAYWGQGTLITVSS |
| 55 | pab1975 VH | QVQLVQSGAEVKKPGASVKVSCKASGYTFTEYAMHWVRQAPGQGLEWMGLIRTYSGGVSYNQKFQGRATMTVDTSISTAYMELSRLRSDDTAVYYCAKSGTVRGFAYWGQGTLVTVSS |
| 56 | pab1979 VH | QVQLVQSGAEVKKPGASVKVSCKASGYTFTEYAMHWVRQAPGQGLEWMGVIRTYSGGVSYNQKFQERVTMTVDTSISTAYMELSRLRSDDTAVYYCAKSGTVRGFAYWGQGTLVTVSS |
| 57 | pab1876 VL | DIVMTQSPDSLAVSLGERATINCKSSQSLLNSGNQKNYLTWYQQKPGQPPKLLIYWASTRESGVPDRFSGSGSGTDFTLTISSLQAEDVAVYHCQNDYSYPYTFGQGTKLEIK |
| 96 | pab1876 VL D97A | DIVMTQSPDSLAVSLGERATINCKSSQSLLNSGNQKNYLTWYQQKPGQPPKLLIYWASTRESGVPDRFSGSGSGTDFTLTISSLQAEDVAVYHCQNAYSYPYTFGQGTKLEIK |
| 58 | pab1967 VL | DIVMTQSPDSLAVSLGERATINCKSSQSLLNSSNQKNYLTWYQQKPGQPPKLLIYWASTRESGVPDRFSGSGSGTDFTLTISSVQAEDVAVYHCQNEYSFPYTFGQGTKLEIK |
| 59 | pab1975/pab1979 | DIVMTQSPDSLAVSLGERATINCKSSQSLLNSGNQKNYLTWYQQKPGQPPKLLIYWASTRESGVPDRFSGSGSGTDFTLTISSLQAEDVAVYYCQNDYSYPYTFGQGTKLEIK |

TABLE 7-continued

Amino acid sequences of exemplary anti-GITR antibodies.*

| SEQ ID NO: | Description* | Amino acid Sequence |
|---|---|---|
| | VL | TDFTLTISSLQAEDVAVYYCQNDYSYPYTFGQGTKLEIK |
| 60 | VH CDR1 | DYAMY |
| 61 | VH CDR1 | GYAMH |
| 62 | VH CDR1 | EYAMH |
| 63 | VH CDR2 | VIRTYSGDVTYNQKFKD |
| 64 | VH CDR2 | VIRTYSGGVTYNQKFKD |
| 65 | VH CDR2 | LIRTYSGGVSYNQKFRE |
| 66 | VH CDR2 | LIRTYSGGVSYNQKFQG |
| 67 | VH CDR2 | VIRTYSGGVSYNQKFQE |
| 68 | VH CDR3 | SGTVRGFAY |
| 97 | VH CDR3 | SGTVAGFAY |
| 69 | VL CDR1 | KSSQSLLNSGNQKNYLT |
| 70 | VL CDR1 | KSSQSLLNSSNQKNYLT |
| 71 | VL CDR2 | WASTRES |
| 72 | VL CDR3 | QNDYSYPYT |
| 98 | VL CDR3 | QNAYSYPYT |
| 73 | VL CDR3 | QNEYSFPYT |
| 74 | GITR VH germ-line | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCAR |
| 75 | GITR VL germ-line | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTP |
| 76 | CDRH1 consensus sequence 1 | $X_1YX_2MX_3$, wherein $X_1$ is D, E or G; $X_2$ is A or V; and $X_3$ is Y or H |
| 77 | CDRH2 consensus sequence 1 | $X_1IX_2TX_3SGX_4X_5X_6YNQKFX_7X_8$, wherein $X_1$ is V or L; $X_2$ is R, K or Q; $X_3$ is Y or F; $X_4$ is D, E or G; $X_5$ is V or L; $X_6$ is T or S; $X_7$ is K, R or Q; and $X_8$ is D, E or G |
| 99 | CDRH3 consensus sequence 1 | SGTVXGFAY, wherein X is R or A |
| 78 | CDRH1 consensus | $X_1YAMX_2$, wherein $X_1$ is D, G, or E, and |

TABLE 7-continued

Amino acid sequences of exemplary anti-GITR antibodies.*

| SEQ ID NO: | Description* | Amino acid Sequence |
|---|---|---|
|  | sequence 2 | $X_2$ is Y or H |
| 79 | CDRH2 consensus sequence 2 | $X_1$IRTYSGX$_2$VX$_3$YNQKFX$_4$X$_5$, wherein $X_1$ is V or L; $X_2$ is D or G; $X_3$ is T or S; $X_4$ is K, R, or Q; and $X_5$ is D, E, or G |
| 80 | CDRL1 consensus sequence 1 | KSSQSLLNSX$_1$NQKNYLX$_2$, wherein $X_1$ is G or S; and $X_2$ is T or S |
| 81 | CDRL3 consensus sequence 1 | QNX$_1$YSX$_2$PYT, wherein $X_1$ is D, E, or A; and $X_2$ is Y, F, or S |
| 82 | CDRL1 consensus sequence 2 | KSSQSLLNSXNQKNYLT, wherein X is G or S |
| 83 | CDRL3 consensus sequence 2 | QNX$_1$YSX$_2$PYT, wherein $X_1$ is D, E, or A; and $X_2$ is Y or F |
| 84 | VH consensus | QVQLVQSGAEVKKPGASVKVSCKX$_1$SGYTFTX$_2$YAMX$_3$WVRQAPGQGLEWX$_4$GX$_5$IRTYSGX$_6$VX$_7$YNQKFX$_8$X$_9$RX$_{10}$TMTVDX$_{11}$SISTAYMELSRLRSDDTAVYYCAKSGTVX$_{12}$GFAYWGQGTLX$_{13}$TVSS<br>$X_1$ is G or A;<br>$X_2$ is D, G, or E;<br>$X_3$ is Y or H;<br>$X_4$ is I or M;<br>$X_5$ is V or L;<br>$X_6$ is D or G;<br>$X_7$ is T or S;<br>$X_8$ is K, R, or Q;<br>$X_9$ is D, E, or G;<br>$X_{10}$ is A or V;<br>$X_{11}$ is K or T;<br>$X_{12}$ is R or A; and<br>$X_{13}$ is V or I |
| 85 | VL consensus | DIVMTQSPDSLAVSLGERATINCKSSQSLLNSX$_1$NQKNYLTWYQQKPGQPPKLLIYWASTRESGVPDRFX$_2$GSGSGTDFTLTISSX$_3$QAEDVAVYX$_4$CQNX$_5$YSX$_6$PYTFGQGTKLEIK<br>$X_1$ is G or S;<br>$X_2$ is S or T;<br>$X_3$ is L or V;<br>$X_4$ is H or Y;<br>$X_5$ is D, E, or A; and<br>$X_6$ is Y or F |
| 86 | pab1876 heavy chain (IgG1) | QVQLVQSGAEVKKPGASVKVSCKGSGYTFTDYAMYWVRQAPGQGLEWIGVIRTYSGDVTYNQKFKDRATMTVDKSISTAYMELSRLRSDDTAVYYCAKSGTVRGFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 87 | pab1876 light chain | DIVMTQSPDSLAVSLGERATINCKSSQSLLNSGNQKNYLTWYQQKPGQPPKLLIYWASTRESGVPDRFSGSGSGTDFTLTISSLQAEDVAVYHCQNDYSYPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

*CDRs are defined according to the Kabat numbering system.

TABLE 8

Heavy chain CDR amino acid sequences of exemplary anti-GITR antibodies.*

| VH (SEQ ID NO:) | VH CDR1 (SEQ ID NO:) | VH CDR2 (SEQ ID NO:) | VH CDR3 (SEQ ID NO:) |
|---|---|---|---|
| pab1876 VH (52) | DYAMY (60) | VIRTYSGDVTYNQKFKD (63) | SGTVRGFAY (68) |
| pab1876 VH D57G (53) | DYAMY (60) | VIRTYSGGVTYNQKFKD (64) | SGTVRGFAY (68) |
| pab1876 VH R103A (95) | DYAMY (60) | VIRTYSGDVTYNQKFKD (63) | SGTVAGFAY (97) |
| pab1967 VH (54) | GYAMH (61) | LIRTYSGGVSYNQKFRE (65) | SGTVRGFAY (68) |
| pab1975 VH (55) | EYAMH (62) | LIRTYSGGVSYNQKFQG (66) | SGTVRGFAY (68) |
| pab1979 VH (56) | EYAMH (62) | VIRTYSGGVSYNQKFQE (67) | SGTVRGFAY (68) |

*Defined according to the Kabat numbering system.

TABLE 9

Light chain CDR amino acid sequences of exemplary anti-GITR antibodies.*

| VL (SEQ ID NO:) | VL CDR1 (SEQ ID NO:) | VL CDR2 (SEQ ID NO:) | VL CDR3 (SEQ ID NO:) |
|---|---|---|---|
| pab1876 VL (57) | KSSQSLLNSGNQKNYLT (69) | WASTRES (71) | QNDYSYPYT (72) |
| pab1876 VL D97A (96) | KSSQSLLNSGNQKNYLT (69) | WASTRES (71) | QNAYSYPYT (98) |
| pab1967 VL (58) | KSSQSLLNSSNQKNYLT (70) | WASTRES (71) | QNEYSFPYT (73) |

TABLE 9-continued

Light chain CDR amino acid sequences of exemplary anti-GITR antibodies.*

| VL (SEQ ID NO:) | VL CDR1 (SEQ ID NO:) | VL CDR2 (SEQ ID NO:) | VL CDR3 (SEQ ID NO:) |
|---|---|---|---|
| pab1975/ pab1979 VL (59) | KSSQSLLNSGNQKNYLT (69) | WASTRES (71) | QNDYSYPYT (72) |

*Defined according to the Kabat numbering system.

TABLE 10

Heavy chain variable region (VH) and light chain variable region (VL) sequences of exemplary anti-GITR antibodies.

| Antibody | Heavy chain variable region | SEQ ID NO: | Light chain variable region | SEQ ID NO: |
|---|---|---|---|---|
| pab1876 | pab1876 VH | 52 | pab1876 VL | 57 |
| pab1876 D57G | pab1876 VH D57G | 53 | pab1876 VL | 57 |
| pab1876 R103A | pab1876 VH R103A | 95 | pab1876 VL | 57 |
| pab1876 D97A | pab1876 VH | 52 | pab1876 VL D97A | 96 |
| pab1967 | pab1967 VH | 54 | pab1967 VL | 58 |
| pab1975 | pab1975 VH | 55 | pab1975 VL | 59 |
| pab1979 | pab1979 VH | 56 | pab1979 VL | 59 |

TABLE 11

Closest germline genes for exemplary anti-GITR antibodies.

| Closest germline gene | SEQ ID NO: |
|---|---|
| IGHV1-2*02 | 74 |
| IGKV4-1*01 | 75 |

In certain embodiments, the instant disclosure provides an isolated antibody that specifically binds to GITR (e.g., human GITR), the antibody comprising a heavy chain variable region comprising one, two, or all three of the CDRs of a heavy chain variable region set forth in Table 7 herein. In certain embodiments, the antibody comprises the CDRH1 of one of heavy chain variable regions set forth in Table 7. In certain embodiments, the antibody comprises the CDRH2 of one of the heavy chain variable regions set forth in Table 7. In certain embodiments, the antibody comprises the CDRH3 of one of the heavy chain variable regions set forth in Table 7.

In certain embodiments, the instant disclosure provides an isolated antibody that specifically binds to GITR (e.g., human GITR), the antibody comprising a light chain variable region comprising one, two, or all three of the CDRs of a light chain variable region disclosed in Table 7 herein. In certain embodiments, the antibody comprises the CDRL1 of one of light chain variable regions set forth in Table 7. In certain embodiments, the antibody comprises the CDRL2 of one of the light chain variable regions set forth in Table 7. In certain embodiments, the antibody comprises the CDRL3 of one of the light chain variable regions set forth in Table 7.

In certain embodiments, the instant disclosure provides an isolated antibody that specifically binds to GITR (e.g., human GITR), the antibody comprising the Chothia V H CDRs of a VH disclosed in Table 7 herein. In certain embodiments, the instant disclosure provides an isolated antibody that specifically binds to GITR (e.g., human GITR), the antibody comprising the Chothia V L CDRs of a VL disclosed in Table 7 herein. In certain embodiments, the instant disclosure provides an isolated antibody that specifically binds to GITR (e.g., human GITR), the antibody comprising the Chothia V H CDRs and Chothia V L CDRs of an antibody disclosed in Table 7 herein. In certain embodiments, antibodies that specifically bind to GITR (e.g., human GITR) comprise one or more CDRs, in which the Chothia and Kabat CDRs have the same amino acid sequence. In certain embodiments, the instant disclosure provides an isolated antibody that specifically binds to GITR (e.g., human GITR) and comprises combinations of Kabat CDRs and Chothia CDRs.

In certain embodiments, the instant disclosure provides antibodies that specifically bind to GITR (e.g., human GITR) and comprise CDRs of an antibody disclosed in Table 7 herein, as determined by the IMGT numbering system, for example, as described in Lefranc M-P (1999) supra and Lefranc M-P et al., (1999) supra.

In certain embodiments, the instant disclosure provides antibodies that specifically bind to GITR (e.g., human GITR) and comprise CDRs of an antibody disclosed in Table 7 herein as determined by the AbM numbering scheme.

In certain embodiments, the instant disclosure provides antibodies that specifically bind to GITR (e.g., human GITR) and comprise CDRs of an antibody disclosed in Table 7 herein as determined by the MacCallum numbering scheme.

In certain embodiments, the instant disclosure provides an isolated antibody that specifically binds to GITR (e.g., human GITR), wherein the antibody comprises a heavy chain variable region comprising the CDRH1, CDRH2, and CDRH3 region amino acid sequences of a heavy chain variable region set forth in SEQ ID NO: 52, 53, 54, 55, 56, or 95, and a light chain variable region comprising the CDRL1, CDRL2, and CDRL3 region amino acid sequences of a light chain variable region set forth in SEQ ID NO: 57, 58, 59, or 96, wherein each CDR is defined in accordance with the MacCallum definition, the Kabat definition, the Chothia definition, the combination of the Kabat definition and the Chothia definition, the IMGT numbering system, or the AbM definition of CDR.

In certain embodiments, the instant disclosure provides an isolated antibody that specifically binds to GITR (e.g., human GITR), wherein the antibody comprises a heavy chain variable region comprising the CDRH1, CDRH2 and CDRH3 amino acid sequences set forth in SEQ ID NOs: 60, 63, and 68; 60, 64, and 68; 60, 63, and 97; 61, 65, and 68; 62, 66, and 68; or 62, 67, and 68, respectively.

In certain embodiments, the instant disclosure provides an isolated antibody that specifically binds to GITR (e.g., human GITR), wherein the antibody comprises a light chain variable region comprising the CDRL1, CDRL2 and CDRL3 amino acid sequences set forth in SEQ ID NOs: 69, 71, and 72; 69, 71, and 98; 70, 71, and 73; or 69, 71, and 72, respectively.

In certain embodiments, the instant disclosure provides an isolated antibody that specifically binds to GITR (e.g., human GITR), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 60, 64, 68, 69, 71, and 72; 60, 63, 97, 69, 71, and 72; 60, 63, 68, 69, 71, and 98, respectively.

In certain embodiments, the instant disclosure provides an isolated antibody that specifically binds to GITR (e.g., human GITR), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 52, 53, 54, 55, 56, or 95. In certain embodiments, the antibody comprises a heavy chain variable region having the amino acid sequence set forth in SEQ ID NO: 52, 53, 54, 55, 56, or 95. In certain embodiments, the antibody comprises a heavy chain variable region having the amino acid sequence set forth in SEQ ID NO: 52. In certain embodiments, the antibody comprises a heavy chain variable region having the amino acid sequence set forth in SEQ ID NO: 53. In certain embodiments, the antibody comprises a heavy chain variable region having the amino acid sequence set forth in SEQ ID NO: 95.

In certain embodiments, the instant disclosure provides an isolated antibody that specifically binds to GITR (e.g., human GITR), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 57, 58, 59, or 96. In certain embodiments, the antibody comprises a light chain variable region having the amino acid sequence set forth in SEQ ID NO: 57, 58, 59, or 96. In certain embodiments, the antibody comprises a light chain variable region having the amino acid sequence set forth in SEQ ID NO: 57. In certain embodiments, the antibody comprises a light chain variable region having the amino acid sequence set forth in SEQ ID NO: 96.

In certain embodiments, the instant disclosure provides an isolated antibody that specifically binds to GITR (e.g., human GITR), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 52, 53, 54, 55, 56, or 95, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 57, 58, 59, or 96. In certain embodiments, the antibody comprises a heavy chain variable region having the amino acid sequence set forth in SEQ ID NO: 52, 53, 54, 55, 56, or 95, and a light chain variable region having the amino acid sequence set forth in SEQ ID NO: 57, 58, 59, or 96. In certain embodiments, the antibody comprises a heavy chain variable region and light chain variable region having the amino acid sequences set forth in SEQ ID NO: 53 and 57; 95 and 57; 52 and 96, respectively. In certain embodiments, the antibody comprises a heavy chain variable region and light chain variable region having the amino acid sequences set forth in SEQ ID NO: 53 and 57, respectively. In certain embodiments, the antibody comprises a heavy chain variable region and light chain variable region having the amino acid sequences set forth in SEQ ID NO: 95 and 57, respectively. In certain embodiments, the antibody comprises a heavy chain variable region and light chain variable region having the amino acid sequences set forth in SEQ ID NO: 52 and 96, respectively.

As further provided herein, antibodies that bind to GITR can increase GITR activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to GITR activity without any antibody or with an unrelated antibody (e.g., an antibody that does not bind to GITR). For instance, an antibody that binds to GITR, e.g., an antibody that binds to GITR and comprises a combination of CDR sequences specified herein, a VH and/or VL sequence having at least 70%, at least 75%, at least 80%, at least 85%, at least 90%, at least 95%, at least 98%, at least 99%, or 100% sequence identity with VH and/or VL sequences specified herein, or heavy and/or light chains specified herein, can increase GITR (e.g., human GITR) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to GITR (e.g., human GITR) activity without any antibody or with an unrelated antibody (e.g., an antibody that does not bind to GITR). Non-limiting examples of GITR (e.g., human GITR) activity can include GITR (e.g., human GITR) signaling, GITR (e.g., human GITR) binding to GITR (e.g., human GITR) ligand, cell proliferation, cell survival, and cytokine production (e.g., IL-2, TNF-α, IFN-γ, IL-4, IL-10, and/or IL-13).

As further provided herein, antibodies that bind to GITR can decrease GITR activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to GITR activity without any antibody or with an unrelated antibody (e.g., an antibody that does not bind to GITR). For instance, an antibody that binds to GITR, e.g., an antibody that binds to GITR and comprises a combination of CDR sequences specified herein, a VH and/or VL sequence having at least 70%, at least 75%, at least 80%, at least 85%, at least 90%, at least 95%, at least 98%, at least 99%, or 100% sequence identity with VH and/or VL sequences specified herein, or heavy and/or light chains specified herein, can decrease GITR (e.g., human GITR) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to GITR (e.g., human GITR) activity without any antibody or with an unrelated antibody (e.g., an antibody that does not bind to GITR). Non-limiting examples of GITR (e.g., human GITR) activity can include GITR (e.g., human GITR) signaling, GITR (e.g., human GITR) binding to GITR (e.g., human GITR) ligand, cell proliferation, cell survival, and cytokine production (e.g., IL-2, TNF-α, IFN-γ, IL-4, IL-10, and/or IL-13).

5.2.3 Multispecific Antibodies that Bind to OX40 and/or GITR

In a specific aspect, provided herein are multispecific antibodies (e.g., bispecific antibodies) which specifically bind to OX40 and/or GITR (e.g., human OX40 and/or human GITR). For instance, a multispecific (e.g., bispecific) antibody provided herein can comprise a first antigen-binding domain that binds to OX40 and a second antigen-binding domain. A multispecific (e.g., bispecific) antibody provided herein can also comprise a first antigen-binding domain and a second antigen-binding domain that binds to GITR. Such multispecific antibodies advantageously show greater specificity for certain subsets of immune cells containing the combination of target proteins than monospecific bivalent antibodies that only bind to OX40 or GITR.

In one instance, an antibody provided herein that specifically binds to OX40 and GITR contains a combination of CDRs shown in a single row of Table 12 below.

TABLE 12

CDR sequences of exemplary anti-OX40/GITR antibodies.*

| SEQ ID NOs of CDRs of the first antigen-binding domain that specifically binds to human OX40 | | | | | | SEQ ID NOs of CDRs of the second antigen-binding domain that specifically binds to human GITR | | | | | |
|---|---|---|---|---|---|---|---|---|---|---|---|
| VH CDR1 | VH CDR2 | VH CDR3 | VL CDR1 | VL CDR2 | VL CDR3 | VH CDR1 | VH CDR2 | VH CDR3 | VL CDR1 | VL CDR2 | VL CDR3 |
| 16 | 21 | 25 | 32 | 33 | 34 | 60 | 64 | 68 | 69 | 71 | 72 |
| 16 | 21 | 25 | 32 | 33 | 34 | 60 | 63 | 97 | 69 | 71 | 72 |
| 16 | 21 | 25 | 32 | 33 | 34 | 60 | 63 | 68 | 69 | 71 | 98 |
| 16 | 21 | 25 | 32 | 33 | 38 | 60 | 64 | 68 | 69 | 71 | 72 |
| 16 | 21 | 25 | 32 | 33 | 38 | 60 | 63 | 97 | 69 | 71 | 72 |
| 16 | 21 | 25 | 32 | 33 | 38 | 60 | 63 | 68 | 69 | 71 | 98 |
| 16 | 22 | 25 | 32 | 33 | 34 | 60 | 63 | 68 | 69 | 71 | 72 |
| 16 | 22 | 25 | 32 | 33 | 34 | 60 | 64 | 68 | 69 | 71 | 72 |
| 16 | 22 | 25 | 32 | 33 | 34 | 60 | 63 | 97 | 69 | 71 | 72 |
| 16 | 22 | 25 | 32 | 33 | 34 | 60 | 63 | 68 | 69 | 71 | 98 |
| 16 | 22 | 25 | 32 | 33 | 34 | 61 | 65 | 68 | 70 | 71 | 73 |
| 16 | 22 | 25 | 32 | 33 | 34 | 62 | 66 | 68 | 69 | 71 | 72 |
| 16 | 22 | 25 | 32 | 33 | 34 | 62 | 67 | 68 | 69 | 71 | 72 |
| 16 | 21 | 26 | 32 | 33 | 34 | 60 | 63 | 68 | 69 | 71 | 72 |
| 16 | 21 | 26 | 32 | 33 | 34 | 60 | 64 | 68 | 69 | 71 | 72 |
| 16 | 21 | 26 | 32 | 33 | 34 | 60 | 63 | 97 | 69 | 71 | 72 |
| 16 | 21 | 26 | 32 | 33 | 34 | 60 | 63 | 68 | 69 | 71 | 98 |
| 16 | 21 | 26 | 32 | 33 | 34 | 61 | 65 | 68 | 70 | 71 | 73 |
| 16 | 21 | 26 | 32 | 33 | 34 | 62 | 66 | 68 | 69 | 71 | 72 |
| 16 | 21 | 26 | 32 | 33 | 34 | 62 | 67 | 68 | 69 | 71 | 72 |
| 16 | 21 | 27 | 32 | 33 | 34 | 60 | 63 | 68 | 69 | 71 | 72 |
| 16 | 21 | 27 | 32 | 33 | 34 | 60 | 64 | 68 | 69 | 71 | 72 |
| 16 | 21 | 27 | 32 | 33 | 34 | 60 | 63 | 97 | 69 | 71 | 72 |
| 16 | 21 | 27 | 32 | 33 | 34 | 60 | 63 | 68 | 69 | 71 | 98 |
| 16 | 21 | 27 | 32 | 33 | 34 | 61 | 65 | 68 | 70 | 71 | 73 |
| 16 | 21 | 27 | 32 | 33 | 34 | 62 | 66 | 68 | 69 | 71 | 72 |
| 16 | 21 | 27 | 32 | 33 | 34 | 62 | 67 | 68 | 69 | 71 | 72 |
| 16 | 21 | 28 | 32 | 33 | 34 | 60 | 63 | 68 | 69 | 71 | 72 |
| 16 | 21 | 28 | 32 | 33 | 34 | 60 | 64 | 68 | 69 | 71 | 72 |
| 16 | 21 | 28 | 32 | 33 | 34 | 60 | 63 | 97 | 69 | 71 | 72 |
| 16 | 21 | 28 | 32 | 33 | 34 | 60 | 63 | 68 | 69 | 71 | 98 |
| 16 | 21 | 28 | 32 | 33 | 34 | 61 | 65 | 68 | 70 | 71 | 73 |
| 16 | 21 | 28 | 32 | 33 | 34 | 62 | 66 | 68 | 69 | 71 | 72 |
| 16 | 21 | 28 | 32 | 33 | 34 | 62 | 67 | 68 | 69 | 71 | 72 |
| 16 | 21 | 29 | 32 | 33 | 34 | 60 | 63 | 68 | 69 | 71 | 72 |
| 16 | 21 | 29 | 32 | 33 | 34 | 60 | 64 | 68 | 69 | 71 | 72 |
| 16 | 21 | 29 | 32 | 33 | 34 | 60 | 63 | 97 | 69 | 71 | 72 |
| 16 | 21 | 29 | 32 | 33 | 34 | 60 | 63 | 68 | 69 | 71 | 98 |
| 16 | 21 | 29 | 32 | 33 | 34 | 61 | 65 | 68 | 70 | 71 | 73 |
| 16 | 21 | 29 | 32 | 33 | 34 | 62 | 66 | 68 | 69 | 71 | 72 |
| 16 | 21 | 29 | 32 | 33 | 34 | 62 | 67 | 68 | 69 | 71 | 72 |
| 17 | 21 | 30 | 32 | 33 | 38 | 60 | 63 | 68 | 69 | 71 | 72 |
| 17 | 21 | 30 | 32 | 33 | 38 | 60 | 64 | 68 | 69 | 71 | 72 |
| 17 | 21 | 30 | 32 | 33 | 38 | 60 | 63 | 97 | 69 | 71 | 72 |
| 17 | 21 | 30 | 32 | 33 | 38 | 60 | 63 | 68 | 69 | 71 | 98 |
| 17 | 21 | 30 | 32 | 33 | 38 | 61 | 65 | 68 | 70 | 71 | 73 |
| 17 | 21 | 30 | 32 | 33 | 38 | 62 | 66 | 68 | 69 | 71 | 72 |
| 17 | 21 | 30 | 32 | 33 | 38 | 62 | 67 | 68 | 69 | 71 | 72 |
| 18 | 23 | 25 | 32 | 33 | 38 | 60 | 63 | 68 | 69 | 71 | 72 |
| 18 | 23 | 25 | 32 | 33 | 38 | 60 | 64 | 68 | 69 | 71 | 72 |
| 18 | 23 | 25 | 32 | 33 | 38 | 60 | 63 | 97 | 69 | 71 | 72 |
| 18 | 23 | 25 | 32 | 33 | 38 | 60 | 63 | 68 | 69 | 71 | 98 |
| 18 | 23 | 25 | 32 | 33 | 38 | 61 | 65 | 68 | 70 | 71 | 73 |
| 18 | 23 | 25 | 32 | 33 | 38 | 62 | 66 | 68 | 69 | 71 | 72 |
| 18 | 23 | 25 | 32 | 33 | 38 | 62 | 67 | 68 | 69 | 71 | 72 |
| 19 | 24 | 25 | 32 | 33 | 38 | 60 | 63 | 68 | 69 | 71 | 72 |
| 19 | 24 | 25 | 32 | 33 | 38 | 60 | 64 | 68 | 69 | 71 | 72 |
| 19 | 24 | 25 | 32 | 33 | 38 | 60 | 63 | 97 | 69 | 71 | 72 |
| 19 | 24 | 25 | 32 | 33 | 38 | 60 | 63 | 68 | 69 | 71 | 98 |
| 19 | 24 | 25 | 32 | 33 | 38 | 61 | 65 | 68 | 70 | 71 | 73 |
| 19 | 24 | 25 | 32 | 33 | 38 | 62 | 66 | 68 | 69 | 71 | 72 |
| 19 | 24 | 25 | 32 | 33 | 38 | 62 | 67 | 68 | 69 | 71 | 72 |
| 20 | 21 | 31 | 32 | 33 | 38 | 60 | 63 | 68 | 69 | 71 | 72 |
| 20 | 21 | 31 | 32 | 33 | 38 | 60 | 64 | 68 | 69 | 71 | 72 |
| 20 | 21 | 31 | 32 | 33 | 38 | 60 | 63 | 97 | 69 | 71 | 72 |

TABLE 12-continued

CDR sequences of exemplary anti-OX40/GITR antibodies.*

| SEQ ID NOs of CDRs of the first antigen-binding domain that specifically binds to human OX40 | | | | | | SEQ ID NOs of CDRs of the second antigen-binding domain that specifically binds to human GITR | | | | | |
|---|---|---|---|---|---|---|---|---|---|---|---|
| VH CDR1 | VH CDR2 | VH CDR3 | VL CDR1 | VL CDR2 | VL CDR3 | VH CDR1 | VH CDR2 | VH CDR3 | VL CDR1 | VL CDR2 | VL CDR3 |
| 20 | 21 | 31 | 32 | 33 | 38 | 60 | 63 | 68 | 69 | 71 | 98 |
| 20 | 21 | 31 | 32 | 33 | 38 | 61 | 65 | 68 | 70 | 71 | 73 |
| 20 | 21 | 31 | 32 | 33 | 38 | 62 | 66 | 68 | 69 | 71 | 72 |
| 20 | 21 | 31 | 32 | 33 | 38 | 62 | 67 | 68 | 69 | 71 | 72 |
| 16 | 21 | 25 | 32 | 33 | 35 | 60 | 63 | 68 | 69 | 71 | 72 |
| 16 | 21 | 25 | 32 | 33 | 35 | 60 | 64 | 68 | 69 | 71 | 72 |
| 16 | 21 | 25 | 32 | 33 | 35 | 60 | 63 | 97 | 69 | 71 | 72 |
| 16 | 21 | 25 | 32 | 33 | 35 | 60 | 63 | 68 | 69 | 71 | 98 |
| 16 | 21 | 25 | 32 | 33 | 35 | 61 | 65 | 68 | 70 | 71 | 73 |
| 16 | 21 | 25 | 32 | 33 | 35 | 62 | 66 | 68 | 69 | 71 | 72 |
| 16 | 21 | 25 | 32 | 33 | 35 | 62 | 67 | 68 | 69 | 71 | 72 |
| 16 | 21 | 25 | 32 | 33 | 36 | 60 | 63 | 68 | 69 | 71 | 72 |
| 16 | 21 | 25 | 32 | 33 | 36 | 60 | 64 | 68 | 69 | 71 | 72 |
| 16 | 21 | 25 | 32 | 33 | 36 | 60 | 63 | 97 | 69 | 71 | 72 |
| 16 | 21 | 25 | 32 | 33 | 36 | 60 | 63 | 68 | 69 | 71 | 98 |
| 16 | 21 | 25 | 32 | 33 | 36 | 61 | 65 | 68 | 70 | 71 | 73 |
| 16 | 21 | 25 | 32 | 33 | 36 | 62 | 66 | 68 | 69 | 71 | 72 |
| 16 | 21 | 25 | 32 | 33 | 36 | 62 | 67 | 68 | 69 | 71 | 72 |
| 16 | 21 | 25 | 32 | 33 | 37 | 60 | 63 | 68 | 69 | 71 | 72 |
| 16 | 21 | 25 | 32 | 33 | 37 | 60 | 64 | 68 | 69 | 71 | 72 |
| 16 | 21 | 25 | 32 | 33 | 37 | 60 | 63 | 97 | 69 | 71 | 72 |
| 16 | 21 | 25 | 32 | 33 | 37 | 60 | 63 | 68 | 69 | 71 | 98 |
| 16 | 21 | 25 | 32 | 33 | 37 | 61 | 65 | 68 | 70 | 71 | 73 |
| 16 | 21 | 25 | 32 | 33 | 37 | 62 | 66 | 68 | 69 | 71 | 72 |
| 16 | 21 | 25 | 32 | 33 | 37 | 62 | 67 | 68 | 69 | 71 | 72 |

*Defined according to the Kabat numbering system.

In one instance, an antibody provided herein that specifically binds to OX40 and GITR contains a combination of two heavy chain variable domains and two light chain variable domains shown in a single row of Table 13 below.

TABLE 13

Heavy chain variable region (VH) and light chain variable region (VL) sequences of exemplary anti-OX40/GITR antibodies.

| SEQ ID NOs of variable regions of the first antigen-binding domain that specifically binds to human OX40 | | SEQ ID NOs of variable regions of the second antigen-binding domain that specifically binds to human GITR | |
|---|---|---|---|
| VH SEQ ID NO: | VL SEQ ID NO: | VH SEQ ID NO: | VL SEQ ID NO: |
| 1 | 11 | 53 | 57 |
| 1 | 11 | 95 | 57 |
| 1 | 11 | 52 | 96 |
| 1 | 15 | 53 | 57 |
| 1 | 15 | 95 | 57 |
| 1 | 15 | 52 | 96 |
| 2 | 11 | 52 | 57 |
| 2 | 11 | 53 | 57 |
| 2 | 11 | 95 | 57 |
| 2 | 11 | 52 | 96 |
| 2 | 11 | 54 | 58 |
| 2 | 11 | 55 | 59 |
| 2 | 11 | 56 | 59 |
| 3 | 11 | 52 | 57 |
| 3 | 11 | 53 | 57 |
| 3 | 11 | 95 | 57 |
| 3 | 11 | 52 | 96 |
| 3 | 11 | 54 | 58 |
| 3 | 11 | 55 | 59 |
| 3 | 11 | 56 | 59 |
| 4 | 11 | 52 | 57 |
| 4 | 11 | 53 | 57 |
| 4 | 11 | 95 | 57 |
| 4 | 11 | 52 | 96 |
| 4 | 11 | 54 | 58 |
| 4 | 11 | 55 | 59 |
| 4 | 11 | 56 | 59 |
| 5 | 11 | 52 | 57 |
| 5 | 11 | 53 | 57 |
| 5 | 11 | 95 | 57 |
| 5 | 11 | 52 | 96 |
| 5 | 11 | 54 | 58 |
| 5 | 11 | 55 | 59 |
| 5 | 11 | 56 | 59 |
| 6 | 11 | 52 | 57 |
| 6 | 11 | 53 | 57 |
| 6 | 11 | 95 | 57 |
| 6 | 11 | 52 | 96 |
| 6 | 11 | 54 | 58 |
| 6 | 11 | 55 | 59 |
| 6 | 11 | 56 | 59 |
| 7 | 15 | 52 | 57 |
| 7 | 15 | 53 | 57 |
| 7 | 15 | 95 | 57 |
| 7 | 15 | 52 | 96 |
| 7 | 15 | 54 | 58 |

TABLE 13-continued

Heavy chain variable region (VH) and light chain variable region (VL) sequences of exemplary anti-OX40/GITR antibodies.

| SEQ ID NOs of variable regions of the first antigen-binding domain that specifically binds to human OX40 | | SEQ ID NOs of variable regions of the second antigen-binding domain that specifically binds to human GITR | |
|---|---|---|---|
| VH SEQ ID NO: | VL SEQ ID NO: | VH SEQ ID NO: | VL SEQ ID NO: |
| 7 | 15 | 55 | 59 |
| 7 | 15 | 56 | 59 |
| 8 | 15 | 52 | 57 |
| 8 | 15 | 53 | 57 |
| 8 | 15 | 95 | 57 |
| 8 | 15 | 52 | 96 |
| 8 | 15 | 54 | 58 |
| 8 | 15 | 55 | 59 |
| 8 | 15 | 56 | 59 |
| 9 | 15 | 52 | 57 |
| 9 | 15 | 53 | 57 |
| 9 | 15 | 95 | 57 |
| 9 | 15 | 52 | 96 |
| 9 | 15 | 54 | 58 |
| 9 | 15 | 55 | 59 |
| 9 | 15 | 56 | 59 |
| 10 | 15 | 52 | 57 |
| 10 | 15 | 53 | 57 |
| 10 | 15 | 95 | 57 |
| 10 | 15 | 52 | 96 |
| 10 | 15 | 54 | 58 |
| 10 | 15 | 55 | 59 |
| 10 | 15 | 56 | 59 |
| 1 | 12 | 52 | 57 |
| 1 | 12 | 53 | 57 |
| 1 | 12 | 95 | 57 |
| 1 | 12 | 52 | 96 |
| 1 | 12 | 54 | 58 |
| 1 | 12 | 55 | 59 |
| 1 | 12 | 56 | 59 |
| 1 | 13 | 52 | 57 |
| 1 | 13 | 53 | 57 |
| 1 | 13 | 95 | 57 |
| 1 | 13 | 52 | 96 |
| 1 | 13 | 54 | 58 |
| 1 | 13 | 55 | 59 |
| 1 | 13 | 56 | 59 |
| 1 | 14 | 52 | 57 |
| 1 | 14 | 53 | 57 |
| 1 | 14 | 95 | 57 |
| 1 | 14 | 52 | 96 |
| 1 | 14 | 54 | 58 |
| 1 | 14 | 55 | 59 |
| 1 | 14 | 56 | 59 |

In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising one, two, or all three of the CDRs of a heavy chain variable region set forth in Table 2 herein. In certain embodiments, the first antigen-binding domain comprises the CDRH1 of one of heavy chain variable regions set forth in Table 2. In certain embodiments, the first antigen-binding domain comprises the CDRH2 of one of the heavy chain variable regions set forth in Table 2. In certain embodiments, the first antigen-binding domain comprises the CDRH3 of one of the heavy chain variable regions set forth in Table 2.

In certain embodiments, the instant disclosure provides an isolated multispecific antibody comprising a first antigen-binding domain, wherein the first antigen-binding domain specifically binds to OX40 (e.g., human OX40) and comprises a light chain variable region comprising one, two, or all three of the CDRs of a light chain variable region disclosed in Table 2 herein. In certain embodiments, the first antigen-binding domain comprises the CDRL1 of one of light chain variable regions set forth in Table 2. In certain embodiments, the first antigen-binding domain comprises the CDRL2 of one of the light chain variable regions set forth in Table 2. In certain embodiments, the first antigen-binding domain comprises the CDRL3 of one of the light chain variable regions set forth in Table 2.

In certain embodiments, the instant disclosure provides an isolated multispecific antibody comprising a first antigen-binding domain, wherein the first antigen-binding domain specifically binds to OX40 (e.g., human OX40) and comprises the Chothia V H CDRs of a VH disclosed in Table 2 herein. In certain embodiments, the instant disclosure provides an isolated multispecific antibody comprising a first antigen-binding domain, wherein the first antigen-binding domain specifically binds to OX40 (e.g., human OX40) and comprises the Chothia V L CDRs of a VL disclosed in Table 2 herein. In certain embodiments, the instant disclosure provides an isolated multispecific antibody comprising a first antigen-binding domain, wherein the first antigen-binding domain specifically binds to OX40 (e.g., human OX40) and comprises the Chothia V H CDRs and Chothia V L CDRs of an antibody disclosed in Table 2 herein. In certain embodiments, the first antigen-binding domain that specifically binds to OX40 (e.g., human OX40) comprises one or more CDRs, in which the Chothia and Kabat CDRs have the same amino acid sequence. In certain embodiments, the instant disclosure provides an isolated multispecific antibody comprising a first antigen-binding domain, wherein the first antigen-binding domain specifically binds to OX40 (e.g., human OX40) and comprises combinations of Kabat CDRs and Chothia CDRs.

In certain embodiments, the instant disclosure provides an isolated multispecific antibody comprising a first antigen-binding domain, wherein the first antigen-binding domain specifically binds to OX40 (e.g., human OX40) and comprises CDRs of an antibody disclosed in Table 2 herein, as determined by the IMGT numbering system, for example, as described in Lefranc M-P (1999) supra and Lefranc M-P et al., (1999) supra.

In certain embodiments, the instant disclosure provides an isolated multispecific antibody comprising a first antigen-binding domain, wherein the first antigen-binding domain specifically binds to OX40 (e.g., human OX40) and comprises CDRs of an antibody disclosed in Table 2 herein as determined by the AbM numbering scheme.

In certain embodiments, the instant disclosure provides an isolated multispecific antibody comprising a first antigen-binding domain, wherein the first antigen-binding domain specifically binds to OX40 (e.g., human OX40) and comprises CDRs of an antibody disclosed in Table 2 herein as determined by the MacCallum numbering scheme.

In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising the CDRH1, CDRH2, and CDRH3 region amino acid sequences of a heavy chain variable region set forth in SEQ ID NO: 1, 2, 3, 4, 5, 6, 7, 8, 9, or 10, and a light chain variable region comprising the CDRL1, CDRL2, and CDRL3 region amino acid sequences of a light chain variable region set forth in SEQ ID NO: 11, 12, 13, 14, or 15, wherein each CDR is defined in accordance with the MacCallum definition, the Kabat definition, the Chothia definition, the combination of the Kabat definition and the Chothia definition, the IMGT numbering system, or the AbM definition of CDR.

In certain embodiments, the instant disclosure provides an isolated multispecific antibody comprising a first antigen-binding domain, wherein the first antigen-binding domain specifically binds to OX40 (e.g., human OX40) and comprises:
(a) a CDRH1 comprises the amino acid sequence of $X_1X_2X_3MI-1$ (SEQ ID NO: 41), wherein
  $X_1$ is G, Q, H, or E,
  $X_2$ is S, E, or Y, and
  $X_3$ is A, S, or G; and/or
(b) a CDRH2 comprises the amino acid sequence of RIRSK$X_1X_2X_3X_4X_5$TAYAASVKG (SEQ ID NO: 42), wherein
  $X_1$ is A, S, or Y,
  $X_2$ is N, E, or Y,
  $X_3$ is S, Q, or G,
  $X_4$ is Y, E, or Q, and
  $X_5$ is A, E, or L; and/or
(c) a CDRH3 comprises the amino acid sequence of GI$X_1X_2X_3X_4X_5X_6X_7$Y (SEQ ID NO: 43), wherein
  $X_1$ is Y or A,
  $X_2$ is D or A,
  $X_3$ is S, T, or W,
  $X_4$ is S, E, or L,
  $X_5$ is G or A,
  $X_6$ is Y or A, and
  $X_7$ is D or A; and/or
(d) a CDRL1 comprises the amino acid sequence of RSSQSLLHSNGYNYLD (SEQ ID NO: 32); and/or
(e) a CDRL2 comprises the amino acid sequence of LGSNRAS (SEQ ID NO: 33); and/or
(f) a CDRL3 comprises the amino acid sequence of MQ$X_1X_2X_3X_4$PLT (SEQ ID NO: 46), wherein
  $X_1$ is A or G,
  $X_2$ is L or S,
  $X_3$ is Q or K, and
  $X_4$ is T or W,
and wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively,
and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and comprises:
(a) a CDRH1 comprises the amino acid sequence of $X_1X_2X_3MH$ (SEQ ID NO: 41), wherein
  $X_1$ is G, Q, H, or E,
  $X_2$ is S, E, or Y, and
  $X_3$ is A, S, or G; and/or
(b) a CDRH2 comprises the amino acid sequence of RIRSK$X_1X_2X_3X_4X_5$TAYAASVKG (SEQ ID NO: 42), wherein
  $X_1$ is A, S, or Y,
  $X_2$ is N, E, or Y,
  $X_3$ is S, Q, or G,
  $X_4$ is Y, E, or Q, and
  $X_5$ is A, E, or L; and/or
(c) a CDRH3 comprises the amino acid sequence of GI$X_1X_2X_3X_4X_5X_6X_7$Y (SEQ ID NO: 43), wherein
  $X_1$ is Y or A,
  $X_2$ is D or A,
  $X_3$ is S, T, or W,
  $X_4$ is S, E, or L,
  $X_5$ is G or A,
  $X_6$ is Y or A, and
  $X_7$ is D or A; and/or
(d) a CDRL1 comprises the amino acid sequence of RSSQSLLHSNGYNYLD (SEQ ID NO: 32); and/or
(e) a CDRL2 comprises the amino acid sequence of LGSNRAS (SEQ ID NO: 33); and/or
(f) a CDRL3 comprises the amino acid sequence of MQ$X_1X_2X_3X_4$PLT (SEQ ID NO: 46), wherein
  $X_1$ is A or G,
  $X_2$ is L or S,
  $X_3$ is Q or K, and
  $X_4$ is T or W,
and wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively,
and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and comprises:
(a) a CDRH1 comprises the amino acid sequence of $X_1X_2X_3MH$ (SEQ ID NO: 41), wherein
  $X_1$ is G, Q, H, or E,
  $X_2$ is S, E, or Y, and
  $X_3$ is A, S, or G; and/or
(b) a CDRH2 comprises the amino acid sequence of RIRSK$X_1X_2X_3X_4X_5$TAYAASVKG (SEQ ID NO: 42), wherein
  $X_1$ is A, S, or Y,
  $X_2$ is N, E, or Y,
  $X_3$ is S, Q, or G,
  $X_4$ is Y, E, or Q, and
  $X_5$ is A, E, or L; and/or
(c) a CDRH3 comprises the amino acid sequence of GI$X_1X_2X_3X_4X_5X_6X_7$Y (SEQ ID NO: 43), wherein
  $X_1$ is Y or A,
  $X_2$ is D or A,
  $X_3$ is S, T, or W,
  $X_4$ is S, E, or L,
  $X_5$ is G or A,
  $X_6$ is Y or A, and
  $X_7$ is D or A; and/or
(d) a CDRL1 comprises the amino acid sequence of RSSQSLLHSNGYNYLD (SEQ ID NO: 32); and/or
(e) a CDRL2 comprises the amino acid sequence of LGSNRAS (SEQ ID NO: 33); and/or
(f) a CDRL3 comprises the amino acid sequence of MQ$X_1X_2X_3X_4$PLT (SEQ ID NO: 46), wherein
  $X_1$ is A or G,
  $X_2$ is L or S,
  $X_3$ is Q or K, and
  $X_4$ is T or W,
and wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38,
and wherein the isolated multispecific antibody further comprises a second antigen-binding domain.

In certain embodiments, CDRH2 of the first antigen-binding domain that specifically binds to human OX40 comprises the amino acid sequence of RIR-SKAXSYATAYAASVKG (SEQ ID NO: 44), wherein: X is N or Y. In certain embodiments, CDRH3 of the first antigen-binding domain that specifically binds to human OX40 comprises the amino acid sequence of GIX$_1$X$_2$SSGX$_3$X$_4$Y (SEQ ID NO: 45), wherein: X$_1$ is Y or A; X$_2$ is D or A; X$_3$ is Y or A; and X$_4$ is D or A. In certain embodiments, CDRH1 of the first antigen-binding domain that specifically binds to human OX40 comprises an amino acid sequence selected from the group consisting of SEQ ID NOs: 16-20. In certain embodiments, CDRH2 of the first antigen-binding domain that specifically binds to human OX40 comprises an amino acid sequence selected from the group consisting of SEQ ID NOs: 21-24. In certain embodiments, CDRH3 of the first antigen-binding domain that specifically binds to human OX40 comprises an amino acid sequence selected from the group consisting of SEQ ID NOs: 25-31. In certain embodiments, CDRL3 of the first antigen-binding domain that specifically binds to human OX40 comprises an amino acid sequence selected from the group consisting of SEQ ID NOs: 34-38.

In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising the CDRH1, CDRH2 and CDRH3 amino acid sequences set forth in SEQ ID NOs: 16, 21, and 25; 16, 22, and 25; 16, 21, and 26; 16, 21, and 27; 16, 21, and 28; 16, 21, and 29; 17, 21, and 30; 18, 23, and 25; 19, 24, and 25; or 20, 21, and 31, respectively, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising the CDRH1, CDRH2 and CDRH3 amino acid sequences set forth in SEQ ID NOs: 16, 21, and 25; 16, 22, and 25; 16, 21, and 26; 16, 21, and 27; 16, 21, and 28; 16, 21, and 29; 17, 21, and 30; 18, 23, and 25; 19, 24, and 25; or 20, 21, and 31, respectively, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising the CDRH1, CDRH2 and CDRH3 amino acid sequences set forth in SEQ ID NOs: 16, 21, and 25; 16, 22, and 25; 16, 21, and 26; 16, 21, and 27; 16, 21, and 28; 16, 21, and 29; 17, 21, and 30; 18, 23, and 25; 19, 24, and 25; or 20, 21, and 31, respectively, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and comprises a light chain variable region comprising the CDRL1, CDRL2 and CDRL3 amino acid sequences set forth in SEQ ID NOs: 32, 33, and 34; 32, 33, and 35; 32, 33, and 36; 32, 33, and 37; or 32, 33, and 38, respectively, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a light chain variable region comprising the CDRL1, CDRL2 and CDRL3 amino acid sequences set forth in SEQ ID NOs: 32, 33, and 34; 32, 33, and 35; 32, 33, and 36; 32, 33, and 37; or 32, 33, and 38, respectively, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a light chain variable region comprising the CDRL1, CDRL2 and CDRL3 amino acid sequences set forth in SEQ ID NOs: 32, 33, and 34; 32, 33, and 35; 32, 33, and 36; 32, 33, and 37; or 32, 33, and 38, respectively, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions of the first antigen-binding domain that specifically binds to OX40 (e.g., human OX40) comprise the amino acid sequences set forth in SEQ ID NOs: 16, 22, 25, 32, 33, and 34; 16, 21, 26, 32, 33, and 34; 16, 21, 27, 32, 33, and 34; 16, 21, 28, 32, 33, and 34; 16, 21, 29, 32, 33, and 34; 17, 21, 30, 32, 33, and 38; 18, 23, 25, 32, 33, and 38; 19, 24, 25, 32, 33, and 38; 20, 21, 31, 32, 33, and 38; 16, 21, 25, 32, 33, and 35; 16, 21, 25, 32, 33, and 36; or 16, 21, 25, 32, 33, and 37, respectively, and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence of SEQ ID NO: 47 or 48, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence of SEQ ID NO: 47 or 48, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence of SEQ ID NO: 47 or 48, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain. In certain embodiments, the first antigen-binding domain that specifically binds to OX40 (e.g., human OX40) comprises a heavy chain variable region having the amino acid sequence set forth in SEQ ID NO: 1, 2, 3, 4, 5, 6, 7, 8, 9, or 10. In certain embodiments, the first antigen-binding domain that specifically binds to OX40 (e.g., human OX40) comprises a heavy chain variable region having the amino acid sequence set forth in SEQ ID NO: 1. In certain embodiments, the first antigen-binding domain that specifically binds to OX40 (e.g., human OX40) comprises a heavy chain variable region having the amino acid sequence set forth in SEQ ID NO: 2. In certain embodiments, the first antigen-binding domain that specifically binds to OX40 (e.g., human OX40) comprises a heavy chain variable region having the amino acid sequence set forth in SEQ ID NO: 3. In certain embodiments, the first antigen-binding domain that specifically binds to OX40 (e.g., human OX40) comprises a heavy chain variable region having the amino acid sequence set forth in SEQ ID NO: 4. In certain embodiments, the first antigen-binding domain that specifically binds to OX40 (e.g., human OX40) comprises a heavy chain variable region having the amino acid sequence set forth in SEQ ID NO: 5. In certain embodiments, the first antigen-binding domain that specifically binds to OX40 (e.g., human OX40) comprises a heavy chain variable region having the amino acid sequence set forth in SEQ ID NO: 6. In certain embodiments, the first antigen-binding domain that specifically binds to OX40 (e.g., human OX40) comprises a heavy chain variable region having the amino acid sequence set forth in SEQ ID NO: 7. In certain embodiments, the first antigen-binding domain that specifically binds to OX40 (e.g., human OX40) comprises a heavy chain variable region having the amino acid sequence set forth in SEQ ID NO: 8. In certain embodiments, the first antigen-binding domain that specifically binds to OX40 (e.g., human OX40) comprises a heavy chain variable region having the amino acid sequence set forth in SEQ ID NO: 9. In certain embodiments, the first antigen-binding domain that specifically binds to OX40 (e.g., human OX40) comprises a heavy chain variable region having the amino acid sequence set forth in SEQ ID NO: 10.

In certain embodiments, the instant disclosure provides an isolated multispecific antibody comprising a first antigen-binding domain, wherein the first antigen-binding domain specifically binds to OX40 (e.g., human OX40) and comprises a light chain variable region comprising an amino acid sequence of SEQ ID NO: 49, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a light chain variable region comprising an amino acid sequence of SEQ ID NO: 49, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a light chain variable region comprising an amino acid sequence of SEQ ID NO: 49, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and comprises a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain. In certain embodiments, the first antigen-binding domain that specifically binds to OX40 (e.g., human OX40) comprises a light chain variable region having the amino acid sequence set forth in SEQ ID NO: 11, 12, 13, 14, or 15. In certain embodiments, the first antigen-binding domain that specifically binds to OX40 (e.g., human OX40) comprises a light chain variable region having the amino acid sequence set forth in SEQ ID NO: 11. In certain embodiments, the first antigen-binding domain that specifically binds to OX40 (e.g., human OX40) comprises a light chain variable region having the amino acid sequence set forth in SEQ ID NO: 12. In certain embodiments, the first antigen-binding domain that specifically binds to OX40 (e.g., human OX40) comprises a light chain variable region having the amino acid sequence set forth in SEQ ID NO: 13. In certain embodiments, the first antigen-binding domain that specifically binds to OX40 (e.g., human OX40) comprises a light chain variable region having the amino acid sequence set forth in SEQ ID NO: 14. In certain embodiments, the first antigen-binding domain that specifically binds to OX40 (e.g., human OX40) comprises a light chain variable region having the amino acid sequence set forth in SEQ ID NO: 15.

In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence of SEQ ID NO: 47 or 48, and a light chain variable region comprising an amino acid sequence of SEQ ID NO: 49, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence of SEQ ID NO: 47 or 48, and a light chain variable region comprising an amino acid sequence of SEQ ID NO: 49, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence of SEQ ID NO: 47 or 48, and a light chain variable region comprising an amino acid sequence of SEQ ID NO: 49, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 2, 3, 4, 5, 6, 7, 8, 9, or 10, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 11, 12, 13, 14, or 15, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain. In certain embodiments, the first antigen-binding domain that specifically binds to OX40 (e.g., human OX40) comprises a heavy chain variable region having the amino acid sequence set forth in SEQ ID NO: 1, 2, 3, 4, 5, 6, 7, 8, 9, or 10, and a light chain variable region having the amino acid sequence set forth in SEQ ID NO: 11, 12, 13, 14, or 15. In certain embodiments, the first antigen-binding domain that specifically binds to OX40 (e.g., human OX40) comprises a heavy chain variable region and light chain variable region having the amino acid sequences set forth in SEQ ID NO: 2 and 11; 3 and 11; 4 and 11; 5 and 11; 6 and 11; 7 and 15; 8 and 15; 9 and 15; 10 and 15; 1 and 12; 1 and 13; or 1 and 14, respectively. In certain embodiments, the first antigen-binding domain that specifically binds to OX40 (e.g., human OX40) comprises a heavy chain variable region and light chain variable region having the amino acid sequences set forth in SEQ ID NO: 2 and 11, respectively. In certain embodiments, the first antigen-binding domain that specifically binds to OX40 (e.g., human OX40) comprises a heavy chain variable region and light chain variable region having the amino acid sequences set forth in SEQ ID NO: 3 and 11, respectively. In certain embodiments, the first antigen-binding domain that specifically binds to OX40 (e.g., human OX40) comprises a heavy chain variable region and light chain variable region having the amino acid sequences set forth in SEQ ID NO: 4 and 11, respectively. In certain embodiments, the first antigen-binding domain that specifically binds to OX40 (e.g., human OX40) comprises a heavy chain variable region and light chain variable region having the amino acid sequences set forth in SEQ ID NO: 5 and 11, respectively. In certain embodiments, the first antigen-binding domain that specifically binds to OX40 (e.g., human OX40) comprises a heavy chain variable region and light chain variable region having the amino acid sequences set forth in SEQ ID NO: 6 and 11, respectively. In certain embodiments, the first antigen-binding domain that specifically binds to OX40 (e.g., human OX40) comprises a heavy chain variable region and light chain variable region having the amino acid sequences set forth in SEQ ID NO: 7 and 15, respectively. In certain embodiments, the first antigen-binding domain that specifically binds to OX40 (e.g., human OX40) comprises a heavy chain variable region and light chain variable region having the amino acid sequences set forth in SEQ ID NO: 8 and 15, respectively. In certain embodiments, the first antigen-binding domain that specifically binds to OX40 (e.g., human OX40) comprises a heavy chain variable region and light chain variable region having the amino acid sequences set forth in SEQ ID NO: 9 and 15, respectively. In certain embodiments, the first antigen-binding domain that specifically binds to OX40 (e.g., human OX40) comprises a heavy chain variable region and light chain variable region having the amino acid sequences set forth in SEQ ID NO: 10 and 15, respectively. In certain embodiments, the first antigen-binding domain that specifically binds to OX40 (e.g., human OX40) comprises a heavy chain variable region and light chain variable region having the amino acid sequences set forth in SEQ ID NO: 1 and 12, respectively. In certain embodiments, the first antigen-binding domain that specifically binds to OX40 (e.g., human OX40) comprises a heavy chain variable region and light chain variable region having the amino acid sequences set forth in SEQ ID NO: 1 and 13, respectively. In certain embodiments, the first antigen-binding domain that specifically binds to OX40 (e.g., human OX40) comprises a heavy chain variable region and light chain variable region having the amino acid sequences set forth in SEQ ID NO: 1 and 14, respectively.

In certain embodiments, the instant disclosure provides an isolated multispecific antibody comprising a first antigen-binding domain, wherein the first antigen-binding domain specifically binds to OX40 (e.g., human OX40) and comprises a heavy chain variable region having an amino acid sequence derived from a human IGHV3-73 germline sequence (e.g., IGHV3-73*01, e.g., having the amino acid sequence of SEQ ID NO: 39), wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region having an amino acid sequence derived from a human IGHV3-73 germline sequence (e.g., IGHV3-73*01, e.g., having the amino acid sequence of SEQ ID NO: 39), wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region having an amino acid sequence derived from a human IGHV3-73 germline sequence (e.g., IGHV3-73*01, e.g., having the amino acid sequence of SEQ ID NO: 39), wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain. One or more regions selected from framework 1, framework 2, framework 3, CDRH1, and CDRH2 (e.g., two, three, four or five of these regions) of the first antigen-binding domain that specifically binds to OX40 (e.g., human OX40) can be derived from a human IGHV3-73 germline sequence (e.g., IGHV3-73*01, e.g., having the amino acid sequence of SEQ ID NO: 39). In one embodiment, framework 1, framework 2, framework 3, CDRH1, and CDRH2 of the first antigen-binding domain that specifically binds to OX40 (e.g., human OX40) are all derived from a human IGHV3-73 germline sequence (e.g., IGHV3-73*01, e.g., having the amino acid sequence of SEQ ID NO: 39).

In certain embodiments, the instant disclosure provides an isolated multispecific antibody comprising a first antigen-binding domain, wherein the first antigen-binding domain specifically binds to OX40 (e.g., human OX40) and comprises a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain. One or more regions selected from framework 1, framework 2, framework 3, CDRL1, and CDRL2 (e.g., two, three, four or five of these regions) of the first antigen-binding domain that specifically binds to OX40 (e.g., human OX40) can be derived from a human IGKV2-28 germline sequence (e.g., IGKV2-28*01, e.g., having the amino acid sequence of SEQ ID NO: 40). In one embodiment, framework 1, framework 2, framework 3, CDRL1, and CDRL2 of the first antigen-binding domain that specifically binds to OX40 (e.g., human OX40) are all derived from a human IGKV2-28 germline sequence (e.g., IGKV2-28*01, e.g., having the amino acid sequence of SEQ ID NO: 40).

In certain embodiments, the instant disclosure provides an isolated multispecific antibody comprising a first antigen-binding domain, wherein the first antigen-binding domain specifically binds to OX40 (e.g., human OX40) and comprises a heavy chain variable region having an amino acid sequence derived from a human IGHV3-73 germline sequence (e.g., IGHV3-73*01, e.g., having the amino acid sequence of SEQ ID NO: 39), and a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 34, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region having an amino acid sequence derived from a human IGHV3-73 germline sequence (e.g., IGHV3-73*01, e.g., having the amino acid sequence of SEQ ID NO: 39), and a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the first antigen-binding domain that specifically binds to human OX40 are not SEQ ID NOs: 16, 21, 25, 32, 33, and 38, respectively, and wherein the isolated multispecific antibody further comprises a second antigen-binding domain. In certain embodiments, the instant disclosure provides an isolated multispecific antibody comprising a first antigen-binding domain, wherein the first antigen-binding domain specifically binds to OX40 (e.g., human OX40) and comprises a heavy chain variable region having an amino acid sequence derived from a human IGHV3-73 germline sequence (e.g., IGHV3-73*01, e.g., having the amino acid sequence of SEQ ID NO: 39), and a light chain variable region having an amino acid sequence derived from a human IGKV2-28 germline sequence (e.g., IGKV2-28*01, e.g., having the amino acid sequence of SEQ ID NO: 40), wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and cross-competes for binding to OX40 (e.g., human OX40) with an antibody comprising the heavy and light chain variable region amino acid sequences set forth in SEQ ID NOs: 2 and 11; 3 and 11; 4 and 11; 5 and 11; 6 and 11; 7 and 15; 8 and 15; 9 and 15; 10 and 15; 1 and 12; 1 and 13; or 1 and 14, respectively, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain.

In certain embodiments, the instant disclosure provides an isolated multispecific antibody comprising a first antigen-binding domain, wherein the first antigen-binding domain specifically binds to OX40 (e.g., human OX40) and binds to the same or an overlapping epitope of OX40 (e.g., an epitope of human OX40) as an antibody described herein, e.g., an antibody comprising the heavy and light chain variable region amino acid sequences set forth in SEQ ID NOs: 2 and 11; 3 and 11; 4 and 11; 5 and 11; 6 and 11; 7 and 15; 8 and 15; 9 and 15; 10 and 15; 1 and 12; 1 and 13; or 1 and 14, respectively, wherein the CDRH1, CDRH2, CDRH3, CDRL1, CDRL2, and CDRL3 sequences of the first antigen-binding domain that specifically binds to human OX40 are not respectively either SEQ ID NOs: 16, 21, 25, 32, 33, and 34 or SEQ ID NOs: 16, 21, 25, 32, 33, and 38, and wherein the isolated multispecific antibody further comprises a second antigen-binding domain.

In some embodiments, the second antigen-binding domain of an isolated multispecific antibody disclosed herein specifically binds to human GITR.

In certain embodiments, the second antigen-binding domain that specifically binds to GITR (e.g., human GITR) comprises a heavy chain variable region comprising one, two, or all three of the CDRs of a heavy chain variable region set forth in Table 7 herein. In certain embodiments, the second antigen-binding domain that specifically binds to GITR (e.g., human GITR) comprises the CDRH1 of one of heavy chain variable regions set forth in Table 7. In certain embodiments, the second antigen-binding domain that specifically binds to GITR (e.g., human GITR) comprises the CDRH2 of one of the heavy chain variable regions set forth in Table 7. In certain embodiments, the second antigen-binding domain that specifically binds to GITR (e.g., human GITR) comprises the CDRH3 of one of the heavy chain variable regions set forth in Table 7.

In certain embodiments, the second antigen-binding domain that specifically binds to GITR (e.g., human GITR) comprises a light chain variable region comprising one, two, or all three of the CDRs of a light chain variable region disclosed in Table 7 herein. In certain embodiments, the second antigen-binding domain that specifically binds to GITR (e.g., human GITR) comprises the CDRL1 of one of light chain variable regions set forth in Table 7. In certain embodiments, the second antigen-binding domain that specifically binds to GITR (e.g., human GITR) comprises the CDRL2 of one of the light chain variable regions set forth in Table 7. In certain embodiments, the second antigen-binding domain that specifically binds to GITR (e.g., human GITR) comprises the CDRL3 of one of the light chain variable regions set forth in Table 7.

In certain embodiments, the second antigen-binding domain that specifically binds to GITR (e.g., human GITR) comprises the Chothia V H CDRs of a VH disclosed in Table 7 herein. In certain embodiments, the second antigen-binding domain that specifically binds to GITR (e.g., human GITR) comprises the Chothia V L CDRs of a VL disclosed in Table 7 herein. In certain embodiments, the second antigen-binding domain that specifically binds to GITR (e.g., human GITR) comprises the Chothia V H CDRs and Chothia V L CDRs of an antibody disclosed in Table 7 herein. In certain embodiments, the second antigen-binding domain that specifically binds to GITR (e.g., human GITR) comprises one or more CDRs, in which the Chothia and Kabat CDRs have the same amino acid sequence. In certain embodiments, the second antigen-binding domain that specifically binds to GITR (e.g., human GITR) comprises combinations of Kabat CDRs and Chothia CDRs.

In certain embodiments, the second antigen-binding domain that specifically binds to GITR (e.g., human GITR) comprise CDRs of an antibody disclosed in Table 7 herein, as determined by the IMGT numbering system, for example, as described in Lefranc M-P (1999) supra and Lefranc M-P et al., (1999) supra.

In certain embodiments, the second antigen-binding domain that specifically binds to GITR (e.g., human GITR) comprises CDRs of an antibody disclosed in Table 7 herein as determined by the AbM numbering scheme.

In certain embodiments, the second antigen-binding domain that specifically binds to GITR (e.g., human GITR) comprises a heavy chain variable region comprising the CDRH1, CDRH2, and CDRH3 region amino acid sequences of a heavy chain variable region set forth in SEQ ID NO: 52, 53, 54, 55, 56, or 95, and a light chain variable region comprising the CDRL1, CDRL2, and CDRL3 region amino acid sequences of a light chain variable region set forth in SEQ ID NO: 57, 58, 59, or 96, wherein each CDR is defined in accordance with the MacCallum definition, the Kabat definition, the Chothia definition, the combination of the Kabat definition and the Chothia definition, the IMGT numbering system, or the AbM definition of CDR.

In certain embodiments, the second antigen-binding domain that specifically binds to GITR (e.g., human GITR) comprises a heavy chain variable region comprising the CDRH1, CDRH2, and CDRH3 region amino acid sequences of a heavy chain variable region set forth in SEQ ID NO: 52, 53, 54, 55, 56, or 95, and a light chain variable region comprising the CDRL1, CDRL2, and CDRL3 region amino acid sequences of a light chain variable region set forth in SEQ ID NO: 57, 58, 59, or 96, wherein each CDR is defined in accordance with the MacCallum definition, the Kabat definition, the Chothia definition, the combination of the Kabat definition and the Chothia definition, the IMGT numbering system, or the AbM definition of CDR.

In certain embodiments, the second antigen-binding domain that specifically binds to GITR (e.g., human GITR) comprises:
(a) a CDRH1 comprises the amino acid sequence of $X_1YX_2MX_3$ (SEQ ID NO: 76), wherein
　$X_1$ is D, E or G,
　$X_2$ is A or V, and
　$X_3$ is Y or H; and/or
(b) a CDRH2 comprises the amino acid sequence of $X_1IX_2TX_3SGX_4X_5X_6YNQKFX_7X_8$ (SEQ ID NO: 77), wherein
　$X_1$ is V or L,
　$X_2$ is R, K or Q,
　$X_3$ is Y or F,
　$X_4$ is D, E or G,
　$X_5$ 1S V or L,
　$X_6$ is T or S,
　$X_7$ is K, R or Q, and
　$X_8$ is D, E or G; and/or (c) a CDRH3 comprises the amino acid sequence of SGTVXGFAY (SEQ ID NO: 99), wherein
X is R or A; and/or
(d) a CDRL1 comprises the amino acid sequence of KSSQSLLNSX$_1$NQKNYLX$_2$ (SEQ ID NO: 80), wherein
X$_1$ is G or S, and
X$_2$ is T or S; and/or
(e) a CDRL2 comprises the amino acid sequence of WASTRES (SEQ ID NO: 71); and/or
(f) a CDRL3 comprises the amino acid sequence of QNX$_1$YSX$_2$PYT (SEQ ID NO: 81), wherein
X$_1$ is D, E, or A; and
X$_2$ is Y, F, or S.

In certain embodiments, CDRH1 of the second antigen-binding domain that specifically binds to human GITR comprises the amino acid sequence of X$_1$YAMX$_2$ (SEQ ID NO: 78), wherein: X$_1$ is D, G, or E; and X$_2$ is Y or H. In certain embodiments, CDRH2 of the second antigen-binding domain that specifically binds to human GITR comprises the amino acid sequence of X$_1$IRTYSGX$_2$VX$_3$YNQKFX$_4$X$_5$ (SEQ ID NO: 79), wherein: X$_1$ is V or L; X$_2$ is D or G; X$_3$ is T or S; X$_4$ is K, R, or Q; and X$_5$ is D, E, or G. In certain embodiments, CDRL1 of the second antigen-binding domain that specifically binds to human GITR comprises the amino acid sequence of KSSQSLLNSXNQKNYLT (SEQ ID NO: 82), wherein: X is G or S. In certain embodiments, CDRL3 of the second antigen-binding domain that specifically binds to human GITR comprises the amino acid sequence of QNX$_1$YSX$_2$PYT (SEQ ID NO: 83), wherein: X$_1$ is D, E, or A; and X$_2$ is Y or F. In certain embodiments, CDRH1 of the second antigen-binding domain that specifically binds to human GITR comprises an amino acid sequence selected from the group consisting of SEQ ID NOs: 60-62. In certain embodiments, CDRH2 of the second antigen-binding domain that specifically binds to human GITR comprises an amino acid sequence selected from the group consisting of SEQ ID NOs: 63-67. In certain embodiments, CDRH3 of the second antigen-binding domain that specifically binds to human GITR comprises an amino acid sequence selected from the group consisting of SEQ ID NOs: 68 and 97. In certain embodiments, CDRL1 of the second antigen-binding domain that specifically binds to human GITR comprises an amino acid sequence selected from the group consisting of SEQ ID NOs: 69 and 70. In certain embodiments, CDRL3 of the second antigen-binding domain that specifically binds to human GITR comprises an amino acid sequence selected from the group consisting of SEQ ID NOs: 72, 73, and 98.

In certain embodiments, the second antigen-binding domain that specifically binds to human GITR comprises a heavy chain variable region comprising the CDRH1, CDRH2 and CDRH3 amino acid sequences set forth in SEQ ID NOs: 60, 63, and 68; 60, 64, and 68; 60, 63, and 97; 61, 65, and 68; 62, 66, and 68; or 62, 67, and 68, respectively.

In certain embodiments, the second antigen-binding domain that specifically binds to human GITR comprises a light chain variable region comprising the CDRL1, CDRL2 and CDRL3 amino acid sequences set forth in SEQ ID NOs: 69, 71, and 72; 69, 71, and 98; 70, 71, and 73; or 69, 71, and 72, respectively.

In certain embodiments, the second antigen-binding domain that specifically binds to human GITR comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 60, 63, 68, 69, 71, and 72; 60, 64, 68, 69, 71, and 72; 60, 63, 97, 69, 71, and 72; 60, 63, 68, 69, 71, and 98; 61, 65, 68, 70, 71, and 73; 62, 66, 68, 69, 71, and 72; or 62, 67, 68, 69, 71, and 72, respectively.

In certain embodiments, the second antigen-binding domain that specifically binds to human GITR comprises a heavy chain variable region comprising an amino acid sequence of SEQ ID NO: 84. In certain embodiments, the second antigen-binding domain that specifically binds to human GITR comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 52, 53, 54, 55, 56, or 95. In certain embodiments, the second antigen-binding domain that specifically binds to human GITR comprises a heavy chain variable region having the amino acid sequence set forth in SEQ ID NO: 52, 53, 54, 55, 56, or 95. In certain embodiments, the second antigen-binding domain that specifically binds to human GITR comprises a heavy chain variable region having the amino acid sequence set forth in SEQ ID NO: 52. In certain embodiments, the second antigen-binding domain that specifically binds to human GITR comprises a heavy chain variable region having the amino acid sequence set forth in SEQ ID NO: 53. In certain embodiments, the second antigen-binding domain that specifically binds to human GITR comprises a heavy chain variable region having the amino acid sequence set forth in SEQ ID NO: 95.

In certain embodiments, the second antigen-binding domain that specifically binds to human GITR comprises a light chain variable region comprising an amino acid sequence of SEQ ID NO: 85. In certain embodiments, the second antigen-binding domain that specifically binds to human GITR comprises a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 57, 58, 59, or 96. In certain embodiments, the second antigen-binding domain that specifically binds to human GITR comprises a light chain variable region having the amino acid sequence set forth in SEQ ID NO: 57, 58, 59, or 96. In certain embodiments, the second antigen-binding domain that specifically binds to human GITR comprises a light chain variable region having the amino acid sequence set forth in SEQ ID NO: 57. In certain embodiments, the second antigen-binding domain that specifically binds to human GITR comprises a light chain variable region having the amino acid sequence set forth in SEQ ID NO: 96.

In certain embodiments, the second antigen-binding domain that specifically binds to human GITR comprises a heavy chain variable region comprising an amino acid sequence of SEQ ID NO: 84, and a light chain variable region comprising an amino acid sequence of SEQ ID NO: 85. In certain embodiments, the second antigen-binding domain that specifically binds to human GITR comprises a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 52, 53, 54, 55, 56, or 95, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 57, 58, 59, or 96. In certain embodiments, the second antigen-binding domain that specifically binds to human GITR comprises a heavy chain variable region having the amino acid sequence set forth in SEQ ID NO: 52, 53, 54, 55, 56, or 95, and a light chain variable region having the amino acid sequence set forth in SEQ ID NO: 57, 58, 59, or 96. In certain embodiments, the second antigen-binding domain that specifically binds to human GITR comprises a heavy chain variable region and light chain variable region having the amino acid sequences set forth in SEQ ID NO: 53 and 57; 95 and 57; 52 and 96, respectively. In certain embodiments, the second antigen-binding domain that specifically binds to human GITR comprises a heavy chain variable region and light chain variable region having the amino acid sequences set forth in SEQ ID NO: 53 and 57, respectively. In certain embodiments, the second antigen-binding domain that specifically binds to human GITR comprises a heavy chain variable region and light chain variable region having the amino acid sequences set forth in SEQ ID NO: 95 and 57, respectively. In certain embodiments, the second antigen-binding domain that specifically binds to human GITR comprises a heavy chain variable region and light chain variable region having the amino acid sequences set forth in SEQ ID NO: 52 and 96, respectively.

In certain embodiments, the instant disclosure provides an isolated multispecific antibody comprising a first antigen-binding domain that specifically binds to OX40 (e.g., human OX40) and a second antigen-binding domain that specifically binds to GITR (e.g., human GITR), wherein CDRH1, CDRH2, CDRH3, CDRL1, CDRL2, and CDRL3 of the first antigen-binding domain and CDRH1, CDRH2, CDRH3, CDRL1, CDRL2, and CDRL3 of the second antigen-binding domain comprise the amino acid sequences listed in a single row of Table 12. In certain embodiments, the instant disclosure provides an isolated multispecific antibody comprising a first antigen-binding domain that specifically binds to OX40 (e.g., human OX40) and a second antigen-binding domain that specifically binds to GITR (e.g., human GITR), wherein CDRH1, CDRH2, CDRH3, CDRL1, CDRL2, and CDRL3 of the first antigen-binding domain and CDRH1, CDRH2, CDRH3, CDRL1, CDRL2, and CDRL3 of the second antigen-binding domain comprise the amino acid sequences set forth in SEQ ID NOs: 16, 21, 25, 32, 33, 34, 60, 64, 68, 69, 71, and 72; 16, 21, 25, 32, 33, 34, 60, 63, 97, 69, 71, and 72; 16, 21, 25, 32, 33, 34, 60, 63, 68, 69, 71, and 98; 16, 21, 25, 32, 33, 38, 60, 64, 68, 69, 71, and 72; 16, 21, 25, 32, 33, 38, 60, 63, 97, 69, 71, and 72; 16, 21, 25, 32, 33, 38, 60, 63, 68, 69, 71, and 98; 16, 22, 25, 32, 33, 34, 60, 63, 68, 69, 71, and 72; 16, 22, 25, 32, 33, 34, 60, 64, 68, 69, 71, and 72; 16, 22, 25, 32, 33, 34, 60, 63, 97, 69, 71, and 72; 16, 22, 25, 32, 33, 34, 60, 63, 68, 69, 71, and 98; 16, 22, 25, 32, 33, 34, 61, 65, 68, 70, 71, and 73; 16, 22, 25, 32, 33, 34, 62, 66, 68, 69, 71, and 72; 16, 22, 25, 32, 33, 34, 62, 67, 68, 69, 71, and 72; 16, 21, 26, 32, 33, 34, 60, 63, 68, 69, 71, and 72; 16, 21, 26, 32, 33, 34, 60, 64, 68, 69, 71, and 72; 16, 21, 26, 32, 33, 34, 60, 63, 97, 69, 71, and 72; 16, 21, 26, 32, 33, 34, 60, 63, 68, 69, 71, and 98; 16, 21, 26, 32, 33, 34, 61, 65, 68, 70, 71, and 73; 16, 21, 26, 32, 33, 34, 62, 66, 68, 69, 71, and 72; 16, 21, 26, 32, 33, 34, 62, 67, 68, 69, 71, and 72; 16, 21, 27, 32, 33, 34, 60, 63, 68, 69, 71, and 72; 16, 21, 27, 32, 33, 34, 60, 64, 68, 69, 71, and 72; 16, 21, 27, 32, 33, 34, 60, 63, 97, 69, 71, and 72; 16, 21, 27, 32, 33, 34, 60, 63, 68, 69, 71, and 98; 16, 21, 27, 32, 33, 34, 61, 65, 68, 70, 71, and 73; 16, 21, 27, 32, 33, 34, 62, 66, 68, 69, 71, and 72; 16, 21, 27, 32, 33, 34, 62, 67, 68, 69, 71, and 72; 16, 21, 28, 32, 33, 34, 60, 63, 68, 69, 71, and 72; 16, 21, 28, 32, 33, 34, 60, 64, 68, 69, 71, and 72; 16, 21, 28, 32, 33, 34, 60, 63, 97, 69, 71, and 72; 16, 21, 28, 32, 33, 34, 60, 63, 68, 69, 71, and 98; 16, 21, 28, 32, 33, 34, 61, 65, 68, 70, 71, and 73; 16, 21, 28, 32, 33, 34, 62, 66, 68, 69, 71, and 72; 16, 21, 28, 32, 33, 34, 62, 67, 68, 69, 71, and 72; 16, 21, 29, 32, 33, 34, 60, 63, 68, 69, 71, and 72; 16, 21, 29, 32, 33, 34, 60, 64, 68, 69, 71, and 72; 16, 21, 29, 32, 33, 34, 60, 63, 97, 69, 71, and 72; 16, 21, 29, 32, 33, 34, 60, 63, 68, 69, 71, and 98; 16, 21, 29, 32, 33, 34, 61, 65, 68, 70, 71, and 73; 16, 21, 29, 32, 33, 34, 62, 66, 68, 69, 71, and 72; 16, 21, 29, 32, 33, 34, 62, 67, 68, 69, 71, and 72; 17, 21, 30, 32, 33, 38, 60, 63, 68, 69, 71, and 72; 17, 21, 30, 32, 33, 38, 60, 64, 68, 69, 71, and 72; 17, 21, 30, 32, 33, 38, 60, 63, 97, 69, 71, and 72; 17, 21, 30, 32, 33, 38, 60, 63, 68, 69, 71, and 98; 17, 21, 30, 32, 33, 38, 61, 65, 68, 70, 71, and 73; 17, 21, 30, 32, 33, 38, 62, 66, 68, 69, 71, and 72; 17, 21, 30, 32, 33, 38, 62, 67, 68, 69, 71, and 72; 18, 23, 25, 32, 33, 38, 60, 63, 68, 69, 71, and 72; 18, 23, 25, 32, 33, 38, 60, 64, 68, 69, 71, and 72; 18, 23, 25, 32, 33, 38, 60, 63, 97, 69, 71, and 72; 18, 23, 25, 32, 33, 38, 60, 63, 68, 69, 71, and 98; 18, 23, 25, 32, 33, 38, 61, 65, 68, 70, 71, and 73; 18, 23, 25, 32, 33, 38, 62, 66, 68, 69, 71, and 72; 18, 23, 25, 32, 33, 38, 62, 67, 68, 69, 71, and 72; 19, 24, 25, 32, 33, 38, 60, 63, 68, 69, 71, and 72; 19, 24, 25, 32, 33, 38, 60, 64, 68, 69, 71, and 72; 19, 24, 25, 32, 33, 38, 60, 63, 97, 69, 71, and 72; 19, 24, 25, 32, 33, 38, 60, 63, 68, 69, 71, and 98; 19, 24, 25, 32, 33, 38, 61, 65, 68, 70, 71, and 73; 19, 24, 25, 32, 33, 38, 62, 66, 68, 69, 71, and 72; 19, 24, 25, 32, 33, 38, 62, 67, 68, 69, 71, and 72; 20, 21, 31, 32, 33, 38, 60, 63, 68, 69, 71, and 72; 20, 21, 31, 32, 33, 38, 60, 64, 68, 69, 71, and 72; 20, 21, 31, 32, 33, 38, 60, 63, 97, 69, 71, and 72; 20, 21, 31, 32, 33, 38, 60, 63, 68, 69, 71, and 98; 20, 21, 31, 32, 33, 38, 61, 65, 68, 70, 71, and 73; 20, 21, 31, 32, 33, 38, 62, 66, 68, 69, 71, and 72; 20, 21, 31, 32, 33, 38, 62, 67, 68, 69, 71, and 72; 16, 21, 25, 32, 33, 35, 60, 63, 68, 69, 71, and 72; 16, 21, 25, 32, 33, 35, 60, 64, 68, 69, 71, and 72; 16, 21, 25, 32, 33, 35, 60, 63, 97, 69, 71, and 72; 16, 21, 25, 32, 33, 35, 60, 63, 68, 69, 71, and 98; 16, 21, 25, 32, 33, 35, 61, 65, 68, 70, 71, and 73; 16, 21, 25, 32, 33, 35, 62, 66, 68, 69, 71, and 72; 16, 21, 25, 32, 33, 35, 62, 67, 68, 69, 71, and 72; 16, 21, 25, 32, 33, 36, 60, 63, 68, 69, 71, and 72; 16, 21, 25, 32, 33, 36, 60, 64, 68, 69, 71, and 72; 16, 21, 25, 32, 33, 36, 60, 63, 97, 69, 71, and 72; 16, 21, 25, 32, 33, 36, 60, 63, 68, 69, 71, and 98; 16, 21, 25, 32, 33, 36, 61, 65, 68, 70, 71, and 73; 16, 21, 25, 32, 33, 36, 62, 66, 68, 69, 71, and 72; 16, 21, 25, 32, 33, 36, 62, 67, 68, 69, 71, and 72; 16, 21, 25, 32, 33, 37, 60, 63, 68, 69, 71, and 72; 16, 21, 25, 32, 33, 37, 60, 64, 68, 69, 71, and 72; 16, 21, 25, 32, 33, 37, 60, 63, 97, 69, 71, and 72; 16, 21, 25, 32, 33, 37, 60, 63, 68, 69, 71, and 98; 16, 21, 25, 32, 33, 37, 61, 65, 68, 70, 71, and 73; 16, 21, 25, 32, 33, 37, 62, 66, 68, 69, 71, and 72; or 16, 21, 25, 32, 33, 37, 62, 67, 68, 69, 71, and 72, respectively.

In certain embodiments, the instant disclosure provides an isolated multispecific antibody comprising a first antigen-binding domain that specifically binds to OX40 (e.g., human OX40) and a second antigen-binding domain that specifically binds to GITR (e.g., human GITR), wherein the heavy chain variable region and the light chain variable region of the first antigen-binding domain and the heavy chain variable region and the light chain variable region of the second antigen-binding domain comprise the amino acid sequences listed in a single row of Table 13. In certain embodiments, the instant disclosure provides an isolated multispecific antibody comprising a first antigen-binding domain that specifically binds to OX40 (e.g., human OX40) and a second antigen-binding domain that specifically binds to GITR (e.g., human GITR), wherein the heavy chain variable region and the light chain variable region of the first antigen-binding domain and the heavy chain variable region and the light chain variable region of the second antigen-binding domain comprise the amino acid sequences set forth in SEQ ID NOs: 1, 11, 53, and 57; 1, 11, 95, and 57; 1, 11, 52, and 96; 1, 15, 53, and 57; 1, 15, 95, and 57; 1, 15, 52, and 96; 2, 11, 52, and 57; 2, 11, 53, and 57; 2, 11, 95, and 57; 2, 11, 52, and 96; 2, 11, 54, and 58; 2, 11, 55, and 59; 2, 11, 56, and 59; 3, 11, 52, and 57; 3, 11, 53, and 57; 3, 11, 95, and 57; 3, 11, 52, and 96; 3, 11, 54, and 58; 3, 11, 55, and 59; 3, 11, 56, and 59; 4, 11, 52, and 57; 4, 11, 53, and 57; 4, 11, 95, and 57; 4, 11, 52, and 96; 4, 11, 54, and 58; 4, 11, 55, and 59; 4, 11, 56, and 59; 5, 11, 52, and 57; 5, 11, 53, and 57; 5, 11, 95, and 57; 5, 11, 52, and 96; 5, 11, 54, and 58; 5, 11, 55, and 59; 5, 11, 56, and 59; 6, 11, 52, and 57; 6, 11, 53, and 57; 6, 11, 95, and 57; 6, 11, 52, and 96; 6, 11, 54, and 58; 6, 11, 55, and 59; 6, 11, 56, and 59; 7, 15, 52, and 57; 7, 15, 53, and 57; 7, 15, 95, and 57; 7, 15, 52, and 96; 7, 15, 54, and 58; 7, 15, 55, and 59; 7, 15, 56, and 59; 8, 15, 52, and 57; 8, 15, 53, and 57; 8, 15, 95, and 57; 8, 15, 52, and 96; 8, 15, 54, and 58; 8, 15, 55, and 59; 8, 15, 56, and 59; 9, 15, 52, and 57; 9, 15, 53, and 57; 9, 15, 95, and 57; 9, 15, 52, and 96; 9, 15, 54, and 58; 9, 15, 55, and 59; 9, 15, 56, and 59; 10, 15, 52, and 57; 10, 15, 53, and 57; 10, 15, 95, and 57; 10, 15, 52, and 96; 10, 15, 54, and 58; 10, 15, 55, and 59; 10, 15, 56, and 59; 1, 12, 52, and 57; 1, 12, 53, and 57; 1, 12, 95, and 57; 1, 12, 52, and 96; 1, 12, 54, and 58; 1, 12, 55, and 59; 1, 12, 56, and 59; 1, 13, 52, and 57; 1, 13, 53, and 57; 1, 13, 95, and 57; 1, 13, 52, and 96; 1, 13, 54, and 58; 1, 13, 55, and 59; 1, 13, 56, and 59; 1, 14, 52, and 57; 1, 14, 53, and 57; 1, 14, 95, and 57; 1, 14, 52, and 96; 1, 14, 54, and 58; 1, 14, 55, and 59; or 1, 14, 56, and 59, respectively.

As further provided herein, antibodies that bind to OX40 and GITR can increase OX40 and/or GITR activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to OX40 and/or GITR activity without any antibody or with an unrelated antibody (e.g., an antibody that does not bind to OX40 or GITR). For instance, an antibody that binds to OX40 and GITR, e.g., an antibody that binds to OX40 and GITR and comprises a combination of CDR sequences specified herein, a combination of VH and/or VL sequences having at least 70%, at least 75%, at least 80%, at least 85%, at least 90%, at least 95%, at least 98%, at least 99%, or 100% sequence identity with a combination of VH and/or VL sequences specified herein, or a combination of heavy and/or light chains specified herein, can increase OX40 (e.g., human OX40) and/or GITR (e.g., human GITR) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to OX40 (e.g., human OX40) and/or GITR (e.g., human GITR) activity without any antibody or with an unrelated antibody (e.g., an antibody that does not bind to OX40 or GITR). Non-limiting examples of OX40 (e.g., human OX40) activity can include OX40 (e.g., human OX40) signaling, OX40 (e.g., human OX40) binding to OX40 (e.g., human OX40) ligand, cell proliferation, cell survival, and cytokine production (e.g., IL-2, TNF-α, IFN-γ, IL-4, IL-10, and/or IL-13). Non-limiting examples of GITR (e.g., human GITR) activity can include GITR (e.g., human GITR) signaling, GITR (e.g., human GITR) binding to GITR (e.g., human GITR) ligand, cell proliferation, cell survival, and cytokine production (e.g., IL-2, TNF-α, IFN-γ, IL-4, IL-10, and/or IL-13).

As further provided herein, antibodies that bind to OX40 and GITR can agonize OX40 and/or GITR function, for example, by stimulating T cell activation. For instance, an antibody that binds to OX40 and GITR, e.g., an antibody that binds to OX40 and GITR and comprises a combination of CDR sequences specified herein, a combination of VH and/or VL sequences having at least 70%, at least 75%, at least 80%, at least 85%, at least 90%, at least 95%, at least 98%, at least 99%, or 100% sequence identity with a combination of VH and/or VL sequences specified herein, or a combination of heavy and/or light chains specified herein, can stimulate T cell activation, optionally wherein T cell activation is a substantially increasing function of antibody concentrations.

As further provided herein, antibodies that bind to OX40 and GITR can agonize OX40 and/or GITR function, for example, by stimulating IL-2 release in an SEA assay. For instance, an antibody that binds to OX40 and GITR, e.g., an antibody that binds to OX40 and GITR and comprises a combination of CDR sequences specified herein, a combination of VH and/or VL sequences having at least 70%, at least 75%, at least 80%, at least 85%, at least 90%, at least 95%, at least 98%, at least 99%, or 100% sequence identity with a combination of VH and/or VL sequences specified herein, or a combination of heavy and/or light chains specified herein, can, in combination with *Staphylococcus* Enterotoxin A (SEA) (e.g., 100 ng/ml), induce IL-2 production in, e.g., PBMCs upon stimulation for, e.g., 5 days at, e.g., 37° C., 5% $CO_2$, and 97% humidity, as measured by, e.g., electrochemiluminescence. In some embodiments, the IL-2 production is a substantially increasing function of antibody concentrations. In certain embodiments, an antibody that binds to OX40 and GITR, e.g., an antibody that binds to OX40 and GITR and comprises a combination of CDR sequences specified herein, a combination of VH and/or VL sequences having at least 70%, at least 75%, at least 80%, at least 85%, at least 90%, at least 95%, at least 98%, at least 99%, or 100% sequence identity with a combination of VH and/or VL sequences specified herein, or a combination of heavy and/or light chains specified herein, can, in combination with *Staphylococcus* Enterotoxin A (SEA), induce IL-2 production in, e.g., PBMCs, wherein the IL-2 production is a substantially increasing function of antibody concentrations as assessed in, e.g., an assay comprising the following steps: (a) culturing the PBMCs (e.g., $10^5$ cells in a well) in the absence or presence of varying concentrations of the antibody and, e.g., 100 ng/ml of SEA for, e.g., 5 days at, e.g., 37° C., 5% $CO_2$, and 97% humidity; and (b) collecting clarified supernatant and measuring the titer of IL-2 by, e.g., electrochemiluminescence.

As further provided herein, antibodies that bind to OX40 and GITR can agonize OX40 and/or GITR function, for example, by stimulating NF-κB signaling. For instance, an antibody that binds to OX40 and GITR, e.g., an antibody that binds to OX40 and GITR and comprises a combination of CDR sequences specified herein, a combination of VH and/or VL sequences having at least 70%, at least 75%, at least 80%, at least 85%, at least 90%, at least 95%, at least 98%, at least 99%, or 100% sequence identity with a combination of VH and/or VL sequences specified herein, or a combination of heavy and/or light chains specified herein, can stimulate NF-κB signaling, e.g., in a Jurkat-huOX40-NF-κB-luciferase reporter assay as described in the examples herein, optionally wherein the NF-κB signaling is a substantially increasing function of antibody concentrations.

As further provided herein, antibodies that bind to OX40 and GITR can decrease OX40 and/or GITR activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to OX40 and/or GITR activity without any antibody or with an unrelated antibody (e.g., an antibody that does not bind to OX40 or GITR). For instance, an antibody that binds to OX40 and GITR, e.g., an antibody that binds to OX40 and GITR and comprises a combination of CDR sequences specified herein, a combination of VH and/or VL sequences having at least 70%, at least 75%, at least 80%, at least 85%, at least 90%, at least 95%, at least 98%, at least 99%, or 100% sequence identity with a combination of VH and/or VL sequences specified herein, or a combination of heavy and/or light chains specified herein, can decrease OX40 (e.g., human OX40) and/or GITR (e.g., human GITR) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to OX40 (e.g., human OX40) and/or GITR (e.g., human GITR) activity without any antibody or with an unrelated antibody (e.g., an antibody that does not bind to OX40 or GITR). Non-limiting examples of OX40 (e.g., human OX40) activity can include OX40 (e.g., human OX40) signaling, OX40 (e.g., human OX40) binding to OX40 (e.g., human OX40) ligand, cell proliferation, cell survival, and cytokine production (e.g., IL-2, TNF-α, IFN-γ, IL-4, IL-10, and/or IL-13). Non-limiting examples of GITR (e.g., human GITR) activity can include GITR (e.g., human GITR) signaling, GITR (e.g., human GITR) binding to GITR (e.g., human GITR) ligand, cell proliferation, cell survival, and cytokine production (e.g., IL-2, TNF-α, IFN-γ, IL-4, IL-10, and/or IL-13).

A multispecific antibody, e.g., a bispecific antibody, that binds to OX40 and/or GITR as provided herein can be prepared by chemically linking two different monoclonal antibodies or by fusing two hybridoma cell lines to produce a hybrid-hybridoma. Other multivalent formats that can be used include, for example, Kλ-bodies, dAbs, diabodies, TandAbs, nanobodies, SMIPs, DNLs, strand-exchange engineered domain bodies (SEEDbodies), Affibodies, Fynomers, Kunitz Domains, Albu-dabs, DARTs, DVD-IG, Covx-bodies, peptibodies, scFv-Igs, SVD-Igs, dAb-Igs, Knobs-in-Holes, and triomAbs. Exemplary bispecific formats are discussed in Garber et al., *Nature Reviews Drug Discovery* 13:799-801 (2014), which is herein incorporated by reference in its entirety.

Exemplary bispecific antibody molecules of the invention comprise (i) a single antibody that has two arms comprising different antigen-binding regions, one with a specificity to a first antigen such as OX40 and one with a specificity to a second antigen such as GITR, (ii) a single antibody that has one antigen-binding region or arm specific to a first antigen such as OX40 and a second antigen-binding region or arm specific to a second antigen such as GITR, (iii) a single chain antibody that has a first specificity to a first antigen such as OX40 and a second specificity to a second antigen such as GITR, e.g., via two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab)$_2$ fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody.

Examples of different classes of bispecific antibodies include but are not limited to IgG-like molecules with complementary CH3 domains to force heterodimerisation; recombinant IgG-like dual targeting molecules, wherein the two sides of the molecule each contain the Fab fragment or part of the Fab fragment of at least two different antibodies; IgG fusion molecules, wherein full length IgG antibodies are fused to extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

Examples of Fab fusion bispecific antibodies include but are not limited to F(ab)$_2$ (Medarex/AMGEN), Dual-Action or Bis-Fab (Genentech), Dock-and-Lock (DNL) (Immuno-Medics), Bivalent Bispecific (Biotecnol) and Fab-Fv (UCB-Celltech). Examples of ScFv-, diabody-based and domain antibodies include but are not limited to Bispecific T Cell Engager (BITE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), and dual targeting heavy chain only domain antibodies.

5.2.4 Constant Regions

Any heavy chain or light chain constant region can be used in the antibodies (e.g., monospecific or multispecific antibodies) disclosed herein. In certain embodiments, the antibodies (e.g., monospecific or multispecific antibodies) disclosed herein comprise an Ig region that is a human IgG, IgE, IgM, IgD, IgA, or IgY immunoglobulin molecule, any class (e.g., Ig IgG$_2$, IgG3, IgG4, IgA$_1$, and IgA$_2$), or any subclass (e.g., IgG2a and IgG2b) of immunoglobulin molecule. Exemplary constant region sequences that can be used in the antibodies (e.g., monospecific or multispecific antibodies) disclosed herein are disclosed in Table 14.

TABLE 14

Exemplary constant region sequences.

| SEQ ID NO: | Description | Amino acid Sequence |
|---|---|---|
| 88 | Human IgG1 constant | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKX$_1$VEPKSCDKTHTCPP |

TABLE 14-continued

Exemplary constant region sequences.

| SEQ ID NO: | Description | Amino acid Sequence |
|---|---|---|
| | region consensus sequence | CPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRX$_2$EX$_3$TKNQVSLTCLVKGFYPSDIAVEWESNGQPENNYKTTPPVLDSDGSFFLYSKLTVDKSRWQQGNVFSCSVMHEX$_4$LHNHYTQKSLSLSPG, wherein<br>X$_1$ is K or R<br>X$_2$ is D or E<br>X$_3$ is L or M<br>X$_4$ is G or A |
| 89 | Human IgG1 G1m3 allotype | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 90 | Human IgG1 G1m17,1 allotype | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| 91 | Human IgG1, G1m17,1,2 allotype | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEGLHNHYTQKSLSLSPG |
| 92 | Human IgG1 G1m3 allotype N297A | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 107 | Human IgG1 S239D/I332E | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPDVFLFPPKPKDTLMISRTPEVTCVVVDVSHEDPEVKFNWYVDGVEVHNAKTKPREEQYNSTYRVVSVLTVLHQDWLNGKEYKCKVSNKALPAPEEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 108 | Human IgG1 S239D/A330L/I332E | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPDVFLFPPKPKDTLMISRTPEVTCVVVDVSHEDPEVKFNWYVDGVEVHNAKTKPREEQYNSTYRVVSVLTVLHQDWLNGKEYKCKVSNKALPLPEEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 109 | Human IgG1 | ASTKGPSVFPLAPSSKSTSGGTAALGCLVKDYFPEPVTVSWNSGALTSGVHTFPAVLQSSGLYSLSSVVTVPSS |
| | L235V/F243L/R292P/Y300L/P396L | SLGTQTYICNVNHKPSNTKVDKRVEPKSCDKTHTCPPCPAPELVGGPSVFLLPPKPKDTLMISRTPEVTCVVVDVSHEDPEVKFNWYVDGVEVHNAKTKPPEEQYNSTLRVVSVLTVLHQDWLNGKEYKCKVSNKALPAPIEKTISKAKGQPREPQVYTLPPSREEMTKNQVSLTCLVKGFYPSDIAVEWESNGQPENNYKTTPLVLDSDGSFFLYSKLTVDKSRWQQGNVFSCSVMHEALHNHYTQKSLSLSPG |
| 93 | Human IgG4 S228P | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| 94 | Human kappa light chain constant region IGKC*01 Km3 allotype | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

In certain embodiments, the antibodies (e.g., monospecific or multispecific antibodies) disclosed herein comprise a human IgG heavy chain constant region that is a variant of a wild type human IgG heavy chain constant region, wherein the variant human IgG heavy chain constant region binds to human Fc gamma receptors with higher affinity than the wild type human IgG heavy chain constant region binds to the human Fc gamma receptors.

In certain embodiments, the variant human IgG heavy chain constant region comprises one or more of the following amino acid mutations, numbered according to the EU numbering system: S239D, A330L, and I332E. In certain embodiments, the variant human IgG heavy chain constant region comprises the following amino acid mutations, numbered according to the EU numbering system: S239D and I332E. In certain embodiments, the variant human IgG heavy chain constant region is a variant human IgG$_1$ heavy chain constant region comprising the following amino acid mutations, numbered according to the EU numbering system: S239D and I332E. In certain embodiments, the variant human IgG heavy chain constant region comprises the following amino acid mutations, numbered according to the EU numbering system: S239D, A330L, and I332E. In certain embodiments, the variant human IgG heavy chain constant region is a variant human IgG$_1$ heavy chain constant region comprising the following amino acid mutations, numbered according to the EU numbering system: S239D, A330L, and I332E.

In certain embodiments, the variant human IgG heavy chain constant region comprises one or more of the following amino acid mutations, numbered according to the EU numbering system: L235V, F243L, R292P, Y300L, and P396L. In certain embodiments, the variant human IgG heavy chain constant region comprises the following amino acid mutations, numbered according to the EU numbering system: L235V, F243L, R292P, Y300L, and P396L. In certain embodiments, the variant human IgG heavy chain constant region is a variant human IgG$_1$ heavy chain constant region comprising the following amino acid mutations, numbered according to the EU numbering system: L235V, F243L, R292P, Y300L, and P396L.

In certain embodiments, the variant human IgG heavy chain constant region comprises one or more of the following amino acid mutations, numbered according to the EU numbering system: G236A, S239D, F243L, T256A, K290A, R292P, S298A, Y300L, V305I, A330L, I332E, E333A, K334A, A339T, and P396L. In certain embodiments, the variant human IgG heavy chain constant region comprises a set of amino acid mutations selected from the group consisting of: S239D; T256A; K290A; S298A; I332E; E333A; K334A; A339T; S239D and I332E; S239D, A330L, and I332E; S298A, E333A, and K334A; G236A, S239D, and I332E; and F243L, R292P, Y300L, V305I, and P396L, numbered according to the EU numbering system. In certain embodiments, the variant human IgG heavy chain constant region comprises S267E or L328F amino acid mutation, numbered according to the EU numbering system. In certain embodiments, the variant human IgG heavy chain constant region comprises the following amino acid mutations, numbered according to the EU numbering system: S267E and L328F. In certain embodiments, the variant human IgG heavy chain constant region is a variant human IgG$_1$ heavy chain constant region comprising the following amino acid mutations, numbered according to the EU numbering system: S267E and L328F. In certain embodiments, the variant human IgG heavy chain constant region comprises P238D amino acid mutation, numbered according to the EU numbering system. In certain embodiments, the variant human IgG heavy chain constant region is a variant human IgG$_1$ heavy chain constant region comprising P238D amino acid mutation, numbered according to the EU numbering system. In certain embodiments, the variant human IgG heavy chain constant region comprises one or more of the following amino acid mutations, numbered according to the EU numbering system: P238D, E233D, G237D, H268D, P271G, and A330R. In certain embodiments, the variant human IgG heavy chain constant region comprises the following amino acid mutations, numbered according to the EU numbering system: P238D, E233D, G237D, H268D, P271G, and A330R. In certain embodiments, the variant human IgG heavy chain constant region is a variant human IgG$_1$ heavy chain constant region comprising the following amino acid mutations, numbered according to the EU numbering system: P238D, E233D, G237D, H268D, P271G, and A330R. In certain embodiments, the variant human IgG heavy chain constant region comprises C127S amino acid mutation, numbered according to the EU numbering system. In certain embodiments, the variant human IgG heavy chain constant region is a variant human IgG2 heavy chain constant region comprising C127S amino acid mutation, numbered according to the EU numbering system.

In certain embodiments, the antibodies (e.g., monospecific or multispecific antibodies) provided herein comprise an afucosylated Fc region.

In certain embodiments, the antibodies (e.g., monospecific or multispecific antibodies) disclosed herein comprise a human IgG heavy chain constant region that is a variant of a wild type human IgG heavy chain constant region, wherein the variant human IgG heavy chain constant region binds to human Fc gamma receptors with lower affinity than the wild type human IgG heavy chain constant region binds to the human Fc gamma receptors. In certain embodiments, the variant human IgG heavy chain constant region comprises a mutation selected from the group consisting of N297A, N297Q, D265A, and a combination thereof, numbered according to the EU numbering system. In certain embodiments, the variant human IgG heavy chain constant region comprises a mutation selected from the group consisting of D265A, P329A, and a combination thereof, numbered according to the EU numbering system.

In certain embodiments, one, two, or more mutations (e.g., amino acid substitutions) are introduced into the Fc region of an antibody (e.g., a monospecific or multispecific antibody) described herein (e.g., CH2 domain (residues 231-340 of human IgG$_1$) and/or CH3 domain (residues 341-447 of human IgG$_1$) and/or the hinge region numbered according to the EU numbering system to alter one or more functional properties of the antibody (e.g., a monospecific or multispecific antibody), such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain may be altered to, e.g., facilitate assembly of the light and heavy chains, or to alter (e.g., increase or decrease) the stability of the antibody (e.g., a monospecific or multispecific antibody).

In some embodiments, one, two, or more mutations (e.g., amino acid substitutions) are introduced into the Fc region of an antibody (e.g., a monospecific or multispecific antibody) described herein (e.g., CH2 domain (residues 231-340 of human IgG$_1$) and/or CH3 domain (residues 341-447 of human IgG$_1$) and/or the hinge region numbered according to the EU numbering system to increase or decrease the affinity of the antibody (e.g., a monospecific or multispecific antibody) for an Fc receptor (e.g., an activated Fc receptor) on the surface of an effector cell. Mutations in the Fc region of an antibody (e.g., a monospecific or multispecific antibody) that decrease or increase the affinity of an antibody (e.g., a monospecific or multispecific antibody) for an Fc receptor and techniques for introducing such mutations into the Fc receptor or fragment thereof are known to one of skill in the art. Examples of mutations in the Fc receptor of an antibody (e.g., a monospecific or multispecific antibody) that can be made to alter the affinity of the antibody (e.g., a monospecific or multispecific antibody) for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In a specific embodiment, one, two, or more amino acid mutations (i.e., substitutions, insertions or deletions) are introduced into an IgG constant domain, or FcRn-binding fragment thereof (for example an Fc or hinge-Fc domain fragment) to alter (e.g., decrease or increase) half-life of an antibody (e.g., a monospecific or multispecific antibody) in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody (e.g., a monospecific or multispecific antibody) in vivo. In some embodiments, one, two or more amino acid mutations (i.e., substitutions, insertions, or deletions) are introduced into an IgG constant domain, or FcRn-binding fragment thereof (for example an Fc or hinge-Fc domain fragment) to decrease the half-life of the antibody (e.g., a monospecific or multispecific antibody) in vivo. In other embodiments, one, two or more amino acid mutations (i.e., substitutions, insertions or deletions) are introduced into an IgG constant domain, or FcRn-binding fragment thereof (for example an Fc or hinge-Fc domain fragment) to increase the half-life of the antibody (e.g., a monospecific or multispecific antibody) in vivo. In a specific embodiment, the antibodies (e.g., monospecific or multispecific antibodies) may have one or more amino acid mutations (e.g., substitutions) in the second constant (CH2) domain (residues 231-340 of human $IgG_1$) and/or the third constant (CH3) domain (residues 341-447 of human $IgG_1$), numbered according to the EU numbering system. In a specific embodiment, the constant region of the $IgG_1$ of an antibody (e.g., a monospecific or multispecific antibody) described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In certain embodiments, an antibody (e.g., a monospecific or multispecific antibody) comprises an IgG constant domain comprising one, two, three or more amino acid substitutions of amino acid residues at positions 251-257, 285-290, 308-314, 385-389, and 428-436, numbered according to the EU numbering system.

In certain embodiments, one or more amino acids selected from amino acid residues 329, 331, and 322 in the constant region of an antibody (e.g., a monospecific or multispecific antibody) described herein, numbered according to the EU numbering system, can be replaced with a different amino acid residue such that the antibody (e.g., a monospecific or multispecific antibody) has altered C1q binding and/or reduced or abolished complement dependent cytotoxicity (CDC). This approach is described in further detail in U.S. Pat. No. 6,194,551 (Idusogie et al). In some embodiments, one or more amino acid residues within amino acid positions 231 to 238 in the N-terminal region of the CH2 domain of an antibody (e.g., a monospecific or multispecific antibody) described herein are altered to thereby alter the ability of the antibody (e.g., a monospecific or multispecific antibody) to fix complement. This approach is described further in International Publication No. WO 94/29351. In certain embodiments, the Fc region of an antibody (e.g., a monospecific or multispecific antibody) described herein is modified to increase the ability of the antibody (e.g., a monospecific or multispecific antibody) to mediate antibody dependent cellular cytotoxicity (ADCC) and/or to increase the affinity of the antibody (e.g., a monospecific or multispecific antibody) for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072.

In certain embodiments, an antibody (e.g., a monospecific or multispecific antibody) described herein comprises the constant region of an IgG4 antibody and the serine at amino acid residue 228 of the heavy chain, numbered according to the EU numbering system, is substituted for proline.

In certain embodiments, an antibody (e.g., a monospecific or multispecific antibody) described herein comprises the constant region of an IgG2 antibody and the cysteine at amino acid residue 127 of the heavy chain, numbered according to the EU numbering system, is substituted for serine.

Antibodies with reduced fucose content have been reported to have an increased affinity for Fc receptors, such as, e.g., FcγRIIIa. Accordingly, in certain embodiments, the antibodies (e.g., monospecific or multispecific antibodies) described herein have reduced fucose content or no fucose content. Such antibodies (e.g., monospecific or multispecific antibodies) can be produced using techniques known to one skilled in the art. For example, the antibodies (e.g., monospecific or multispecific antibodies) can be expressed in cells deficient or lacking the ability of fucosylation. In a specific example, cell lines with a knockout of both alleles of α1,6-fucosyltransferase can be used to produce antibodies (e.g., monospecific or multispecific antibodies) with reduced fucose content. The Potelligent® system (Lonza) is an example of such a system that can be used to produce antibodies (e.g., monospecific or multispecific antibodies) with reduced fucose content. Alternatively, antibodies (e.g., monospecific or multispecific antibodies) with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies (e.g., monospecific or multispecific antibodies) thereof which are not fucsoylated. See, e.g., Longmore G D & Schachter H (1982) Carbohydr Res 100: 365-92 and Imai-Nishiya H et al., (2007) BMC Biotechnol. 7: 84 for methods for producing antibodies (e.g., monospecific or multispecific antibodies) with no fucose content or reduced fucose content.

Engineered glycoforms may be useful for a variety of purposes, including but not limited to enhancing or reducing effector function. Methods for generating engineered glycoforms in an antibody (e.g., a monospecific or multispecific antibody) described herein include but are not limited to those disclosed, e.g., in Umaña P et al., (1999) Nat Biotechnol 17: 176-180; Davies J et al., (2001) Biotechnol Bioeng 74: 288-294; Shields R L et al., (2002) J Biol Chem 277: 26733-26740; Shinkawa T et al., (2003) J Biol Chem 278: 3466-3473; Niwa R et al., (2004) Clin Cancer Res 1: 6248-6255; Presta L G et al., (2002) Biochem Soc Trans 30: 487-490; Kanda Y et al., (2007) Glycobiology 17: 104-118; U.S. Pat. Nos. 6,602,684; 6,946,292; and 7,214,775; U.S. Patent Publication Nos. US 2007/0248600; 2007/0178551; 2008/0060092; and 2006/0253928; International Publication Nos. WO 00/61739; WO 01/292246; WO 02/311140; and WO 02/30954; Potillegent™ technology (Biowa, Inc. Princeton, N.J.); and GlycoMAb® glycosylation engineering technology (Glycart biotechnology AG, Zurich, Switzerland). See also, e.g., Ferrara C et al., (2006) Biotechnol Bioeng 93: 851-861; International Publication Nos. WO 07/039818; WO 12/130831; WO 99/054342; WO 03/011878; and WO 04/065540.

In certain embodiments, the technology used to engineer the Fc domain of an antibody (e.g., a monospecific or multispecific antibody) described herein is the Xmab® Technology of Xencor (Monrovia, Calif.). See, e.g., U.S.

Pat. Nos. 8,367,805; 8,039,592; 8,124,731; 8,188,231; U.S. Patent Publication No. 2006/0235208; International Publication Nos. WO 05/077981; WO 11/097527; and Richards J O et al., (2008) Mol Cancer Ther 7: 2517-2527.

In certain embodiments, any of the constant region mutations or modifications described herein can be introduced into one or both heavy chain constant regions of an antibody (e.g., a monospecific or multispecific antibody) described herein having two heavy chain constant regions.

5.3 Antibody Production

Antibodies, including monospecific or multispecific (e.g., bispecific) antibodies, that immunospecifically bind to OX40 and/or GITR, (e.g., human OX40 and/or GITR) can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., a recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In a certain aspect, provided herein is a method of making an antibody which immunospecifically binds to OX40 and/or GITR (including, e.g., monospecific or multispecific antibodies that bind to human OX40 and/or human GITR) comprising culturing a cell or host cell described herein. In a certain aspect, provided herein is a method of making an antibody which immunospecifically binds to OX40 and/or GITR (including, e.g., monospecific or multispecific antibodies that bind to human OX40 and/or human GITR) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein.

In specific embodiments, a "monoclonal antibody," as used herein, is an antibody produced by a single cell (e.g., hybridoma or host cell producing a recombinant antibody), wherein the antibody immunospecifically binds to OX40 and/or GITR (including, e.g., monospecific or multispecific antibodies that bind to human OX40 and/or GITR) as determined, e.g., by ELISA or other antigen-binding or competitive binding assay known in the art or in the Examples provided herein. In particular embodiments, a monoclonal antibody can be a chimeric antibody or a humanized antibody. In certain embodiments, a monoclonal antibody is a monovalent antibody or multivalent (e.g., bivalent) antibody. In certain embodiments, a monoclonal antibody can be a Fab fragment or a F(ab')$_2$ fragment. Monoclonal antibodies described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., OX40 or GITR (e.g., human OX40 or GITR)) used for immunization. Alternatively, lymphocytes can be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) Hybridoma 16:381-9, incorporated by reference in its entirety).

In some embodiments, mice (or other animals, such as rats, monkeys, donkeys, pigs, sheep, hamster, or dogs) can be immunized with an antigen (e.g., OX40 or GITR (e.g., human OX40 or GITR)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that optionally contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against OX40 and/or GITR (e.g., human OX40 and/or GITR). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of a tetrameric antibody molecule and contains the complete light chain paired with the VH and CH1 domains of the heavy chain. A F(ab')$_2$ fragment contains the two antigen-binding arms of a tetrameric antibody molecule linked by disulfide bonds in the hinge region.

Further, the antibodies or antigen-binding fragments described herein can also be generated using various phage display methods known in the art. In phage display methods, proteins are displayed on the surface of phage particles which carry the polynucleotide sequences encoding them. In particular, DNA sequences encoding heavy and light chain variable regions are amplified from animal cDNA libraries (e.g., human or murine cDNA libraries of affected tissues). The DNA encoding the heavy and light chain variable regions are recombined together with a scFv linker by PCR and cloned into a phagemid vector. The vector is electroporated in E. coli and the E. coli is infected with helper phage. Phage used in these methods are typically filamentous phage including fd and M13, and the heavy and light chain variable regions are usually recombinantly fused to either the phage gene III or gene VIII. Phage expressing an antibody that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/11236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

As described in the above references, after phage selection, the antibody coding regions from the phage can be isolated and used to generate antibodies, including human antibodies, and expressed in any desired host, including mammalian cells, insect cells, plant cells, yeast, and bacteria, e.g., as described below. Techniques to recombinantly produce antibodies such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In one aspect, to generate antibodies, PCR primers including heavy or light chain variable region nucleotide sequences, a restriction site, and a flanking sequence to protect the restriction site can be used to amplify the heavy or light chain variable region sequences from a template, e.g., scFv clones. Utilizing cloning techniques known to those of skill in the art, the PCR amplified heavy chain variable regions can be cloned into vectors expressing a heavy chain constant region, and the PCR amplified light chain variable regions can be cloned into vectors expressing a light chain constant region, e.g., human kappa or lambda constant regions. The heavy and light chain variable regions can also be cloned into one vector expressing the necessary constant regions. The heavy chain conversion vectors and light chain conversion vectors are then co-transfected into cell lines to generate stable or transient cell lines that express antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, IgG2, IgG3 and IgG4. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is incorporated by reference herein in its entirety.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301.

Further, antibodies that immunospecifically bind to an OX40 and/or GITR antigen can, in turn, be utilized to generate anti-idiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438).

In particular embodiments, an antibody or antigen-binding fragment thereof described herein, which binds to the same epitope of OX40 and/or GITR (e.g., human OX40 and/or GITR) as an anti-OX40 or GITR antibody or antigen-binding fragment thereof described herein, is a human antibody. In particular embodiments, an antibody described herein, which competitively blocks (e.g., in a dose-dependent manner) any one of the antibodies described herein, from binding to OX40 or GITR (e.g., human OX40 or GITR), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., OX40 or GITR). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the XENOMOUSE™ (Abgenix, Inc.; U.S. Pat. Nos. 6,075,181 and 6,150,184), the HUABMOUSE™ (Mederex, Inc./Gen Pharm; U.S. Pat. Nos. 5,545,806 and 5,569,825), the TRANSCHROMO MOUSE™ (Kirin) and the KM MOUSE™ (Medarex/Kirin).

Human antibodies or antigen-binding fragments which specifically bind to OX40 and/or GITR (including, e.g., monospecific or multispecific antibodies that bind to human OX40 and/or GITR) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., OX40 or GITR, e.g., human OX40 or GITR). Such methods are known and are described in the art, see, e.g., Shinmoto H et al., (2004) Cytotechnology 46: 19-23; Naganawa Y et al., (2005) Human Antibodies 14: 27-31.

Bispecific, bivalent antibodies, and methods of making them, are described, for instance in U.S. Pat. Nos. 5,731,168, 5,807,706, 5,821,333, and U.S. Appl. Publ. Nos. 2003/

020734 and 2002/0155537; each of which is herein incorporated by reference in its entirety. Bispecific tetravalent antibodies, and methods of making them are described, for instance, in Int. Appl. Publ. Nos. WO02/096948 and WO00/44788, the disclosures of both of which are herein incorporated by reference in its entirety. See generally, Int. Appl. Publ. Nos. WO93/17715, WO92/08802, WO91/00360, and WO92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992); each of which is herein incorporated by reference in its entirety.

One method for generating bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, compositions of the invention have immunoglobulin chains in which the CH3 domains have been modified by mutating selected amino acids that interact at the interface between two polypeptides to form a bispecific antibody. The bispecific antibodies can be composed of immunoglobulin chains of the same subclass (e.g., IgG1 or IgG3) or different subclasses (e.g., IgG1 and IgG3, or IgG3 and IgG4)

In one embodiment, a bispecific antibody that binds to OX40 and/or GITR comprises a T366W mutation in the "knobs chain" and T366S, L368A, Y407V mutations in the "hole chain," and optionally an additional interchain disulfide bridge between the CH3 domains by, e.g., introducing a Y349C mutation into the "knobs chain" and a E356C mutation or a S354C mutation into the "hole chain;" R409D, K370E mutations in the "knobs chain" and D399K, E357K mutations in the "hole chain;" R409D, K370E mutations in the "knobs chain" and D399K, E357K mutations in the "hole chain;" a T366W mutation in the "knobs chain" and T366S, L368A, Y407V mutations in the "hole chain;" R409D, K370E mutations in the "knobs chain" and D399K, E357K mutations in the "hole chain;" Y349C, T366W mutations in one of the chains and E356C, T366S, L368A, Y407V mutations in the counterpart chain; Y349C, T366W mutations in one chain and S354C, T366S, L368A, Y407V mutations in the counterpart chain; Y349C, T366W mutations in one chain and S354C, T366S, L368A, Y407V mutations in the counterpart chain; and Y349C, T366W mutations in one chain and S354C, T366S, L368A, Y407V mutations in the counterpart chain, numbering according to the EU numbering system.

Bispecific antibodies that bind to OX40 and/or GITR can, in some instances contain, IgG4 and IgG1, IgG4 and IgG2, IgG4 and IgG2, IgG4 and IgG3, or IgG1 and IgG3 chain heterodimers. Such heterodimeric heavy chain antibodies, can routinely be engineered by, for example, modifying selected amino acids forming the interface of the CH3 domains in human IgG4 and the IgG1 or IgG3 so as to favor heterodimeric heavy chain formation.

In particular embodiments, a multispecific (e.g., bispecific) antibody can be a chimeric antibody or a humanized antibody. In certain embodiments, a multispecific (e.g., bispecific) antibody can be a F(ab')$_2$ fragment. A F(ab')$_2$ fragment contains the two antigen-binding arms of a tetrameric antibody molecule linked by disulfide bonds in the hinge region.

Multispecific (e.g., bispecific) antibodies described herein can be generated by any technique known to those of skill in the art. For example, F(ab')$_2$ fragments described herein can be produced by proteolytic cleavage of immunoglobulin molecules, using enzymes such as pepsin.

5.3.1 Polynucleotides

In certain aspects, provided herein are polynucleotides comprising a nucleotide sequence encoding an antibody described herein or a fragment thereof (e.g., a light chain variable region and/or heavy chain variable region) that immunospecifically binds to an OX40 and/or GITR (e.g., human OX40 and/or GITR) antigen, and vectors, e.g., vectors comprising such polynucleotides for recombinant expression in host cells (e.g., E. coli and mammalian cells). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which immunospecifically bind to an OX40 and/or GITR polypeptide (e.g., human OX40 and/or GITR) and comprises an amino acid sequence as described herein, as well as antibodies that compete with such antibodies for binding to an OX40 and/or GITR polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL CDRs of antibodies described herein (see, e.g., Tables 2, 4, 7, 9, and 12). The polynucleotides can comprise nucleotide sequences encoding a heavy chain comprising the VH CDRs of antibodies described herein (see, e.g., Tables 2, 3, 7, 8, and 12). In specific embodiments, a polynucleotide described herein encodes a heavy chain variable region and/or a light chain variable region comprising an amino acid sequence set forth in Tables 2, 5, 7, 10, or 13.

In particular embodiments, provided herein are polynucleotides comprising a nucleotide sequence encoding an anti-OX40 and/or GITR antibody comprising three VL chain CDRs, e.g., containing VL CDR1, VL CDR2, and VL CDR3 of any one of antibodies described herein (e.g., see Tables 4, 9, and 12). In specific embodiments, provided herein are polynucleotides comprising three VH chain CDRs, e.g., containing VH CDR1, VH CDR2, and VH CDR3 of any one of antibodies described herein (e.g., see Tables 3, 8, and 12). In specific embodiments, provided herein are polynucleotides comprising a nucleotide sequence encoding an anti-OX40 and/or GITR antibody comprising three VH chain CDRs, e.g., containing VL CDR1, VL CDR2, and VL CDR3 of any one of antibodies described herein (e.g., see Tables 4, 9, and 12) and three VH chain CDRs, e.g., containing VH CDR1, VH CDR2, and VH CDR3 of any one of antibodies described herein (e.g., see Tables 3, 8, and 12).

In certain embodiments, a polynucleotide described herein comprises a nucleotide sequence encoding an antibody or antigen-binding fragment thereof provided herein comprising a light chain variable region comprising an amino acid sequence described herein (e.g., see Tables 2, 5, 7, 10, and 13), wherein the antibody immunospecifically binds to OX40 and/or GITR (e.g., human OX40 and/or GITR).

In certain embodiments, a polynucleotide described herein comprises a nucleotide sequence encoding an antibody or antigen-binding fragment thereof provided herein comprising a heavy chain variable region comprising an amino acid sequence described herein (e.g., see Tables 2, 5, 7, 10, and 13), wherein the antibody immunospecifically binds to OX40 and/or GITR (e.g., human OX40 and/or GITR).

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody, which immunospecifically binds to OX40 and/or GITR (e.g., human OX40 and/or GITR), wherein the antibody comprises a light chain, and wherein the amino acid sequence of the light chain variable region can comprise a light chain variable region amino acid sequence set forth in Tables 2, 5, 7, 10, or 13, and wherein the constant region of the light chain comprises the amino acid sequence of a human kappa light chain constant region. In another particular embodiment, a polynucleotide provided herein comprises a nucleotide sequence encoding an antibody, which immunospecifically binds to OX40 and/or GITR (e.g., human OX40 and/or GITR), and comprises a light chain, wherein the amino acid sequence of the light chain variable region can comprise a light chain variable region amino acid sequence set forth in Tables 2, 5, 7, 10, or 13, and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to OX40 (e.g., human OX40), wherein the antibody comprises a heavy chain, wherein the amino acid sequence of the heavy chain variable region can comprise the VH amino acid sequence set forth in Tables 2, 5, 7, 10, or 13, and wherein the constant region of the heavy chain comprises the amino acid sequence of a human gamma (γ) heavy chain constant region.

In a certain embodiment, a polynucleotide provided herein comprises a nucleotide sequence(s) encoding a heavy chain variable region and/or a light chain variable region of an antibody described herein (e.g., see Tables 2, 5, 7, 10, and 13), which immunospecifically binds to OX40 and/or GITR (e.g., human OX40 and/or GITR).

In yet another specific embodiment, a polynucleotide provided herein comprises a nucleotide sequence encoding an antibody described herein, which immunospecifically binds OX40 and/or GITR (e.g., human OX40 and/or GITR), wherein the antibody comprises a light chain variable region and a heavy chain variable region comprising any amino acid sequences described herein, and wherein the constant regions comprise the amino acid sequences of the constant regions of a human IgG$_1$ (e.g., allotype 1, 17, or 3), human IgG2, or human IgG4.

In a specific embodiment, provided herein are polynucleotides comprising a nucleotide sequence encoding an anti-OX40 and/or GITR antibody or domain thereof, designated herein, see, e.g., Tables 1-5, 7-10, 12, and 13.

Also provided herein are polynucleotides encoding an anti-OX40 and/or GITR antibody or a fragment thereof that are optimized, e.g., by codon/RNA optimization, replacement with heterologous signal sequences, and elimination of mRNA instability elements. Methods to generate optimized nucleic acids encoding an anti-OX40 antibody or a fragment thereof (e.g., light chain, heavy chain, heavy chain variable region, or light chain variable region) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding an anti-OX40 and/or GITR antibody described herein or a fragment thereof (e.g., heavy chain variable region or light chain variable region) can hybridize to an antisense (e.g., complementary) polynucleotide of an unoptimized polynucleotide sequence encoding an anti-OX40 and/or GITR antibody described herein or a fragment thereof (e.g., heavy chain variable region or light chain variable region). In specific embodiments, an optimized nucleotide sequence encoding an anti-OX40 and/or GITR antibody described herein or a fragment hybridizes under high stringency conditions to antisense polynucleotide of an unoptimized polynucleotide sequence encoding an anti-OX40 and/or GITR antibody described herein or a fragment thereof. In a specific embodiment, an optimized nucleotide sequence encoding an anti-OX40 and/or GITR antibody described herein or a fragment thereof hybridizes under high stringency, intermediate or lower stringency hybridization conditions to an antisense polynucleotide of an unoptimized nucleotide sequence encoding an anti-OX40 and/or GITR antibody described herein or a fragment thereof. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, e.g., antibodies described in Tables 2-5, 7-10, and 12-14, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-246), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody or fragment thereof described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody or fragment thereof is not available, but the sequence of the antibody molecule or fragment thereof is known, a nucleic acid encoding the immunoglobulin or fragment can be chemically synthesized or obtained from a suitable source (e.g., an antibody cDNA library or a cDNA library generated from, or nucleic acid, for example poly A+RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-OX40 and/or GITR antibodies described herein can be readily isolated and sequenced using conventional procedures (e.g., by using oligonucleotide probes that are capable of binding specifically to genes encoding the heavy and light chains of the anti-OX40 and/or GITR antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS® System (Lonza)), or myeloma cells that do not otherwise produce immunoglobulin protein, to obtain the synthesis of anti-OX40 antibodies in the recombinant host cells.

To generate antibodies, PCR primers including heavy or light chain variable region nucleotide sequences, a restriction site, and a flanking sequence to protect the restriction site can be used to amplify the heavy or light chain variable region sequences in scFv clones. Utilizing cloning techniques known to those of skill in the art, the PCR amplified heavy chain variable regions can be cloned into vectors expressing a heavy chain constant region, e.g., the human gamma 4 constant region, and the PCR amplified light chain variable regions can be cloned into vectors expressing a light chain constant region, e.g., human kappa or lambda constant regions. In certain embodiments, the vectors for expressing the heavy or light chain variable regions comprise an EF-1α promoter, a secretion signal, a cloning site for the variable domain, constant domains, and a selection marker such as neomycin. The heavy and light chain variable regions can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a heavy chain variable region and/or light chain variable region (e.g., see Tables 2, 5, 7, 10, and 13) provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

5.3.2 Cells and Vectors

In certain aspects, provided herein are cells (e.g., host cells) expressing (e.g., recombinantly) antibodies described herein which specifically bind to OX40 (including, e.g., antibodies that bind to human OX40 and GITR) and related polynucleotides and expression vectors. Provided herein are vectors (e.g., expression vectors) comprising polynucleotides comprising nucleotide sequences encoding anti-OX40 and/or GITR antibodies or a fragment for recombinant expression in host cells, for example in mammalian cells. Also provided herein are host cells comprising such vectors for recombinantly expressing anti-OX40 antibodies (including, e.g., antibodies that bind to human OX40 and GITR described herein (e.g., human or humanized antibody). In a particular aspect, provided herein are methods for producing an antibody described herein, comprising expressing such antibody in a host cell.

Recombinant expression of an antibody or fragment thereof described herein (e.g., a heavy or light chain of an antibody described herein) that specifically binds to OX40 and/or GITR (including, e.g., monospecific or multispecific antibodies that bind to human OX40 and/or GITR) involves construction of an expression vector containing a polynucleotide that encodes the antibody or fragment. Once a polynucleotide encoding an antibody or fragment thereof (e.g., heavy or light chain variable domains) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein (e.g., a monospecific or multispecific antibody comprising the CDRs in Tables 2, 3, 4, 7, 8, 9, and/or 12) or a fragment thereof. Thus, provided herein are host cells containing a polynucleotide encoding an antibody described herein (e.g., a monospecific or multispecific antibody comprising the CDRs in Tables 2, 3, 4, 7, 8, 9, and/or 12) or fragments thereof (e.g., a heavy or light chain thereof, or fragment thereof), operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein (e.g., a monospecific or multispecific antibody comprising the CDRs in Tables 2, 3, 4, 7, 8, 9, and/or 12), or a fragment thereof. In specific embodiments, a host cell contains two different vectors, a first vector comprising a polynucleotide encoding a heavy chain or a heavy chain variable region of an antibody described herein (e.g., a monospecific or multispecific antibody comprising the CDRs in Tables 2, 3, 4, 7, 8, 9, and/or 12), or a fragment thereof, and a second vector comprising a polynucleotide encoding a light chain or a light chain variable region of an antibody described herein (e.g., a monospecific or multispecific antibody comprising the CDRs in Tables 2, 3, 4, 7, 8, 9, and/or 12), or a fragment thereof. In other embodiments, a first host cell comprises a first vector comprising a polynucleotide encoding a heavy chain or a heavy chain variable region of an antibody described herein (e.g., a monospecific or multispecific antibody comprising the CDRs in Tables 2, 3, 4, 7, 8, 9, and/or 12), or a fragment thereof, and a second host cell comprises a second vector comprising a polynucleotide encoding a light chain or a light chain variable region of an antibody described herein (e.g., a monospecific or multispecific antibody comprising the CDRs in Tables 2, 3, 4, 7, 8, 9, and/or 12). In specific embodiments, a heavy chain/heavy chain variable region expressed by a first cell associated with a light chain/light chain variable region of a second cell to form an anti-OX40 and/or GITR antibody described herein (e.g., a monospecific or multispecific antibody comprising the CDRs in Tables 2, 3, 4, 7, 8, 9, and/or 12). In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-OX40 and/or GITR antibody described herein (e.g., a monospecific or multispecific antibody comprising the CDRs in Tables 2, 3, 4, 7, 8, 9, and/or 12), and a second vector comprising a polynucleotide encoding a heavy chain/heavy chain variable region of an anti-OX40 antibody described herein (e.g., a monospecific or multispecific antibody comprising the CDRs in Tables 2, 3, 4, 7, 8, 9, and/or 12).

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein (e.g., a monospecific or multispecific antibody comprising the CDRs in Tables 2, 3, 4, 7, 8, 9, and/or 12) are CHO cells, for example CHO cells from the CHO GS® System (Lonza). In a particular embodiment, cells for expressing antibodies described herein are human cells, e.g., human cell lines. In a specific embodiment, a mammalian expression vector is POPTIVEC™-TOPO® vector (ThermoFisher Scientific) or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain embodiments, antibodies described herein are produced by CHO cells or NS0 cells. In a specific embodiment, the expression of nucleotide sequences encoding antibodies described herein which immunospecifically bind OX40 and/or GITR (e.g., human OX40 and/or GITR) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81: 3655-3659). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-OX40 and/or GITR antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of $\alpha 1,6$-fucosyltransferase can be used to produce antibodies with reduced fucose content. The POTELLIGENT® system (Lonza) is an example of such a system that can be used to produce antibodies with reduced fucose content.

For long-term, high-yield production of recombinant proteins, stable expression cells can be generated. For example, cell lines which stably express an anti-OX40 and/or GITR antibody described herein can be engineered.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-OX40 and/or GITR antibody described herein or a fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler M et al., (1977) Cell 11(1): 223-232), hypoxanthineguanine phosphoribosyltransferase (Szybalska E H & Szybalski W (1962) PNAS 48(12): 2026-2034) and adenine phosphoribosyltransferase (Lowy I et al., (1980) Cell 22(3): 817-823) genes can be employed in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-3570; O'Hare K et al., (1981) PNAS 78: 1527-1531); gpt, which confers resistance to mycophenolic acid (Mulligan R C & Berg P (1981) PNAS 78(4): 2072-2076); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-215); and hygro, which confers resistance to hygromycin (Santerre R F et al., (1984) Gene 30(1-3): 147-156). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbére-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody. When the antibody or fragment is recombinantly produced, it is also generally substantially free of culture medium, i.e., culture medium represents less than about 20%, 10%, 2%, 1%, 0.5%, or 0.1% of the volume of the protein preparation. When the antibody or fragment is produced by chemical synthesis, it is generally substantially free of chemical precursors or other chemicals, i.e., it is separated from chemical precursors or other chemicals which are involved in the synthesis of the protein. Accordingly, such preparations of the antibody or fragment have less than about 30%, 20%, 10%, or 5% (by dry weight) of chemical precursors or compounds other than the antibody or fragment of interest. In a specific embodiment, antibodies described herein are isolated or purified.

5.4 Pharmaceutical Compositions

Provided herein are compositions comprising an antibody described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed.

Pharmaceutical compositions described herein can be useful in enhancing, inducing, or activating an OX40 and/or GITR activity and treating a condition, such as cancer or an infectious disease. In one embodiment, the present invention relates to a pharmaceutical composition of the present invention comprising an antibody (e.g., a monospecific or multispecific antibody) of the present invention for use as a medicament. In another embodiment, the present invention relates to a pharmaceutical composition of the present invention for use in a method for the treatment of cancer or an infectious disease. Examples of cancer that can be treated in accordance with the methods described herein include, but are not limited to, B cell lymphomas (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

Pharmaceutical compositions described herein that comprise an antagonistic antibody described herein can be useful in diminishing, reducing, inhibiting, or deactivating an OX40 and/or GITR activity and treating a condition, such as an inflammatory or autoimmune disease or disorder or an infectious disease.

Pharmaceutical compositions described herein that comprise an antagonistic antibody described herein can be useful in reducing, deactivating, or inhibiting an OX40 and/or GITR activity and treating a condition selected from the group consisting of infections (viral, bacterial, fungal and parasitic), endotoxic shock associated with infection, arthritis, rheumatoid arthritis, asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, uveitis, autoimmune uveitis, immune mediated inflammatory disorders of the central and peripheral nervous system such as multiple sclerosis, lupus (such as systemic lupus erythematosus) and Guillain-Barr syndrome, dermatitis, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma (surgery), graft-versus-host disease, transplant rejection, heart disease (i.e., cardiovascular disease) including ischaemic diseases such as myocardial infarction as well as atherosclerosis, intravascular coagulation, bone resorption, osteoporosis, osteoarthritis, periodontitis, hypochlorhydia, and neuromyelitis optica. In one embodiment, the present invention relates to a pharmaceutical composition of the present invention comprising an antibody (e.g., a monospecific or multispecific antibody) of the present invention for use as a medicament. In another embodiment, the present invention relates to a pharmaceutical composition of the present invention for use in a method for the treatment of an autoimmune or inflammatory disease or disorder.

The compositions to be used for in vivo administration can be sterile. This is readily accomplished by filtration through, e.g., sterile filtration membranes.

5.5 Uses and Methods

5.5.1 Therapeutic Uses and Methods

In one aspect, presented herein are methods for modulating one or more immune functions or responses in a subject, comprising to a subject in need thereof administering an anti-OX40 and/or GITR antibody (including, e.g., monospecific or multispecific antibodies that bind to human OX40 and/or GITR) described herein, or a composition thereof. In a specific aspect, presented herein are methods for activating, enhancing or inducing one or more immune functions or responses in a subject, comprising to a subject in need thereof administering an anti-OX40 and/or GITR antibody (including, e.g., monospecific or multispecific antibodies that bind to human OX40 and/or GITR) or a composition thereof. In a specific embodiment, presented herein are methods for preventing and/or treating diseases in which it is desirable to activate or enhance one or more immune functions or responses, comprising administering to a subject in need thereof an anti-OX40 and/or GITR antibody (including, e.g., monospecific or multispecific antibodies that bind to human OX40 and/or GITR) described herein or a composition thereof. In a certain embodiment, presented herein are methods of treating an infectious disease comprising administering to a subject in need thereof an anti-OX40 and/or GITR antibody (including, e.g., monospecific or multispecific antibodies that bind to human OX40 and/or GITR) or a composition thereof. In a certain embodiment, presented herein are methods of treating cancer comprising administering to a subject in need thereof an anti-OX40 and/or GITR antibody (including, e.g., monospecific or multispecific antibodies that bind to human OX40 and/or GITR) or a composition thereof. The cancer can be selected from a group consisting of melanoma, renal cancer, and prostate cancer. The cancer can be selected from a group consisting of melanoma, renal cancer, prostate cancer, colon cancer, and lung cancer. In a certain embodiment, presented herein are methods of treating melanoma comprising administering to a subject in need thereof an anti-OX40 and/or GITR antibody (including, e.g., monospecific or multispecific antibodies that bind to human OX40 and/or GITR) or a composition thereof. In a certain embodiment, presented herein are methods of treating renal cancer comprising administering to a subject in need thereof an anti-OX40 and/or GITR antibody (including, e.g., monospecific or multispecific antibodies that bind to human OX40 and/or GITR) or a composition thereof. In a certain embodiment, presented herein are methods of treating prostate cancer comprising administering to a subject in need thereof an anti-OX40 and/or GITR antibody (including, e.g., monospecific or multispecific antibodies that bind to human OX40 and/or GITR) or a composition thereof. In certain embodiments, presented herein are methods of treating colon cancer comprising administering to a subject in need thereof an anti-OX40 and/or GITR antibody (including, e.g., monospecific or multispecific antibodies that bind to human OX40 and/or GITR) or a composition thereof. In certain embodiments, presented herein are methods of treating lung cancer comprising administering to a subject in need thereof an anti-OX40 and/or GITR antibody (including, e.g., monospecific or multispecific antibodies that bind to human OX40 and/or GITR) or a composition thereof. In certain embodiments, presented herein are methods of treating non-small cell lung cancer (NSCLC) comprising administering to a subject in need thereof an anti-OX40 and/or GITR antibody (including, e.g., monospecific or multispecific antibodies that bind to human OX40 and/or GITR) or a composition thereof.

In a certain embodiment, presented herein are methods of treating a cancer selected from the group consisting of: B cell lymphomas (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

In another embodiment, an anti-OX40 and/or GITR antibody (including, e.g., monospecific or multispecific antibodies that bind to human OX40 and/or GITR) is administered to a patient diagnosed with cancer to increase the proliferation and/or effector function of one or more immune cell populations (e.g., T cell effector cells, such as CD4$^+$ and CD8$^+$ T cells) in the patient.

In a specific embodiment, an anti-OX40 and/or GITR antibody (including, e.g., monospecific or multispecific antibodies that bind to human OX40 and/or GITR) described herein activates or enhances or induces one or more immune functions or responses in a subject by at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the anti-OX40 and/or GITR antibody (including, e.g., monospecific or multispecific antibodies that bind to human OX40 and/or GITR) described herein using assays well known in the art, e.g., ELISPOT, ELISA, and cell proliferation assays. In a specific embodiment, the immune function is cytokine production (e.g., IL-2, TNF-α, IFN-γ, IL-4, IL-10, and/or IL-13 production). In another embodiment, the immune function is T cell proliferation/expansion, which can be assayed, e.g., by flow cytometry to detect the number of cells expressing markers of T cells (e.g., CD3, CD4, or CD8). In another embodiment, the immune function is antibody production, which can be assayed, e.g., by ELISA. In some embodiments, the immune function is effector function, which can be assayed, e.g., by a cytotoxicity assay or other assays well known in the art. In another embodiment, the immune function is a Th1 response. In another embodiment, the immune function is a Th2 response. In another embodiment, the immune function is a memory response.

In specific embodiments, non-limiting examples of immune functions that can be enhanced or induced by an anti-OX40 and/or GITR antibody (including, e.g., monospecific or multispecific antibodies that bind to human OX40 and/or GITR) are proliferation/expansion of effector lymphocytes (e.g., increase in the number of effector T lymphocytes), and inhibition of apoptosis of effector lymphocytes (e.g., effector T lymphocytes). In particular embodiments, an immune function enhanced or induced by an anti-OX40 and/or GITR antibody (including, e.g., monospecific or multispecific antibodies that bind to human OX40 and/or GITR) described herein is proliferation/expansion in the number of or activation of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer (NK) cells), macrophages, monocytes, dendritic cells, mast cells, eosinophils, basophils or polymorphonucleated leukocytes. In one embodiment, an anti-OX40 and/or GITR antibody (including, e.g., monospecific or multispecific antibodies that bind to human OX40 and/or GITR) described herein activates or enhances the proliferation/expansion or number of lymphocyte progenitors. In some embodiments, an anti-OX40 and/or GITR antibody (including, e.g., monospecific or multispecific antibodies that bind to human OX40 and/or GITR) described herein increases the number of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer cells (NK cells), macrophages, monocytes, dendritic cells, mast cells, eosinophils, basophils or polymorphonucleated leukocytes by approximately at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative a negative control (e.g., number of the respective cells not treated, cultured, or contacted with an anti-OX40 and/or GITR antibody (including, e.g., monospecific or multispecific antibodies that bind to human OX40 and/or GITR) described herein.

In some embodiments, an anti-OX40 and/or GITR antibody (including, e.g., monospecific or multispecific antibodies that bind to human OX40 and/or GITR) described herein is administered to a subject in combination with a chemotherapeutic, a radiotherapeutic, or a checkpoint targeting agent. In some embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, and an agonist anti-OX40 antibody.

In some embodiments, an anti-OX40 and/or GITR antibody (including, e.g., monospecific or multispecific antibodies that bind to human OX40 and/or GITR) described herein is administered to a subject in combination with a compound that targets an immunomodulatory enzyme(s) such as IDO (indoleamine-(2,3)-dioxygenase) and TDO (tryptophan 2,3-dioxygenase). In particular embodiments, such compound is selected from the group consisting of epacadostat (Incyte Corp), F001287 (Flexus Biosciences), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919.

In some embodiments, an anti-OX40 and/or GITR antibody (including, e.g., monospecific or multispecific antibodies that bind to human OX40 and/or GITR) described herein is administered to a subject in combination with a vaccine.

In some embodiments, an anti-OX40 and/or GITR antibody (including, e.g., monospecific or multispecific antibodies that bind to human OX40 and/or GITR) described herein is administered to a subject in combination with a heat shock protein based tumor vaccine or a heat shock protein based pathogen vaccine. In a specific embodiment, an anti-OX40 and/or GITR antibody (including, e.g., monospecific or multispecific antibodies that bind to human OX40 and/or GITR) is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In some embodiments, HSPPCs used in methods disclosed herein comprise one or more heat shock proteins from the hsp60, hsp70, or hsp90 family of stress proteins complexed with antigenic peptides. In some embodiments, HSPPCs comprise hsc70, hsp70, hsp90, hsp110, grp170, gp96, calreticulin, or combinations of two or more thereof.

In a specific embodiment, an anti-OX40 and/or GITR antibody (including, e.g., monospecific or multispecific antibodies that bind to human OX40 and/or GITR) is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In some embodiments, this fingerprint contains unique antigens that are present only in that particular subject's specific cancer cells and injection of the vaccine is intended to stimulate the subject's immune system to recognize and attack any cells with the specific cancer fingerprint.

In some embodiments, the HSPPC, e.g., HSPPC-96, is produced from the tumor tissue of a subject. In a specific embodiment, the HSPPC (e.g., HSPPC-96) is produced from tumor of the type of cancer or metastasis thereof being treated. In another specific embodiment, the HSPPC (e.g., HSPPC-96) is autologous to the subject being treated. In some embodiments, the tumor tissue is non-necrotic tumor tissue. In some embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In some embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In some embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, which are incorporated herein by reference in their entireties for all purposes, U.S. Pat. Nos. 6,391,306, 6,383,492, 6,403,095, 6,410,026, 6,436,404, 6,447,780, 6,447,781 and 6,610,659.

In one aspect, the methods for modulating one or more immune functions or responses in a subject as presented herein are methods for deactivating, reducing, or inhibiting one or more immune functions or responses in a subject, comprising to a subject in need thereof administering an anti-OX40 and/or GITR antagonistic antibody (including, e.g., monospecific or multispecific antibodies that bind to human OX40 and/or GITR) or a composition thereof. In a specific embodiment, presented herein are methods for preventing and/or treating diseases in which it is desirable to deactivate, reduce, or inhibit one or more immune functions or responses, comprising administering to a subject in need thereof an anti-OX40 and/or GITR antagonistic antibody (including, e.g., monospecific or multispecific antibodies that bind to human OX40 and/or GITR) described herein or a composition thereof. In a certain embodiment, presented herein are methods of treating an autoimmune or inflammatory disease or disorder comprising administering to a subject in need thereof an effective amount of an anti-OX40 and/or GITR antagonistic antibody (including, e.g., monospecific or multispecific antibodies that bind to human OX40 and/or GITR) described herein or a composition thereof. In certain embodiments, the subject is a human. In certain embodiments, the disease or disorder is selected from the group consisting of: infections (viral, bacterial, fungal and parasitic), endotoxic shock associated with infection, arthritis, rheumatoid arthritis, asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, uveitis, autoimmune uveitis, immune mediated inflammatory disorders of the central and peripheral nervous system such as multiple sclerosis, lupus (such as systemic lupus erythematosus) and Guillain-Barr syndrome, dermatitis, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, pancreatitis, trauma (surgery), graft-versus-host disease, transplant rejection, heart disease (i.e., cardiovascular disease) including ischaemic diseases such as myocardial infarction as well as atherosclerosis, intravascular coagulation, bone resorption, osteoporosis, osteoarthritis, periodontitis, hypochlorhydia, and neuromyelitis optica. In certain embodiments, the disease or disorder is selected from the group consisting of: transplant rejection, graft-versus-host disease, vasculitis, asthma, rheumatoid arthritis, dermatitis, inflammatory bowel disease, uveitis, lupus, colitis, diabetes, multiple sclerosis, and airway inflammation.

In another embodiment, an anti-OX40 and/or GITR antagonistic antibody (including, e.g., monospecific or multispecific antibodies that bind to human OX40 and/or GITR) described herein is administered to a patient diagnosed with an autoimmune or inflammatory disease or disorder to decrease the proliferation and/or effector function of one or more immune cell populations (e.g., T cell effector cells, such as CD4$^+$ and CD8$^+$ T cells) in the patient.

In a specific embodiment, an anti-OX40 and/or GITR antagonistic antibody (including, e.g., monospecific or multispecific antibodies that bind to human OX40 and/or GITR) described herein deactivates or reduces or inhibits one or more immune functions or responses in a subject by at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the anti-OX40 and/or GITR antagonistic antibody (including, e.g., monospecific or multispecific antibodies that bind to human OX40 and/or GITR) described herein using assays well known in the art, e.g., ELISPOT, ELISA, and cell proliferation assays. In a specific embodiment, the immune function is cytokine production (e.g., IL-2, TNF-α, IFN-γ, IL-4, IL-10, and/or IL-13 production). In another embodiment, the immune function is T cell proliferation/expansion, which can be assayed, e.g., by flow cytometry to detect the number of cells expressing markers of T cells (e.g., CD3, CD4, or CD8). In another embodiment, the immune function is antibody production, which can be assayed, e.g., by ELISA. In some embodiments, the immune function is effector function, which can be assayed, e.g., by a cytotoxicity assay or other assays well known in the art. In another embodiment, the immune function is a Th1 response. In another embodiment, the immune function is a Th2 response. In another embodiment, the immune function is a memory response.

In specific embodiments, non-limiting examples of immune functions that can be reduced or inhibited by an anti-OX40 and/or GITR antagonistic antibody (including, e.g., monospecific or multispecific antibodies that bind to human OX40 and/or GITR) are proliferation/expansion of effector lymphocytes (e.g., decrease in the number of effector T lymphocytes), and stimulation of apoptosis of effector lymphocytes (e.g., effector T lymphocytes). In particular embodiments, an immune function reduced or inhibited by an anti-OX40 and/or GITR antagonistic antibody (including, e.g., monospecific or multispecific antibodies that bind to human OX40 and/or GITR) described herein is proliferation/expansion in the number of or activation of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer (NK) cells), macrophages, monocytes, dendritic cells, mast cells, eosinophils, basophils or polymorphonucleated leukocytes. In one embodiment, an anti-OX40 and/or GITR antagonistic antibody (including, e.g., monospecific or multispecific antibodies that bind to human OX40 and/or GITR) described herein deactivates or reduces or inhibits the proliferation/expansion or number of lymphocyte progenitors. In some embodiments, an anti-OX40 and/or GITR antagonistic antibody (including, e.g., monospecific or multispecific antibodies that bind to human OX40 and/or GITR) described herein decreases the number of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, tumor-resident T cells, CD122$^+$ T cells, natural killer cells (NK cells), macrophages, monocytes, dendritic cells, mast cells, eosinophils, basophils or polymorphonucleated leukocytes by approximately at least 99%, at least 98%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative a negative control (e.g., number of the respective cells not treated, cultured, or contacted with an anti-OX40 and/or GITR antagonistic antibody (including, e.g., monospecific or multispecific antibodies that bind to human OX40 and/or GITR) described herein.

In one embodiment, the present invention relates to an antibody (e.g., a monospecific or multispecific antibody) and/or pharmaceutical composition of the present invention for use in a method of the present invention, wherein the method further comprises administering an additional therapeutic agent to the subject. In one embodiment, the present invention relates to (a) an antibody (e.g., a monospecific or multispecific antibody) and/or pharmaceutical composition of the present invention and (b) an additional therapeutic agent for use as a medicament. In one embodiment, the present invention relates to (a) an antibody (e.g., a monospecific or multispecific antibody) and/or pharmaceutical composition of the present invention, and (b) an additional therapeutic agent for use in a method for the treatment of cancer or an infectious disease. In one embodiment, the present invention relates to (a) an antibody (e.g., a monospecific or multispecific antibody) and/or pharmaceutical composition of the present invention, and (b) an additional therapeutic agent for use in a method for the treatment of an autoimmune or inflammatory disease or disorder. In one embodiment, the present invention relates to a pharmaceutical composition, kit or kit-of-parts comprising (a) an antibody (e.g., a monospecific or multispecific antibody) and/or pharmaceutical composition of the present invention and (b) an additional therapeutic agent.

5.5.1.1 Routes of Administration & Dosage

An antibody or composition described herein can be delivered to a subject by a variety of routes.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the disease, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Generally, human antibodies have a longer half-life within the human body than antibodies from other species due to the immune response to the foreign polypeptides. Thus, lower dosages of human antibodies and less frequent administration is often possible.

5.5.2 Detection & Diagnostic Uses

An anti-OX40 and/or GITR antibody (including, e.g., monospecific or multispecific antibodies that bind to human OX40 and/or GITR) described herein (see, e.g., Section 5.2) can be used to assay OX40 and/or GITR protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-OX40 and/or GITR antibody (including, e.g., monospecific or multispecific antibodies that bind to human OX40 and/or GITR) described herein can be labeled and used in combination with an anti-OX40 and/or GITR antibody (including, e.g., monospecific or multispecific antibodies that bind to human OX40 and/or GITR) to detect OX40 protein levels.

Assaying for the expression level of OX40 protein and/or GITR protein is intended to include qualitatively or quantitatively measuring or estimating the level of an OX40 and/or GITR protein in a first biological sample either directly (e.g., by determining or estimating absolute protein level) or relatively (e.g., by comparing to the disease associated protein level in a second biological sample). OX40 and/or GITR polypeptide expression level in the first biological sample can be measured or estimated and compared to a standard OX40 and/or GITR protein level, the standard being taken from a second biological sample obtained from an individual not having the disorder or being determined by averaging levels from a population of individuals not having the disorder. As will be appreciated in the art, once the "standard" OX40 and/or GITR polypeptide level is known, it can be used repeatedly as a standard for comparison.

As used herein, the term "biological sample" refers to any biological sample obtained from a subject, cell line, tissue, or other source of cells potentially expressing OX40 and/or GITR. Methods for obtaining tissue biopsies and body fluids from animals (e.g., humans) are well known in the art. Biological samples include peripheral mononuclear blood cells.

An anti-OX40 and/or GITR antibody (including, e.g., monospecific or multispecific antibodies that bind to human OX40 and/or GITR) described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

In one embodiment, the present invention relates to an anti-OX40 and/or GITR antibody (including, e.g., monospecific or multispecific antibodies that bind to human OX40 and/or GITR) and/or pharmaceutical composition of the present invention for use as a diagnostic.

In one embodiment, an anti-OX40 and/or GITR antibody (including, e.g., monospecific or multispecific antibodies that bind to human OX40 and/or GITR) can be used in immunohistochemistry of biopsy samples.

In another embodiment, an anti-OX40 and/or GITR antibody (including, e.g., monospecific or multispecific antibodies that bind to human OX40 and/or GITR) can be used to detect levels of OX40 and/or GITR, or levels of cells which contain OX40 and/or GITR on their membrane surface, which levels can then be linked to certain disease symptoms. Anti-OX40 and/or GITR antibodies (including, e.g., monospecific or multispecific antibodies that bind to human OX40 and/or GITR) described herein can carry a detectable or functional label. When fluorescence labels are used, currently available microscopy and fluorescence-activated cell sorter analysis (FACS) or combination of both methods procedures known in the art can be utilized to identify and to quantitate the specific binding members. Anti-OX40 and/or GITR antibodies (including, e.g., monospecific or multispecific antibodies that bind to human OX40 and/or GITR) described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-OX40 antibody can carry a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of an anti-OX40 and/or GITR antibody (including, e.g., monospecific or multispecific antibodies that bind to human OX40 and/or GITR). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-OX40 and/or GITR antibody (including, e.g., monospecific or multispecific antibodies that bind to human OX40 and/or GITR) described herein under conditions that allow for the formation of a complex between the antibody and OX40 and/or GITR. Any complexes formed between the antibody and OX40 and/or GITR are detected and compared in the sample and the control. In light of the specific binding of the antibodies described herein for OX40 and/or GITR, the antibodies thereof can be used to specifically detect OX40 and/or GITR expression on the surface of cells. The antibodies described herein can also be used to purify OX40 and/or GITR via immunoaffinity purification.

Also included herein is an assay system which can be prepared in the form of a test kit for the quantitative analysis of the extent of the presence of, for instance, OX40, OX40/OX40L, GITR, and/or GITR/GITRL complexes. The system or test kit can comprise a labeled component, e.g., a labeled antibody, and one or more additional immunochemical reagents. See, e.g., Section 5.6 below for more on kits.

5.6 Kits

Provided herein are kits comprising one or more antibodies described herein or conjugates thereof. In a specific embodiment, provided herein is a pharmaceutical pack or kit comprising one or more containers filled with one or more of the ingredients of the pharmaceutical compositions described herein, such as one or more antibodies provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises an antibody described herein, for example a purified antibody, in one or more containers. In a specific embodiment, kits described herein contain a substantially isolated anti-OX40 and/or GITR antigen (e.g., human OX40 and/or GITR) that can be used as a control. In another specific embodiment, the kits described herein further comprise a control antibody which does not react with an OX40 and/or GITR antigen. In another specific embodiment, kits described herein contain one or more elements for detecting the binding of an antibody to an OX40 and/or GITR antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized OX40 and/or GITR antigen. The OX40 and/or GITR antigen provided in the kit can also be attached to a solid support. In a more specific embodiment, the detecting means of the above described kit includes a solid support to which an OX40 and/or GITR antigen is attached. Such a kit can also include a non-attached reporter-labeled anti-human antibody or anti-mouse/rat antibody. In this embodiment, binding of the antibody to the OX40 and/or GITR antigen can be detected by binding of the said reporter-labeled antibody.

The following examples are offered by way of illustration and not by way of limitation.

6. EXAMPLES

The examples in this Section (i.e., Section 6) are offered by way of illustration, and not by way of limitation.

6.1 Example 1: Characterization of Antibodies Against Human OX40

This example describes the characterization of antibodies that bind to human OX40. The sequence information of the variable regions of these anti-OX40 antibodies is listed in Table 5.

6.1.1 Antibody Binding to OX40-Expressing Cells

The binding characteristics of the anti-OX40 antibodies to cells expressing human OX40 were analyzed by flow cytometry. Briefly, Jurkat cells were transduced to recombinantly express human OX40. Stable clones were generated via single-cell sorting (FACSARIA™ fusion flow cytometer, BD biosciences). OX40 expression was verified by flow cytometry using positive control antibodies. For binding analysis, OX40-expressing Jurkat cells were incubated with anti-OX40 antibodies (12-point dose titration, 10 µg/ml to 0.00005 µg/ml) for 30 minutes at 4° C. The samples were washed twice and then incubated with FITC-conjugated mouse anti-human kappa detection antibody (Life Technologies, Catalog number: HP6062) for 30 minutes at 4° C. The samples were then washed twice and analyzed using the LSRFORTESSA™ flow cytometer (BD Biosciences). The flow cytometry plots were analyzed using a combination of FACS-DIVA™ (BD Biosciences) and WEHI Weasel flow cytometry analysis software.

As shown in FIGS. 1A-1J, all the anti-OX40 antibodies tested bound to OX40-expressing cells in a dose-dependent manner.

6.1.2 Effect of Anti-OX40 Antibodies in Blocking OX40L Induced NF-κB Signaling

An OX40 reporter assay was developed to test the activity of the anti-OX40 antibodies. This reporter assay was built using Jurkat cells which expressed minimum amount, if any, of FcR, diminishing the possibility of FcR-mediated clustering of OX40 molecules.

Cells ectopically expressing OX40 as well as NF-κB-luciferase (Nano luciferase, NANOLUC®, Promega Corporation) reporter were generated by transduction of lentiviral vectors (EF1a promoter) into Jurkat cells. Stable clones were generated via single-cell sorting (FACSARIA™ fusion). Expression of OX40 was verified by flow cytometry. To evaluate the ability of anti-OX40 antibodies to neutralize OX40L-induced NF-κB signaling, Jurkat-huOX40-NF-κB-luciferase cells were incubated with increasing concentrations of anti-OX40 antibodies or an isotype control antibody (8-point dose titration, 20 μg/ml to 0.01 μg/ml) for 30 minutes in RPMI media, supplemented with 10% heat-inactivated FBS at 37° C. and 5% $CO_2$. The samples were then washed twice, resuspended in 1 μg/ml of multimeric OX40L, and incubated for two additional hours at 37° C. For detection of luciferase activities, the samples were incubated with prepared NANO-GLO® luciferase assay substrate (Promega Corporation, 1:1 v/v) in passive lysis buffer for 5 minutes at room temperature. Data were collected using the ENVISION® multilabel plate reader (Perkin-Elmer Inc). To determine % OX40L activity, the RLU value for OX40L (1 μg/ml) without addition of antibody was established as 100% activity. Relative values for anti-OX40 antibodies and the isotype control were calculated accordingly.

As shown in FIGS. 2A-2I, pre-incubation of Jurkat-huOX40-NF-κB-luciferase reporter cells with increasing concentrations of anti-OX40 antibodies tested here significantly reduced OX40L-induced NF-κB-luciferase activity in a dose-dependent manner.

6.2 Example 2: Characterization of Antibodies Against Human GITR

This example describes the characterization of antibodies that bind to human GITR. The sequence information of the variable regions of these anti-GITR antibodies is listed in Table 10.

6.2.1 Antibody Binding to GITR-Expressing Cells

In this example, anti-GITR antibodies were tested for their binding to GITR-expressing cells by flow cytometry. Cells ectopically expressing human GITR were generated by transduction of lentiviral vectors (EF1a promoter) into the Jurkat cell line. Stable clones were generated via single-cell sorting (FACSARIA™ fusion flow cytometer). GITR expression was verified by flow cytometry using positive control antibodies. For binding analysis, GITR-expressing Jurkat cells were incubated with anti-GITR antibodies or an isotype control antibody for 30 minutes at 4° C. The samples were washed twice and then incubated with FITC-conjugated mouse anti-human kappa detection antibody (Life Technologies, Catalog number: HP6062) for 30 minutes at 4° C. The samples were then washed twice and analyzed using the LSRFORTESSA™ flow cytometer (BD Biosciences). The flow cytometry plots were analyzed using a combination of FACSDIVA™ (BD Biosciences) and WEHI Weasel flow cytometry analysis software.

All the anti-GITR antibodies tested exhibited dose-dependent binding to GITR-expressing cells (FIGS. 3A-3G).

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

---

What is claimed:

1. An isolated antibody that specifically binds to human OX40, the antibody comprising a heavy chain variable region comprising complementarity determining regions CDRH1, CDRH2, and CDRH3 and a light chain variable region comprising complementarity determining regions CDRL1, CDRL2, and CDRL3, wherein:
   (a) CDRH1 comprises the amino acid sequence of $X_1X_2X_3$MH (SEQ ID NO: 41), wherein
      $X_1$ is G, Q, H, or E,
      $X_2$ is S, E, or Y, and
      $X_3$ is A, S, or G;
   (b) CDRH2 comprises the amino acid sequence of RIRSK$X_1X_2X_3X_4X_5$TAYAASVKG (SEQ ID NO: 42), wherein
      $X_1$ is A, S, or Y,
      $X_2$ is N, E, or Y,
      $X_3$ is S, Q, or G,
      $X_4$ is Y, E, or Q, and
      $X_5$ is A, E, or L;
   (c) CDRH3 comprises the amino acid sequence of GI$X_1X_2X_3X_4X_5X_6X_7$Y (SEQ ID NO: 43), wherein
      $X_1$ is Y or A,
      $X_2$ is D or A,
      $X_3$ is S, T, or W,
      $X_4$ is S, E, or L,
      $X_5$ is G or A,
      $X_6$ is Y or A, and
      $X_7$ is D or A;
   (d) CDRL1 comprises the amino acid sequence of SEQ ID NO: 32;
   (e) CDRL2 comprises the amino acid sequence of SEQ ID NO: 33; and
   (f) CDRL3 comprises the amino acid sequence of MQ$X_1X_2X_3X_4$PLT (SEQ ID NO: 46), wherein
      $X_1$ is A or G,
      $X_2$ is L or S,
      $X_3$ is Q or K, and
      $X_4$ is T or W,
   and wherein the CDRH1, CDRH2, CDRH3, CDRL1, CDRL2, and CDRL3 sequences of the antibody are not respectively either SEQ ID NOs: 16, 21, 25, 32, 33, and 34 or SEQ ID NOs: 16, 21, 25, 32, 33, and 38, optionally wherein:
   (g) CDRH1 comprises an amino acid sequence selected from the group consisting of SEQ ID NOs: 16-20;
   (h) CDRH2 comprises the amino acid sequence of RIR-SKAXSYATAYAASVKG (SEQ ID NO: 44), wherein: X is N or Y, or an amino acid sequence selected from the group consisting of SEQ ID NOs: 21-24;

(i) CDRH3 comprises the amino acid sequence of GIX$_1$X$_2$SSGX$_3$X$_4$Y (SEQ ID NO: 45), wherein: X$_1$ is Y or A; X$_2$ is D or A; X$_3$ is Y or A; and X$_4$ is D or A, or an amino acid sequence selected from the group consisting of SEQ ID NOs: 25-31;

(j) CDRL3 comprises an amino acid sequence selected from the group consisting of SEQ ID NOs: 34-38;

(k) CDRH1, CDRH2, and CDRH3 comprise the amino acid sequences set forth in SEQ ID NOs: 16, 21, and 25; 16, 22, and 25; 16, 21, and 26; 16, 21, and 27; 16, 21, and 28; 16, 21, and 29; 17, 21, and 30; 18, 23, and 25; 19, 24, and 25; or 20, 21, and 31, respectively;

(l) CDRL1, CDRL2, and CDRL3 comprise the amino acid sequences set forth in SEQ ID NOs: 32, 33, and 34; 32, 33, and 35; 32, 33, and 36; 32, 33, and 37; or 32, 33, and 38, respectively; or (m) CDRH1, CDRH2, CDRH3, CDRL1, CDRL2, and CDRL3 comprise the amino acid sequences set forth in SEQ ID NOs: 16, 22, 25, 32, 33, and 34; 16, 21, 26, 32, 33, and 34; 16, 21, 27, 32, 33, and 34; 16, 21, 28, 32, 33, and 34; 16, 21, 29, 32, 33, and 34; 17, 21, 30, 32, 33, and 38; 18, 23, 25, 32, 33, and 38; 19, 24, 25, 32, 33, and 38; 20, 21, 31, 32, 33, and 38; 16, 21, 25, 32, 33, and 35; 16, 21, 25, 32, 33, and 36; or 16, 21, 25, 32, 33, and 37, respectively.

2. The isolated antibody of claim 1, wherein the antibody comprises:
(a) a heavy chain variable region comprising
  (i) the amino acid sequence of SEQ ID NO: 47 or 48;
  (ii) an amino acid sequence which is at least 75%, 80%, 85%, 90%, 95%, or 100% identical to an amino acid sequence selected from the group consisting of SEQ ID NOs: 1-10; or
  (iii) an amino acid sequence selected from the group consisting of SEQ ID NOs: 1-10; and/or
(b) a light chain variable region comprising
  (i) the amino acid sequence of SEQ ID NO: 49;
  (ii) an amino acid sequence which is at least 75%, 80%, 85%, 90%, 95%, or 100% identical to an amino acid sequence selected from the group consisting of SEQ ID NOs: 11-15; or
  (iii) an amino acid sequence selected from the group consisting of SEQ ID NOs: 11-15.

3. An isolated antibody that specifically binds to human GITR, the antibody comprising:
a heavy chain variable region comprising complementarity determining regions CDRH1, CDRH2, and CDRH3 and a light chain variable region comprising complementarity determining regions CDRL1, CDRL2, and CDRL3, wherein the CDRH1, CDRH2, CDRH3, CDRL1, CDRL2, and CDRL3 regions comprise the amino acid sequences set forth in SEQ ID NOs: 60, 64, 68, 69, 71, and 72, respectively.

4. An isolated multispecific antibody comprising a first antigen-binding domain and a second antigen-binding domain, wherein the second antigen-binding domain specifically binds to human GITR and comprises:
a heavy chain variable region comprising complementarity determining regions CDRH1, CDRH2, and CDRH3 and a light chain variable region comprising complementarity determining regions CDRL1, CDRL2, and CDRL3, wherein the CDRH1, CDRH2, CDRH3, CDRL1, CDRL2, and CDRL3 regions of the second antigen-binding domain that specifically binds to human GITR comprise the amino acid sequences set forth in SEQ ID NOs: 60, 64, 68, 69, 71, and 72, respectively.

5. The isolated multispecific antibody of claim 4, wherein the first antigen-binding domain specifically binds to human OX40.

6. A pharmaceutical composition comprising the antibody of claim 3 and a pharmaceutically acceptable carrier or excipient.

7. A pharmaceutical composition comprising the antibody of claim 4 and a pharmaceutically acceptable carrier or excipient.

8. The isolated antibody of claim 3, wherein the heavy chain variable region comprises the amino acid sequence of SEQ ID NO: 53.

9. The isolated antibody of claim 3, wherein the light chain variable region comprises the amino acid sequence of SEQ ID NO: 57.

10. The isolated antibody of claim 8, wherein the light chain variable region comprises the amino acid sequence of SEQ ID NO: 57.

11. The isolated multispecific antibody of claim 5, wherein the first antigen-binding domain that specifically binds to human OX40 comprises a heavy chain variable region comprising complementarity determining regions CDRH1, CDRH2, and CDRH3 and a light chain variable region comprising complementarity determining regions CDRL1, CDRL2, and CDRL3, wherein:
(a) CDRH1 comprises the amino acid sequence of X$_1$X$_2$X$_3$MH (SEQ ID NO: 41), wherein
  X$_1$ is G, Q, H, or E,
  X$_2$ is S, E, or Y, and
  X$_3$ is A, S, or G;
(b) CDRH2 comprises the amino acid sequence of RIRSKX$_1$X$_2$X$_3$X$_4$X$_5$TAYAASVKG (SEQ ID NO: 42), wherein
  X$_1$ is A, S, or Y,
  X$_2$ is N, E, or Y,
  X$_3$ is S, Q, or G,
  X$_4$ is Y, E, or Q, and
  X$_5$ is A, E, or L;
(c) CDRH3 comprises the amino acid sequence of GIX$_1$X$_2$X$_3$X$_4$X$_5$X$_6$X$_7$Y (SEQ ID NO: 43), wherein
  X$_1$ is Y or A,
  X$_2$ is D or A,
  X$_3$ is S, T, or W,
  X$_4$ is S, E, or L,
  X$_5$ is G or A,
  X$_6$ is Y or A, and
  X$_7$ is D or A;
(d) CDRL1 comprises the amino acid sequence of SEQ ID NO: 32;
(e) CDRL2 comprises the amino acid sequence of SEQ ID NO: 33; and
(f) CDRL3 comprises the amino acid sequence of MQX$_1$X$_2$X$_3$X$_4$PLT (SEQ ID NO: 46), wherein
  X$_1$ is A or G,
  X$_2$ is L or S,
  X$_3$ is Q or K, and
X$_4$ is T or W.

12. The isolated multispecific antibody of claim 11, wherein the CDRH1, CDRH2, CDRH3, CDRL1, CDRL2, and CDRL3 regions of the first antigen-binding domain that specifically binds to human OX40 comprise the amino acid sequences set forth in SEQ ID NOs: 16, 21, 25, 32, 33, and 34, respectively.

13. The isolated multispecific antibody of claim 11, wherein the CDRH1, CDRH2, CDRH3, CDRL1, CDRL2, and CDRL3 regions of the first antigen-binding domain that specifically binds to human OX40 comprise the amino acid sequences set forth in SEQ ID NOs: 16, 21, 25, 32, 33, and 38, respectively.

14. The isolated antibody of claim 4, wherein the heavy chain variable region comprises the amino acid sequence of SEQ ID NO: 53.

15. The isolated antibody of claim 4, wherein the light chain variable region comprises the amino acid sequence of SEQ ID NO: 57.

16. The isolated antibody of claim 14, wherein the light chain variable region comprises the amino acid sequence of SEQ ID NO: 57.

* * * * *